US012584844B2

(12) United States Patent
Goldberg et al.

(10) Patent No.: US 12,584,844 B2
(45) Date of Patent: *Mar. 24, 2026

(54) FLOW CYTOMETRY IMMUNOPROFILING OF PERIPHERAL BLOOD

(71) Applicant: BostonGene Corporation, Waltham, MA (US)

(72) Inventors: Michael F. Goldberg, Brookline, MA (US); Alexander Bagaev, Waltham, MA (US); Daniiar Dyikanov, Waltham, MA (US); Aleksandr Zaitsev, Yerevan (AM); Boris Shpak, Yerevan (AM); Evgenii Tikhonov, Yerevan (AM); Polina Turova, Yerevan (AM); Arsenii Sokolov, Yerevan (AM); Anna Gantseva, Yerevan (AM)

(73) Assignee: BostonGene Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,357

(22) Filed: Nov. 17, 2023

(65) Prior Publication Data

US 2024/0167933 A1      May 23, 2024

Related U.S. Application Data

(60) Provisional application No. 63/490,214, filed on Mar. 14, 2023, provisional application No. 63/426,153, filed on Nov. 17, 2022.

(51) Int. Cl.
| | |
|---|---|
| *G01N 15/1429* | (2024.01) |
| *G01N 15/01* | (2024.01) |
| *G16B 25/10* | (2019.01) |
| *G16B 40/20* | (2019.01) |
| *G16B 40/30* | (2019.01) |
| *G16H 50/20* | (2018.01) |

(52) U.S. Cl.
CPC ......... *G01N 15/1429* (2013.01); *G16B 25/10* (2019.02); *G16B 40/20* (2019.02); *G16B 40/30* (2019.02); *G16H 50/20* (2018.01); *G01N 2015/016* (2024.01)

(58) Field of Classification Search
CPC ......... G01N 15/1429; G01N 2015/016; G16H 50/20
See application file for complete search history.

(56) References Cited

U.S. PATENT DOCUMENTS

| | | | |
|---|---|---|---|
| 11,302,420 | B2 | 4/2022 | Bagaev et al. |
| 11,315,658 | B2 | 4/2022 | Zaitsev et al. |
| 11,587,642 | B2 | 2/2023 | Zaitsev et al. |
| 2005/0048463 | A1 | 3/2005 | Deng et al. |
| 2014/0066323 | A1 | 3/2014 | Buerki et al. |
| 2018/0357374 | A1 | 12/2018 | Bagaev et al. |
| 2019/0233898 | A1 | 8/2019 | Newman et al. |
| 2019/0324038 | A1 | 10/2019 | Ginhoux et al. |
| 2020/0058377 | A1 | 2/2020 | Bagaev et al. |
| 2020/0210852 | A1 | 7/2020 | Igartua et al. |
| 2020/0340909 | A1 | 10/2020 | Ohsaka et al. |
| 2021/0118526 | A1 | 4/2021 | Barber |
| 2021/0151128 | A1 | 5/2021 | Abe et al. |
| 2021/0287759 | A1 | 9/2021 | Zaitsev et al. |
| 2021/0388418 | A1 | 12/2021 | Skanderup et al. |
| 2022/0186318 | A1 | 6/2022 | Meerson et al. |
| 2022/0230707 | A1 | 7/2022 | Zaitsev et al. |
| 2022/0319638 | A1 | 10/2022 | Hsieh et al. |
| 2022/0372580 | A1 | 11/2022 | Zaitsev et al. |
| 2022/0389512 | A1 | 12/2022 | Bagaev et al. |
| 2023/0178178 | A1 | 6/2023 | Zaitsev et al. |
| 2023/0245479 | A1 | 8/2023 | Ataullakhanov et al. |
| 2024/0170096 | A1 | 5/2024 | Goldberg et al. |
| 2024/0177803 | A1 | 5/2024 | Goldberg et al. |
| 2024/0347211 | A1 | 10/2024 | Kust et al. |

FOREIGN PATENT DOCUMENTS

| | | | |
|---|---|---|---|
| EP | | 3 349 006 A1 | 7/2018 |
| WO | WO 2019/018684 A1 | | 1/2019 |
| WO | WO 2020/081582 A1 | | 4/2020 |
| WO | WO 2021/092071 A1 | | 5/2021 |
| WO | WO 2021/183917 A1 | | 9/2021 |
| WO | WO 2021/202917 A1 | | 10/2021 |
| WO | WO 2021/247868 A1 | | 12/2021 |
| WO | WO 2022/133131 A1 | | 6/2022 |
| WO | WO 2022/192393 A1 | | 9/2022 |
| WO | WO 2022/232615 A1 | | 11/2022 |

OTHER PUBLICATIONS

Geissler, Katharina, et al. "Immune signature of tumor infiltrating immune cells in renal cancer." Oncoimmunology 4.1 (2015): e985082. (Year: 2015).*
Wang, Weiwei, et al. "Clinical applications of monitoring immune status with 90 immune cell subsets in human whole blood by 10-color flow cytometry." International Journal of Laboratory Hematology 43.5 (2021): 1132-1144. (Year: 2021).*
Nassar, Mariam, et al. "Label-free identification of white blood cells using machine learning." Cytometry Part A 95.8 (2019): 836-842. (Year: 2019).*

(Continued)

*Primary Examiner* — Larry D Riggs, II
*Assistant Examiner* — Kettip Kriangchaivech
(74) *Attorney, Agent, or Firm* — Wolf, Greenfield & Sacks, P.C.

(57) ABSTRACT

Aspects of the disclosure relate to methods, systems, and computer-readable storage media, that are useful for characterizing subjects having cancer. The disclosure is based, in part, on methods for immunoprofiling a cancer subject and the subject's prognosis and/or likelihood of responding to an immunotherapy based upon analysis of leukocyte populations in the peripheral blood of the subject.

14 Claims, 70 Drawing Sheets

(56) References Cited

OTHER PUBLICATIONS

Czystowska, Malgorzata, et al. "The immune signature of CD8+ CCR7+ T cells in the peripheral circulation associates with disease recurrence in patients with HNSCC." Clinical Cancer Research 19.4 (2013): 889-899. (Year: 2013).*

Zhou, Min, et al. "Development and evaluation of a leukemia diagnosis system using deep learning in real clinical scenarios." Frontiers in Pediatrics 9 (2021): 693676. (Year: 2021).*

Bell, R. Bryan, et al. "Developing an immunotherapy strategy for the effective treatment of oral, head and neck squamous cell carcinoma." Journal of Oral and Maxillofacial Surgery 73.12 (2015): S107-S115. (Year: 2015).*

Communication pursuant to Article 94(3) EPC for European Application No. 21716903.6 dated Jul. 31, 2023.

International Preliminary Report on Patentability for International Application No. PCT/US2021/022155 dated Sep. 22, 2022.

International Preliminary Report on Patentability for International Application No. PCT/US2022/027088 dated Nov. 9, 2023.

International Search Report and Written Opinion for International Application No. PCT/US2021/022155 dated Jul. 5, 2021.

International Search Report and Written Opinion for International Application No. PCT/US2022/027088 dated Aug. 16, 2022.

International Search Report and Written Opinion for International Application No. PCT/US2023/012003 mailed May 12, 2023.

[No Author Listed], Artyomov Lab Systems Immunology. Maxim N. Artyomov. 2013. https://artyomovlab.wustl.edu/site/index.html [last accessed Jun. 7, 2021]. 3 pages.

[No Author Listed], Deconvolution of ABsolute Immune Signal. shinyapps.io. 2021. https://giannimonaco.shinyapps.io/ABIS/ [last accessed Jun. 7, 2021]. 1 page.

[No Author Listed], MCP-counter. CIT. 2021. https://cit.ligue-cancer.net/mcp-counter/ [last accessed Jun. 7, 2021]. 2 pages.

[No Author Listed], Using Epic to estimate the proportion of various cell types in bulk samples. Epic. 2021. http://epic.gfellerlab.org/ [last accessed Jun. 7, 2021]. 1 page.

[No Author Listed], Wikipedia Gradient Boosting. 2022. 10 pages. https://en.wikipedia.org/wiki/Gradient_boosting [Last accessed May 25, 2022].

[No Author Listed], Wikipedia Nonlinear Regression. 2021. https://en.wikipedia.org/wiki/Nonlinear_regression [Last accessed Aug. 29, 2022].

Abbas et al., Immune response in silico (IRIS): immune-specific genes identified from a compendium of microarray expression data. Genes & Immunity. Jun. 2005;6(4):319-31.

Altman et al., Transcriptome networks identify mechanisms of viral and nonviral asthma exacerbations in children. Nature immunology. May 2019;20(5):637-51.

Aran et al., Systematic pan-cancer analysis of tumour purity. Nature communications. Dec. 4, 2015;6(1):1-11.

Aran et al., xCell. UCSF Institute for Computational Health Sciences. 2017. https://xcell.ucsf.edu/ [last accessed Jun. 7, 2021]. 2 pages.

Aran et al., xCell: digitally portraying the tissue cellular heterogeneity landscape. Genome biology. Dec. 2017;18(1):1-14.

Araujo B. De Lima et al., Immune Cell Profiling of Peripheral Blood as Signature for Response During Checkpoint Inhibition Across Cancer Types. Front Oncol. Mar. 25, 2021;11:558248. doi: 10.3389/fonc.2021.558248. PMID: 33842304.

Becht et al., Estimating the population abundance of tissue-infiltrating immune and stromal cell populations using gene expression. Genome biology. Dec. 2016;17(1):1-20.

Ben-Moshe et al., mRNA-seq whole transcriptome profiling of fresh frozen versus archived fixed tissues. BMC genomics. Dec. 2018;19(1):11 pages.

Bray et al., Near-optimal probabilistic RNA-seq quantification. Nat Biotechnol. May 2016;34(5):525-7. doi: 10.1038/nbt.3519. PMID: 27043002.

Butler et al., Integrating single-cell transcriptomic data across different conditions, technologies, and species. Nature biotechnology. May 2018;36(5):411-20.

Chen et al., Profiling tumor infiltrating immune cells with Cibersort. Cancer systems biology. 2018:243-259.

Cieslik et al., The use of exome capture RNA-seq for highly degraded RNA with application to clinical cancer sequencing. Genome research. Sep. 1, 2015;25(9):1372-81.

Duraiswamy et al., Phenotype, function, and gene expression profiles of programmed death-1(hi) CD8 T cells in healthy human adults. J Immunol. Apr. 1, 2011;186(7):4200-12. doi: 10.4049/jimmunol.1001783. PMID: 21383243.

Eisenberg et al., Human housekeeping genes, revisited. Trends in Genetics. Oct. 1, 2013;29(10):569-74.

Finotello et al., Molecular and pharmacological modulators of the tumor immune contexture revealed by deconvolution of RNA-seq data. Genome medicine. Dec. 2019;11(1):1-20.

Finotello et al., quanTIseq documentation. quanTIseq. Feb. 25, 2019. https://icbi.i-med.ac.at/software/quantiseq/doc/ [last accessed Jun. 7, 2021]. 9 pages.

Frankish et al., Gencode reference annotation for the human and mouse genomes. Nucleic acids research. Jan. 8, 2019;47(D1):D766-73.

Galon et al., Type, density, and location of immune cells within human colorectal tumors predict clinical outcome. Science. Sep. 29, 2006;313(5795):1960-4.

George et al., Hemophilia B gene therapy with a high-specific-activity factor IX variant. New England Journal of Medicine. Dec. 7, 2017;377(23):2215-27.

Griffiths et al., Detection and removal of barcode swapping in single-cell RNA-seq data. Nature communications. Jul. 10, 2018;9(1):1-6.

Hao et al., Fast and robust deconvolution of tumor infiltrating lymphocyte from expression profiles using least trimmed squares. PLoS computational biology. May 6, 2019;15(5):e1006976. 21 pages.

Hirata et al., Tumor microenvironment and differential responses to therapy. Cold Spring Harbor perspectives in medicine. Jul. 1, 2017;7(7):a026781. 14 pages.

Hoek et al., A cell-based systems biology assessment of human blood to monitor immune responses after influenza vaccination. PLoS one. Feb. 23, 2015;10(2):e0118528. 24 pages.

Holik et al., RNA-seq mixology: designing realistic control experiments to compare protocols and analysis methods. Nucleic acids research. Mar. 17, 2017;45(5):e30. 18 pages.

Izar et al., A Single-Cell Landscape of High-Grade Serous Ovarian Cancer. Nature medicine. 2020;26:1271-1279. 23 pages.

Ke et al., Lightgbm: A highly efficient gradient boosting decision tree. Advances in neural information processing systems (NIPS). 2017;30:3146-54.

Kitano et al., Computational algorithm-driven evaluation of monocytic myeloid-derived suppressor cell frequency for prediction of clinical outcomes. Cancer Immunol Res. Aug. 2014;2(8):812-21. doi: 10.1158/2326-6066.CIR-14-0013. PMID: 24844912.

Lambrechts et al., Phenotype molding of stromal cells in the lung tumor microenvironment. Nature medicine. Aug. 2018;24(8):1277-89. 19 pages.

Levine et al., Data-driven phenotypic dissection of AML reveals progenitor-like cells that correlate with prognosis. Cell. Jul. 2, 2015;162(1):184-97. 31 pages.

Linsley et al., Copy number loss of the interferon gene cluster in melanomas is linked to reduced T cell infiltrate and poor patient prognosis. PLoS one. Oct. 14, 2014;9(10):e109760. 9 pages.

Lun et al., EmptyDrops: distinguishing cells from empty droplets in droplet-based single-cell RNA sequencing data. Genome biology. Dec. 2019;20(1):1-9.

Ma et al., PD1 Hi CD8+ T cells correlate with exhausted signature and poor clinical outcome in hepatocellular carcinoma. Journal for immunotherapy of cancer. Dec. 2019;7(1):331. 15 pages.

Macosko et al., Highly parallel genome-wide expression profiling of individual cells using nanoliter droplets. Cell. May 21, 2015;161(5):1202-14. 25 pages.

Marioni et al., RNA-seq: an assessment of technical reproducibility and comparison with gene expression arrays. Genome research. Sep. 1, 2008;18(9):1509-17.

(56)     References Cited

OTHER PUBLICATIONS

Martens et al., Baseline Peripheral Blood Biomarkers Associated with Clinical Outcome of Advanced Melanoma Patients Treated with Ipilimumab. Clin Cancer Res. Jun. 15, 2016;22(12):2908-18. doi: 10.1158/1078-0432.CCR-15-2412. PMID: 26787752.

Melsted et al., Modular and efficient pre-processing of single-cell RNA-seq. BioRxiv. Jun. 17, 2019:673285. 16 pages.

Meyer et al., Frequencies of circulating MDSC correlate with clinical outcome of melanoma patients treated with ipilimumab. Cancer Immunol Immunother. Mar. 2014;63(3):247-57. doi: 10.1007/s00262-013-1508-5. PMID: 24357148.

Möller et al., Blood Immune Cell Biomarkers in Patient with Lung Cancer Undergoing Treatment With Checkpoint Blockade. J Immunother. Feb./Mar. 2020;43(2):57-66. doi: 10.1097/CJI.0000000000000297. PMID: 31592989.

Monaco et al., RNA-Seq signatures normalized by mRNA abundance allow absolute deconvolution of human immune cell types. Cell reports. Feb. 5, 2019;26(6):1627-40.e7.

Neftel et al., An integrative model of cellular states, plasticity, and genetics for glioblastoma. Cell. Aug. 8, 2019;178(4):835-49.e29. 37 pages.

Newman et al., Cibersort. Stanford University. 2021. https://cibersort.stanford.edu/ [last accessed Jun. 7, 2021]. 1 page.

Newman et al., Cibersortx. Stanford University. 2021. https://cibersortx.stanford.edu/ [last accessed Jun. 7, 2021]. 1 page.

Newman et al., Determining cell type abundance and expression from bulk tissues with digital cytometry. Nature biotechnology. Jul. 2019;37(7):773-82.

Newman et al., Robust enumeration of cell subsets from tissue expression profiles. Nature methods. May 2015;12(5):453-7. 20 pages.

Norton et al., Pancreatic cancer associated fibroblasts (CAF): under-explored target for pancreatic cancer treatment. Cancers. May 2020;12(5):1347. 18 pages.

Ottonello et al., Association Between Response to Nivolumab Treatment and Peripheral Blood Lymphocyte Subsets in Patients with Non-small Cell Lung Cancer. Front Immunol. Feb. 7, 2020;11:125. doi: 10.3389/fimmu.2020.00125. PMID: 32117275.

Parish et al., The molecular signature of CD8+ T cells undergoing deletional tolerance. Blood. May 7, 2009;113(19):4575-85. doi: 10.1182/blood-2008-10-185223. PMID: 19204323.

Pico De Coaña et al. PD-1 checkpoint blockade in advanced melanoma patients: NK cells, monocytic subsets and host PD-L1 expression as predictive biomarker candidates. Oncoimmunology. Aug. 28, 2020;9(1):1786888. doi: 10.1080/2162402X.2020.1786888. PMID: 32939320.

Puram et al., Single-cell transcriptomic analysis of primary and metastatic tumor ecosystems in head and neck cancer. Cell. Dec. 14, 2017;171(7):1611-24.e24. 40 pages.

Racle et al., Epic: a tool to estimate the proportions of different cell types from bulk gene expression data. Bioinformatics for Cancer Immunotherapy. 2020:233-248.

Racle et al., Simultaneous enumeration of cancer and immune cell types from bulk tumor gene expression data. elife. Nov. 13, 2017;6:e26476. 25 pages.

Rakaee et al.,Prognostic value of macrophage phenotypes in resectable non-small cell lung cancer assessed by multiplex immunohistochemistry. Neoplasia. Mar. 1, 2019;21(3):282-93.

Roider et al., Dissecting intratumour heterogeneity of nodal B-cell lymphomas at the transcriptional, genetic and drug-response levels. Nature Cell Biology. Jul. 2020;22(7):896-906. 27 pages.

Saltz et al., Spatial organization and molecular correlation of tumor-infiltrating lymphocytes using deep learning on pathology images. Cell reports. Apr. 3, 2018;23(1):181-93.e7. 21 pages.

Shin et al., Variation in RNA-Seq transcriptome profiles of peripheral whole blood from healthy individuals with and without globin depletion. PloS one. Mar. 7, 2014;9(3):e91041. 11 pages.

Shishkova et al., Deep immune profiling by mass cytometry revealed an association between the state of immune system before treatment and response to checkpoint inhibitor therapy in clear cell renal cell carcinoma. Cancer Research. Jun. 15, 2022;82(12_Supplement):2061.

Simon et al., PD-1 and TIGIT coexpression identifies a circulating CD8 T cell subset predictive of response to anti-PD-1 therapy. J Immunother Cancer. Nov. 2020;8(2):e001631. doi: 10.1136/jitc-2020-001631. PMID: 33188038.

Stuart et al., Comprehensive integration of single-cell data. Cell. Jun. 13, 2019;177(7):1888-902.e21. 52 pages.

Sturm et al., Comprehensive evaluation of transcriptome-based cell-type quantification methods for immuno-oncology. Bioinformatics. Jul. 15, 2019;35(14):1436-45.

Sun et al., An efficient and flexible method for deconvoluting bulk RNA-seq data with single-cell RNA-seq data. Cells. Oct. 2019;8(10):1161.

Tirosh et al., Dissecting the multicellular ecosystem of metastatic melanoma by single-cell RNA-seq. Science. Apr. 8, 2016;352(6282):189-96.

Van Gassen et al., FlowSOM: Using self-organizing maps for visualization and interpretation of cytometry data. Cytometry Part A. Jul. 2015;87(7):636-45.

Vivian et al., Toil enables reproducible, open source, big biomedical data analyses. Nat Biotechnol. Apr. 11, 2017;35(4):314-16. doi: 10.1038/nbt.3772. PMID: 28398314.

Vivian et al., Toil enables reproducible, open source, big biomedical data analyses. Nature biotechnology. Apr. 2017;35(4):314-6.

Wagner et al., Measurement of mRNA abundance using RNA-seq data: RPKM measure is inconsistent among samples. Theory in biosciences. Dec. 1, 2012;131(4):281-5.

Weber et al., Phase I/II Study of Metastatic Melanoma Patients Treated with Nivolumab Who Had Progressed after Ipilimumab. Cancer Immunol Res. Apr. 2016;4(4):345-53. doi: 10.1158/2326-6066.CIR-15-0193. PMID: 26873574.

Wistuba-Hamprecht et al., Proportions of blood-borne Vδ1+ and Vδ2+ T-cells are associated with overall survival of melanoma patients treated with ipilimumab. Eur J Cancer. Sep. 2016;64:116-26. doi: 10.1016/j.ejca.2016.06.001. PMID: 27400322.

Wu et al., Stromal PD-L1-positive regulatory T cells and PD-1-positive CD8-positive T cells define the response of different subsets of non-small cell lung cancer to PD-1/PD-L1 blockade immunotherapy. Journal of Thoracic Oncology. Apr. 1, 2018;13(4):521-32.

Xu et al., Mapping of γ/δ T cells reveals Vδ2+ T cells resistance to senescence. EBioMedicine. Jan. 1, 2019;39:44-58.

Zaitsev et al., Complete deconvolution of cellular mixtures based on linearity of transcriptional signatures. Nature communications. May 17, 2019;10(1):2209. 16 pages.

Zaitsev et al., Precise reconstruction of the TME using bulk RNA-seq and a machine learning algorithm trained on artificial transcriptomes. Cancer Cell. Aug. 8, 2022;40(8):879-894.e16. doi: 10.1016/j.ccell.2022.07.006. PMID: 35944503.

Zhang et al., Spectral clustering of single-cell multi-omics data on multilayer graphs. Bioinformatics. Jul. 11, 2022;38(14):3600-8. doi: 10.1093/bioinformatics/btac378. PMID: 35652725.

Zheng et al., Massively parallel digital transcriptional profiling of single cells. Nature communications. Jan. 16, 2017;8(1):1-12.

Zimmermann et al., System-wide associations between DNA-methylation, gene expression, and humoral immune response to influenza vaccination. PloS one. Mar. 31, 2016;11(3):e0152034. 21 pages.

International Search Report and Written Opinion for International Application No. PCT/US2023/080339 mailed Jun. 5, 2024.

Dyikanov et al., Comprehensive immunoprofiling of peripheral blood reveals five conserved immunotypes with implications for immunotherapy in cancer patients. Cancer Research. Apr. 4, 2023;83(7_Supplement):6664.

Newman et al., Determining cell type abundance and expression from bulk tissues with digital cytometry. Nature biotechnology. Jul. 2019;37(7):773-82 and supplementary information. 16 pages.

Schelker et al., Estimation of immune cell content in tumour tissue using single-cell RNA-seq data. Nature communications. Dec. 11, 2017;8(1):2032.

(56)　　　　References Cited

OTHER PUBLICATIONS

International Search Report and Written Opinion for International Application No. PCT/US2024/024323 mailed Jul. 25, 2024.

Bagaev et al., Conserved pan-cancer microenvironment subtypes predict response to immunotherapy. Cancer Cell. Jun. 14, 2021;39(6):845-865.e7. doi: 10.1016/j.ccell.2021.04.014. Epub May 20, 2021. PMID: 34019806.

Bai et al., Mechanisms of Cancer Resistance to Immunotherapy. Front Oncol. Aug. 6, 2020;10:1290. 12 pages. doi: 10.3389/fonc.2020.01290. 12 pages. PMID: 32850400; PMCID: PMC7425302.

Barbie et al., Systematic RNA interference reveals that oncogenic KRAS-driven cancers require TBK1. Nature. Nov. 5, 2009;462(7269):108-12.

Camus et al., Coordination of intratumoral immune reaction and human colorectal cancer recurrence. Cancer research. Mar. 15, 2009;69(6):2685-93.

Chen et al., Elements of cancer immunity and the cancer-immune set point. Nature 541. 2017: 321-30. https://doi.org/10.1038/nature21349.

Chen et al., Pan-cancer molecular subtypes revealed by mass-spectrometry-based proteomic characterization of more than 500 human cancers. Nat Commun. Dec. 12, 2019;10(1):5679. 15 pages. doi: 10.1038/s41467-019-13528-0. PMID: 31831737; PMCID: PMC6908580.

Ferlay et al., Cancer statistics for the year 2020: An overview. International journal of cancer. Aug. 15, 2021;149(4):778-89.

Galon et al., Approaches to treat immune hot, altered and cold tumors with combination immunotherapies. Nat Rev Drug Discov. Mar. 2019;18(3):197-218. doi: 10.1038/s41573-018-0007-y. PMID: 30610226.

Gautier et al., affy—analysis of Affymetrix GeneChip data at the probe level. Bioinformatics. Feb. 12, 2004;20(3):307-15.

Gerritse et al., High-dose administration of tyrosine kinase inhibitors to improve clinical benefit: A systematic review. Cancer Treatment Reviews. Jun. 1, 2021;97:102171.

Hanahan, Hallmarks of Cancer: New Dimensions. Cancer Discov. Jan. 2022;12(1):31-46. doi: 10.1158/2159-8290.CD-21-1059. PMID: 35022204.

Kim et al., The Evasion Mechanisms of Cancer Immunity and Drug Intervention in the Tumor Microenvironment. Front Pharmacol. May 24, 2022;13:868695. 16 pages. doi: 10.3389/fphar.2022.868695. PMID: 35685630; PMCID: PMC9171538.

Le Louedec et al., Cancer immunotherapy dosing: a pharmacokinetic/pharmacodynamic perspective. Vaccines. Oct. 31, 2020;8(4):632.

Luca et al., Atlas of clinically distinct cell states and ecosystems across human solid tumors. Cell. Oct. 14, 2021;184(21):5482-5496.e28. doi: 10.1016/j.cell.2021.09.014. Epub Sep. 30, 2021. PMID: 34597583; PMCID: PMC8526411.

Rassy et al., Tyrosine kinase inhibitors and immunotherapy combinations in renal cell carcinoma. Therapeutic advances in medical oncology. Mar. 2020;12:1758835920907504. 13 pages.

Ren et al., Immunological Classification of Tumor Types and Advances in Precision Combination Immunotherapy. Front Immunol. Feb. 28, 2022;13:790113. 11 pages. doi: 10.3389/fimmu.2022.790113. PMID: 35296094; PMCID: PMC8918549.

Ritchie et al., limma powers differential expression analyses for RNA-sequencing and microarray studies. Nucleic Acids Res. Apr. 20, 2015;43(7):e47. 20. doi.org/10.1093/nar/gkv007PMID: 25605792, PMCID: PMC4402510.

Schubert et al., Perturbation-response genes reveal signaling footprints in cancer gene expression. Nat Commun. Jan. 2, 2018;9(1):20. 11 pages. doi: 10.1038/s41467-017-02391-6. PMID: 29295995; PMCID: PMC5750219.

Tamborero et al., A Pan-cancer Landscape of Interactions between Solid Tumors and Infiltrating Immune Cell Populations. Clin Cancer Res. Aug. 1, 2018;24(15):3717-3728. doi: 10.1158/1078-0432.CCR-17-3509. Epub Apr. 17, 2018. PMID: 29666300.

Thorsson et al., The Immune Landscape of Cancer. Immunity. Apr. 17, 2018;48(4):812-830.e14. doi: 10.1016/j.immuni.2018.03.023.

Torre et al., Global cancer statistics, 2012. CA Cancer J Clin. Mar. 2015;65(2):87-108. doi: 10.3322/caac.21262. PMID: 25651787.

Vaught et al., Biological sample collection, processing, storage and information management. IARC Sci Publ. Jan. 1, 2011;163(163):23-42.

Vaught et al., Biospecimens and biorepositories: from afterthought to science. Cancer Epidemiology, Biomarkers & Prevention. Feb. 1, 2012;21(2):253-5.

Wang et al., Therapeutic targets and biomarkers of tumor immunotherapy: response versus non-response. Signal transduction and targeted therapy. Sep. 19, 2022;7(1):331. 27 pages.

Ward, Hierarchical grouping to optimize an objective function. Journal of the American statistical association. 1963;58(301):236-244.

Wu et al., gcrma: Background Adjustment Using Sequence Information. R package version 2.66.0. 2022. 14 pages.

International Search Report and Written Opinion for International Application No. PCT/US2024/053934 mailed Feb. 7, 2025.

Cheng et al., Uncoupling protein 2 reprograms the tumor microenvironment to support the anti-tumor immune cycle. Nat Immunol. 2016;20:206.17.

* cited by examiner

300

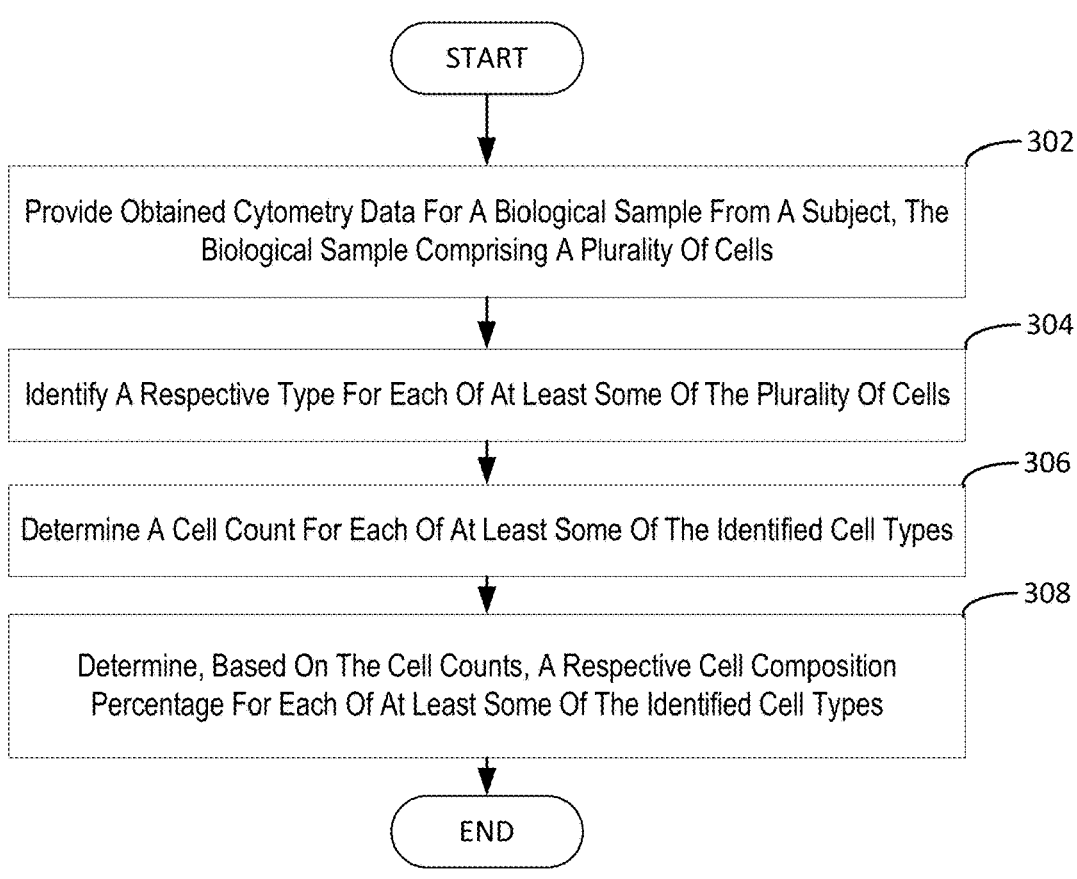

START

302

Provide Obtained Cytometry Data For A Biological Sample From A Subject, The Biological Sample Comprising A Plurality Of Cells

304

Identify A Respective Type For Each Of At Least Some Of The Plurality Of Cells

306

Determine A Cell Count For Each Of At Least Some Of The Identified Cell Types

308

Determine, Based On The Cell Counts, A Respective Cell Composition Percentage For Each Of At Least Some Of The Identified Cell Types

END

FIG. 3

Cohort

|  | Cancer patients<br>n = 442 (52%) | Healthy donors<br>n = 408 (48%) |
|---|---|---|
| Age (Median) | 61.5 | 47 |
| Gender | 50.8% female | 48.5% female |
| Diagnosis   sarcoma<br>breast<br>colorectal<br>pancreatic<br>NSCLC<br>melanoma<br>prostate<br>other | 133 (30%)<br>65 (14.7%)<br>41 (9.3%)<br>37 (8.3%)<br>32 (7.2%)<br>19 (4.3%)<br>18 (4.1%)<br>97 (22%) | |
| Therapy data avaliable | 276 (62.4%) | |
| RNA-seq data avaliable | 423 (95.7%) | 400 (98%) |

FIG. 5B

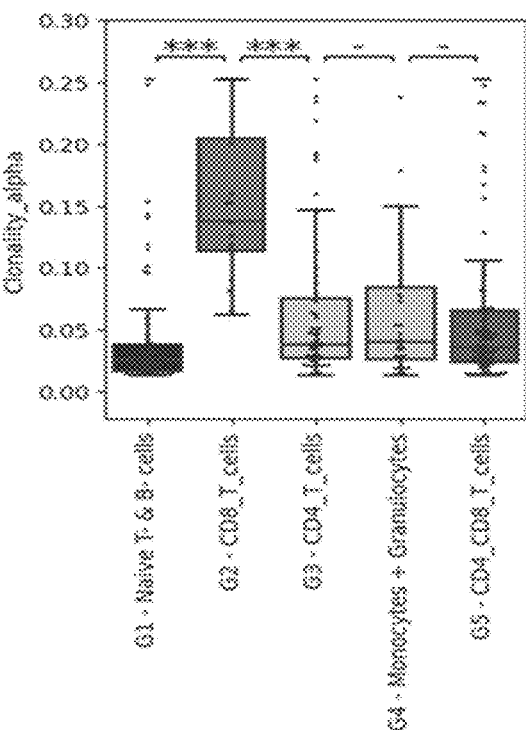
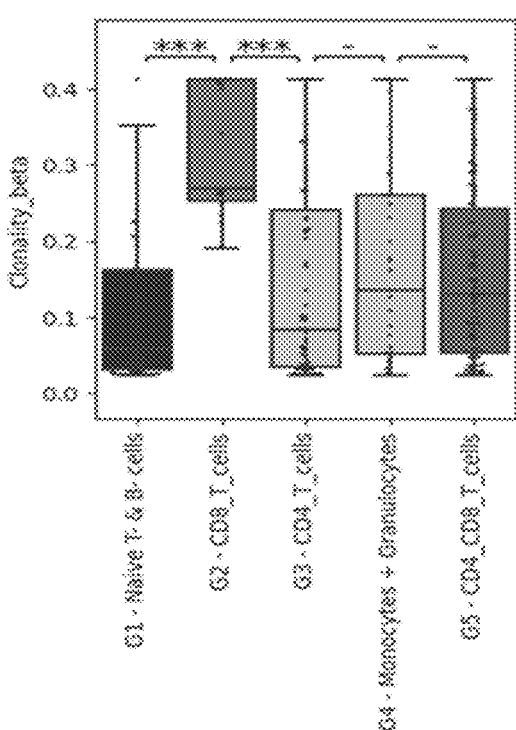
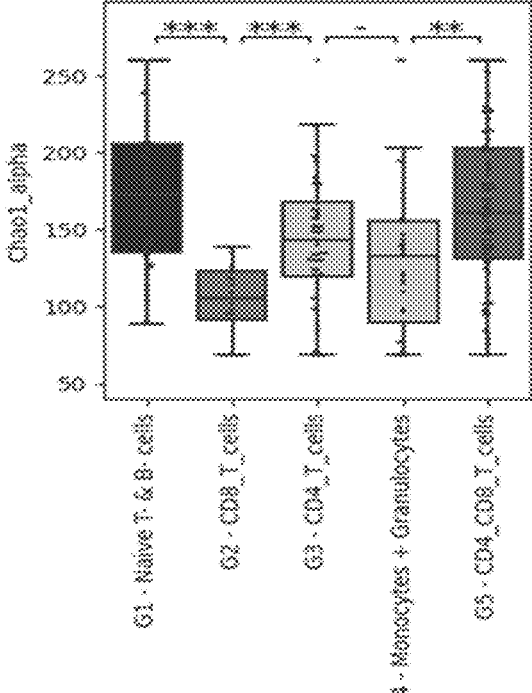
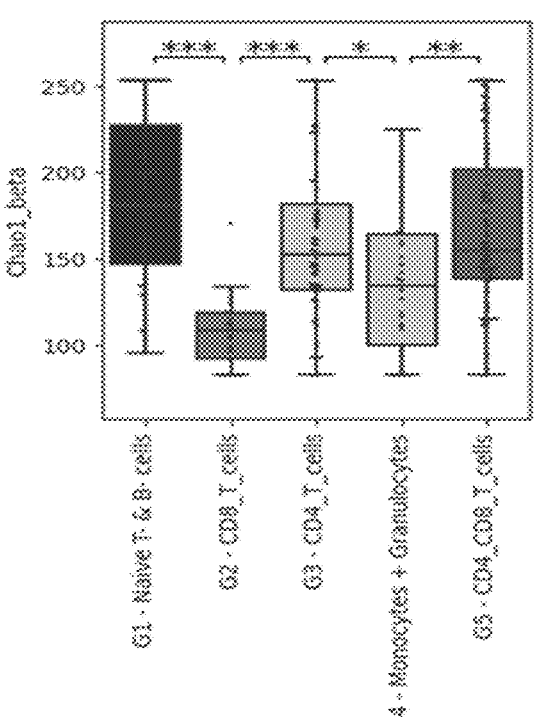
FIG. 9A

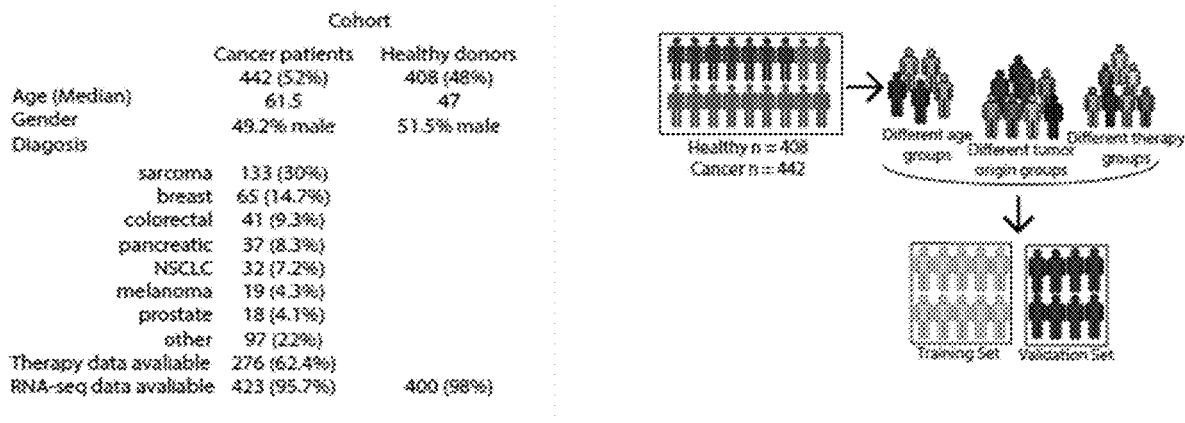
FIG. 17A
FIG. 17B
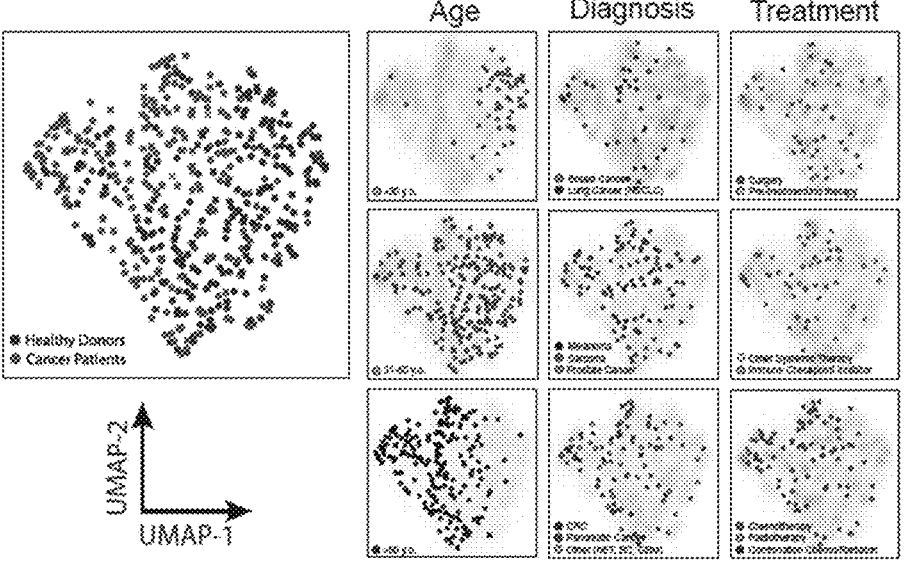
FIG. 17C

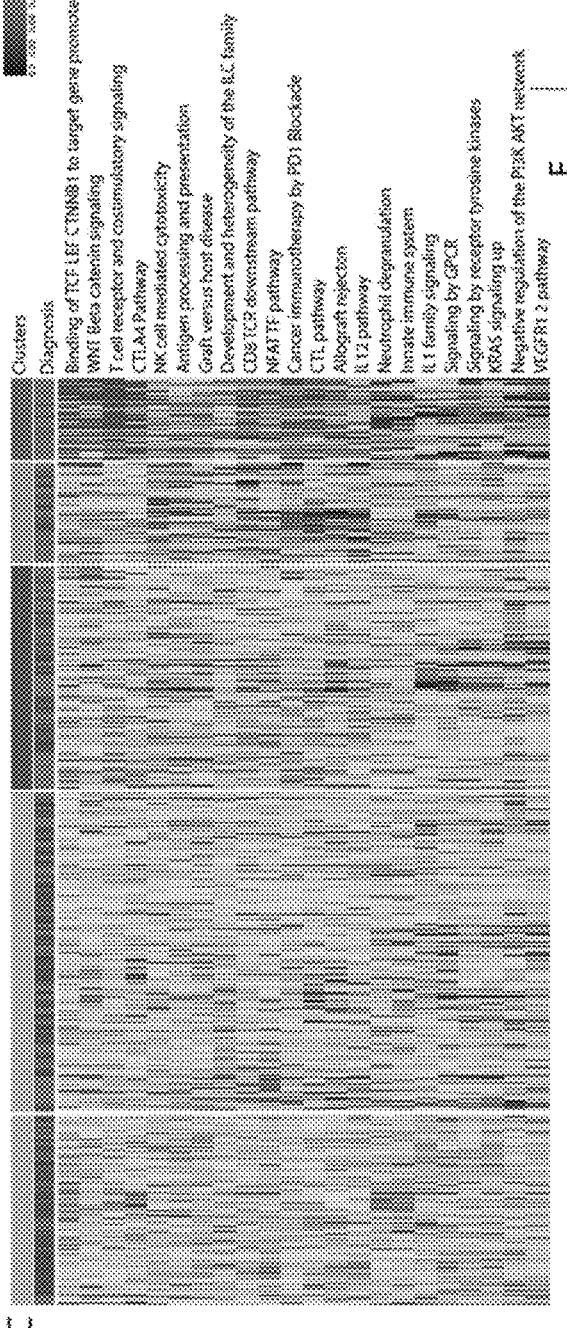
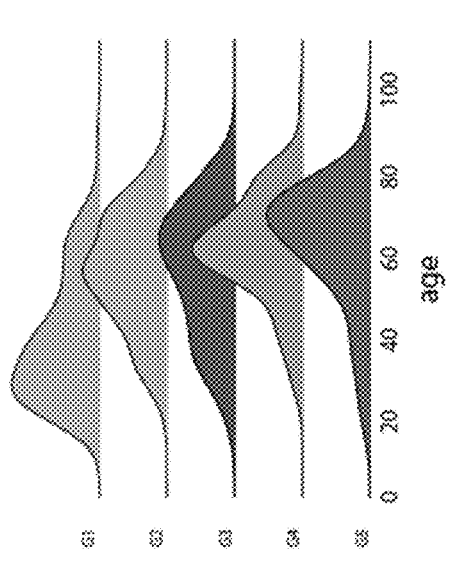
FIG. 18C

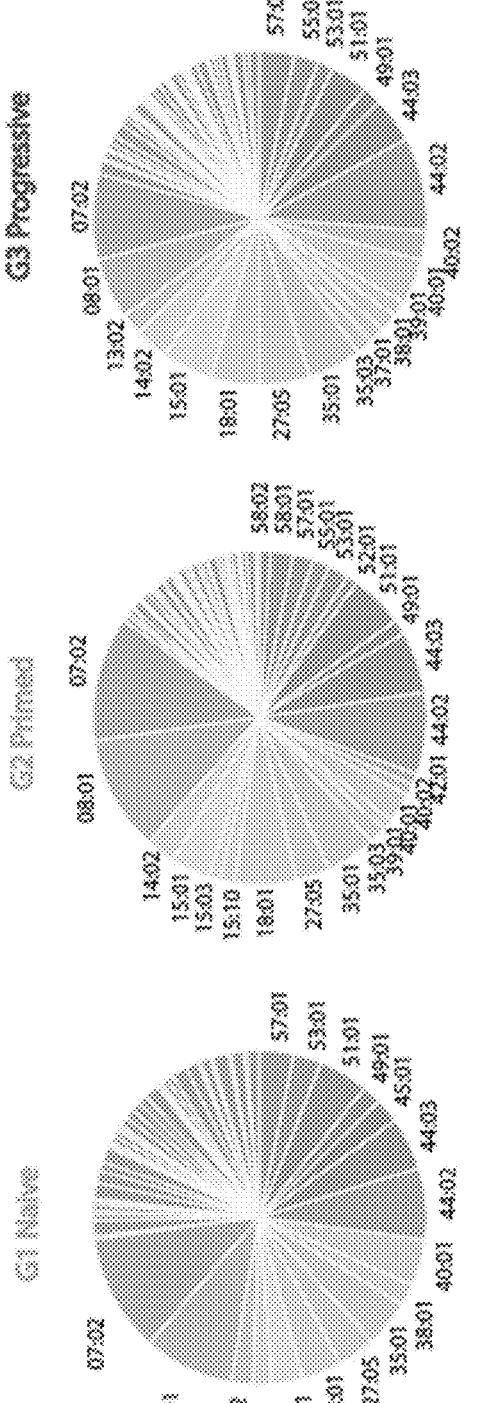
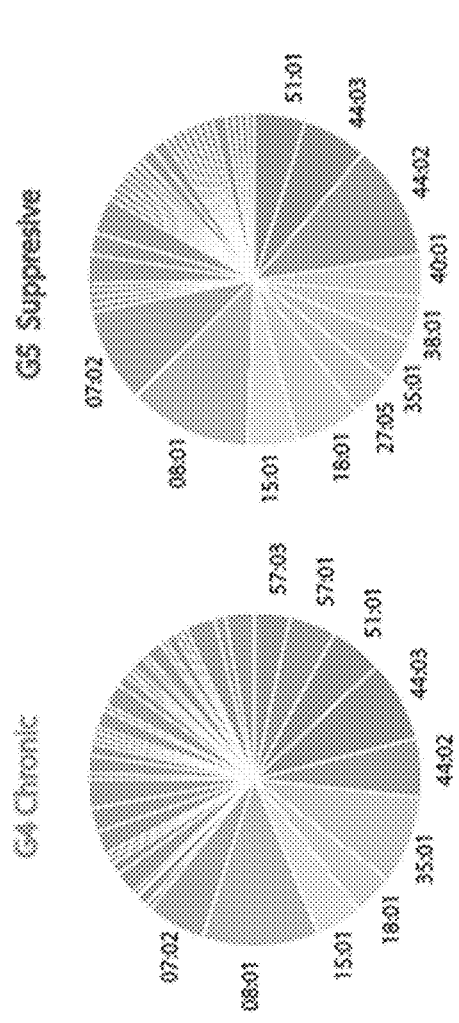
FIG. 20A

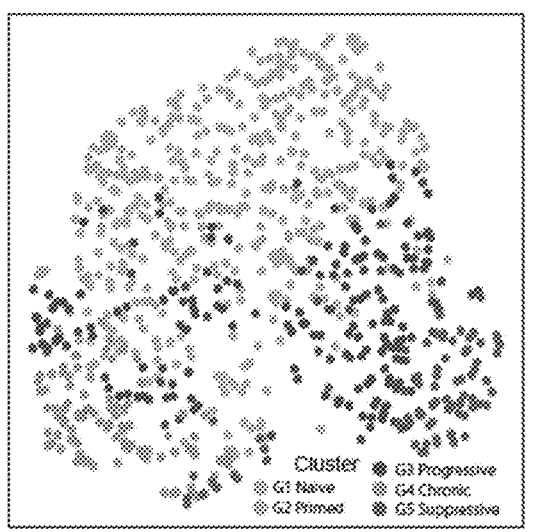
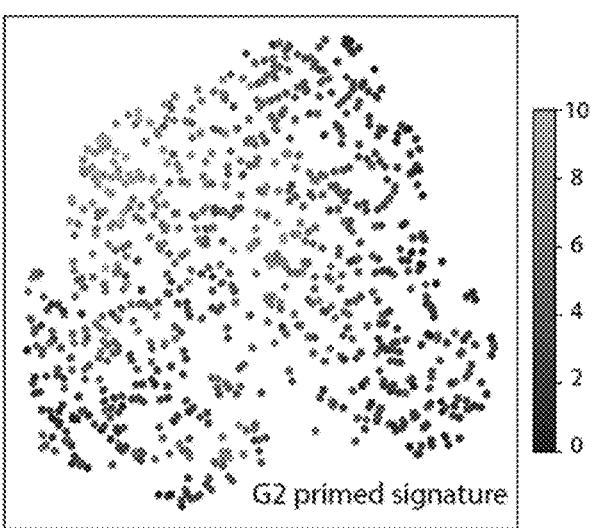
FIG. 22D
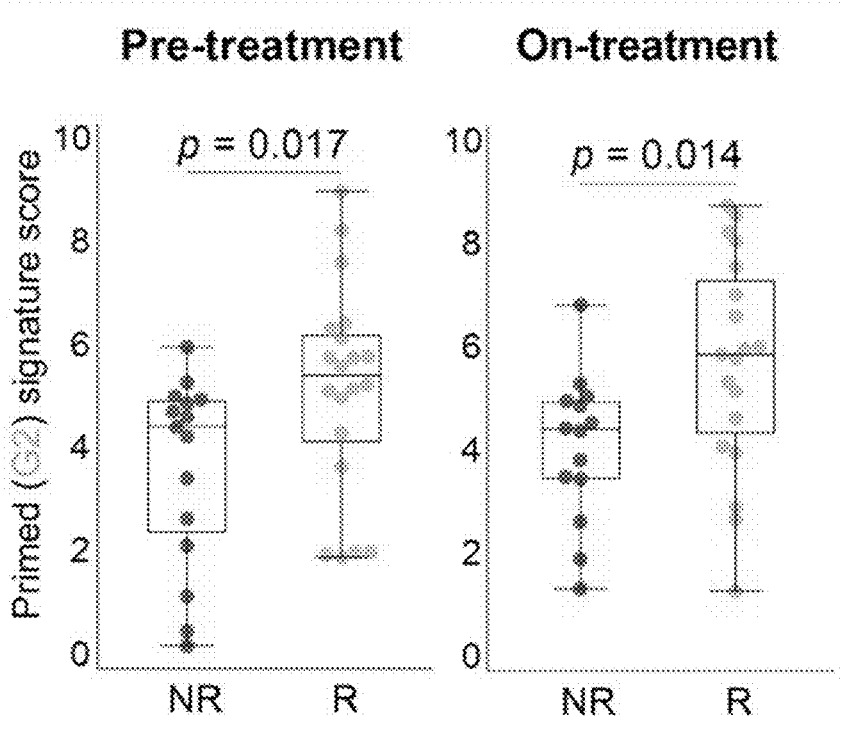
FIG. 22E

FIG. 23A

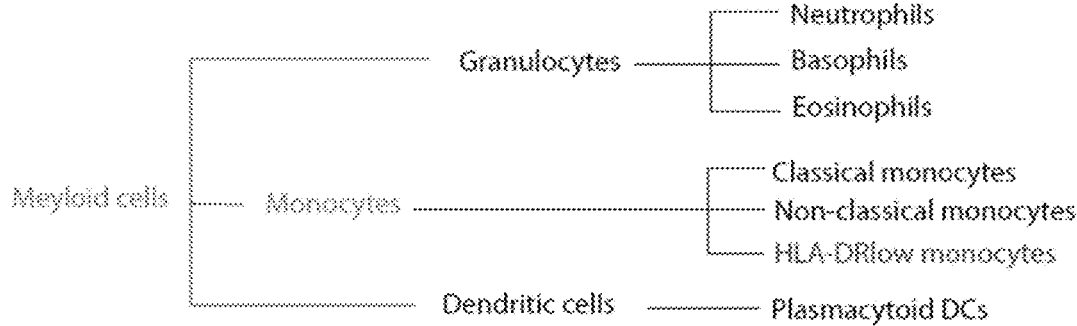

Granulocytes ——— Neutrophils
                  Basophils
                  Eosinophils Meyloid cells Monocytes ——— Classical monocytes
             Non-classical monocytes
             HLA-DRlow monocytes Dendritic cells ——— Plasmacytoid DCs B cells ——— Naive B cells
           Non-switched IgM B cells
           Class-switched B cells Lymphoid cells T cells CD4 T cells ——— CD4 Memory ——— CD4 TEMRA
                              CD4 TEM
                              CD4 TTM
                              CD4 TCM
               CD4 Naive
               Tregs ——— CD39 Tregs
                        Naive Tregs gd Vdelta2+

CD8 T cells ——— CD8 Memory ——— CD8 TEMRA
                              CD8 TEM
                              CD8 TTM
                              CD8 TCM
               CD8 Naive
               PD-1+ TIGIT+ CD8 T cells NKT cells NK cells ——— Mature NK
            Immature NK

FIG. 23B

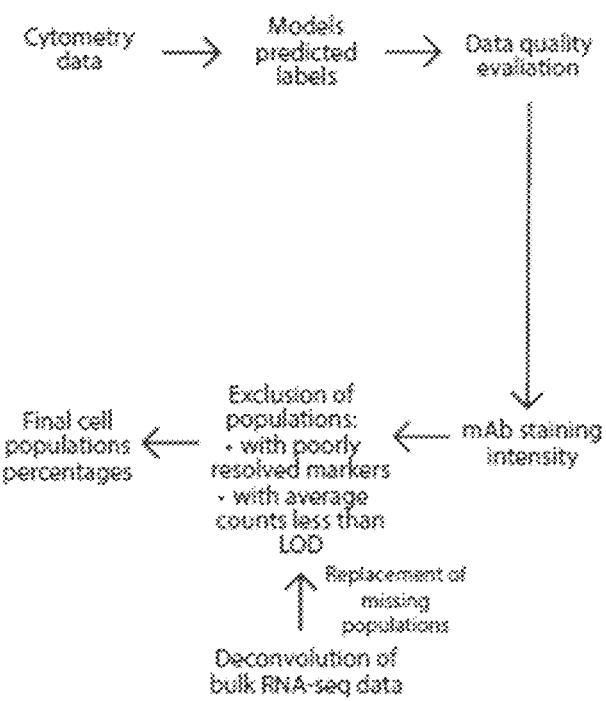
FIG. 26A
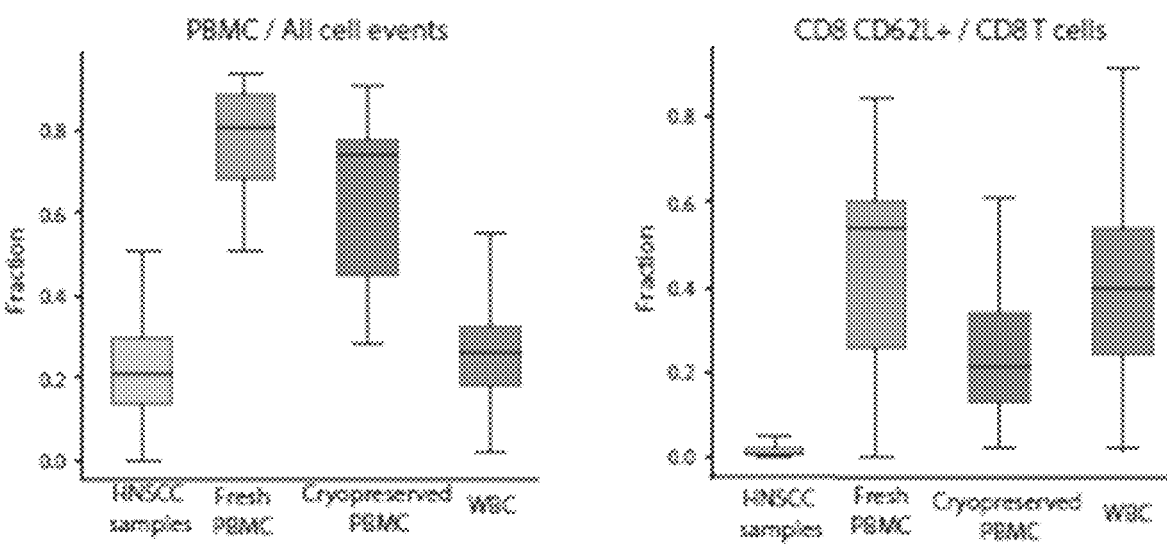
FIG. 26B                    FIG. 26C

FLOW CYTOMETRY IMMUNOPROFILING OF PERIPHERAL BLOOD

CROSS-REFERENCE TO RELATED APPLICATIONS

This application claims the benefit under 35 U.S.C. § 119 (e) of the filing date of U.S. provisional Application Ser. No. 63/490,214, filed Mar. 14, 2023, titled "COMPREHENSIVE IMMUNOPROFILING OF PERIPHERAL BLOOD", and U.S. provisional Application Ser. No. 63/426,153, filed Nov. 17, 2022, titled "COMPREHENSIVE IMMUNOPROFIL- ING OF PERIPHERAL BLOOD REVEALS FIVE CON- SERVED IMMUNOTYPES WITH IMPLICATIONS FOR IMMUNOTHERAPY IN CANCER PATIENTS" the entire contents of each of which are incorporated by reference herein.

BACKGROUND

Methods for immunoprofiling, include, but are not limited to RNA sequencing (RNAseq) and cytometry. RNAseq is a method that may be used to determine the sequence and/or the relative amount of RNA in a sample (e.g., RNAs expressed by an immune cell). The sequences and relative expression levels of the RNAs can be indicative of the properties of a cell. Cytometry is a laboratory technique used for analyzing single cells or particles in a biological sample. Cytometry is used in a variety of applications such as immunology and molecular biology. Cytometry may be used to measure characteristics of individual cells or particles. Types of cytometry include flow cytometry and mass cytom- etry.

Flow cytometry measures the intensity produced by fluo- rescent markers that are used to label cells in the biological sample. For example, a cell labelled with one or more markers may be processed by a flow cytometry platform, which measures the fluorescence intensities of the markers. The measured fluorescence intensities may be termed "marker values" and may be used for various applications such as cell counting, cell sorting, and/or determining vari- ous cell characteristics. Other types of cytometry (e.g., mass cytometry) may also be used for such applications.

SUMMARY

Aspects of the disclosure relate to methods, systems, and computer-readable storage media that are useful for charac- terizing a subject's leukocyte (e.g., white blood cell (WBC) or peripheral blood mononuclear cell (PBMC)) immunopro- file type. A leukocyte immunoprofile type may be deter- mined independent of a patient's health status, for example, a healthy patient or a patient having or suspected of having or at risk of having cancer.

The disclosure is based, in part, on methods for immu- noprofiling a cancer subject and the subject's prognosis and/or likelihood of responding to an immunotherapy based upon analysis of leukocyte populations in the peripheral blood of the subject. In some embodiments, methods described by the disclosure are useful for determining the leukocyte immunoprofile type of a subject having cancer. In some embodiments, the leukocyte immunoprofile type of a subject is indicative of a subject's cancer prognosis (e.g., pancreatic cancer, breast cancer, non-small cell lung carci- noma, colorectal cancer, melanoma, prostate cancer, etc.) and/or the likelihood of whether the subject will respond to treatment with particular therapeutic agents, for example immunotherapeutic agents such as immune checkpoint inhibitors (ICI). In some embodiments, the leukocyte immu- noprofile type of a subject is indicative of a subject's Head and neck squamous cell carcinoma (HNSCC) prognosis and/or the likelihood of whether the subject having HNSCC will respond to treatment with particular therapeutic agents, for example immunotherapeutic agents such as ICIs.

Accordingly, in some aspects, the disclosure provides a method for determining a leukocyte immunoprofile type of a subject having, suspected of having, or at risk of having cancer, the method comprising using at least one computer hardware processor to perform obtaining cytometry data or RNA expression data from a biological sample obtained from the subject; processing the cytometry data or the RNA expression data to determine cell composition percentages for at least 20 cell types listed in Table 4; generating a leukocyte signature for the subject using the determined cell composition percentages for the at least 20 cell types, the leukocyte signature comprising the cell composition per- centages for the at least 20 cell types; and identifying, using the leukocyte signature and from among a plurality of leukocyte immunoprofile types, a leukocyte immunoprofile type for the subject.

In some aspects, the disclosure provides a system, com- prising at least one computer hardware processor; and at least one computer-readable storage medium storing proces- sor-executable instructions that, when executed by the at least one computer hardware processor, cause the at least one computer hardware processor to perform a method for determining a leukocyte immunoprofile type of a subject having, suspected of having, or at risk of having cancer, the method comprising using at least one computer hardware processor to perform obtaining cytometry data or RNA expression data from a biological sample obtained from the subject; processing the cytometry data or the RNA expres- sion data to determine cell composition percentages for at least 20 cell types listed in Table 4; generating a leukocyte signature for the subject using the determined cell compo- sition percentages for the at least 20 cell types, the leukocyte signature comprising the cell composition percentages for the at least 20 cell types; and identifying, using the leukocyte signature and from among a plurality of leukocyte immu- noprofile types, a leukocyte immunoprofile type for the subject.

In some aspects, the disclosure provides at least one computer-readable storage medium storing processor-ex- ecutable instructions that, when executed by at least one computer hardware processor, cause the at least one com- puter hardware processor to perform a method for determin- ing a leukocyte immunoprofile type of a subject having, suspected of having, or at risk of having cancer, the method comprising using at least one computer hardware processor to perform obtaining cytometry data or RNA expression data from a biological sample obtained from the subject; pro- cessing the cytometry data or the RNA expression data to determine cell composition percentages for at least 20 cell types listed in Table 4; generating a leukocyte signature for the subject using the determined cell composition percent- ages for the at least 20 cell types, the leukocyte signature comprising the cell composition percentages for the at least 20 cell types; and identifying, using the leukocyte signature and from among a plurality of leukocyte immunoprofile types, a leukocyte immunoprofile type for the subject.

Embodiments of any of the above aspects may have one or more of the following features.

In some embodiments, cytometry data comprises flow cytometry data. In some embodiments, flow cytometry data is obtained from a biological sample consisting of white blood cells.

In some embodiments, processing flow cytometry data comprises determining cell composition percentages for each cell type listed in Table 1. In some embodiments, flow cytometry data is obtained from a biological sample consisting of peripheral blood mononuclear cells (PBMCs).

In some embodiments, processing flow cytometry data comprises determining cell composition percentages for each cell type listed in Table 2.

In some embodiments, processing cytometry data comprises applying one or more machine learning models to the cytometry data to obtain cell composition percentages for the at least 20 cell types listed in Table 4.

In some embodiments, obtaining RNA expression data comprises obtaining sequencing data previously obtained by sequencing the biological sample obtained from the subject. In some embodiments, sequencing data comprises at least 1 million reads, at least 5 million reads, at least 10 million reads, at least 20 million reads, at least 50 million reads, or at least 100 million reads.

In some embodiments, the method further comprises normalizing the RNA expression data to transcripts per million (TPM) units prior to processing the RNA expression data to determine the cell composition percentages.

In some embodiments, a plurality of leukocyte immunoprofile types is associated with a respective plurality of leukocyte immunoprofile types, and identifying, using the leukocyte signature and from among a plurality of leukocyte immunoprofile types, the leukocyte immunoprofile type for the subject comprises associating the leukocyte signature of the subject with a particular one of the plurality of leukocyte immunoprofile types, and identifying the leukocyte immunoprofile type for the subject as the leukocyte immunoprofile type corresponding to the particular one of the plurality of leukocyte immunoprofile types to which the leukocyte signature of the subject is associated In some embodiments, associating a leukocyte signature of a subject with a particular one of a plurality of leukocyte immunoprofile types comprises processing the leukocyte signature with a trained classifier to obtain an output indicative of the particular one of the plurality of leukocyte immunoprofile types. In some embodiments, a trained classifier comprises a trained neural network classifier, optionally, a tabular prior-data fitted network transformer (TabPFN) classifier.

In some embodiments, associating a leukocyte signature of the subject with a particular one of a plurality of leukocyte immunoprofile types comprises determining, for each particular one of the plurality of leukocyte immunoprofile types, a score indicating whether the leukocyte signature of the subject is associated with that particular leukocyte immunoprofile type, wherein determining the score for a particular leukocyte immunoprofile type comprises applying a linear regression model associated with the particular leukocyte immunoprofile type, to the cell composition percentages in the leukocyte signature.

In some embodiments, the method further comprises generating a plurality of leukocyte immunoprofile types, the generating comprising obtaining multiple sets of cytometry data or RNA expression data from biological samples obtained from multiple respective subjects, each of the multiple sets of cytometry data or RNA expression data indicating cell composition percentages for at least 20 cell types listed in Table 4; generating multiple leukocyte signatures from the multiple sets of cytometry data or RNA expression data, each of the multiple leukocyte signatures comprising cell composition percentages for at least 20 cell types listed in Table 4, the generating comprising, for each particular one of the multiple leukocyte signatures: determining the leukocyte signature by determining the cell composition percentages using the cytometry data or RNA expression data in the particular set of cytometry data or RNA expression data for which the particular one leukocyte signature is being generated; and clustering the multiple leukocyte signatures to obtain the plurality of leukocyte immunoprofile types.

In some embodiments, the method further comprises updating the plurality of leukocyte immunoprofile types using the leukocyte signature of the subject, wherein the leukocyte signature of the subject is one of a threshold number of leukocyte signatures for a threshold number of subjects, wherein when the threshold number of leukocyte signatures is generated the leukocyte immunoprofile types are updated, wherein the threshold number of leukocyte signatures is at least 50, at least 75, at least 100, at least 200, at least 500, at least 1000, or at least 5000 leukocyte signatures.

In some embodiments, updating clusters is performed using a clustering algorithm selected from the group consisting of a dense clustering algorithm, spectral clustering algorithm, k-means clustering algorithm, hierarchical clustering algorithm, and an agglomerative clustering algorithm.

In some embodiments, the method further comprises determining a leukocyte immunoprofile type of a second subject, wherein the leukocyte immunoprofile type of the second subject is identified using the updated leukocyte immunoprofile types, wherein the identifying comprises determining a leukocyte signature of the second subject from cytometry data or RNA expression data from a biological sample obtained from the second subject; associating the leukocyte signature of the second subject with a particular one of the plurality of the updated leukocyte immunoprofile types; and identifying the leukocyte immunoprofile type for the second subject as the leukocyte immunoprofile type corresponding to the particular one of the plurality of updated leukocyte immunoprofile types to which the leukocyte signature of the second subject is associated.

In some embodiments, clustering is performed using a dense clustering algorithm, a spectral clustering algorithm, a k-means clustering algorithm, hierarchical clustering algorithm, and/or an agglomerative clustering algorithm. In some embodiments, clustering is performed using a spectral clustering algorithm.

In some embodiments, a plurality of leukocyte immunoprofile types comprises: a Naïve type, a Primed type, a Progressive type, a Chronic type, and a Suppressive type.

In some embodiments, the method further comprises identifying a subject as a candidate for treatment with an immunotherapy based upon the identifying the leukocyte immunoprofile type for the subject. In some embodiments, the method further comprises identifying a subject as a candidate for treatment with an immunotherapy when the subject is identified as having a Primed type.

In some embodiments, the method further comprises administering a therapeutic agent to a subject based upon identification of the subject's leukocyte immunoprofile type. In some embodiments, the method further comprises administering an immunotherapy to a subject when the subject is identified as having a Primed type.

In some aspects, the disclosure provides a method for determining a leukocyte immunoprofile type of a subject having, suspected of having, or at risk of having cancer, the method comprising using at least one computer hardware processor to perform: obtaining flow cytometry data for white blood cells (WBC) isolated from a biological sample obtained from the subject; processing the flow cytometry data to determine cell composition percentages for at least 20 cell types listed in Table 1; generating a leukocyte signature for the subject using the determined cell composition percentages for the at least 20 cell types, the leukocyte signature comprising the cell composition percentages for the at least 20 cell types; and identifying, using the leukocyte signature and from among a plurality of leukocyte immunoprofile types, a leukocyte immunoprofile type for the subject.

In some embodiments, the WBC consist of granulocyte white blood cells and agranulocyte white blood cells.

In some embodiments, processing flow cytometry data comprises applying one or more machine learning models to the flow cytometry data to obtain cell composition percentages for at least 20 cell types listed in Table 1.

In some embodiments, processing flow cytometry data comprises determining cell composition percentages for: Naive CD4+ Tregs, Naive CD4+ T cells, Naive CD8+ T cells, Naive B cells, Effector memory CD4+ T cells, Effector memory CD8+ T cells, Classical monocytes, and Non-classical monocytes.

In some embodiments, processing flow cytometry data comprises determining cell composition percentages for: Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, All memory CD4+ T cells, CD4+ T cells, CD39+ CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, and HLA-DRlow monocytes.

In some embodiments, a leukocyte signature comprises cell composition percentages for: Naive CD4+ Tregs, Naive CD4+ T cells, Naive CD8+ T cells, Naive B cells, Effector memory CD4+ T cells, Effector memory CD8+ T cells, Classical monocytes, and Non-classical monocytes.

In some embodiments, a leukocyte signature comprises cell composition percentages for: Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, All memory CD4+ T cells, CD4+ T cells, CD39+CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, and HLA-DRlow monocytes.

In some embodiments, a plurality of leukocyte immunoprofile types is associated with a respective plurality of leukocyte immunoprofile types, and identifying, using the leukocyte signature and from among a plurality of leukocyte immunoprofile types, the leukocyte immunoprofile type for the subject comprises associating the leukocyte signature of the subject with a particular one of the plurality of leukocyte immunoprofile types, and identifying the leukocyte immunoprofile type for the subject as the leukocyte immunoprofile type corresponding to the particular one of the plurality of leukocyte immunoprofile types to which the leukocyte signature of the subject is associated In some embodiments, associating a leukocyte signature of a subject with a particular one of a plurality of leukocyte immunoprofile types comprises processing the leukocyte signature with a trained classifier to obtain an output indicative of the particular one of the plurality of leukocyte immunoprofile types. In some embodiments, a trained classifier comprises a trained neural network classifier, optionally, a tabular prior-data fitted network transformer (TabPFN) classifier.

In some embodiments, associating a leukocyte signature of the subject with a particular one of a plurality of leukocyte immunoprofile types comprises determining, for each particular one of the plurality of leukocyte immunoprofile types, a score indicating whether the leukocyte signature of the subject is associated with that particular leukocyte immunoprofile type, wherein determining the score for a particular leukocyte immunoprofile type comprises applying a linear regression model associated with the particular leukocyte immunoprofile type, to the cell composition percentages in the leukocyte signature.

In some embodiments, generating a plurality of leukocyte immunoprofile types comprises obtaining multiple sets of flow cytometry data from white blood cells (WBC) isolated from biological samples obtained from multiple respective subjects, each of the multiple sets of flow cytometry data indicating cell composition percentages for at least 20 cell types listed in Table 1; generating multiple leukocyte signatures from the multiple sets of flow cytometry data, each of the multiple leukocyte signatures comprising cell composition percentages for at least 20 cell types listed in Table 1, the generating comprising, for each particular one of the multiple leukocyte signatures determining the leukocyte signature by determining the cell composition percentages using the flow cytometry data in the particular set of flow cytometry data for which the particular one leukocyte signature is being generated; and clustering the multiple leukocyte signatures to obtain the plurality of leukocyte immunoprofile types.

In some embodiments, the method further comprises updating a plurality of leukocyte immunoprofile types using the leukocyte signature of the subject, wherein the leukocyte signature of the subject is one of a threshold number of leukocyte signatures for a threshold number of subjects, wherein when the threshold number of leukocyte signatures is generated the leukocyte immunoprofile types are updated, wherein the threshold number of leukocyte signatures is at least 50, at least 75, at least 100, at least 200, at least 500, at least 1000, or at least 5000 leukocyte signatures.

In some embodiments, updating is performed using a clustering algorithm selected from the group consisting of a dense clustering algorithm, spectral clustering algorithm, k-means clustering algorithm, hierarchical clustering algorithm, and an agglomerative clustering algorithm.

In some embodiments, the method further comprises determining a leukocyte immunoprofile type of a second subject, wherein the leukocyte immunoprofile type of the second subject is identified using the updated leukocyte immunoprofile types, wherein the identifying comprises determining a leukocyte signature of the second subject from flow cytometry data from white blood cells isolated from a biological sample obtained from the second subject; associating the leukocyte signature of the second subject with a particular one of the plurality of the updated leukocyte immunoprofile types; and identifying the leukocyte immunoprofile type for the second subject as the leukocyte immunoprofile type corresponding to the particular one of the plurality of updated leukocyte immunoprofile types to which the leukocyte signature of the second subject is associated.

In some embodiments, clustering is performed using a dense clustering algorithm, a spectral clustering algorithm, a k-means clustering algorithm, hierarchical clustering algorithm, and/or an agglomerative clustering algorithm. In some embodiments, clustering is performed using a spectral clustering algorithm.

In some embodiments, a plurality of leukocyte immunoprofile types comprises: a Naïve type, a Primed type, a Progressive type, a Chronic type, and a Suppressive type.

In some embodiments, the method further comprises identifying a subject as a candidate for treatment with an immunotherapy based upon the identifying the leukocyte immunoprofile type for the subject. In some embodiments, the method further comprises identifying the subject as a candidate for treatment with an immunotherapy when the subject is identified as having a Primed type.

In some embodiments, the method further comprises administering a therapeutic agent to a subject based upon identification of the subject's leukocyte immunoprofile type. In some embodiments, the method further comprises administering an immunotherapy to a subject when the subject is identified as having a Primed type.

In some embodiments, a subject has head and neck squamous cell carcinoma (HNSCC).

In some aspects, the disclosure provides a method for determining a leukocyte immunoprofile type of a subject having, suspected of having, or at risk of having cancer, the method comprising using at least one computer hardware processor to perform obtaining RNA expression data for peripheral blood mononuclear cells (PBMC) isolated from a biological sample obtained from the subject; processing the RNA expression data to determine cell composition percentages for at least 20 cell types listed in Table 3; generating a leukocyte signature for the subject using the determined cell composition percentages for the at least 20 cell types, the leukocyte signature comprising the cell composition percentages for the at least 20 cell types; and identifying, using the leukocyte signature and from among a plurality of leukocyte immunoprofile types, a leukocyte immunoprofile type for the subject.

In some embodiments, RNA expression data comprises bulk RNA expression data. In some embodiments, processing RNA expression data comprises applying a cell deconvolution technique comprising one or more machine learning models to obtain the cell composition percentages.

In some embodiments, cell composition percentages comprise cell composition percentages for: Naive CD4+ Tregs, Naive CD4+ T cells, Naive CD8+ T cells, Naive B cells, Effector memory CD8+ T cells, Classical monocytes, and Non-classical monocytes.

In some embodiments, composition percentages comprise cell composition percentages for: Naive CD4+ T cells, Naive CD8+ T cells, Naive B cells, Non-switched Memory IgM B cells, Class-switched memory B cells, Central memory, CD4+ T cells, CD4+ Tregs, Transitional memory CD4+ T cells, Central memory CD4+ T cells, All memory CD4+ T cells, CD4+ T cells, CD4+ T cells, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, CD8+ TEMRA, Effector memory CD8+ T cells, Neutrophils, Granulocytes, Classical monocytes, and Non-classical monocytes.

In some embodiments, a leukocyte signature comprises cell composition percentages for: Naive CD4+ Tregs, Naive CD4+ T cells, Naive CD8+ T cells, Naive B cells, Effector memory CD8+ T cells, Classical monocytes, and Non-classical monocytes.

In some embodiments, a leukocyte signature comprises cell composition percentages for: Naive CD4+ T cells, Naive CD8+ T cells, Naive B cells, Non-switched Memory IgM B cells, Class-switched memory B cells, Central memory, CD4+ T cells, CD4+ Tregs, Transitional memory CD4+ T cells, Central memory CD4+ T cells, All memory CD4+ T cells, CD4+ T cells, CD4+ T cells, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, CD8+ TEMRA, Effector memory CD8+ T cells, Neutrophils, Granulocytes, Classical monocytes, and Non-classical monocytes.

In some embodiments, a plurality of leukocyte immunoprofile types is associated with a respective plurality of leukocyte immunoprofile types, and identifying, using the leukocyte signature and from among a plurality of leukocyte immunoprofile types, the leukocyte immunoprofile type for the subject comprises associating the leukocyte signature of the subject with a particular one of the plurality of leukocyte immunoprofile types, and identifying the leukocyte immunoprofile type for the subject as the leukocyte immunoprofile type corresponding to the particular one of the plurality of leukocyte immunoprofile types to which the leukocyte signature of the subject is associated In some embodiments, associating a leukocyte signature of a subject with a particular one of a plurality of leukocyte immunoprofile types comprises processing the leukocyte signature with a trained classifier to obtain an output indicative of the particular one of the plurality of leukocyte immunoprofile types. In some embodiments, a trained classifier comprises a trained neural network classifier, optionally, a tabular prior-data fitted network transformer (TabPFN) classifier.

In some embodiments, associating a leukocyte signature of the subject with a particular one of a plurality of leukocyte immunoprofile types comprises determining, for each particular one of the plurality of leukocyte immunoprofile types, a score indicating whether the leukocyte signature of the subject is associated with that particular leukocyte immunoprofile type, wherein determining the score for a particular leukocyte immunoprofile type comprises applying a linear regression model associated with the particular leukocyte immunoprofile type, to the cell composition percentages in the leukocyte signature.

In some embodiments, the method further comprises generating a plurality of leukocyte immunoprofile types, the generating comprising obtaining multiple sets of RNA expression data from white blood cells (WBC) isolated from biological samples obtained from multiple respective subjects, each of the multiple sets of RNA expression data indicating cell composition percentages for at least 20 cell types listed in Table 3; generating multiple leukocyte signatures from the multiple sets of RNA expression data, each of the multiple leukocyte signatures comprising cell composition percentages for at least 20 cell types listed in Table 3, the generating comprising, for each particular one of the multiple leukocyte signatures determining the leukocyte signature by determining the cell composition percentages using the RNA expression data in the particular set of RNA expression data for which the particular one leukocyte signature is being generated; and clustering the multiple leukocyte signatures to obtain the plurality of leukocyte immunoprofile types.

In some embodiments, the method further comprises updating a plurality of leukocyte immunoprofile types using the leukocyte signature of the subject, wherein the leukocyte signature of the subject is one of a threshold number of leukocyte signatures for a threshold number of subjects, wherein when the threshold number of leukocyte signatures is generated the leukocyte immunoprofile types are updated, wherein the threshold number of leukocyte signatures is at least 50, at least 75, at least 100, at least 200, at least 500, at least 1000, or at least 5000 leukocyte signatures.

In some embodiments, updating is performed using a clustering algorithm selected from the group consisting of a dense clustering algorithm, spectral clustering algorithm, k-means clustering algorithm, hierarchical clustering algorithm, and an agglomerative clustering algorithm.

In some embodiments, the method further comprises determining a leukocyte immunoprofile type of a second subject, wherein the leukocyte immunoprofile type of the second subject is identified using the updated leukocyte immunoprofile types, wherein the identifying comprises: determining a leukocyte signature of the second subject from RNA expression data from white blood cells isolated from a biological sample obtained from the second subject; associating the leukocyte signature of the second subject with a particular one of the plurality of the updated leukocyte immunoprofile types; and identifying the leukocyte immunoprofile type for the second subject as the leukocyte immunoprofile type corresponding to the particular one of the plurality of updated leukocyte immunoprofile types to which the leukocyte signature of the second subject is associated.

In some embodiments, clustering is performed using a dense clustering algorithm, a spectral clustering algorithm, a k-means clustering algorithm, hierarchical clustering algorithm, and/or an agglomerative clustering algorithm. In some embodiments, clustering is performed using a spectral clustering algorithm.

In some embodiments, a plurality of leukocyte immunoprofile types comprises: a Naïve type (G1), a Primed type (G2), a Progressive type (G3), a Chronic type (G4), and a Suppressive type (G5).

In some embodiments, the method further comprises identifying a subject as a candidate for treatment with an immunotherapy based upon the identifying the leukocyte immunoprofile type for the subject. In some embodiments, the method further comprises identifying the subject as a candidate for treatment with an immunotherapy when the subject is identified as having a Primed type.

In some embodiments, the method further comprises administering a therapeutic agent to a subject based upon identification of the subject's leukocyte immunoprofile type. In some embodiments, the method further comprises administering an immunotherapy to a subject when the subject is identified as having a Primed type.

In some embodiments, a subject has head and neck squamous cell carcinoma (HNSCC).

BRIEF DESCRIPTION OF THE DRAWINGS

FIG. 3 is a flowchart of an illustrative process for determining cell composition percentages based on cell counts determined for a plurality of cells of a biological sample, according to some embodiments of the technology described herein.

FIGS. 5A-5B show schematics representing exemplary cohorts used to produce leukocyte immunoprofile types, according to some embodiments of the technology as described herein.

FIG. 9A top panels describe clonality and Chao1 metrics data for alpha T cell receptor (TCR) variants among the 5 leukocyte immunoprofile types. The middle panels describe clonality and Chao1 metrics data for beta TCR variants among the 5 leukocyte immunoprofile types. The bottom panels describe representative data for clonality of heavy, lambda and kappa chains of BCR clonotypes in samples among the 5 leukocyte immunoprofile types. FIG. 9B shows representative data for TCR clonality, TCR diversity, and lambda and kappa chains of BCR clonotypes for the 5 leukocyte immunoprofile types.

FIG. 10B shows representative data for cytometry panels of cell populations shown as heatmaps of normalized signal intensities and t-distributed stochastic neighbor embedding (tSNE) of immune cell populations, according to some embodiments of the technology described herein.

FIG. 11A shows a representative Uniform Manifold Approximation and Projection (UMAP) plotted with 450 immune cell populations. FIG. 11B shows a volcano plot demonstrating the differentially represented populations between healthy and cancer patients. FIG. 11C shows UMAP for selected populations with true and predicted labels were compared, showing a gradient between cancer patients and healthy individuals. FIG. 11D shows representative data for ROC-AUC for the model's classification quality of training (left) and validation cohort (right) on 20 selected populations compared to the T and B Natural Killer Cells (TBNK) panel, which comprises the most common populations that are used in cytometry studies.

FIG. 12A shows unsupervised spectral clustering analysis applied to normalized flow cytometry percentages revealed 5 distinct leukocyte immunoprofile types. FIG. 12B shows matched RNA-seq (n=824) data that provided orthogonal validation to the flow cytometry (FC) analysis of cell percentages, using the cellular deconvolution algorithm Kassandra. FIG. 12C shows another example of matched RNA-seq data that provided orthogonal validation to the flow cytometry (FC) analysis of cell percentages, using the cellular deconvolution algorithm Kassandra. FIG. 12D shows a representative flow cytometry data-based pseudo-time analysis graph, which analyzes the connection between different peripheral blood samples using cell percentages obtained from flow cytometry data analysis.

FIGS. 13A-13C show representative data indicating cytokine pathways are differentially expressed in leukocyte immunoprofile types, according to some embodiments of the technology described herein. FIGS. 13A-13B show a representative heatmaps indicating correlations between functional gene signatures from MSigDB database for cytokine-related pathways were found with leukocyte immunoprofile types G1-G5. The health status for each patient is also shown. FIG. 13C shows representative data indicating comparison of differential gene expression levels of cytokine and chemokine genes, FLT3LG, CCL4, CXCL16, CCR7, TGFBR3 and ILIR1, the 5 leukocyte immunoprofile types.

FIG. 16A shows one embodiment of an overall workflow of cluster development: the blood draw, hematology analyzer, sample processing, flow cytometry run, manual data labeling, machine learning models training and implementation and following cohort analysis. FIG. 16B shows a representative heatmap with cell population-wise various cell surface marker signal intensities combined through different panels with tSNE-based panel-wise visualization of immune cell populations. FIG. 16C shows representative data indicating differences between healthy donors and cancer patients in a polar graph-like tree-shaped scatter plot visualization.

FIGS. 17A-17G show a representative data describing a patient cohort, according to some embodiments of the technology described herein. FIG. 17A shows a cohort description with disease-wise breakdown and clinical annotation. FIG. 17B shows the cohort was analyzed by different clinical groups and was split into training and validation sets for machine learning applications. FIG. 17C shows representative uMAP analysis visualization of raw cytometry data. Representative age, diagnosis, and treatment groups are highlighted separately. FIG. 17D shows a representative volcano plot showing differentially represented populations between healthy and cancer patients that were selected with a Max-Relevance and Min-Redundancy (MRMR) algorithm. FIG. 17E shows representative boxplots showing cell population distribution between healthy and cancer patients for Naïve CD4 T cells, monocytes, IgM unswitched memory B cells, and CX3CR1-CD8 TEMRA. FIG. 17F shows representative uMAP analysis visualizations of selected cell populations with several characteristics highlighted. FIG. 17G shows a representative ROC AUC analysis of healthy/cancer classifier trained on selected populations and on TBNK panel, respectively. Training and validation cohort split are shown.

FIGS. 18A-18E show representative data for clustering of cell populations, according to some embodiments of the technology described herein. FIG. 18A shows a clustered heatmap with 5 separate leukocyte immunotype clusters selected (G1-Naïve, G2-Primed, G3-Progressive, G4-Chronic, and G5-Suppressive); healthy and cancer patients are highlighted.

FIG. 18B shows representative flow cytometry data-based and Kassandra deconvolution data-based cell median percentages bubble plots. FIG. 18C shows a representative heatmap with GSEA scores for RNA-seq data samples grouped by the five clusters and age distribution between the clusters shown as histogram plots. FIG. 18D shows representative violin plots showing distribution of selected cytokines expressions. FIG. 18E shows representative pseudotime analysis plots visualization. Samples representing the 5 clusters are highlighted.

FIG. 19A shows a 3D principal components analysis (PCA) representation of blood RNA-seq datasets processed by Kassandra cell deconvolution algorithm. FIG. 19B shows bar plots showing distribution of five clusters within each disease group (G1-Naïve, G2-Primed, G3-Progressive, G4-Chronic, and G5-Suppressive). FIG. 19C shows representative data indicating statistical differences between leukocyte immunotypes within each disease group compared with healthy samples. Color intensity depends on log p-value, size of a circle is proportional to the fraction within the disease group.

FIGS. 20A-20F show representative data for analysis of HLA alleles and TCR/BCR repertoire, according to some embodiments of the technology described herein. FIG. 20A shows HLA allelic distribution for I type HLA genes. Only alleles with 5 counts or more are shown with different color and labeled. FIG. 20B shows representative TCR-beta clonality distribution within the five clusters (G1-Naïve, G2-Primed, G3-Progressive, G4-Chronic, and G5-Suppressive) using a swarm plot. FIG. 20C shows representative TCR-beta chao1 (diversity metric) distribution within the five clusters using a swarm plot. FIG. 20D shows a representative TCR-beta landscape. On the top line the CDR3 beta coverage is shown, on the middle deck explicit TCR-beta fractions are highlighted, and on the bottom line the cluster and healthy/cancer state are shown. FIG. 20E shows representative GSEA scores for different gene groups as well as distribution of differentially expressed genes (with ID3, TCF7 and LEF1 overexpressed in G1 cluster, TBX21, EOMES and TOX being overexpressed in G4 cluster) across the five clusters. FIG. 20F shows representative PD1 signaling and Cancer immunotherapy by PD1 blockade gene group scores among the patients receiving ICB across the five clusters.

FIG. 21A shows a representative HNSCC cohort description. Treatment and blood draw time points are shown. FIG. 21B shows representative uMAP analysis of data from a pan-cancer patient cohort relative to a representative HNSCC patient cohort. FIG. 21C shows a representative heatmap of the HNSCC cohort with corresponding cell populations across the five clusters (G1-G5). Responders and non-responders as well as pre- and post-treatment time points are highlighted. FIG. 21D shows representative bar plots for cluster-based analysis (left) and response-based analysis (right) for the pre-treatment samples across the five PBMC immunoprofile clusters (G1-G5). FIG. 21E shows a representative Sankey plot indicating the five clusters shifting after treatment. FIG. 21F shows representative data for cluster-based analysis (left) and response-based analysis (right) bar plots for the post-treatment samples across the five clusters (G1-G5).

FIGS. 22A-22F show representative data for HNSCC sample analysis, according to some embodiments of the technology described herein. FIG. 22A shows a representative volcano plot showing differentially represented populations between responders and non-responders within pre-treatment samples of the HNSCC cohort. Populations with p-value <0.05 and more than 20% difference are highlighted. FIG. 22B shows a representative waterfall plot with over-represented cell populations with p-value <0.05 and more than 20% difference for pre-treatment samples. FIG. 22C shows representative boxplots showing distribution of selected cell populations between responders and non-responders within a pre-treatment cohort. FIG. 22D shows representative uMAP visualizations of cluster (G1-G5) distribution (left) and Primed (G2) cluster signature scores (right). FIG. 22E shows representative data for Primed (G2) signature distribution between non-responders and responders shown on a box plot for pre-treatment samples (on the left) and for post-treatment samples (on the right). FIG. 22F shows a representative ROC-AUC curve based on median cohort-based cutoff.

FIGS. 23A-23B show representative data for blood immunoprofile cluster analysis, according to some embodiments of the technology described herein. FIG. 23A shows a representative heatmap, showing gene set enrichment analysis scores performed on RNA-seq samples aligned on the 5 clusters using gene sets from mSigDB. FIG. 23B shows a representative cell tree for cell populations used in the cluster analysis. Clinical value-adding populations are highlighted.

FIGS. 24A and 24B show bubble plots showing HLA-B allele distribution between the five clusters with an average TCR beta and alpha clonality highlighted. FIG. 24C shows a representative distribution of percentages of first clonotype for TCR beta categorized by the five clusters. FIG. 24D shows a representative TCR-alpha clonality distribution compared by cluster type (G1-G5) using a swarm plot. FIG. 24E shows a representative TCR-alpha chao1 (a diversity metric) distribution for the five clusters using a swarm plot. FIG. 24F shows a representative distribution of percentages of first clonotype for TCR alpha within the five clusters. FIG. 24G shows swarm plot, showing a representative distribution of percentages of common (intersecting with tumor) clonotypes in the five clusters. FIG. 24H shows a swarm plot, showing a representative distribution of percentages of common (intersecting with blood) clonotypes in the five clusters by cluster type. FIG. 24I shows a scatter plot showing representative percentages of both blood and tumor for common clonotypes (G1, G2, G3, G4, and G5. FIG. 24J shows BCR heavy chao1 (diversity metric) distribution within the five clusters using a swarm plot. FIG. 24K shows BCR lambda chao1 (diversity metric) distribution within the five clusters using a swarm plot. FIG. 24L shows BCR kappa chao1 (diversity metric) distribution within the five clusters shown in a swarm plot. FIG. 24M shows a representative TCR-alpha landscape. On the top line the CDR3 beta coverage is shown, on the middle deck explicit TCR-alpha fractions are highlighted, on the bottom line the cluster (G1-G5) and healthy/cancer state are shown.

FIGS. 26A-26C show a representative head and neck squamous cell carcinoma (HNSCC) cohort immunoprofiling analysis, according to some embodiments of the technology described herein. FIG. 26A shows a representative HNSCC cohort analysis workflow schema. FIG. 26B shows box plots showing a representative distribution of PBMC fraction of all cell events for HNSCC frozen PBMC in comparison with other blood source processing techniques. FIG. 26C shows box plots showing distribution of CD62L+ CD8 cells percentage from PBMC in comparison with other blood source processing techniques.

FIG. 27A shows a representative healthy/cancer classifier training workflow schema. FIG. 27B shows correlations between model cell type predictions and manual markups. FIG. 27C shows DE volcano plot of genes (fold change vs. false discovery rate) for each of five clusters G1-G5. FIG. 27D shows a representative Kassandra deconvolution heatmap with labels based on flow cytometry clustering. FIG. 27E shows representative data for a cytometry/deconvolution comparison with values, normalized on internal cohort distribution. FIG. 27F shows a representative machine learning model for flow cytometry data analysis training workflow schema.

DETAILED DESCRIPTION

Figure 1:
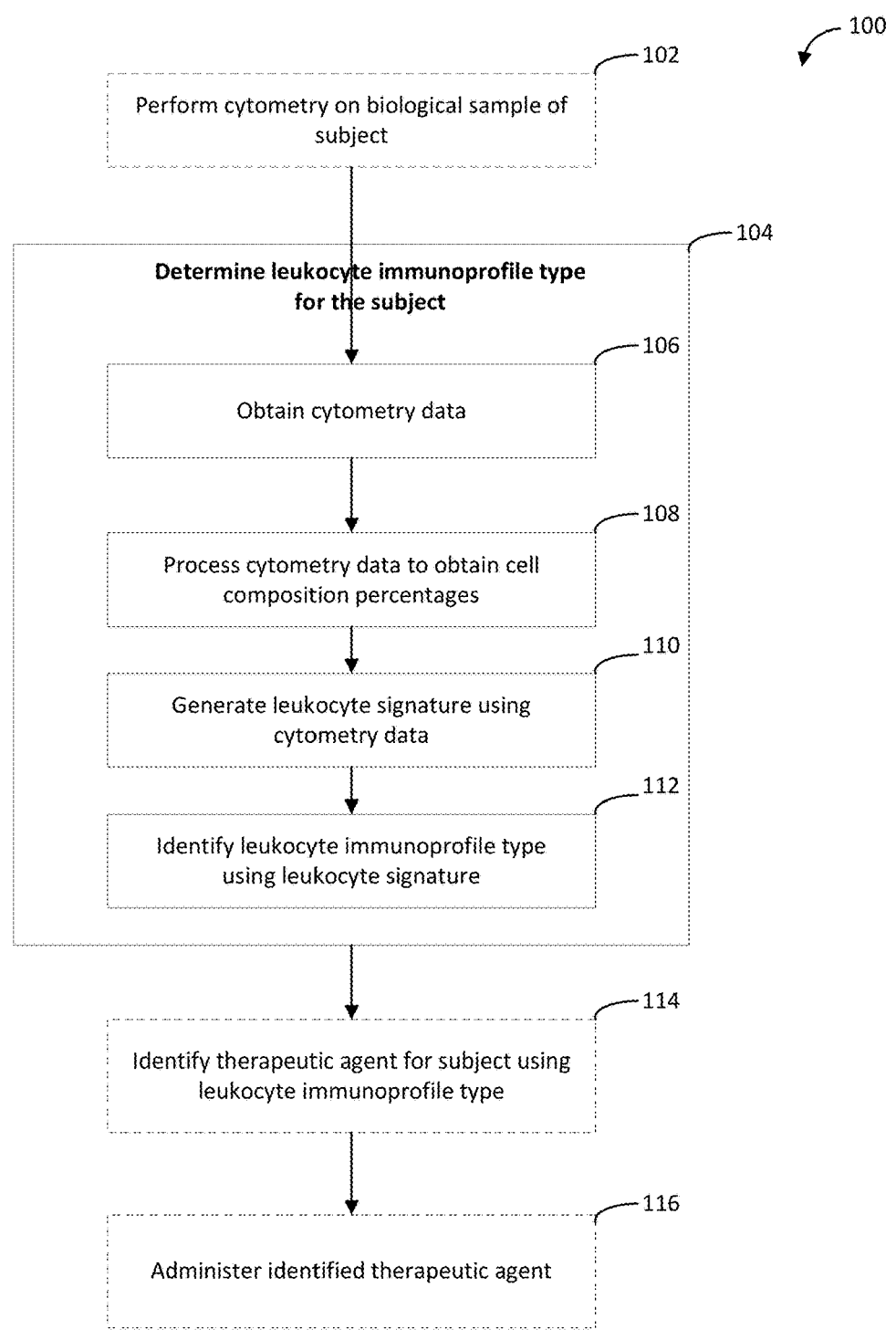
FIG. 1 provides a representative example of a process for identifying the leukocyte immunoprofile type of a subject using cytometry data, according to some embodiments of the technology described herein.

Aspects of the disclosure relate to methods, systems, and computer-readable storage media that are useful for characterizing an immunoprofile of a subject (e.g., healthy subject or subject diagnosed with cancer). In some embodiments, methods described by the disclosure are useful for determining the leukocyte immunoprofile of a subject. In some embodiments, a leukocyte immunoprofile type is determined from a biological sample comprising or consisting of (or consisting essentially of) white blood cells (WBC) of a subject. In some embodiments, a leukocyte immunoprofile is determined from a biological sample comprising or consisting of (or consisting essentially of) peripheral blood mononuclear cells (PBMC) of a subject. The disclosure is based, in part, on methods for immunoprofiling a cancer subject and the subject's prognosis and/or likelihood of responding to an immunotherapy based upon analysis of leukocyte populations in the blood of the subject. In some embodiments, methods described by the disclosure are useful for determining the leukocyte immunoprofile type (also referred to in some embodiments, as a white blood cells (WBC) or peripheral blood mononuclear cell (PBMC) immunoprofile type) of a subject having cancer. In some embodiments, the leukocyte immunoprofile type of a subject is indicative of a subject's cancer prognosis and/or the likelihood of whether the subject will respond to treatment with particular therapeutic agents, for example immunotherapeutic agents such as immune checkpoint inhibitors (ICI).

The highly heterogenous nature of cancer presents significant therapeutic challenges. For example, different patients diagnosed with the same cancer may have different responses to the same treatment. Thus, there is a need to identify patient and cancer characteristics which are indicative of the type of therapies to which the patient is likely to respond. Previous methods for identifying these characteristics focused on classifying patients according to cancer sub-types, for example, using cancer cell histology or RNA sequencing data and statistical analysis. This classification was then used to determine whether a given therapy is expected to be effective for a particular subject. These methods require obtaining a tumor tissue sample from the subject, which is often highly invasive (e.g., requiring surgery), time consuming, and expensive.

Aspects of this disclosure relate to methods for determining a subject's leukocyte immunoprofile type (e.g., a WBC or PBMC immunoprofile type) using machine learning-based techniques to analyze WBC or PBMC cytometry data (e.g., flow cytometry data or CYTOF data) or RNA-seq data, which is obtained from a healthy subject or a diseased subject (e.g., subjects with cancer, infection, autoimmune, or inflammatory disease). The inventors have recognized that the percentage composition certain cell types in the peripheral blood of a subject can be analyzed to determine leukocyte signatures (also referred to in some embodiments, as WBC signatures or PBMC signatures) that characterize a subject's immunotype and whether the subject is healthy or diseased, independent of disease type. The inventors also recognized that there is a set of five reproducible leukocyte immunotypes (Naïve type, Primed type, Progressive type, Chronic type, and Suppressive type, described further below) that are independent of the subject's healthy or diseased state, and that can be identified based on WBC or PBMC flow cytometry data and/or RNA expression data of a subject. This is an improvement over previous immunotyping technologies because previous techniques focused on sub-classifying patients having the same cancer type, whereas immunotypes identified by methods described herein are conserved across healthy subjects and subjects having different cancer types. Therefore, leukocyte immunoprofile types described herein may have pan-cancer utility in determining effective therapeutics for a given patient. The inventors have also recognized that specific immunotypes described herein are indicative of positive response to certain therapeutics in patients diagnosed with certain cancers, for example, head and neck squamous cell carcinoma (HNSCC), and thus may be used to determine which therapeutics to administer (or not administer) to a given patient.

Aspects of the disclosure relate to methods for identifying a subject as having one of five distinct leukocyte immunotypes (Naïve, Primed, Progressive, Chronic, and Suppressive) by analyzing WBC or PBMC cytometry data and/or RNA sequencing data indicative of WBC or PBMC cell composition in the subject. The five leukocyte immunotypes identified are characterized by a different distributions of immune cell types and activation states and reflect underlying immunological processes and tissue microenvironments. Analysis of over 18,000 transcriptomes from white blood cells and PBMCs demonstrated that these immunotypes are highly conserved across different patient groups and diseases.

In some embodiments, the methods described herein comprise determining the leukocyte immunoprofile type (selected from among the Naïve, Primed, Progressive, Chronic, or Suppressive immunoprofile types) of a subject having head and neck squamous cell carcinoma (HNSCC) and determining a treatment strategy based on the leukocyte (e.g., PBMC) immunoprofile type. As described further in the Examples, data indicates that HNSCC patients identified as having a Primed immunotype are more likely to respond to immunotherapy than patients having other immunoprofile types. The Primed type is characterized as having greater percentages of differentiated CD4+ central and transitional memory T cells, and CD39+ regulatory T cells (Tregs) than other leukocyte immunoprofile types.

Accordingly, in some aspects, the disclosure provides a method for determining a leukocyte immunoprofile type of a subject (e.g., healthy or having cancer), the method comprising using at least one computer hardware processor to perform: obtaining cytometry data or RNA expression data from blood of the subject (e.g., obtaining cytometry data or RNA expression data for one or more whole blood samples comprising WBC or PBMC obtained from the subject); processing the cytometry data or RNA expression data to determine cell composition percentages for at least some cell types (e.g., at least 15, 16, 17, 18, 19, 20, 21, 22, 23, 24, 25, 26, 27, 28, 29, 30, 31, 32, 33, or 34 cell types) of a plurality of cell types listed in any one of Tables 1 to 3; generating a leukocyte signature for the subject using the cytometry data or RNA expression data, the leukocyte signature comprising the cell composition percentages for respective cell types (e.g., at least 15, 16, 17, 18, 19, 20, 21, 22, 23, 24, 25, 26, 27, 28, 29, 30, 31, 32, 33, or 34 cell types) in the at least some of the plurality of cell types; and identifying, using the leukocyte signature and from among a plurality of leukocyte immunoprofile types, a leukocyte immunoprofile type for the subject. In some embodiments, the method comprises obtaining WBC or PMBC flow cytometry data from whole blood of the subject. Flow cytometry has several advantages over CYTOF, including, but not limited to lower cost, more widespread access, and case in controlling measurement signals. In some embodiments, the method comprises obtaining WBC or PMBC RNA-seq data from whole blood of the subject.

In some embodiments, WBC cytometry data is processed and the cell composition percentages comprise cell composition percentages for 15 or more (e.g., at least 15, 16, 17, 18, 19, 20, 21, 22, 23, 24, 25, 26, 27, 28, 29, 30, 31, 32, 33, or 34), or each of the cell types set forth in Table 1. In some embodiments, PMBC cytometry data is processed and the cell composition percentages comprise cell composition percentages for 15 or more (e.g., at least 15, 16, 17, 18, 19, 20, 21, 22, 23, 24, 25, 26, 27, 28, 29, 30, 31, 32, 33, or 34), or each of the cell types set forth in Table 2. In some embodiments, RNA-seq data is processed and cell composition percentages comprise cell composition percentages for 15 or more (e.g., at least 15, 16, 17, 18, 19, 20, 21, 22, 23, 24, 25, 26, 27, 28, 29, 30, 31, 32, 33, or 34), or each of the cell types set forth in Table 3.

In some embodiments, the method comprises processing the data (e.g., cytometry data or RNA expression data) to determine cell composition percentages for a plurality of cell types selected from Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, All memory CD4+ T cells, CD4+ T cells, CD39+CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, HLA-DRlow monocytes for Flow Cytometry data; and Naive CD4+ T cells, Naive CD8+ T cells, Naive B cells, Non-switched Memory IgM B cells, Class-switched memory B cells, Central memory CD4+ T cells, CD4+ Tregs, Transitional memory CD4+ T cells, Central memory CD4+ T cells, All memory CD4+ T cells, CD4+ T cells, Eosinophils, Basophils, Plasmacytoid dendritic cells, Dendritic cells, PD1high CD8+ T cells, Transitional memory CD8+ T cells, Cytotoxic NK cells, Regulatory NK cells, All memory CD8+ T cells, CD8+ T cells, CD8+ TEMRA, Effector memory CD8+ T cells, Neutrophils, Granulocytes, Classical monocytes, and Non-classical monocytes, for RNA-seq cell deconvolution data.

In some embodiments, the plurality of leukocyte immunoprofile types are clusters that have been identified by clustering a plurality of leukocyte signatures associated with respective subjects in a cohort of subjects. The cohort may comprise subjects that have been diagnosed as having cancer. The cohort may comprise healthy subjects. The cohort may comprise subjects that have been diagnosed as having cancer and that have a known prognosis and/or a known likelihood of responding to a particular therapy, such as an immunotherapy.

Following below are more detailed descriptions of various concepts related to, and embodiments of, the cell type determination systems and methods developed by the inventors. It should be appreciated that various aspects described herein may be implemented in any of numerous ways. Examples of specific implementations are provided herein for illustrative purposes only. In addition, the various aspects described in the embodiments below may be used alone or in any combination and are not limited to the combinations explicitly described herein.

FIG. 1 depicts an illustrative process 100 for determining a determining a leukocyte (e.g., PBMC) immunoprofile type of a subject. In some embodiments, the subject is a healthy subject. In some embodiments, a subject is a subject having, suspected of having, or at risk of having cancer. In some embodiments, the subject may include any of the embodiments described herein including with respect to the "Subjects" section.

In some embodiments, the illustrated process 100 may be implemented in a clinical or laboratory setting. For example, the illustrated process 100 may be implemented on a computing device that is located within the clinical or laboratory setting. In some embodiments, the computing device may directly obtain cytometry data from a cytometry platform within the clinical or laboratory setting. For example, a computing device included within the cytometry platform may directly obtain cytometry data from the cytometry platform. In some embodiments, the computing device may indirectly obtain cytometry data from a cytometry platform that is located within or external to the clinical or laboratory setting. For example, a computing device that is located within the clinical or laboratory setting may obtain cytometry data via a communication network, such as Internet or any other suitable network, as aspects of the technology described herein are not limited to any particular communication network.

Additionally, or alternatively, the illustrated process 100 may be implemented in a setting that is remote from a clinical or laboratory setting. For example, the illustrated process 100 may be implemented on a computing device that is located externally from a clinical or laboratory setting. In this case, the computing device may indirectly obtain cytometry data that is generated using a cytometry platform located within or external to a clinical or laboratory setting. For example, the cytometry data may be provided to computing device via a communication network, such as Internet or any other suitable network, as aspects of the technology described herein are not limited to any particular communication network. In some embodiments, the cytometry data may be obtained from a database or data store, and may be data that has been previously obtained from a cytometry platform and stored (possibly after being received from the cytometry platform and partially processed). In some embodiments, obtaining the flow cytometry data comprising obtaining data from subjects having a plurality of different cancers (e.g., pancreatic cancer, breast cancer, non-small cell lung carcinoma, colorectal cancer, melanoma, prostate cancer, etc.). Thus, in some embodiments, the methods described herein have pan-cancer applicability.

As described herein, in some embodiments, process 100 begins with act 102 performing cytometry on a biological sample comprising PBMCs (or WBC, in the case of determining an WBC immunoprofile type) obtained from the subject. In some embodiments, the act 102 involves processing a biological sample using a cytometry platform, which produces cytometry data. The biological sample processed in act 102 may be obtained from a subject having, suspected of having, or at risk of having cancer or any immune-related diseases. The biological sample processed in act 102 may be obtained from a healthy subject. The biological sample may be obtained by performing a biopsy or by obtaining a blood sample, a salivary sample, or any other suitable biological sample from the subject. The biological sample may include diseased tissue (e.g., cancerous), and/or healthy tissue. In some embodiments, the origin or preparation methods of the biological sample may include any of the embodiments described herein including with respect to the "Biological Samples" section.

In some embodiments, the cytometry platform includes any suitable instrument and/or system configured to perform cytometry, as aspects of the technology described herein are not limited to any particular type of cytometry system. For example, the cytometry platform may include any suitable flow cytometry platform. Additionally, or alternatively, the cytometry platform may include any suitable mass cytometry platform. In some embodiments, the biological sample may be prepared according to manufacturer's protocols associated with the cytometry platform. In some embodiments, the biological sample may be prepared according to any suitable protocol, as embodiments of the technology described herein are not limited to any particular preparation protocol. In some embodiments, flow cytometry techniques may include any of the embodiments described herein including with respect to the "Flow Cytometry" section. In some embodiments, mass cytometry techniques may include any of the embodiments described herein including with respect to the "Mass Cytometry" section.

The skilled artisan will recognize that, in some embodiments, act 102 is optional and is not always required to perform process 100. For example, in some instances, the cytometry has already been performed on the biological sample, and the cytometry data exists prior to beginning process 100.

Regardless of whether act 102 is performed, process 100 either proceeds to or begins with act 104, where a leukocyte immunoprofile type for the subject is determined. Act 104 involves acts 106, 108, 110, and 112, and process 100 proceeds through these acts sequentially, starting with act 106 for obtaining cytometry data for the subject. The cytometry data typically comprises information relating to a plurality of cells, for example, information relating to populations of immune cell types (e.g., PBMCs) of the subject. In some embodiments, the cytometry data comprises information relating to the presence, absence, and/or relative amounts of at least some (or all) of the cells of the plurality of cells, for example some or all of the cell types listed in Table 1 or Table 2. In some embodiments, the cytometry data comprises flow cytometry data. In some embodiments, the cytometry data comprises cytometry by time of flight (CyTOF) data.

In some embodiments, the cytometry data comprises information relating to the presence, absence, and/or relative amounts for between 15 and 36 cell types listed in Table 1 or Table 2. In some embodiments, the cytometry data comprises information relating to the presence, absence, and/or relative amounts for between 3 and 8, 5 and 12, 10 and 20, 15 and 25, 18 and 34 or 18 and 36 cell types listed in Table 1 or Table 2. In some embodiments, the cytometry data comprises information relating to the presence, absence, and/or relative amounts for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or 36 cell types listed in Table 1 or Table 2. In some embodiments, the cytometry data comprises information relating to the presence, absence, and/or relative amounts for additional cell types that are not listed in Table 1 or Table 2.

Next, process 100 proceeds to act 108, processing the cytometry data to obtain cell composition percentages. In some embodiments, the cytometry data is processed to obtain cell composition percentages for at least some cell types of a plurality of cell types listed in Table 1 or Table 2. In some embodiments, the cytometry data is processed to obtain cell composition percentages for between 15 and 36 cell types listed in Table 1 or Table 2. In some embodiments, the cytometry data is processed to obtain cell composition percentages for between 2 and 34 cell types listed in Table 1 or Table 2. In some embodiments, the cytometry data is processed to obtain cell composition percentages for between 3 and 8, 5 and 12, 10 and 20, 15 and 25, 18 and 34 or 18 and 36 cell types listed in Table 1 or Table 2. In some embodiments, the cytometry data is processed to obtain cell composition percentages for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or 36 cell types listed in Table 1 or Table 2. In some embodiments, the cytometry data is processed to obtain cell composition percentages for additional cell types that are not listed in Table 1 or Table 2. Methods of processing cytometry data to obtain cell composition percentages are further described herein with respect to FIG. 3.

In some embodiments, processing the cytometry data comprises applying one or more machine learning models to the cytometry data to obtain cell composition percentages for at least some (or all) of the plurality of cell types listed in Table 1 or Table 2. Examples of machine learning models that may be used to process cytometry data to obtain cell composition percentages are described, for example in International Application Publication Number WO2023/147177, filed Jan. 31, 2023, the entire contents of which are incorporated by reference herein. In some embodiments, the machine learning model comprises a Cibersort technique (e.g., as described by Newman et al. Nature Methods volume 12, pages 453-457 (2015)) or CibersortX technique (e.g., as described by Newman et al. Nature Biotechnology volume 37, pages 773-782 (2019)). Aspects of machine learning models are described herein including at least in the section "Cytometry-Based Cellular Deconvolution".

After cell composition percentages have been obtained from the cytometry data in act 108, process 104 proceeds to act 110, generating a leukocyte signature using the cytometry data. In some embodiments, a leukocyte signature comprises cell composition percentages for at least some of the cell types listed in Table 1 or Table 2. In some embodiments, a leukocyte signature comprises cell composition percentages for between 15 and 36 cell types listed in Table 1 or Table 2. In some embodiments, a leukocyte signature comprises cell composition percentages for between 3 and 8, 5 and 12, 10 and 20, 15 and 25, 18 and 34 or 18 and 36 cell types listed in Table 1 or Table 2. In some embodiments, a leukocyte signature comprises cell composition percentages for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or 36 cell types listed in Table 1 or Table 2. In some embodiments, a leukocyte signature comprises cell composition percentages for additional cell types that are not listed in Table 1 or Table 2. In some embodiments, the leukocyte signature is outputted as a vector comprising the cell composition percentages.

In some embodiments, the cytometry data is processed using computing device. In some embodiments, computing device can be one or multiple computing devices of any suitable type. For example, the computing device may be a portable computing device (e.g., a laptop, a smartphone) or a fixed computing device (e.g., a desktop computer, a server). When computing device includes multiple computing devices, the device(s) may be physically co-located (e.g., in a single room) or distributed across multiple physical locations. In some embodiments, the computing device may be part of a cloud computing infrastructure. In some embodiments, one or more computer(s) may be co-located in a facility operated by an entity (e.g., a hospital, a research institution). In some embodiments, the one or more computing device(s) may be physically co-located with a medical device, such as a cytometry platform. For example, a cytometry platform may include computing device.

In some embodiments, the computing device may be operated by a user such as a doctor, clinician, researcher, patient, or other individual. For example, the user may provide the cytometry data as input to the computing device (e.g., by uploading a file), and/or may provide user input specifying processing or other methods to be performed using the cytometry data.

In some embodiments, computing device includes software configured to perform various functions with respect to the cytometry data. An example of computing device including such software is described herein including at least with respect to FIG. 15.

Next, process 100 proceeds to act 112, where a leukocyte immunoprofile type is identified for the subject using the leukocyte signature generated at act 110. This may be done in any suitable way. For example, in some embodiments, the each of the possible leukocyte immunoprofile types is associated with (e.g., defined by or characterized by) a respective plurality of leukocyte immunoprofile types. In such embodiments, a leukocyte immunoprofile type for the subject may be identified by associating the leukocyte signature of the subject with a particular one of the plurality of leukocyte immunoprofile types (e.g., the type identified may be the type associated with (e.g., defined by or characterized by) the leukocyte signature cluster to which the leukocyte signature of the subject is closest according to a distance measure or any suitable measure of distance or similarity); and identifying the leukocyte immunoprofile type for the subject as the leukocyte immunoprofile type corresponding to the particular one of the plurality of leukocyte immunoprofile types to which the leukocyte signature of the subject is associated. Examples of leukocyte immunoprofile types are described herein. Aspects of identifying a leukocyte immunoprofile type for a subject are described herein including in the sections titled "Generating Leukocyte Signature and Identifying Leukocyte Immunoprofile Type" and "Techniques for Associating Leukocyte Signatures to Leukocyte Immunoprofile Types", and in FIG. 4.

As described above, a subject's leukocyte immunoprofile type is identified at act 112. In some embodiments, the leukocyte immunoprofile type of a subject is identified to be one of the following leukocyte immunoprofile types: Naïve type, Primed type, Progressive type, Chronic type, or Suppressive type. In some embodiments, process 104 ends once act 112 is complete.

In some embodiments, process 100 proceeds to act 114, where the subject's likelihood of responding to a therapy is identified using the leukocyte immunoprofile type identified at act 112. In some embodiments, when a subject is identified as having a Naïve leukocyte immunoprofile type at act 112, the subject is identified as having an increased likelihood of responding to an immunotherapy (e.g., an immune checkpoint inhibitor, such as a PD1 antibody, such as pembrolizumab) relative to a subject having other leukocyte immunoprofile types, at act 114. In some embodiments, when a subject is identified as having a Primed leukocyte immunoprofile type at act 112, the subject is identified as having an increased likelihood of responding to an immunotherapy (e.g., an immune checkpoint inhibitor, such as a PD1 antibody, such as pembrolizumab) relative to a subject having other leukocyte immunoprofile types, at act 114. In some embodiments, when a subject is identified as having a Suppressive leukocyte immunoprofile type at act 112, the subject is identified as having a decreased likelihood of responding to an immunotherapy (e.g., an immune checkpoint inhibitor, such as a PD1 antibody, such as pembrolizumab) relative to a subject having other leukocyte immunoprofile types, at act 114, and a therapy that is not an immunotherapy may be identified for the subject. Aspects of identifying whether or not a subject is likely to respond to a therapy are described herein including in the section below titled "Therapeutic Indications."

In some embodiments, process 100 completes after act 114 completes. In some such embodiments, the determined leukocyte signature and/or identified leukocyte immunoprofile type, and/or the identified likelihood the subject will respond to a therapy may be stored for subsequent use, provided to one or more recipients (e.g., a clinician, a researcher, etc.), and/or used to update the leukocyte immunoprofile types.

However, in some embodiments, one or more other acts are performed after act 114. For example, in the illustrated embodiment of FIG. 1, process 100 may include optional act 116, shown using dashed lines in FIG. 1. For example, at act 116, the subject is administered one or more therapeutic agents (e.g., immunotherapies, such as immune checkpoint inhibitors).

Examples of immunotherapies and other therapies are provided herein. It should be appreciated that although acts 102, 114, and 116 are indicated as optional in the example of FIG. 1, in other embodiments, one or more other acts may be optional (in addition to or instead of acts 102, 114, and 116).

In some aspects, the disclosure provides a method for determining a leukocyte immunoprofile type of a subject, the method comprising using at least one computer hardware processor to perform: obtaining RNA expression data for WBC or PBMC of the subject; processing the RNA expression data using a cell deconvolution technique to determine cell composition percentages for at least some cell types (e.g., at least 15, 16, 17, 18, 19, 20, 21, 22, 23, 24, 25, 26, 27, or 28) of a plurality of cell types listed in Table 3; generating a leukocyte signature for the subject using the RNA expression data, the leukocyte signature comprising the cell composition percentages for respective cell types (e.g., at least 15, 16, 17, 18, 19, 20, 21, 22, 23, 24, 25, 26, 27, or 28) in the at least some of the plurality of cell types; and identifying, using the leukocyte signature and from among a plurality of leukocyte immunoprofile types, a leukocyte immunoprofile type for the subject. In some embodiments, method comprises determining the leukocyte immunoprofile type of a subject having, suspected of having, or at risk of having cancer.

Figure 2:
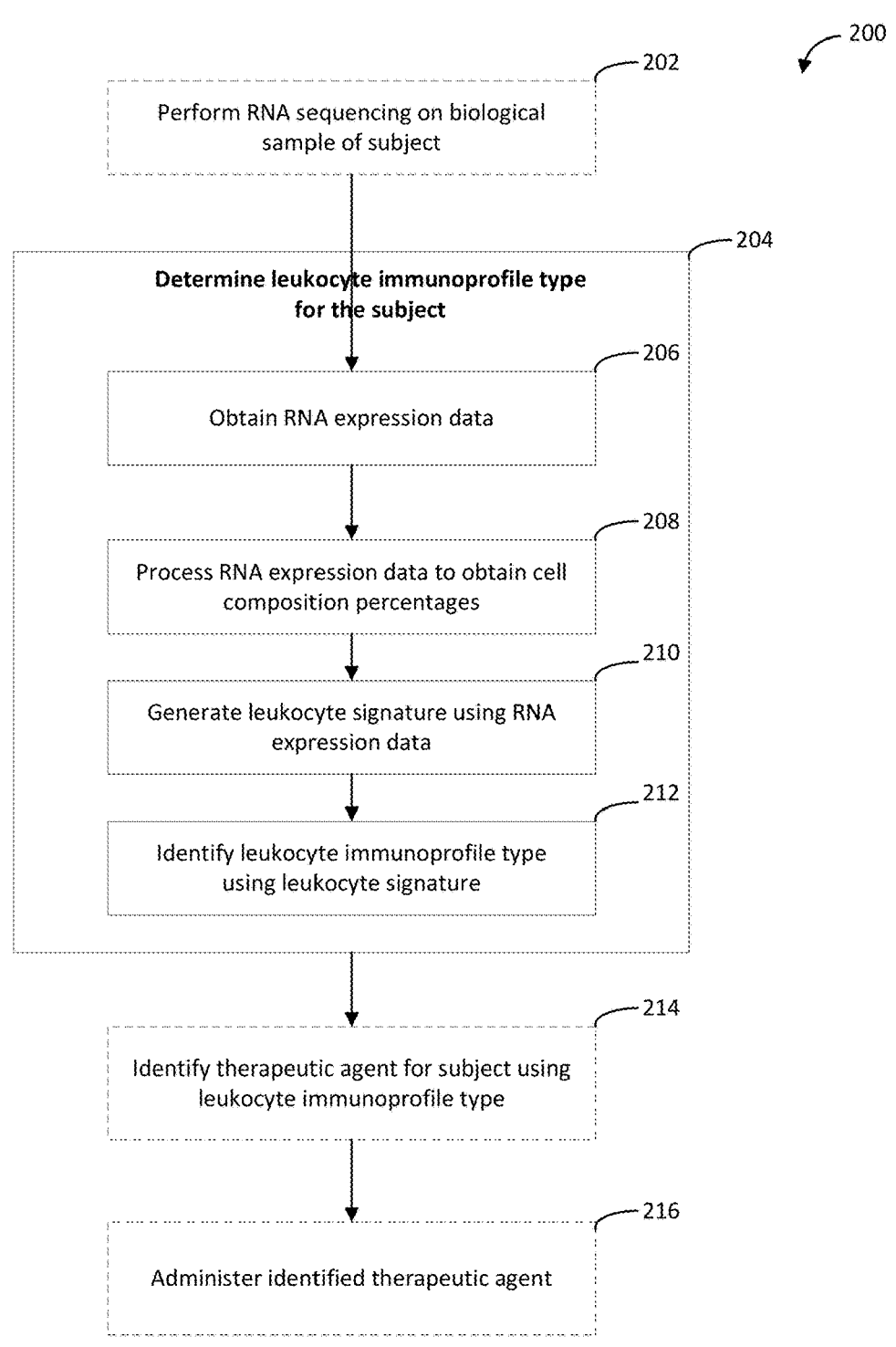
FIG. 2 provides a representative example of a process for identifying the leukocyte immunoprofile type of a subject using RNA expression data, according to some embodiments of the technology described herein.

FIG. 2 depicts an illustrative process 200 for determining a determining a peripheral blood leukocyte immunoprofile type of a subject having, suspected of having, or at risk of having cancer. In some embodiments, the subject may include any of the embodiments described herein including with respect to the "Subjects" section.

In some embodiments, the illustrated process 200 may be implemented in a clinical or laboratory setting. For example, the illustrated process 200 may be implemented on a computing device that is located within the clinical or laboratory setting. In some embodiments, the computing device may directly obtain RNA expression data from a sequencing platform (e.g., nucleic acid sequencing platform) within the clinical or laboratory setting. For example, a computing device included within the sequencing platform may directly obtain RNA expression data from the sequencing platform. In some embodiments, the computing device may indirectly obtain RNA expression data from a sequencing platform that is located within or external to the clinical or laboratory setting. For example, a computing device that is located within the clinical or laboratory setting may obtain RNA expression data via a communication network, such as Internet or any other suitable network, as aspects of the technology described herein are not limited to any particular communication network.

Additionally, or alternatively, the illustrated process 200 may be implemented in a setting that is remote from a clinical or laboratory setting. For example, the illustrated process 200 may be implemented on a computing device that is located externally from a clinical or laboratory setting. In this case, the computing device may indirectly obtain RNA expression data that is generated using a sequencing platform located within or external to a clinical or laboratory setting. For example, the RNA expression data may be provided to computing device via a communication network, such as Internet or any other suitable network, as aspects of the technology described herein are not limited to any particular communication network.

As described herein, in some embodiments, process 200 begins with act 202 performing RNA sequencing on a biological sample obtained from the subject. In some embodiments, the act 202 involves processing a biological sample using a sequencing platform, which produces sequencing data. In some embodiments, the RNA sequencing data is processed to obtain RNA expression data. The biological sample processed in act 202 may be obtained from a subject having, suspected of having, or at risk of having cancer or any immune-related diseases. The biological sample may be obtained by performing a biopsy or by obtaining a blood sample, a salivary sample, or any other suitable biological sample from the subject. The biological sample may include diseased tissue (e.g., cancerous), and/or healthy tissue. In some embodiments, the origin or preparation methods of the biological sample may include any of the embodiments described herein including with respect to the "Biological Samples" section.

In some embodiments, the sequencing platform includes any suitable instrument and/or system configured to perform nucleic acid sequencing (e.g., RNA sequencing), as aspects of the technology described herein are not limited to any particular type of sequencing system. In some embodiments, the biological sample may be prepared according to manufacturer's protocols associated with the sequencing platform. In some embodiments, the biological sample may be prepared according to any suitable protocol, as embodiments of the technology described herein are not limited to any particular preparation protocol. As one illustrative example, in some embodiments, the sequencing data may comprise bulk sequencing data. The bulk sequencing data may comprise at least 1 million reads, at least 5 million reads, at least 10 million reads, at least 20 million reads, at least 50 million reads, or at least 100 million reads. In some embodiments, the sequencing data comprises bulk RNA sequencing (RNA-seq) data, single cell RNA sequencing (scRNA-seq) data, or next generation sequencing (NGS) data. In some embodiments, RNA sequencing techniques may include any of the embodiments described herein including with respect to the "RNA Expression Data" section.

The skilled artisan will recognize that, in some embodiments, act 202 is optional and is not always required to perform process 200. For example, in some instances, the RNA sequencing has already been performed on the biological sample and processed to generate RNA expression data, and the RNA expression data exists prior to beginning process 200.

Regardless of whether 202 is performed, process 200 either proceeds to or begins at act 204, where a leukocyte immunoprofile type for the subject is determined. Act 204 involves acts 206, 208, 210, and 212 and process 200 proceeds through these acts sequentially, starting with act 206 for obtaining RNA expression data for the subject. The RNA expression data, in some embodiments, comprises RNA expression levels for genes expressed by a plurality of cells, for example, a plurality of immune cell types (e.g., PBMCs), of the subject. In some embodiments, the RNA expression data comprises information (e.g., RNA expression levels) relating to the presence, absence, and/or relative amounts of at least some (or all) of the cells of the plurality of cells, for example some or all of the cell types listed in Table 3.

In some embodiments, the RNA expression data comprises RNA expression levels of genes associated with (e.g., defined by or characterized by) between 2 and 28 cell types listed in Table 3. In some embodiments, the RNA expression data comprises RNA expression levels of genes associated with between 3 and 8, 5 and 12, 10 and 20, 15 and 25, 18 and 26 or 18 and 28 cell types listed in Table 3. In some embodiments, the RNA expression data comprises RNA expression levels of genes associated with at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 cell types listed in Table 3. In some embodiments, the RNA expression data comprises RNA expression levels of genes associated with (e.g., defined by or characterized by) additional cell types that are not listed in Table 3.

Next, process 200 proceeds to act 208, processing the RNA expression data to obtain cell composition percentages. In some embodiments, the RNA expression data is processed to obtain cell composition percentages for at least some cell types of a plurality of cell types listed in Table 3. In some embodiments, the RNA expression data is processed to obtain cell composition percentages for between 20 and 28 cell types listed in Table 3. In some embodiments, the RNA expression data is processed to obtain cell composition percentages for between 3 and 8, 5 and 12, 10 and 20, 15 and 25, 18 and 26 or 18 and 28 cell types listed in Table 3. In some embodiments, the RNA expression data is processed to obtain cell composition percentages for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 cell types listed in Table 3. In some embodiments, the RNA expression data is processed to obtain cell composition percentages for additional cell types that are not listed in Table 3.

In some embodiments, act 208 comprises processing the RNA expression levels using a cell deconvolution technique to determine the cell composition percentages for at least some (or all) cell types of a plurality of cell types listed in Table 3. In some embodiments, processing the RNA expression data comprises applying one or more machine learning models to the RNA expression data to obtain cell composition percentages for at least some (or all) of the plurality of cell types listed in Table 3. Examples of machine learning models that may be used to process RNA expression data to obtain cell composition percentages are described, for example in International Application No. PCT/US2021/022155, published as International Publication No. WO2021/183917 on Sep. 16, 2021; and International Application No. PCT/US2022/027088, published as International Publication No. WO2022/232615 on Nov. 3, 2022, the entire contents of each of which are incorporated by reference herein. Aspects of machine learning models are described herein including at least in the section "RNA-Based Cellular Deconvolution".

After cell composition percentages have been obtained from the RNA expression data in act 208, process 204 proceeds to act 210, generating a leukocyte signature using the RNA expression data. In some embodiments, a leukocyte signature comprises cell composition percentages for at least some (e.g., at least 20, 21, 22, 23, 24, 25, 26, 27, or 28) of the cell types listed in Table 3. In some embodiments, a leukocyte signature comprises cell composition percentages for between 2 and 28 cell types listed in Table 3. In some embodiments, a leukocyte signature comprises cell composition percentages for between 3 and 8, 5 and 12, 10 and 20, 15 and 25, 16 and 26 or 18 and 28 cell types listed in Table 3. In some embodiments, a leukocyte signature comprises cell composition percentages for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 cell types listed in Table 3. In some embodiments, a leukocyte signature comprises cell composition percentages for additional cell types that are not listed in Table 3. In some embodiments, the leukocyte signature is outputted as a vector comprising the cell composition percentages.

In some embodiments, the RNA expression data is processed using computing device. In some embodiments, computing device can be one or multiple computing devices of any suitable type. For example, the computing device may be a portable computing device (e.g., a laptop, a smartphone) or a fixed computing device (e.g., a desktop computer, a server). When computing device includes multiple computing devices, the device(s) may be physically co-located (e.g., in a single room) or distributed across multiple physical locations. In some embodiments, the computing device may be part of a cloud computing infrastructure. In some embodiments, one or more computer(s) may be co-located in a facility operated by an entity (e.g., a hospital, a research institution). In some embodiments, the one or more computing device(s) may be physically co-located with a medical device, such as a sequencing platform. For example, a sequencing platform may include computing device.

In some embodiments, the computing device may be operated by a user such as a doctor, clinician, researcher, patient, or other individual. For example, the user may provide the RNA expression data as input to the computing device (e.g., by uploading a file), and/or may provide user input specifying processing or other methods to be performed using the RNA expression data.

In some embodiments, computing device includes software configured to perform various functions with respect to the RNA expression data. An example of computing device including such software is described herein including at least with respect to FIG. 15.

Next, process 200 proceeds to act 212, where a leukocyte immunoprofile type is identified for the subject using the leukocyte signature generated at act 210. This may be done in any suitable way. For example, in some embodiments, the each of the possible leukocyte immunoprofile types is associated with (e.g., defined by or characterized by) a respective plurality of leukocyte immunoprofile types. In such embodiments, a leukocyte immunoprofile type for the subject may be identified by associating the leukocyte signature of the subject with a particular one of the plurality of leukocyte immunoprofile types (e.g., the type identified may be the type associated with the leukocyte cluster to which the leukocyte signature of the subject is closest according to a distance measure or any suitable measure of distance or similarity); and identifying the leukocyte immunoprofile type for the subject as the leukocyte immunoprofile type corresponding to the particular one of the plurality of leukocyte immunoprofile types to which the leukocyte signature of the subject is associated. Examples of leukocyte immunoprofile types are described herein. Aspects of identifying a leukocyte immunoprofile type for a subject are described herein including in the sections titled "Generating Leukocyte Signature and Identifying Leukocyte Immunoprofile Type" and "Techniques for Associating Leukocyte Signatures to Leukocyte Immunoprofile Types", and in FIG. 4.

As described above, a subject's leukocyte immunoprofile type is identified at act 212. In some embodiments, the leukocyte immunoprofile type of a subject is identified to be one of the following leukocyte immunoprofile types: Naïve type, Primed type, Progressive type, Chronic type, or Suppressive type. In some embodiments, process 204 ends once act 212 is complete.

In some embodiments, process 200 proceeds to act 214, where the subject's likelihood of responding to a therapy is identified using the leukocyte immunoprofile type identified at act 212. In some embodiments, when a subject is identified as having a Naïve leukocyte immunoprofile type at act 212, the subject is identified as having an increased likelihood of responding to an immunotherapy (e.g., an immune checkpoint inhibitor, such as a PD1 antibody, such as pembrolizumab) relative to a subject having other leukocyte immunoprofile types, at act 214. In some embodiments, when a subject is identified as having a Primed leukocyte immunoprofile type at act 212, the subject is identified as having an increased likelihood of responding to an immunotherapy (e.g., an immune checkpoint inhibitor, such as a PD1 antibody, such as pembrolizumab) relative to a subject having other leukocyte immunoprofile types, at act 214. In some embodiments, when a subject is identified as having a Suppressive leukocyte immunoprofile type at act 212, the subject is identified as having a decreased likelihood of responding to an immunotherapy (e.g., an immune checkpoint inhibitor, such as a PD1 antibody, such as pembrolizumab) relative to a subject having other leukocyte immunoprofile types, at act 214, and a therapy that is not an immunotherapy may be identified for the subject. Aspects of identifying whether or not a subject is likely to respond to a therapy are described herein including in the section below titled "Therapeutic Indications."

In some embodiments, process 200 completes after act 214 completes. In some such embodiments, the determined WBC or PBMC signature and/or identified leukocyte immunoprofile type, and/or the identified likelihood the subject will respond to a therapy may be stored for subsequent use, provided to one or more recipients (e.g., a clinician, a researcher, etc.), and/or used to update the leukocyte immunoprofile types.

However, in some embodiments, one or more other acts are performed after act 214. For example, in the illustrated embodiment of FIG. 2, process 200 may include optional act 216, shown using dashed lines in FIG. 2. For example, at act 216, the subject is administered one or more therapeutic agents (e.g., immunotherapies, such as immune checkpoint inhibitors). Examples of immunotherapies and other therapies are provided herein.

It should be appreciated that although acts 202, 214, and 216 are indicated as optional in the example of FIG. 2, in other embodiments, one or more other acts may be optional (in addition to or instead of acts 202, 214, and 216).

TABLE 1

| Exemplary cell types used in WBC signatures |
| --- |
| Naive CD4+ Tregs |
| Naive CD4+ T cells |
| Naive CD8+ T cells |
| Naive B cells |
| Non-switched memory IgM B cells |
| Vδ2+ γδ T cells |
| Class-switched memory B cells |
| Central memory CD8+ T cells |
| CD4+ Tregs |
| Transitional memory CD4+ T cells |
| Central memory CD4+ T cells |
| All memory CD4+ T cells |
| CD4+ T cells |
| CD39+ CD4+ Tregs |
| Eosinophils |
| Basophils |
| Plasmacytoid dendritic cells |
| Dendritic cells |
| PD1high CD8+ T cells |
| Transitional memory CD8+ T cells |
| Cytotoxic NK cells |
| Regulatory NK cells |
| All memory CD8+ T cells |
| CD8+ T cells |
| Effector memory CD4+ T cells |
| NKT cells |
| CD8+ TEMRA |
| Effector memory CD8+ T cells |
| CD4+ TEMRA |
| Neutrophils |
| Granulocytes |
| Classical monocytes |
| Non-classical monocytes |
| HLA-DRlow monocytes |

TABLE 2

| Exemplary cell types used in PBMC signatures |
| --- |
| Naive CD4+ Tregs |
| Naive CD4+ T cells |
| Naive CD8+ T cells |
| Naive B cells |

TABLE 2-continued

| Exemplary cell types used in PBMC signatures |
| --- |
| Non-switched memory IgM B cells |
| Vδ2+ γδ T cells |
| Class-switched memory B cells |
| Central memory CD8+ T cells |
| CD4+ Tregs |
| Transitional memory CD4+ T cells |
| Central memory CD4+ T cells |
| All memory CD4+ T cells |
| CD4+ T cells |
| CD39+ CD4+ Tregs |
| Plasmacytoid dendritic cells |
| Dendritic cells |
| PD1high CD8+ T cells |
| Transitional memory CD8+ T cells |
| Cytotoxic NK cells |
| Regulatory NK cells |
| All memory CD8+ T cells |
| CD8+ T cells |
| Effector memory CD4+ T cells |
| NKT cells |
| CD8+ TEMRA |
| Effector memory CD8+ T cells |
| CD4+ TEMRA |
| Classical monocytes |
| Non-classical monocytes |
| HLA-DRlow monocytes |

TABLE 3

| Exemplary cell types used in RNAseq cell deconvolution signatures |
| --- |
| Naive CD4+ T cells |
| Naive CD8+ T cells |
| Naive B cells |
| Non-switched Memory IgM B cells |
| Class-switched memory B cells |
| Central memory CD4+ T cells |
| CD4+ Tregs |
| Transitional memory CD4+ T cells |
| Central memory CD4+ T cells |
| All memory CD4+ T cells |
| CD4+ T cells |
| CD4+ T cells |
| Eosinophils |
| Basophils |
| Plasmacytoid dendritic cells |
| Dendritic cells |
| PD1high CD8+ T cells |
| Transitional memory CD8+ T cells |
| Cytotoxic NK cells |
| Regulatory NK cells |
| All memory CD8+ T cells |
| CD8+ T cells |
| CD8+ TEMRA |
| Effector memory CD8+ T cells |
| Neutrophils |
| Granulocytes |
| Classical monocytes |
| Non-classical monocytes |

TABLE 4

| Exemplary cell types used to produce Leukocyte Signature |
| --- |
| Naive CD4+ T cells |
| Naive CD8+ T cells |
| Naive B cells |
| Non-switched Memory IgM B cells |
| Class-switched memory B cells |
| Central memory CD4+ T cells |
| CD4+ Tregs |
| Transitional memory CD4+ T cells |

TABLE 4-continued

| Exemplary cell types used to produce Leukocyte Signature |
| --- |
| Central memory CD4+ T cells |
| All memory CD4+ T cells |
| CD4+ T cells |
| Plasmacytoid dendritic cells |
| Dendritic cells |
| PD1high CD8+ T cells |
| Transitional memory CD8+ T cells |
| Cytotoxic NK cells |
| Regulatory NK cells |
| All memory CD8+ T cells |
| CD8+ T cells |
| Effector memory CD4+ T cells |
| CD8+ TEMRA |
| Effector memory CD8+ T cells |
| Classical monocytes |
| Non-classical monocytes |

Subjects

Aspects of this disclosure relate to a biological sample that has been obtained from a subject. In some embodiments, a subject is a mammal (e.g., a human, a mouse, a cat, a dog, a horse, a hamster, a cow, a pig, or other animal). A subject may be a human. The subject may be an adult human (e.g., of 18 years of age or older) or a child (e.g., less than 18 years of age). The human may be or may have been diagnosed with at least one form of cancer.

In some embodiments, a cancer from which a subject suffers is a carcinoma, a sarcoma, a myeloma, a leukemia, a lymphoma, or a mixed type of cancer that comprises more than one of a carcinoma, a sarcoma, a myeloma, a leukemia, and a lymphoma. Carcinoma refers to a malignant neoplasm of epithelial origin or cancer of the internal or external lining of the body. Sarcoma refers to cancer that originates in supportive and connective tissues such as bones, tendons, cartilage, muscle, and fat. Myeloma is cancer that originates in the plasma cells of bone marrow. Leukemias ("liquid cancers" or "blood cancers") are cancers of the bone marrow (the site of blood cell production). Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Non-limiting examples of a mixed type of cancer include adenosquamous carcinoma, mixed mesodermal tumor, carcinosarcoma, and teratocarcinoma. In some embodiments, a subject has a tumor. A tumor may be benign or malignant. In some embodiments, a cancer is any one of the following: skin cancer, lung cancer, breast cancer, prostate cancer, colon cancer, rectal cancer, cervical cancer, and cancer of the uterus. In some embodiments, a cancer is any one of the following: sarcoma, breast cancer, colorectal cancer, pancreatic cancer, non-small cell lung carcinoma (NSCLC), melanoma, or prostate cancer. In some embodiments, the cancer is head and neck squamous cell carcinoma (HNSCC).

In some embodiments, a subject is at risk for developing cancer, e.g., because the subject has one or more genetic risk factors, or has been exposed to or is being exposed to one or more carcinogens (e.g., cigarette smoke, or chewing tobacco).

Biological Samples

Any of the methods, systems, or other claimed elements may use or be used to analyze a biological sample from a subject. In some embodiments, a biological sample is obtained from a subject having, suspected of having cancer, or at risk of having cancer. In some embodiments, a biological sample comprises a bodily fluid (e.g., blood, urine or cerebrospinal fluid) and/or a tumor.

A sample of a tumor, in some embodiments, refers to a sample comprising cells from a tumor. In some embodiments, the sample of the tumor comprises cells from a benign tumor, e.g., non-cancerous cells. In some embodiments, the sample of the tumor comprises cells from a premalignant tumor, e.g., precancerous cells. In some embodiments, the sample of the tumor comprises cells from a malignant tumor, e.g., cancerous cells.

Examples of tumors include, but are not limited to, adenomas, fibromas, hemangiomas, lipomas, cervical dysplasia, metaplasia of the lung, leukoplakia, carcinoma, sarcoma, germ cell tumors, and blastoma.

A sample of blood, in some embodiments, refers to a sample comprising cells, e.g., cells from a blood sample. In some embodiments, the sample of blood comprises non-cancerous cells. In some embodiments, the sample of blood comprises precancerous cells. In some embodiments, the sample of blood comprises cancerous cells. In some embodiments, the sample of blood comprises blood cells. In some embodiments, the sample of blood comprises red blood cells. In some embodiments, the sample of blood comprises or consists of white blood cells, "WBC", or peripheral blood mononuclear cells, "PBMC". In some embodiments, the sample of blood comprises platelets. Examples of cancerous blood cells include, but are not limited to, leukemia, lymphoma, and myeloma. In some embodiments, a sample of blood is collected to obtain the cell-free nucleic acid (e.g., cell-free DNA, cell-free RNA, etc.) in the blood.

A sample of blood may be a sample of whole blood or a sample of fractionated blood. In some embodiments, the sample of blood comprises whole blood. In some embodiments, the whole blood sample comprises anti-coagulation agents. In some embodiments, the sample of blood comprises fractionated blood. In some embodiments, the sample of blood comprises buffy coat. In some embodiments, the sample of blood comprises serum. In some embodiments, the sample of blood comprises plasma. In some embodiments, the sample of blood comprises a blood clot.

A sample of a tissue, in some embodiments, refers to a sample comprising cells from a tissue. In some embodiments, the sample of the tumor comprises non-cancerous cells from a tissue. In some embodiments, the sample of the tumor comprises precancerous cells from a tissue.

Any of the biological samples described herein may be obtained from the subject using any known technique. See, for example, the following publications on collecting, processing, and storing biological samples, each of which are incorporated by reference herein in its entirety: Biospecimens and biorepositories: from afterthought to science by Vaught et al. (Cancer Epidemiol Biomarkers Prev. 2012 February; 21(2):253-5), and Biological sample collection, processing, storage and information management by Vaught and Henderson (IARC Sci Publ. 2011; (163):23-42).

Any of the biological samples from a subject described herein may be stored using any method that preserves stability of the biological sample. In some embodiments, preserving the stability of the biological sample means inhibiting components (e.g., DNA, RNA, protein, or tissue structure or morphology) of the biological sample from degrading until they are measured so that when measured, the measurements represent the state of the sample at the time of obtaining it from the subject. In some embodiments, a biological sample is stored in a composition that is able to penetrate the same and protect components (e.g., DNA, RNA, protein, or tissue structure or morphology) of the biological sample from degrading. As used herein, degradation is the transformation of a component from one from to another such that the first form is no longer detected at the same level as before degradation.

In some embodiments, the biological sample is stored using cryopreservation. Non-limiting examples of cryopreservation include, but are not limited to, step-down freezing, blast freezing, direct plunge freezing, snap freezing, slow freezing using a programmable freezer, and vitrification. In some embodiments, the biological sample is stored using lyophilization. In some embodiments, a biological sample is placed into a container that already contains a preservant (e.g., RNALater to preserve RNA) and then frozen (e.g., by snap-freezing), after the collection of the biological sample from the subject. In some embodiments, such storage in frozen state is done immediately after collection of the biological sample. In some embodiments, a biological sample may be kept at either room temperature or 4° C. for some time (e.g., up to an hour, up to 8 h, or up to 1 day, or a few days) in a preservant or in a buffer without a preservant, before being frozen.

Non-limiting examples of preservants include formalin solutions, formaldehyde solutions, RNALater or other equivalent solutions, TriZol or other equivalent solutions, DNA/RNA Shield or equivalent solutions, EDTA (e.g., Buffer AE (10 mM Tris·Cl; 0.5 mM EDTA, pH 9.0)) and other coagulants, and Acids Citrate Dextronse (e.g., for blood specimens). In some embodiments, special containers may be used for collecting and/or storing a biological sample. For example, a vacutainer may be used to store blood. In some embodiments, a vacutainer may comprise a preservant (e.g., a coagulant, or an anticoagulant). In some embodiments, a container in which a biological sample is preserved may be contained in a secondary container, for the purpose of better preservation, or for the purpose of avoid contamination.

Any of the biological samples from a subject described herein may be stored under any condition that preserves stability of the biological sample. In some embodiments, the biological sample is stored at a temperature that preserves stability of the biological sample. In some embodiments, the sample is stored at room temperature (e.g., 25° C.). In some embodiments, the sample is stored under refrigeration (e.g., 4° C.). In some embodiments, the sample is stored under freezing conditions (e.g., −20° C.). In some embodiments, the sample is stored under ultralow temperature conditions (e.g., −50° C. to −800° C.). In some embodiments, the sample is stored under liquid nitrogen (e.g., −1700° C.). In some embodiments, a biological sample is stored at −60° C. to −80° C. (e.g., −70° C.) for up to 5 years (e.g., up to 1 month, up to 2 months, up to 3 months, up to 4 months, up to 5 months, up to 6 months, up to 7 months, up to 8 months, up to 9 months, up to 10 months, up to 11 months, up to 1 year, up to 2 years, up to 3 years, up to 4 years, or up to 5 years). In some embodiments, a biological sample is stored as described by any of the methods described herein for up to 20 years (e.g., up to 5 years, up to 10 years, up to 15 years, or up to 20 years).

Methods of the present disclosure encompass obtaining one or more biological samples from a subject for analysis. In some embodiments, one biological sample is collected from a subject for analysis. In some embodiments, more than one (e.g., 2, 3, 4, 5, 6, 7, 8, 9, 10, 11, 12, 13, 14, 15, 16, 17, 18, 19, 20, or more) biological samples are collected from a subject for analysis. In some embodiments, one biological sample from a subject will be analyzed. In some embodiments, more than one (e.g., 2, 3, 4, 5, 6, 7, 8, 9, 10, 11, 12, 13, 14, 15, 16, 17, 18, 19, 20, or more) biological samples may be analyzed. If more than one biological sample from a subject is analyzed, the biological samples may be procured at the same time (e.g., more than one biological sample may be taken in the same procedure), or the biological samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure).

A second or subsequent biological sample may be taken or obtained from the subject after one or more treatments and may be taken from the same region or a different region. As a non-limiting example, the second or subsequent biological sample may be useful in determining whether the cancer in each biological sample has different characteristics (e.g., in the case of biological samples taken from two physically separate tumors in a patient) or whether the cancer has responded to one or more treatments (e.g., in the case of two or more biological samples from the same tumor or different tumors prior to and subsequent to a treatment). In some embodiments, each of the at least one biological sample is a bodily fluid sample, a cell sample, or a tissue biopsy sample.

Flow Cytometry

Aspects of the disclosure relate to processing cytometry data to produce cell composition percentages. In some embodiments, the cytometry data may include flow cytometry data. In some embodiments, a flow cytometry platform may be used to perform flow cytometry investigation of a fluid (e.g., blood) sample. The fluid sample may include target particles with particular particle attributes. The flow cytometry investigation of the fluid sample may provide a flow cytometry result for the fluid sample.

In some embodiments, the fluid sample may be exposed to a stain or dye that provides response radiation when exposed to investigation excitation radiation that may be measured by the radiation detection system of the flow cytometry platform. In some embodiments, a multiplicity of photodetectors is included in the flow cytometry platform. When a particle passes through the laser beam, time correlated pulses on forward scatter (FSC) and side scatter (SSC) detectors, and possibly also fluorescent emission detectors will occur. This may be considered an "event," and for each event the magnitude of the detector output for each detector, FSC, SSC and fluorescence detectors is stored. The data obtained comprise the signals measured for each of the light scatter parameters and the fluorescence emissions.

Flow cytometry platforms may further comprise components for storing the detector outputs and analyzing the data. For example, data storage and analysis may be carried out using a computer connected to the detection electronics. For example, the data can be stored logically in tabular form, where each row corresponds to data for one particle (or one event), and the columns correspond to each of the measured parameters. The use of standard file formats, such as an "FCS" file format, for storing data from a flow cytometer facilitates analyzing data using separate programs and/or machines. In some embodiments, the data may be displayed in 2-dimensional (2D) plots for case of visualization, but other methods may be used to visualize multidimensional data.

In some embodiments, the parameters measured using a flow cytometer may include FSC, which refers to the excitation light that is scattered by the particle along a generally forward direction, SSC, which refers to the excitation light that is scattered by the particle in a generally sideways direction, and the light emitted from fluorescent molecules in one or more channels (frequency bands) of the spectrum, referred to as FL1, FL2, etc., or by the name of the fluorescent dye that emits primarily in that channel.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated by reference herein. Fluorescence imaging microscopy is described in, for example, Pawley (ed.), Handbook of Biological Confocal Microscopy, 2nd Edition, Plenum Press (1989), incorporated by reference herein.

In some embodiments, the cytometry data includes cytometry measurements obtained during respective cytometry events. As described herein, a cytometry event corresponds to an object (e.g., a cell, debris, a bead, a doublet, or an undefined object) being measured by a cytometry platform (e.g., a flow cytometry platform or a mass cytometry platform). In some embodiments, the cytometry events include a subset of events corresponding to cells in the biological sample being measured by the cytometry platform. For example, the subset of events may include one, some, or all of the cytometry events. The number of cells measured using the cytometry platform may include any suitable number of cells, as aspects of the technology described herein are not limited in this respect. For example, the number of cells measured by the cytometry platform may include at least 5,000 cells, at least 10,000 cells, at least 20,000 cells, at least 50,000 cells, at least 100,000 cells, at least 500,000 cells, at least 600,000 cells, at least 900,000 cells, between 500 cells and 1 million cells, between 5,000 cells and 900,000 cells, or between 20,000 cells and 700,000 cells. In some embodiments, flow cytometry is performed using the panel of antibodies described in Table 12.

Mass Cytometry

Aspects of the disclosure relate to processing cytometry data to produce cell composition percentages. In some embodiments, the cytometry data may include mass cytometry data. In some embodiments, a mass cytometry platform may be used to perform mass cytometry investigation of a fluid (e.g., blood) sample. The fluid sample may include target particles with particular particle attributes. The mass cytometry investigation of the fluid sample may provide a mass cytometry result for the fluid sample.

In some embodiments, the fluid sample may be exposed to target-specific antibodies labeled with metal isotopes. In some embodiments, elemental mass spectrometry (e.g., inductively coupled plasma mass spectrometry (ICP-MS) and time of flight mass spectrometry (TOF-MS)) is used to detect the conjugated antibodies. For example, elemental mass spectrometry can discriminate isotopes of different atomic weights and measure electrical signals for isotopes associated with each particle or cell. Data obtained for a single cell or particle is considered an "event." In some embodiments, mass cytometry is also referred to as "cytometry by time of flight" or "CyTOF". CyTOF techniques are described, for example in Shiskova et al. "Deep immune profiling by mass cytometry revealed an association between the state of immune system before treatment and response to checkpoint inhibitor therapy in clear cell renal cell carcinoma", *Cancer Res* (2022) 82 (12_Supplement): 2061.

Mass cytometry platforms may further comprise components for storing the detector outputs and analyzing the data. For example, data storage and analysis may be carried out using a computer connected to the detection elements. The use of standard file formats, such as an "FCS" file format, for storing data from a mass cytometry platform facilitates analyzing data using separate programs and/or machines.

Mass cytometry platforms are commercially available from, for example, Fluidigm (San Francisco, CA). Mass cytometry is described in, for example, Bendall et al., A deep profiler's guide to cytometry, *Trends in Immunology,* 33(7), 323-332 (2012) and Spitzer et al., Mass Cytometry: Single Cells, Many Features, *Cell,* 165(4), 780-791 (2016), both of which are incorporated by reference herein in their entirety.

In some embodiments, the cytometry data includes cytometry measurements obtained during respective cytometry events. As described herein, a cytometry event corresponds to an object (e.g., a cell, debris, a bead, a doublet, or an undefined object) being measured by a cytometry platform (e.g., a flow cytometry platform or a mass cytometry platform). In some embodiments, the cytometry events include a subset of events corresponding to cells in the biological sample being measured by the cytometry platform. For example, the subset of events may include one, some, or all of the cytometry events. The number of cells measured using the cytometry platform may include any suitable number of cells, as aspects of the technology described herein are not limited in this respect. For example, the number of cells measured by the cytometry platform may include at least 5,000 cells, at least 10,000 cells, at least 20,000 cells, at least 50,000 cells, at least 100,000 cells, at least 500,000 cells, at least 600,000 cells, at least 900,000 cells, between 500 cells and 1 million cells, between 5,000 cells and 900,000 cells, or between 20,000 cells and 700,000 cells.

RNA Expression Data

Aspects of the disclosure relate to methods of determining a leukocyte immunoprofile type of a subject using sequencing data or RNA expression data obtained from a biological sample from the subject. The RNA expression data used in methods described herein typically is derived from sequencing data obtained from the biological sample.

The sequencing data may be obtained from the biological sample using any suitable sequencing technique and/or apparatus. In some embodiments, the sequencing apparatus used to sequence the biological sample may be selected from any suitable sequencing apparatus known in the art including, but not limited to, Illumina™, SOLid™, Ion Torrent™, PacBio™, a nanopore-based sequencing apparatus, a Sanger sequencing apparatus, or a 454™ sequencing apparatus. In some embodiments, sequencing apparatus used to sequence the biological sample is an Illumina sequencing (e.g., NovaSeq™, NextSeq™, HiSeq™, MiSeq™, or MiniSeq™) apparatus.

After the sequencing data is obtained, it is processed in order to obtain the RNA expression data. RNA expression data may be acquired using any method known in the art including, but not limited to whole transcriptome sequencing, whole exome sequencing, total RNA sequencing, mRNA sequencing, targeted RNA sequencing, RNA exome capture sequencing, next generation sequencing, and/or deep RNA sequencing. In some embodiments, RNA expression data may be obtained using a microarray assay.

In some embodiments, the sequencing data is processed to produce RNA expression data. In some embodiments, RNA sequence data is processed by one or more bioinformatics methods or software tools, for example RNA sequence quantification tools (e.g., Kallisto) and genome annotation tools (e.g., Gencode v23), in order to produce expression data. The Kallisto software is described in Nicolas L Bray, Harold Pimentel, Pall Melsted and Lior Pachter, Near-optimal probabilistic RNA-seq quantification, Nature Bio-technology 34, 525-527 (2016), doi:10.1038/nbt.3519, which is incorporated by reference in its entirety herein.

In some embodiments, microarray expression data is processed using a bioinformatics R package, such as "affy" or "limma," in order to produce expression data. The "affy" software is described in Bioinformatics. 2004 Feb. 12; 20(3):307-15. Doi: 10.1093/bioinformatics/btg405. "affy-analysis of Affymetrix GeneChip data at the probe level" by Laurent Gautier 1, Leslie Cope, Benjamin M Bolstad, Rafael A Irizarry PMID: 14960456 DOI: 10.1093/bioinformatics/btg405, which is incorporated by reference herein in its entirety. The "limma" software is described in Ritchie M E, Phipson B, Wu D, Hu Y, Law C W, Shi W, Smyth G K "limma powers differential expression analyses for RNA-sequencing and microarray studies." Nucleic Acids Res. 2015 Apr. 20; 43(7):e47. 20. Doi.org/10.1093/nar/gkv007PMID: 25605792, PMCID: PMC4402510, which is incorporated by reference herein in its entirety.

In some embodiments, sequencing data and/or expression data comprises more than 5 kilobases (kb). In some embodiments, the size of the obtained RNA data is at least 10 kb. In some embodiments, the size of the obtained RNA sequencing data is at least 100 kb. In some embodiments, the size of the obtained RNA sequencing data is at least 500 kb. In some embodiments, the size of the obtained RNA sequencing data is at least 1 megabase (Mb). In some embodiments, the size of the obtained RNA sequencing data is at least 10 Mb. In some embodiments, the size of the obtained RNA sequencing data is at least 100 Mb. In some embodiments, the size of the obtained RNA sequencing data is at least 500 Mb. In some embodiments, the size of the obtained RNA sequencing data is at least 1 gigabase (Gb). In some embodiments, the size of the obtained RNA sequencing data is at least 10 Gb. In some embodiments, the size of the obtained RNA sequencing data is at least 100 Gb. In some embodiments, the size of the obtained RNA sequencing data is at least 500 Gb.

In some embodiments, the expression data is acquired through bulk RNA sequencing. Bulk RNA sequencing may include obtaining expression levels for each gene across RNA extracted from a large population of input cells (e.g., a mixture of different cell types.) In some embodiments, the expression data is acquired through single cell sequencing (e.g., scRNA-seq). Single cell sequencing may include sequencing individual cells.

In some embodiments, bulk sequencing data comprises at least 1 million reads, at least 5 million reads, at least 10 million reads, at least 20 million reads, at least 50 million reads, or at least 100 million reads. In some embodiments, bulk sequencing data comprises between 1 million reads and 5 million reads, 3 million reads and 10 million reads, 5 million reads and 20 million reads, 10 million reads and 50 million reads, 30 million reads and 100 million reads, or 1 million reads and 100 million reads (or any number of reads including, and between).

In some embodiments, the expression data comprises next-generation sequencing (NGS) data. In some embodiments, the expression data comprises microarray data.

Expression data (e.g., indicating RNA expression levels) for a plurality of genes may be used for any of the methods or compositions described herein. The number of genes which may be examined may be up to and inclusive of all the genes of the subject. In some embodiments, expression levels may be determined for all of the genes of a subject. As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 35 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein.

In some embodiments, RNA expression data is obtained by accessing the RNA expression data from at least one computer storage medium on which the RNA expression data is stored. Additionally, or alternatively, in some embodiments, RNA expression data may be received from one or more sources via a communication network of any suitable type. For example, in some embodiment, the RNA expression data may be received from a server (e.g., a SFTP server, or Illumina BaseSpace).

The RNA expression data obtained may be in any suitable format, as aspects of the technology described herein are not limited in this respect. For example, in some embodiments, the RNA expression data may be obtained in a text-based file (e.g., in a FASTQ, FASTA, BAM, or SAM format). In some embodiments, a file in which sequencing data is stored may contains quality scores of the sequencing data. In some embodiments, a file in which sequencing data is stored may contain sequence identifier information.

Expression data, in some embodiments, includes gene expression levels. Gene expression levels may be detected by detecting a product of gene expression such as mRNA and/or protein. In some embodiments, gene expression levels are determined by detecting a level of a mRNA in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

In some embodiments, sequencing data is obtained from a biological sample obtained from a subject. The sequencing data is obtained by any suitable method, for example, using any of the methods described herein including in the Section titled "Biological Samples." In some embodiments, the sequencing data comprises RNA-seq data. In some embodiments, the biological sample comprises blood or tissue. In some embodiments, the biological sample comprises one or more tumor cells and/or one or more immune cells (e.g., PBMC).

In some embodiments, the sequencing data that has been obtained is normalized to transcripts per kilobase million (TPM) units. The normalization may be performed using any suitable software and in any suitable way. For example, in some embodiments, TPM normalization may be performed according to the techniques described in Wagner et al. (Theory Biosci. (2012) 131:281-285), which is incorporated by reference herein in its entirety. In some embodiments, the TPM normalization may be performed using a software package, such as, for example, the germa package.

Aspects of the germa package are described in Wu J, Gentry RIwcfJMJ (2021). "germa: Background Adjustment Using Sequence Information. R package version 2.66.0," which is incorporated by reference in its entirety herein. In some embodiments, RNA expression level in TPM units for a particular gene may be calculated according to the following formula:

$$A \cdot \frac{1}{\sum (A)} \cdot 10^6$$

$$\text{Where } A = \frac{\text{total reads mapped to gene} \cdot 10^3}{\text{gene length in } bp}$$

In some embodiments, the RNA expression levels normalized to TPM units may be log transformed. In some embodiments, the RNA expression levels may not be normalized to transcripts per million units and may, instead, be converted to another type of unit (e.g., reads per kilobase million (RPKM) or fragments per kilobase million (FPKM) or any other suitable unit). Additionally, or alternatively, in some embodiments, the log transformation may be omitted. Instead, no transformation may be applied in some embodiments, or one or more other transformations may be applied in lieu of the log transformation.

In some embodiments, RNA expression data can include the sequence data generated by a sequencing protocol (e.g., the series of nucleotides in a nucleic acid molecule identified by next-generation sequencing, sanger sequencing, etc.) as well as information contained therein (e.g., information indicative of source, tissue type, populations of cell types, etc.) which may also be considered information that can be inferred or determined from the sequence data. In some embodiments, expression data can include information included in a FASTA file, a description and/or quality scores included in a FASTQ file, an aligned position included in a BAM file, and/or any other suitable information obtained from any suitable file.

Techniques for Associating Leukocyte Signatures to Leukocyte Immunoprofile Types As discussed herein, a subject may be determined to have a particular leukocyte immunoprofile type. To this end, a leukocyte signature for a subject may be determined (e.g., using cytometry (e.g., flow cytometry) or RNA sequencing) and the leukocyte signature for the subject may be associated with one particular leukocyte signature cluster in a set of leukocyte signature clusters (each corresponding to a respective leukocyte immunoprofile type (e.g., Naïve, Primed, Progressive, Chronic or Suppressive)). The leukocyte signature for the subject may be associated with one of the signature clusters in the set in a variety of ways.

For example, in some embodiments, a leukocyte signature of a subject may be associated with a particular one of the plurality of leukocyte signature clusters by using a distance-based comparison or any other suitable metric and, based on the result of the comparison, the leukocyte signature may be associated with the closest leukocyte signature cluster (when a distance-based comparison is performed, or the "closest" in the sense of whatever metric or measure of distance is used). An example of this is described herein including with reference to FIG. 4.

For example, in some embodiments, a leukocyte signature of a subject may be associated with a particular one of the plurality of leukocyte signature clusters by using a trained classifier. The trained classifier may be a multi-class classifier. The trained classifier may process the leukocyte signature to obtain an output indicative of the particular one of the plurality of leukocyte signature clusters. To this end, the leukocyte signature may be provided as input (optionally, suitable pre-processing, for example, normalization) to the trained classifier to obtain an output indicative of the particular one of the plurality of leukocyte signature clusters. For example, the output may indicate a numeric value (e.g., a score, a likelihood, and/or a probability) for each of the signature clusters and the numeric values may be used to select a signature cluster with which to associate the leukocyte signature of the subject (e.g., selecting the cluster with the largest value (e.g., when the numeric value is a probability) or with the smallest score (e.g., when the score is a log-likelihood)).

For example, in some embodiments, the leukocyte signature may include cell percentages for a number of cell populations (e.g., a respective cell percentage for each of at least some (e.g., all) cell populations listed in Table 1, Table 2, Table 3, and/or Table 4). The cell percentages in the leukocyte signature may be normalized prior to being provided as input features into the trained classifier to produce an output for selecting a signature cluster with which to associate the leukocyte signature. For example, the cell percentages may be renormalized as percentages from PBMC fraction for PBMC populations or as percentages from WBC fraction for granulocyte populations. Additionally, or alternatively, the cell percentages may be recalculated as min-max normalization only with 2 and 98 percentiles of the cohort used to create the signature clusters (e.g., out of 850 samples). Accordingly, in some embodiments, input to the trained classifier may be a one-dimensional vector of normalized cell percentages (e.g., a 30×1 or 34×1 vector of numbers within the range of [0,1]) and the output may be a probability (or other numeric value indicating likelihood) of being assigned to each of the five leukocyte signature clusters (the clusters corresponding to respective immunoprofile types) and, as such, may be a 5×1 vector of numbers within range [0,1] that will sum to 1. In this example, the signature cluster with the highest of the five predicted probabilities may be the signature cluster to which the subject's leukocyte signature is assigned. As a specific non-limiting example, if the output of the trained classifier (for an input of normalized cell percentages for a subject) is [0.8, 0.1, 0.07, 0.0, 0.03], then the leukocyte signature for the subject may be assigned to the first cluster (e.g., "Naïve" or "G1" signature cluster).

Any of numerous types of classifiers may be used to associate the leukocyte signature of a subject with a particular one of the plurality of leukocyte signature clusters. For example a k-nearest neighbors (KNN) classifier, a decision tree classifier, a gradient boosted decision tree classifier, a Bayesian classifier, or a neural network classifier may be used.

As one example, a neural network classifier may be used. For example, in some embodiments, a tabular prior-data fitted network transformer (TabPFN) classifier may be used. For example, a TabPFN classifier may be used that has the architecture described in and is trained using method described in, for example, in N. Hollmann, S. Muller, K. Eggensperger, and F. Hutter, "TABPFN: A transformer that solves small tabular classification problems in a second", The Eleventh International Conference on Learning Representations (ICLR) 2023, which is incorporated by reference herein in its entirety. As one example, the TabPFN classifier may be trained for a cohort with N (e.g., 850) samples with cluster labels and M (e.g., 34) normalized cell population percentages using leave-one-out cross-validation, by taking N−1 samples end evaluating the correctness of prediction on the one that was left and repeating this process N (e.g., 850) times to estimate the error.

As another example, a decision tree classifier may be used. Any suitable type of decision tree classifier may be used and may be trained using any suitable supervised decision tree learning technique. For example, the decision tree classifier may be trained by the iterative dichotomiser technique (e.g., the ID3 algorithm as described, for example, in Quinlan, J. R. 1986. Induction of Decision Trees. Mach. Learn. 1, 1 (March 1986), 81-106)), the C4.5 technique (e.g., as described, for example, in Quinlan, J. R. C4.5: Programs for Machine Learning. Morgan Kaufmann Publishers, 1993), the classification and regression tree (CART) technique (e.g., as described, for example, in Breiman, Leo; Friedman, J. H.; Olshen, R. A.; Stone, C. J. (1984). Classification and regression trees. Monterey, CA: Wadsworth & Brooks/Cole Advanced Books & Software). It should be appreciated that a decision tree classifier may be trained using any other suitable training method, as aspects of the technology described herein are not limited in this respect.

As another example, a gradient-boosted decision tree classifier may be used. The gradient-boosted decision tree classifier may be an ensemble of multiple decision tree classifiers (sometimes called "weak learners"). The prediction (e.g., classification) generated by the gradient-boosted decision tree classifier is formed based on the predictions generated by the multiple decision trees part of the ensemble. The ensemble may be trained using an iterative optimization technique involving calculation of gradients of a loss function (hence the name "gradient" boosting). Any suitable supervised training algorithm may be applied to 30 training a gradient-boosted decision tree classifier including, for example, any of the algorithms described in Hastie, T.; Tibshirani, R.; Friedman, J. H. (2009). "10. Boosting and Additive Trees". The Elements of Statistical Learning (2nd ed.). New York: Springer. pp. 337-384. In some embodiments, the gradient-boosted decision tree classifier may be implemented using any suitable publicly-available gradient boosting framework such as XGBoost (e.g., as described, for example, in Chen, T., & Guestrin, C. (2016). XGBoost: A Scalable Tree Boosting System. In Proceedings of the 22nd ACM SIGKDD International Conference on Knowledge Discovery and Data Mining (pp. 785-794). New York, NY, USA: ACM). The XGBoost software may be obtained from xgboost.ai, for example). Another example framework that may be employed is LightGBM (e.g., as described, for example, in Kc, G., Meng, Q., Finley, T., Wang, T., Chen, W., Ma, W., . . . . Liu, T.-Y. (2017). Lightgbm: A highly efficient gradient boosting decision tree. Advances in Neural Information Processing Systems, 30, 3146-3154). The LightGBM software may be obtained from lightgbm-.readthedocs.io/, for example).

It should be appreciated that although, in some embodiments, a multi-class classifier may be used, in other embodiments multiple classifiers (e.g., multiple binary classifiers) may be used to associate a leukocyte signature to a cluster. For example, each cluster may be associated with a respective binary classifier trained to generate a numeric score that the leukocyte signature belongs to that cluster. Then outputs from the multiple classifiers could be compared to identify the signature cluster with which to associate the leukocyte signature for a subject. Yet another approach to associating the leukocyte signature for a subject with a signature cluster involves determining, for each particular one of the plurality of leukocyte signature clusters, a score indicating whether the leukocyte signature of the subject is associated with that particular cluster, wherein determining the score for a particular cluster comprises applying a linear regression model associated with the particular cluster, to the cell composition percentages in the leukocyte signature. The linear regression model may be trained using regularization and, for example, may be model whose coefficients are determined using Elastic Net linear regression.

Cell Composition Percentages and Applications

Aspects of the disclosure relate to generating leukocyte signature for a subject by processing cytometry data and/or RNA expression data to obtain cell composition percentages. As used herein, a "cell composition percentage" refers to the percentage of a particular cell type in a plurality of cells. For example, if 100 cells of a total cell population of 500 cells are identified as being CD4 T cells, the cell composition percentage of CD4 T cells in the population is 20%.

FIG. 3 is a flowchart of process 300, which may be used to implement act 108 (and is therefore an example implementation of act 108) for determining cell composition percentages using cytometry data. Process 300 may be performed in part or in full by a laptop computer, a desktop computer, one or more servers, in a cloud computing environment, computing device as described herein with respect to FIG. 15 or using any other suitable computing device(s), as aspects of the technology described herein are not limited in this respect.

Process 300 begins at act 302 for obtaining cytometry data for a biological sample from a subject, the biological sample including a plurality of cells. In some embodiments, act 302 may be performed in any suitable way as described herein. For example, cytometry (e.g., flow cytometry) may be performed on the biological sample (e.g., using any suitable flow cytometry device or platform) to obtain the cytometry data.

Next, at act 304, a respective type is identified for each of at least some of the plurality of cells based on the cytometry data obtained at act 302. In some embodiments, act 304 may be performed according to the techniques described herein including at least with respect to FIG. 1 for identifying types for cells in a biological sample.

Next, at act 306, a cell count is determined for each of multiple cell types identified at act 304. In some embodiments, this includes determining a number of cells, or cell count, of each type of cell for which cytometry measurements are obtained at act 302. The cell counts, in some embodiments, may be used to determine a number of cells of each type of cell included in at least a hierarchy of cell types. A hierarchy of cell types may indicate relationships between different cell types. For example, the hierarchy of cell types may include parent cell types and cell types that are children, or subtypes, of the parent cell type. In some embodiments, data indicating a hierarchy of cell types is received as input at act 306. Such data may be provided in any suitable format, as aspects of the technology described herein are not limited in this respect.

In some embodiments, data indicating the types identified (at act 304) for each of multiple objects (e.g., cells, debris, beads, unidentified objects, etc.) in the biological sample may also be received at act 306. For example, the input may include a tab-separated values file having a number of lines corresponding to the number of objects. Each of at least some of the lines may include an indication of the type determined for the object. In some embodiments, at least some of the cell types indicated for the objects are included in the hierarchy of cell types. In some embodiments, one or more cell types are not included in the hierarchy of cell types. For example, the identified cell types may include types for "doubles," which are a combination of two different cell types (e.g., "Monocytes & Neutrophils"). As another example, the identified cell types may include one or more custom cell types which one or more of machine learning models were trained to predict (e.g., "Dead Neutrophils").

In some embodiments, a "raw" cell count is determined for each unique cell type listed in the data indicating the types identified for the subsample. For example, this includes determining counts for types that are included in the hierarchy of cell types and types that are not included in the hierarchy of cell types.

In some embodiments, the determined cell counts are then updated to conform with cell types included in the hierarchy of cell types. For example, this may include attributing a cell count determined for an identified cell type that is not included in the hierarchy to a cell type that is included in the hierarchy. For example, a cell count determined for the identified cell type of "Dead Neutrophils," which is not included in the hierarchy, may be attributed to the cell type "Neutrophils," which is included in the hierarchy. For example, the cell count may be added to the cell count for neutrophils. Accordingly, in some embodiments, since the cell count is accounted for by the "Neutrophil" cell type, the cell count for "Dead Neutrophils" may be discarded. In some embodiments, in updating the determined cell counts to conform with cell types included in the hierarchy of cell types, "doubles" may also be split into two different cell types, and cell counts may be updated for the respective cell types accordingly. For example, a count of "Monocytes & Neutrophils") may be split into a count of Monocytes and a count of Neutrophils. Accordingly, in some embodiments, any existing cell counts for Monocytes and Neutrophils may be updated to include said counts. Since the cell counts are accounted for by the "Monocyte" and "Neutrophil" cell type, the cell count for "Monocyte & Neutrophil" may be discarded.

In some embodiments, cell counts for parent cell types in the hierarchy of cell types are determined as a sum of the cell counts of their descendants (e.g., subtypes). For example, a cell that is identified to be a "Classical Monocyte" is also a "Monocyte," since "Classical Monocyte" is a subtype of "Monocyte." Accordingly, in some embodiments, the cell count of a parent cell type in the hierarchy of cell types may be updated based on the cell counts of its descendants. For example, the cell counts of the descendants may be added to an existing cell count for the parent or added from zero, if there is no existing cell count for the parent cell type. In some embodiments, the techniques for updating cell counts of parent cell types may be carried out sequentially from the bottom of the hierarchy of cell types to the top of the hierarchy of cell types.

Next, at act 308, a cell composition percentage is determined for each of at least some of the identified cell types. In some embodiments, determining a cell composition percentage for a particular cell type includes determining a ratio between the number of cells of a particular type and a total number of cells determined for the biological sample. In some embodiments, determining a cell composition percentage for a particular cell type includes determining a ratio between the number of cells of a particular type and a total number of immune cells determined for the biological sample. In some embodiments, determining a cell composition percentage for a particular cell type includes determining, in the biological sample, a percentage of the particular cell type relative to a cell type class associated with the particular cell type. For example, determining the percentage of naïve T cells relative to the total number of T cells identified in the biological sample. For example, the total number of cells may be determined as the number of leukocytes determined for the biological sample.

In some embodiments, the cell composition percentages determined for particular cell types are used to determine cell concentrations of those cell types in the biological sample. For example, the normalized cell composition percentages may be multiplied by a respective coefficient that converts the cell composition percentage to a cell concentration. Aspects of machine learning models are described herein including at least in the section "Cytometry-Based Cellular Deconvolution".

In other embodiments of the methods described herein, RNA expression data is processed using a cell deconvolution technique to generate cell composition percentages for some (or all) of the cell types listed in Table 3. The use of cell deconvolution techniques, for example the BostonGene Kassandra technique, to generate cell composition percentages has been described, for example by International Application No. PCT/US2021/022155, published as International Publication No. WO2021/183917 on Sep. 16, 2021; and International Application No. PCT/US2022/027088, published as International Publication No. WO2022/232615 on Nov. 3, 2022, the entire contents of each of which are incorporated by reference herein. Aspects of machine learning models are described herein including at least in the section "RNA-Based Cellular Deconvolution".

Other cell deconvolution techniques may also be used in methods described by the disclosure, for example Cibersort (e.g., as described by Newman et al. Nature Methods volume 12, pages 453-457 (2015)) or CibersortX (e.g., as described by Newman et al. *Nature Biotechnology* volume 37, pages 773-782 (2019)). In some embodiments, more than one cell deconvolution approach is used and then a consensus from the more than one cell devolution approach is used to determine the cell deconvolution.

Cytometry-Based Cellular Deconvolution

Cytometry data may be processed to identify cell composition percentages using any suitable technique. Any one of a number of techniques may be used for this purpose, as aspects of the technology described herein are not limited in this respect.

For example, in some embodiments, processing the cytometry data to determine cell composition percentages may include plotting the cytometry data in a series of two-dimensional plots and identifying discrete cell populations based on shared marker expression, commonly referred to as "gating". Gating the cytometry data may include manually gating the cytometry data to separate the discrete cell populations. Additionally, or alternatively, gating may be performed using any suitable gating techniques, such as by using FlowJo™ (FlowJo™ Software. Ashland, OR: Beckton, Dickinson and Company; 2021). In some embodiments, the numbers of cells included in the identified cell populations may be used to determine corresponding cell composition percentages.

Additionally, or alternatively, processing the cytometry data to determine cell composition percentages may include clustering the cytometry data to identify discrete populations of cells. In some embodiments, clustering the cytometry data may include calculating two-dimensional t-SNE plots for a sample and calculating FlowSOM for the sample. FlowSOM is described by Van Gassen et al. ("FlowSOM: Using self-organizing maps for visualization and interpretation of cytometry data," in *Journal of Quantitative Cell Science*, vol. 87, no. 7, pp. 636-645, 2015), which is incorporated by reference herein in its entirety. The resulting clusters may correspond to discrete cell populations. In some embodiments, the numbers of cells included in the identified cell populations may be used to determine corresponding cell composition percentages.

Additionally, or alternatively, processing the cytometry data to determine cell composition percentages may include processing the cytometry data using machine learning techniques. For example, the cytometry data may be processed using the machine learning techniques described by International Application No. PCT/US2023/012003, published as International Publication No. WO 2023/147177 on Aug. 3, 2023, which is incorporated by reference herein in its entirety.

For example, the machine learning techniques may include processing cytometry data using one or multiple machine learning models to identify types of cells present in a biological sample. In some embodiments, the multiple machine learning models used to process the cytometry data include a first machine learning model and a second machine learning model different from the first machine learning model. In some embodiments, the first machine learning model is used to process cytometry measurements corresponding to a particular event to determine an event type for the particular event. An "event" corresponds to an object (e.g., a cell, debris, a bead, a doublet, or an unidentified object) in a biological sample being measured by a cytometry platform (e.g., a flow cytometry platform or a mass cytometry platform). For example, an event may correspond to a cell in the biological sample being measured by a cytometry platform, and the measurements obtained during the event may be included in the cytometry data. The determined event type (e.g., predicted by the first machine learning model) indicate whether an event corresponds to a cell being measured by the cytometry platform, debris being measured by the cytometry platform, or a bead being measured by the cytometry platform. For example, the first machine learning model may include a multiclass classifier trained to distinguish between at least some event types. In some embodiments, when the determined event type indicates that the particular event corresponds to the cell being measured by the cytometry platform, the second machine learning model is used to process the cytometry measurements corresponding to the particular event to determine a type of cell for the particular event. For example, the second machine learning model may include a multiclass classifier trained to distinguish between at least some event cell types.

In some embodiments, the machine learning techniques include processing cytometry data for cells (e.g., a type of event) in the biological sample using a hierarchy of machine learning models corresponding to a hierarchy of cell types. A machine learning model in the hierarchy of machine learning models may be trained to predict a particular type for a cell using the cytometry data corresponding to the cell. Additionally, or alternatively, a machine learning model in the hierarchy of machine learning models may include a multiclass classifier trained to distinguish between at least some cell types at a particular level in the hierarchy. Different levels of the hierarchy of machine learning models may be used to predict a type for a cell with different levels of specificity (e.g., a general cell type or a specific subtype). In some embodiments, the cell types determined for cells in the biological sample are then used to determine cell composition percentages for the cell types.

Figure 30:
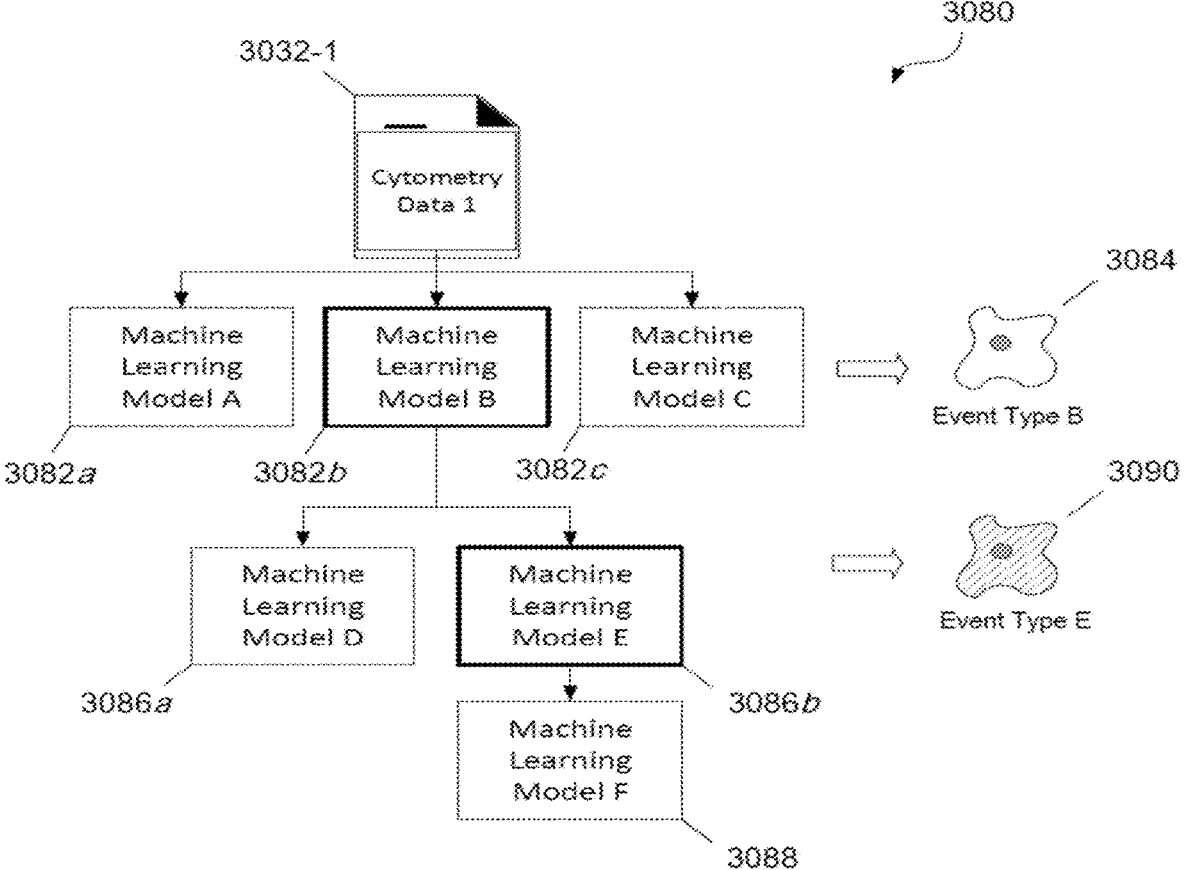
FIG. 30 depicts an illustrative technique for processing cytometry data to determine a respective type for one or more cells, according to some embodiments of the technology described herein.

FIG. 30 depicts an illustrative technique 3080 for processing cytometry data using multiple machine learning models to determine a respective type for one or more events (e.g., cells or particles). In some embodiments, illustrative technique 3080 includes providing first cytometry data 3032-1 for a first event as input to a hierarchy of machine learning models, which is used to determine one or more event types 3084, 3090 for the first event.

The cytometry data processed using illustrative technique 3080 may include cytometry data for each of multiple cells and particles processed using a cytometry platform. For example, the cytometry data includes first cytometry data 3032-1 for a first event. FIG. 30 shows processing the first cytometry data 3032-1 to determine one or more types for the first event. However, it should be appreciated that illustrative technique 3080 can be used to process cytometry data for any suitable number of events, such as second cytometry data for a second event, as aspects of the technology described herein are not limited to processing cytometry data for any particular number of events.

In some embodiments, the technique 3080 includes processing first cytometry data 3032-1 with the hierarchy of machine learning models. FIG. 30 shows an example hierarchy of machine learning models, which includes machine learning models 3082a-c, 3086a-b, 3088.

In some embodiments, a machine learning model may be trained to determine whether the first event is of a particular type, based on the first cytometry data 3032-1. In some embodiments, this may include determining a probability that the first event is of the particular type. For example, the first event may correspond to a cell, and each of at least some (e.g., all) of the machine learning model in the hierarchy may be trained to predict whether a cell is of a particular cell type. The cell type may include any suitable cell type as aspects of the technology described herein are not limited in this respect. For example, the cell type may include any of the cell types listed in Table 1. In the example shown in FIG. 30, Event Type B 3084 and Event Type 3090 may be cell types that are identified for a cell using machine learning models in a hierarchy of machine learning models. Event Type B 3084 and Event Type 3090 may each be any suitable cell type, such as any of the cell types listed in Table 1, for example.

As an example, machine learning model 3082a may be trained to determine whether the first event is of Type A. As another example, machine learning model 3086b may be trained to determine whether the first event is of Type E. Additionally, or alternatively, a machine learning model may include a multiclass classifier trained to determine whether the first event is one of multiple different event types, based on the first cytometry data 3032-1. For example, machine learning model A 3082a may be trained to determine whether the first event is of Type A1, Type A2, or Type A3. For example, the machine learning model may output the most probable type (e.g., of Type A1, Type A2, or Type A3) for the first event. Such a machine learning model may output a type and/or the probability that the event is of the identified type. For example, machine learning model A 3082a may identify that the event is more likely Type A2 than Type A1 or Type A3, along with the probability that the event is Type A2. In some embodiments, the machine learning model may include a decision tree classifier, a gradient boosted decision tree classifier, a neural network, a support vector machine classifier, or any other suitable type of machine learning model, as aspects of the technology described herein are not limited in this respect. In some embodiments, the machine learning model may include an ensemble of machine learning models of any suitable type (the machine learning models part of the ensemble may be termed "weak learners"). For example, the machine learning model may include an ensemble of decision tree classifiers. Aspects of machine learning models are described herein including at least in the section "Machine Learning."

In some embodiments, different levels of the hierarchy of machine learning models may be used to determine event types with different levels of specificity. For example, machine learning models 3082*a-c* may be used to determine that the first event is of Type B 3084, while machine learning models 3086*a-b* may be used to determine that the first event is of Type E 3090, a subtype of Type B 3084.

In some embodiments, outputs of machine learning models 3082*a-c* are used to inform which machine learning model(s) of the hierarchy will subsequently be used to process the first cytometry data 3032-1. For example, the outputs of machine learning models 3082*a-c* may indicate which event type, out of the event types associated with each of the models, is the most probable event type for the first event. As shown in the example, the output of machine learning models 3082*a-c* indicates that the first event is of Type B 3084. Based on the output, the technique 3080 may continue with determining whether the first event is of a subtype of Type B 3084. Therefore, in some embodiments, machine learning models 3086*a-b*, which are trained to determine whether an event is a subtype of Type B 3084, may be used to process the first cytometry data 3032-1.

In some embodiments, a level of the hierarchy of machine learning models may not indicate any type for the first event. For example, the level of the hierarchy including machine learning model 3088 does not indicate a type for the first event. In some embodiments, this may indicate that none of the machine learning models on that level of the hierarchy predicted the first event to be of the particular event type associated with the machine learning model (e.g., for which the machine learning model was trained to determine). For example, machine learning model 3088 predicted that the first event is not of Type F. In some embodiments, if a level of the hierarchy does not indicate an event type, then the event type indicated at the previous level of the hierarchy may be determined to be the type for the first event. For example, Type E 3090 may be determined as the type for the first event. In this case, Type E 3090 represents the most specific type for the first event since Type E 3090 is a subtype of Type B 3084.

In some embodiments, the cell types identified for cells in the biological sample may be used to determine the number of cells of each type in the sample (e.g., cell counts). The cell counts may be used to determine cell composition percentages for different cell types. Example techniques for determining cell composition percentages based on cell counts are described herein including at least with respect to FIG. 3.

RNA-Based Cellular Deconvolution

RNA expression data may be processed to identify cell composition percentages using a suitable cellular deconvolution technique. Any one of a number of cellular deconvolution techniques may be used for this purpose, as aspects of the technology described herein are not limited in this respect. Nonlimiting examples of cellular deconvolution techniques include Kassandra, CIBERSORT, CIBERSORTx, QuanTIseq, FARDEEP, Xcell, ABIS, EPIC, MCP-counter, Scaden, and MuSiC. Kassandra is described in International Application No. PCT/US2021/022155, published as International Publication No. WO2021/183917 on Sep. 16, 2021; and International Application No. PCT/US2022/027088, published as International Publication No. WO2022/232615 on Nov. 3, 2022, the entire contents of each of which are incorporated by reference herein. CIBERSORTx is described by Newman et al. ("Robust enumeration of cell subsets from tissue expression profiles." *Nat. Methods* 12, 453-457 (2015)), which is incorporated by reference herein in its entirety. CIBERSORTx is described by Newman, A., et al. ("Determining cell type abundance and expression from bulk tissues with digital cytometry." *Nature biotechnology* 37.7 (2019): 773-782), which is incorporated by reference herein in its entirety. QuanTIseq is described by Finotello, F., et al. ("Molecular and pharmacological modulators of the tumor immune contexture revealed by deconvolution of RNA-seq data." *Genome medicine* 11.1 (2019): 1-20), which is incorporated by reference herein in its entirety. FARDEEP is described by Hao, Yuning, et al. ("Fast and robust deconvolution of tumor infiltrating lymphocyte from expression profiles using least trimmed squares." *PLoS computational biology* 15.5 (2019): e1006976), which is incorporated by reference herein in its entirety. Xcell is described by Aran, D., et al. ("xCell: digitally portraying the tissue cellular heterogeneity landscape." *Genome biology* 18 (2017): 1-14), which is incorporated by reference herein in its entirety. Abis is described by Monaco, G, et al. ("RNA-Seq signatures normalized by mRNA abundance allow absolute deconvolution of human immune cell types." *Cell reports* 26.6 (2019): 1627-1640), which is incorporated by reference herein in its entirety. EPIC is described by Racle, J. and Gfeller, D. ("EPIC: a tool to estimate the proportions of different cell types from bulk gene expression data." *Bioinformatics for Cancer Immunotherapy: Methods and Protocols* (2020): 233-248), which is incorporated by reference herein in its entirety. MCP-counter is described by Becht, E., et al. ("Estimating the population abundance of tissue-infiltrating immune and stromal cell populations using gene expression." *Genome biology* 17.1 (2016): 1-20), which is incorporated by reference herein in its entirety. Menden, K., et al. ("Deep learning-based cell composition analysis from tissue expression profiles." *Science advances* 6.30 (2020): caba2619), which is incorporated by reference herein in its entirety. MuSiC is described by Wang, X., et al. ("Bulk tissue cell type deconvolution with multi-subject single-cell expression reference." Nature communications 10.1 (2019): 380), which is incorporated by reference herein in its entirety.

In some embodiments, the RNA expression data is processed using the Kassandra cellular deconvolution techniques to identify the cell composition percentages. The Kassandra deconvolution techniques include, in some embodiments, processing RNA expression data using one or more machine learning models to determine cell composition percentages for one or more cell types. For example, determining a cell composition percentage for a particular cell type may include obtaining RNA expression data for a set of genes associated with the cell type (e.g., such as one or more marker genes, which may be specific or semi-specific genes for the particular cell type), and processing the RNA expression data with at least one machine learning model to determine the cell composition percentage for the particular cell type. According to some embodiments, this process may be repeated or performed in parallel for each of multiple cell types in order to achieve deconvolution across the multiple cell types.

Figure 29A:
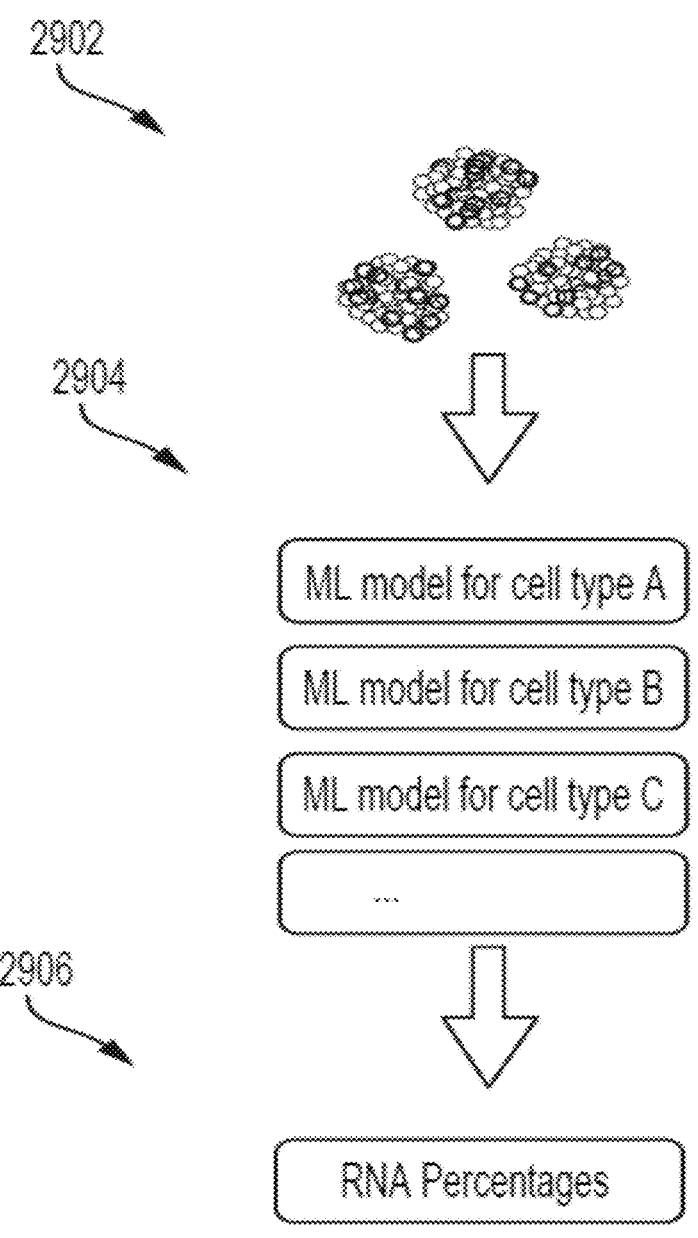
FIG. 29A is a diagram depicting an example technique for determining RNA percentages based on RNA expression data, according to some embodiments of the technology described herein.

In some embodiments, determining a cell composition percentage for a particular cell type using the Kassandra deconvolution technique includes estimating an RNA percentage for the particular cell type, and using the estimated RNA percentage to determine the cell composition percentage. For example, estimating the RNA percentage may include processing the RNA expression data obtained for the cell type using at least one machine learning model trained to predict the RNA percentage for the cell type. FIG. 29A is a diagram depicting an illustrative example of using machine learning techniques for determining RNA percentages based on RNA expression data. In the example, RNA expression data from biological samples 2902 is processed using one or more machine learning models to obtain RNA percentages 2906 for cell type A, cell type B, and cell type C. While three cell types are shown in the example of FIG. 29A, the techniques may be applied to determine RNA percentages for any suitable number of cell types, as aspects of the technology described herein are not limited in this respect. Additionally, the cell types may be any suitable cell type such as, for example, any of the cell types listed in Table 18 and/or any of the cell types listed in International Publication No. WO2021/183917.

In the example shown in FIG. 29A, RNA expression data is obtained for the biological sample 2902. The RNA expression data may be obtained using any suitable techniques such as those described herein.

Regardless of how the RNA expression data is obtained from biological sample 2902, the RNA expression data may be processed using machine learning model(s) 2904. The machine learning model(s) 2904 may include any suitable machine learning model(s) such as, for example, a non-linear regression model (e.g., a logistic regression model), a neural network model, a support vector machine, a Gaussian mixture model, a random forest model, a decision tree model, or any other suitable type of machine learning model, as aspects of the technology described herein are not limited in this respect. For example, the machine learning model(s) 2904 may be non-linear regression model(s). The non-linear regression model(s) may be implemented using a gradient boosting technique (e.g., as implemented in XGBoost). Aspects of machine learning models are described herein including at least in the section "Machine Learning."

In some embodiments, the machine learning model(s) 2904 may comprise a separate machine learning model for each of multiple cell types. In the example shown in FIG. 29A, the machine learning models 2904 include a machine learning model for cell type A, a machine learning model for cell type B, and a machine learning model for cell type C. As shown, additional machine learning models for one or more additional cell types and/or subtypes may be provided, in some embodiments. For example, one or more machine learning models may be provided for one or more cell types listed in Table 18 and/or any of the cell types listed in International Publication No. WO2021/183917.

In some embodiments, the input to each of the machine learning models 2904 may comprise a select subset of the RNA expression data 2902. For example, the input to a machine learning model for a particular cell type may comprise RNA expression data for specific and/or semi-specific genes for that cell type. Table 18 and International Publication No. WO2021/183917 list examples of genes that are specific and/or semi-specific to different cell types. In some embodiments, expression data obtained for genes listed for a particular cell type in Table 18 and/or in International Publication No. WO2021/183917 may be provided as input to a machine learning model trained to predict an RNA percentage for the particular cell type. As a non-limiting example, expression data obtained for genes listed for basophils in Table 18 may be provided as input to a machine learning model trained to predict an RNA percentage for basophils in the biological sample. In some embodiments, other information about the RNA expression data (e.g., a median of the RNA expression data, or any other suitable statistics) may be additionally or alternatively provided as input to the machine learning models.

In some embodiments, the output of machine learning models 2904 may be RNA percentages 2906 for respective cell types and/or subtypes. For example, the machine learning model for cell type A may produce as its output a predicted percentage of RNA from cells of type A in the input RNA expression data. Similarly, the machine learning model for cell type B may produce as its output a predicted percentage of RNA from cells of type B, and the machine learning model for cell type C may produce as its output a predicted percentage of RNA from cells of type C. As described herein, the predicted percentages of RNA may be used to calculate corresponding cell composition percentages for some or all of the cell types and/or subtypes being analyzed.

Figure 29B:
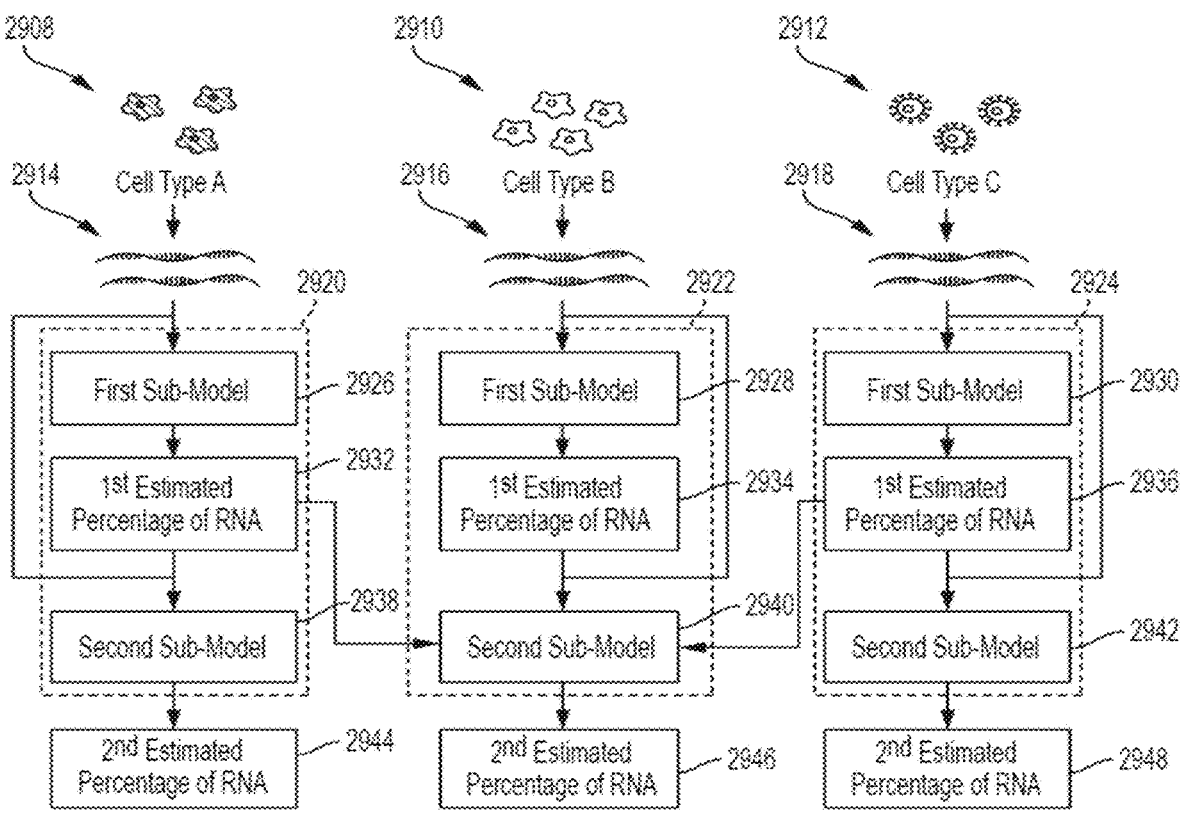
FIG. 29B is a diagram depicting an example of using machine learning model(s) for determining RNA percentages based on RNA expression data, according to some embodiments of the technology described herein.

FIG. 29B is a diagram depicting use of machine learning models 2920, 2922, 2924 comprising first sub-models 2926, 2928, 2930 and second sub-models 2938, 2940, 2942 for determining RNA percentages based on RNA expression data.

As shown in FIG. 29B, a different machine learning model 2920, 2922, 2924 is used to process expression data 2914, 2916, 2918 for genes associated with each cell type: cell type A 2908, cell type B 2910, and cell type C 2912. In some embodiments, each example machine learning model includes a first sub-model 2926, 2928, 2930, for generating a first value 2932, 2934, 2936 for the estimated percentage of RNA from each cell type, and a second sub-model 2938, 2940, 2942 for generating a second value 2944, 2946, 2948 for the estimated percentage of RNA from each cell type.

As a non-limiting example for using a machine learning model that includes one or more sub-models, consider the machine learning model 2922 trained to estimate an RNA percentage for cell type B 2910. In some embodiments, expression data 2916 may be obtained from a set of genes associated with cell type B 2910 and used as input to the machine learning model 2922. For example, cell type B 2910 may include basophils and the expression data 2916 may include expression data for at least some of the genes from the gene set associated with basophils listed in Table 18. In some embodiments, at least some of the expression data 2916 (e.g., expression data associated with a subset of genes, expression data associated with all the genes, etc.) is used as input to the first sub-model 2928. For example, a subset of the expression data 2916 including expression data for a subset of the genes from the gene set associated with basophils may be used input. The first sub-model may then process the input expression data to determine a first value 2934 of the estimated percentage of RNA from cell type B 2910.

In some embodiments, the example machine learning model 2922 may include a second sub-model 2940 to generate a second value 2946 of the estimated percentage of RNA from cell type B 2910. In some embodiments, the second sub-model 2940 may use one or more inputs to generate the second value 2940. For example, in some embodiments, at least some of the expression data 2916 may be used as input. In some embodiments the expression data may include the same expression data input to the first sub-model 2928. In some embodiments, the expression data may include the same expression data input to the first sub-model, as well as additional expression data. In some embodiments, the expression data may include expression data different from the expression data input to the first sub-model.

Additionally, or alternatively, in some embodiments, the second sub-model 2940 may take as input estimate percentages of RNA output by the first sub-models 2926, 2930 of machine learning models 2920, 2924 for other cell types 2908, 2912. As shown, the second sub-model 2940 for cell type B 2910 takes as input the first value 2932 for the estimate percentage of RNA from cell type A 2908 and the first value 2936 for the estimate percentage of RNA from cell type C 2912. This type of input may be informative when trying to determine the percentage of RNA from a cell type that is associated with a same gene or same set of genes as another cell type(s). For example, if cell type B 2910 is associated with a same gene as cell type C 2912, then expression data obtained for that gene may not be highly informative about which of the two cell types is present in the biological sample, since it may be unclear which cell type generated the expression data. However, consider a scenario where the first sub-model 2930 outputs 0% as the first value 2936 of the estimated percentage of RNA determined for cell type C. This indicates that there are no cells of cell type C 2912 in the biological sample. As a result, any expression data obtained for the shared gene must have been expressed by cell type B 2910. In some embodiments, the second sub-model 2940 can use the first values 2932, 2936 to make such inferences.

In some embodiments, the output of the second sub-model 2940 is a second value 2946 for the estimated percentage of RNA from cell type B 2910.

In some embodiments, the estimated RNA percentages may be processed to determine cell composition percentages for each of the cell types. The RNA percentages may be processed using any suitable techniques to obtain the cell composition percentages, as aspects of the technology described herein are not limited in this respect.

As a nonlimiting example, determining cell composition percentages based on RNA percentages may include applying Equation 1 to the RNA percentages:

$$C_{cell} = \frac{R_{cell}}{A_{cell}} / \sum_{cells} \frac{R_{cell}}{A_{cell}}$$ (Equation 1)

where $C_{cell}$ is the cell composition percentage for the cell type, $R_{cell}$ is the RNA percentage for the cell type, and $A_{cell}$ is an RNA per cell coefficient. As shown in Equation 1, the denominator may comprise a sum over all cell types and/or subtypes being analyzed (cells). As such, the expression $$\frac{R_{cell}}{A_{cell}}$$

may be initially computed for all cell types and/or subtypes, then used to compute individual $C_{cell}$ values for each cell type and/or subtype.

The RNA per cell coefficient $A_{cell}$ may represent an RNA concentration per cell. The RNA per cell coefficient can be used to allow the conversion of RNA percentages to corresponding cell composition percentages. In some embodiments, the RNA per cell coefficient $A_{cell}$ may be determined as part of a model training process (e.g., from simulated or artificial data with known percentages of the different cell types.) In some embodiments, the RNA per cell coefficient $A_{cell}$ may be determined experimentally for some or all cell types. For example, RNA per cell coefficients may be obtained by accessing data relating to RNA expression for each cell type (e.g., from available scientific literature, such as PMID: 29130882, PMID: 30726743, or estimated from single cell data, using average or non-linearly transformed UMI count per cell type) and using that data to determine a corresponding RNA per cell coefficient (e.g., by analyzing purity and/or histological TCGA lymphocyte data, for example) for each cell type. In some embodiments, the RNA per cell coefficients may be tissue specific, and could vary based on the disease being analyzed (e.g., from cancer to cancer). In some embodiments, the RNA per cell coefficient may be tissue agnostic, and may not vary based on a disease being analyzed (e.g., because non-malignant microenvironment cells may be represented by the same or substantially similar cellular phenotypes even across different cancers, tissues, or diseases). In the latter case, data from multiple types of cancers, tissues, diseases, etc. may be combined in order to calculate the RNA per cell coefficients. For example, in some embodiments, more than 10,000 different cancer tissues samples from TCGA were analyzed as part of determining RNA per cell coefficients for cell types. The inventors have recognized and appreciated that non-malignant cell composition percentages may correspond to the tumor cellularity defined by histology and WES analysis. As such, in some embodiments, determining RNA per cell coefficients may comprise aligning non-malignant cell composition percentages obtained from RNA to cell composition percentages obtained from DNA in order to develop coefficients for RNA per cell type.

In some embodiments, Equation 1 may be applied independently to each RNA percentage (e.g., in sequence), or may be applied to some or all of the RNA percentages together (e.g., in parallel) in some embodiments. In some embodiments, Equation 1 may be applied initially to RNA percentages for cell types which are not subtypes of one another. In some embodiments, Equation 1 may subsequently be applied to RNA percentages for cell types that are a subtype of one or more initially used cell types. In some embodiments, the calculation of cell composition percentages for cell subtypes may be modified based on the initially calculated cell composition percentages. For example, in some embodiments, subsequently calculated cell composition percentages for cell subtypes may be normalized or otherwise adjusted such that they sum to the cell composition percentage for the total cell type (i.e., the initially-calculated cell type of which they are subtypes).

Generating Leukocyte Signature and Identifying Leukocyte Immunoprofile Type

In some embodiments, the leukocyte immunoprofile types may be generated by: (1) obtaining leukocyte signatures (using the techniques described herein) for a plurality of subjects; and (2) clustering the leukocyte signatures so obtained into a plurality of leukocyte immunoprofile types. Any suitable clustering technique may be used for this purpose including, but not limited to, a dense clustering algorithm, spectral clustering algorithm, k-means clustering algorithm, hierarchical clustering algorithm, and/or an agglomerative clustering algorithm.

In some embodiments, the leukocyte immunoprofile types may have been identified by clustering a plurality of leukocyte signatures for a plurality of subjects. In some embodiment, the leukocyte immunoprofile types have been identified using a clustering algorithm selected from the group consisting of a dense clustering algorithm, spectral clustering algorithm, k-means clustering algorithm, hierarchical clustering algorithm, and/or an agglomerative clustering algorithm. In some embodiments, clustering is performed using a spectral clustering algorithm.

For example, inter-sample similarity may be calculated using a Pearson correlation. A distance matrix may be converted into a graph where each sample forms a node and two nodes form an edge with a weight equal to their Pearson correlation coefficient. Edges with weight lower than a specified threshold may be removed. A Louvain community detection algorithm may be applied to calculate graph partitioning into clusters. To mathematically determine the optimum weight threshold for observed clusters minimum DaviesBouldin, maximum Calinski-Harabasz, and Silhouette techniques may be employed. Separations with low-populated clusters (<5% of samples) may be excluded.

Accordingly, in some embodiments, generating the leukocyte immunoprofile types involves: (A) obtaining multiple sets of data (e.g., cytometry data, RNA expression data, etc.) from biological samples obtained from multiple respective subjects, each of the multiple sets of data comprising information indicative of the presence, absence, and/or respective amounts of certain cell types, such as WBC or PBMC (e.g., some or all of the cell types listed in Table 1, Table 2, Table 3, or Table 4) in the biological sample of the subject; (B) generating multiple leukocyte signatures from the multiple sets of data, each of the multiple leukocyte signatures comprising cell composition percentages for respective cell types (e.g., some or all of the cell types listed in Table 1, Table 2, Table 3, or Table 4) of the biological samples of the respective subjects, and (C) clustering the multiple leukocyte signatures to obtain the plurality of leukocyte immunoprofile types.

The resulting leukocyte immunoprofile types may each contain any suitable number of leukocyte signatures, e.g., at least 10, at least 100, at least 500, at least 500, at least 1000, at least 5000, between 100 and 10,000, between 500 and 20,000, or any other suitable range within these ranges, as aspects of the technology described herein are not limited in this respect.

The number of leukocyte immunoprofile types in this example is five. An important aspect of the present disclosure is the inventors' discovery that certain intrinsic types of leukocyte immunoprofile may be characterized into five types based upon the generation of leukocyte signatures using methods described herein.

Figure 4:
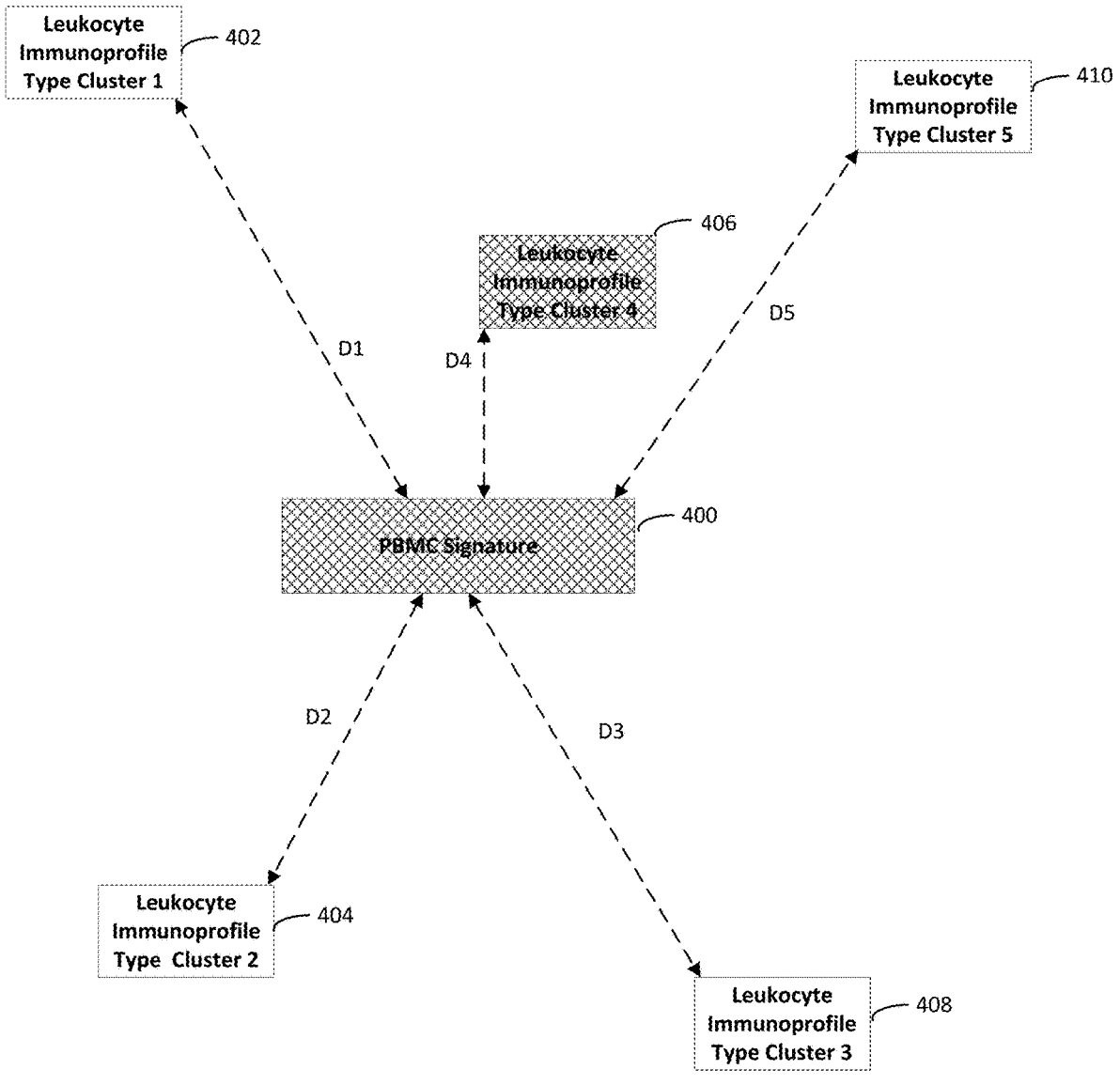
FIG. 4 is a diagram depicting an illustrative technique for identifying a leukocyte immunoprofile type, associated with a respective leukocyte signature cluster, using a leukocyte signature (e.g., a WBC signature or a PBMC signature), according to some embodiments of the technology described herein.

For example, as shown in FIG. 4, a subject's leukocyte signature 400 may be associated with one of five leukocyte immunoprofile types: 402, 404, 406, 408, and 410. Each of the clusters 402, 404, 406, 408, and 410 may be associated with respective leukocyte immunoprofile types. In this example, the leukocyte signature 400 is compared to each cluster (e.g., using a distance-based comparison or any other suitable metric) and, based on the result of the comparison, the leukocyte signature 400 is associated with the closest leukocyte signature cluster (when a distance-based comparison is performed, or the "closest" in the sense of whatever metric or measure of distance is used). In this example, leukocyte signature 400 is associated with leukocyte signature Cluster 4 406 (as shown by the consistent shading) because the measure of distance D4 between the leukocyte signature 400 and (e.g., a centroid or other point representative of) cluster 406 is smaller than the measures of the distance D1, D2, D3, and D5 between the leukocyte signature 400 and (e.g., a centroid or other point(s) representative of) clusters 402, 404, 608, and 410, respectively.

In some embodiments, a subject's leukocyte signature may be associated with one of five leukocyte immunoprofile types by using a machine learning technique (e.g., such as k-nearest neighbors (KNN) or any other suitable classifier) to assign the leukocyte signature to one of the five leukocyte immunoprofile types. The machine learning technique may be trained to assign leukocyte signatures on the meta-cohorts represented by the signatures in the clusters. Aspects of machine learning models are described herein including at least in the section "Techniques for Associating Leukocyte Signatures to Leukocyte Immunoprofile Types".

In some embodiments, a subject's leukocyte signature may be associated with one of five leukocyte immunoprofile types by using a linear regression model, for example Elastic Net linear regression. In some embodiments, associating the leukocyte signature of a subject with a particular one of a plurality of leukocyte immunoprofile types comprises determining, for each particular one of the plurality of leukocyte immunoprofile types, a score indicating whether the leukocyte signature of the subject is associated with that particular cluster. In some embodiments, determining the score for a particular cluster comprises applying a linear regression model associated with the particular cluster, to the cell composition percentages in the leukocyte signature.

In some embodiments, leukocyte immunoprofile types comprise a Naïve type (e.g., G1), a Primed type (e.g., G2), a Progressive type (e.g., G3), a Chronic type (e.g., G4), and a Suppressive type (e.g., G5). The leukocyte immunoprofile types described herein may be described by qualitative characteristics, for example high cell composition percentages for certain cell types or low signals cell composition percentages for other certain cell types. In some embodiments, a high cell composition percentage refers to higher cell composition percentage of the same cell type in the subject being analyzed compared to a subject having a different type of cancer or a healthy subject. In some embodiments, a low cell composition percentage refers to lower cell composition percentage of the same cell type in the subject being analyzed compared to a subject having a different type of cancer or a healthy subject. In some embodiments, a "high" signal refers to a cell composition percentage that is at least 1-fold, 2-fold, 3-fold, 4-fold, 5-fold, 6-fold, 7-fold, 8-fold, 9-fold, 10-fold, 20-fold, 50-fold, 100-fold, 1000-fold, or more increased relative to the cell composition percentage of the same cell type in a subject having a different type of cancer or a healthy subject. In some embodiments, a "low" signal refers to a cell composition percentage that is at least 1-fold, 2-fold, 3-fold, 4-fold, 5-fold, 6-fold, 7-fold, 8-fold, 9-fold, 10-fold, 20-fold, 50-fold, 100-fold, 1000-fold, or more decreased relative to the cell composition percentage of the same cell type in a subject having a different type of cancer or a healthy subject.

In some embodiments, the Suppressive leukocyte immunoprofile type (e.g., G5) is characterized by an increased number of myeloid cell populations, including classical monocytes and neutrophils, relative to the other leukocyte immunoprofile types.

In some embodiments, the Chronic leukocyte immunoprofile type (e.g., G4) is characterized by an increased number of CD8 memory and effector cells as well as the NKT cell population, relative to the other leukocyte immunoprofile types.

In some embodiments, the Primed leukocyte immunoprofile type (e.g., G2) is characterized by an increased number of T-helper memory cells, including CD4 central memory, relative to the other leukocyte immunoprofile types.

In some embodiments, the Progressive cell memory leukocyte immunoprofile type (e.g., G3) is characterized by an increased number of CD4 and CD8 memory cells, and high increase in CD8 transitional memory cells, relative to the other leukocyte immunoprofile types.

In some embodiments, the Naïve leukocyte immunoprofile type (e.g., G1) is characterized by an increased number of Naïve CD4, CD8 and B cells, relative to the other leukocyte immunoprofile types.

In some embodiments, leukocyte immunoprofile types may be characterized by gene expression profiles indicative of biological processes underlying the particular leukocyte immunoprofile type. For example, in some embodiments, leukocyte immunoprofile types are characterized according to Molecular Signatures Database (MSigDB; described by Liberzon et al. *Cell Syst.* 2015 Dec. 23; 1 (6): 417-425) signatures. In some embodiments, the MSigDB signatures are selected from: Binding of TCF LEF CTNNB1 to target promoters, WNT beta catenin signaling, T cell receptor and costimulatory signaling, CTLA4 Pathway, NK cell mediated cytotoxicity, Antigen processing and presentation, Graft versus host disease, Development and heterogeneity of the ILC family, CD8 TCR downstream pathway, NFAT TF pathway, Cancer immunotherapy by PD1 Blockade, CTL pathway, Allograft rejection, IL 12 2pathway, Neutrophil degranulation, Innate immune system, IL1 family signaling, Signaling by GPCR, Signaling by receptor tyrosine kinases, KRAS signaling up, Negative regulation of the PI3K AKT network, VEGFR1 2 pathway, Naive CD8 T cells versus PD-1 high CD8 T cells, Naive versus activated CD8 T cells, PD-1 signaling, and Cancer immunotherapy by PD1 Blockade signatures.

In some embodiments, a "Binding of TCF LEF CTNNB 1 to target promoters" signature comprises gene expression scores (e.g., GSEA scores) for the following genes: AXIN2, CTNNB, LEF1, MYC, RUNX3, TCF7, TCF7L1, and TCF7L2.

In some embodiments, a "WNT beta catenin signaling" signature comprises gene expression scores (e.g., GSEA scores) for the following genes: ADAM17, AXIN1, AXIN2, CCND2, CSNK1E, CTNNB1, CUL1, DKK1, DKK4, DLL1, DVL2, FRAT1, FZD1, FZD8, GNAI1, HDAC11, HDAC2, HDAC5, HEY1, HEY2, JAG1, JAG2, KAT2A, LEF1, MAML1, MYC, NCOR2, NCSTN, NKD1, NOTCH1, NOTCH4, NUMB, PPARD, PSEN2, PTCH1, RBPJ, SKP2, TCF7, TP53, WNT1, WNT5B, and WNT6.

In some embodiments, a "T cell receptor and costimulatory signaling" signature comprises gene expression scores (e.g., GSEA scores) for the following genes: PDK1, NFKB1, NFKB1A, NFATC2, IL2, CSNK1A1, PLCG1, ZAP70, PRKCA, PTPN6, DYRK1A, LCK, PDCD1, PPP3CA, DYRK2, CTLA4, PTEN, GSK3B, GSK3A, FYN, CD28, AKT1, CALM1, RASA1, RASGRP1, CD8A, CALM2, CD8B, and ITK.

In some embodiments, a "CTLA4 Pathway" signature comprises gene expression scores (e.g., GSEA scores) for the following genes: CD247, CD28, CD3D, CD3E, CD3G, CD80, CD86, CTLA4, GRB2, HLA-DRA, HLA-DRB1, HLA-DRB3, HLA-DRB4, HLA-DRB5, ICOS, ICOSLG, IL2, ITK, LCK, PIK3CA, PIK3R1, and PTPN11.

In some embodiments, a "NK cell mediated cytotoxicity" signature comprises gene expression scores (e.g., GSEA scores) for the following genes: ARAF, B1D, BRAF, CASP3, CD244, CD247, CD48, CHP1, CHP2, CSF2, FAS, FASLG, FCER1G, FCGR3A, FCGR3B, FYN, GRB2, GZMB, HCST, HLA-A, HLA-B, HLA-C, HLA-E, HLA-G, HRAS, ICAM1, ICAM2, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNG, IFNGR1, IFNGR2, ITGAL, ITGB2, KIR2DL1, KIR2DL2, KIR2DL3, KIR2DL4, KIR2DL5A, KIR2DS1, KIR2DS3, KIR2DS4, KIR2DS5, KIR3DL1, KIR3DL2, KLRC1, KLRC2, KLRC3, KLRD1, KLRK1, KRAS, LAT, LCK, LCP2, MAP2K1, MAP2K2, MAPK1, MAPK3, MICA, MICB, NCR1, NCR2, NCR3, NFAT5, NFATC1, NFATC2, NFATC3, NFATC4, NRAS, PAK1, PIK3CA, PIK3CB, PIK3CD, PIK3CG, PIK3R1, PIK3R2, PIK3R3, PIK3R5, PLCG1, PLCG2, PPP3CA, PPP3CB, PPP3CC, PPP3R1, PPP3R2, PRF1, PRKCA, PRKCB, PRKCG, PTK2B, PTPN11, PTPN6, RAC1, RAC2, RAC3, RAET1E, RAET1G, RAET1L, RAF1, SH2D1A, SH2D1B, SH3BP2, SHC1, SHC2, SHC3, SHC4, SOS1, SOS2, SYK, TNF, TNFRSF10A, TNFRSF10B, TNFRSF10C, TNFRSF10D, TNFSF10, TYROBP, ULBP1, ULBP2, ULBP3, VAV1, VAV2, VAV3, and ZAP70.

In some embodiments, a "Antigen processing and presentation" signature comprises gene expression scores (e.g., GSEA scores) for the following genes: B2M, CALR, CANX, CD4, CD74, CD8A, CD8B, CIITA, CREB1, CTSB, CTSL, CTSS, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DRA, HLA-DRB1, HLA-DRB3, HLA-DRB4, HLA-DRB5, HLA-E, HLA-F, HLA-G, HSP90AA1, HSP90AB1, HSPA1A, HSPA1B, HSPA1L, HSPA2, HSPA4, HSPA5, HSPA6, HSPA8, IFI30, IFNA1, IFNA10, IFNA13, IFNA14, IFNA16, IFNA17, IFNA2, IFNA21, IFNA4, IFNA5, IFNA6, IFNA7, IFNA8, KIR2DL1, KIR2DL2, KIR2DL3, KIR2DL4, KIR2DL5A, KIR2DS1, KIR2DS3, KIR2DS4, KIR2DS5, KIR3DL1, KIR3DL2, KIR3DL3, KLRC1, KLRC2, KLRC3, KLRC4, KLRD1, LGMN, LTA, NFYA, NFYB, NFYC, PDIA3, PSME1, PSME2, PSME3, RFX5, RFXANK, RFXAP, TAP1, TAP2, and TAPBP.

In some embodiments, a "Graft versus host disease" signature comprises gene expression scores (e.g., GSEA scores) for the following genes: CD28, CD80, CD86, FAS, FASLG, GZMB, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DRA, HLA-DRB1, HLA-DRB3, HLA-DRB4, HLA-DRB5, HLA-E, HLA-F, HLA-G, IFNG, IL1A, IL1B, IL2, IL6, KIR2DL1, KIR2DL2, KIR2DL3, KIR2DL5A, KIR3DL1, KIR3DL2, KLRC1, KLRD1, PRF1, and TNF.

In some embodiments, a "Development and heterogeneity of the ILC family" signature comprises gene expression scores (e.g., GSEA scores) for the following genes: AHR, AREG, BCL11B, EOMES, GATA3, GFI1, HNF1A, ID2, IFNG, IL12A, IL12B, IL13, IL15, IL 17A, IL18, IL1B, IL22, IL23A, IL25, IL33, IL4, IL5, IL6, IL7, IL9, NFIL3, RORA, TBX21, TNF, TOX, TSLP, and ZBTB16.

In some embodiments, a "CD8 TCR downstream pathway" signature comprises gene expression scores (e.g., GSEA scores) for the following genes: B2M, BRAF, CD247, CD3D, CD3E, CD3G, CD8A, CD8B, EGR1, EGR4, ELK1, EOMES, FASLG, FOS, FOSL1, GZMB, HLA-A, HRAS, IFNA1, IFNA10, IFNA14, IFNA16, IFNA17, IFNA2, IFNA21, IFNA4, IFNA5, IFNA6, IFNA7, IFNA8, IFNAR1, IFNAR2, IFNG, IL2, IL2RA, IL2RB, IL2RG, JUN, JUNB, KRAS, MAP2K1, MAP2K2, MAPK1, MAPK3, MAPK8, MAPK9, NFATC1, NFATC2, NFATC3, NRAS, PPP3CA, PPP3CB, PPP3R1, PRF1, PRKCA, PRKCB, PRKCE, PRKCQ, PTPN7, RAF1, STAT4, TNF, TNFRSF18, TNFRSF4, and TNERSF9.

In some embodiments, a "NFAT TF pathway" signature comprises gene expression scores (e.g., GSEA scores) for the following genes: BATF3, CASP3, CBLB, CD40LG, CDK4, CSF2, CTLA4, CXCL8, DGKA, E2F1, EGR1, EGR2, EGR3, EGR4, FASLG, FOS, FOSL1, FOXP3, GATA3, GBP3, IFNG, IKZF1, IL2, IL2RA, IL3, IL4, IL5, IRF4, ITCH, JUN, JUNB, MAF, NFATC1, NFATC2, NFATC3, POU2F1, PPARG, PRKCQ, PTGS2, PTPN1, PTPRK, RNF128, SLC3A2, TBX21, and TNF.

In some embodiments, a "Cancer immunotherapy by PD1 Blockade" signature comprises gene expression scores (e.g., GSEA scores) for the following genes: NFKB1, PTPN11, PDCD1, NFATC1, STAT3, NFATC2, HLA-DRB1, BATF, NFAT5, IFNG, HLA-A, CD274, PDCD1LG2, ZAP70, NFATC3, NFATC4, CD8A, CD3D, LCK, CD8B, CD3E, JUN, and CD3G.

In some embodiments, a "CTL pathway" signature comprises gene expression scores (e.g., GSEA scores) for the following genes: B2M, CD247, CD3D, CD3E, CD3G, FAS, FASLG, GZMB, HLA-A, ICAM1, ITGAL, ITGB2, and PRF1.

In some embodiments, an "Allograft rejection" signature comprises gene expression scores (e.g., GSEA scores) for the following genes: AARS1, ABCE1, ABI1, ACHE, ACVR2A, AKT1, APBB1, B2M, BCAT1, BCL10, BCL3, BRCA1, C2, CAPG, CARTPT, CCL11, CCL13, CCL19, CCL2, CCL22, CCL4, CCL5, CCL7, CCND2, CCND3, CCR1, CCR2, CCR5, CD1D, CD2, CD247, CD28, CD3D, CD3E, CD3G, CD4, CD40, CD40LG, CD47, CD7, CD74, CD79A, CD80, CD86, CD8A, CD8B, CD96, CDKN2A, CFP, CRTAM, CSF1, CSK, CTSS, CXCL13, CXCL9, CXCR3, DARS1, DEGS1, DYRK3, EGFR, EIF3A, EIF3D, EIF3J, EIF4G3, EIF5A, ELANE, ELF4, EREG, ETS1, F2, F2R, FAS, FASLG, FCGR2B, FGR, FLNA, FYB1, GALNT1, GBP2, GCNT1, GLMN, GPR65, GZMA, GZMB, HCLS1, HDAC9, HIF1A, HLA-A, HLA-DMA, HLA-DMB, HLA-DOA, HLA-DOB, HLA-DQA1, HLA-DRA, HLA-E, HLA-G, ICAM1, ICOSLG, IFNAR2, IFNG, IFNGR1, IFNGR2, IGSF6, IKBKB, IL10, IL11, IL12A, IL12B, IL12RB1, IL13, IL15, IL16, IL18, IL18RAP, IL1B, IL2, IL27RA, IL2RA, IL2RB, IL2RG, IL4, IL4R, IL6, IL7, IL9, INHBA, INHBB, IRF4, IRF7, IRF8, ITGAL, ITGB2, ITK, JAK2, KLRD1, KRT1, LCK, LCP2, LIF, LTB, LY75, LY86, LYN, MAP3K7, MAP4K1, MBL2, MMP9, MRPL3, MTIF2, NCF4, NCK1, NCR1, NLRP3, NME1, NOS2, NPM1, PF4, PRF1, PRKCB, PRKCG, PSMB10, PTPN6, PTPRC, RARS1, RIPK2, RPL39, RPL3L, RPL9, RPS19, RPS3A, RPS9, SIT1, SOCS1, SOCS5, SPI1, SRGN, ST8SIA4, STAB1, STAT1, STAT4, TAP1, TAP2, TAPBP, TGFB1, TGFB2, THY1, TIMP1, TLR1, TLR2, TLR3, TLR6, TNF, TPD52, TRAF2, TRAT1, UBE2D1, UBE2N, WARS1, WAS, and ZAP70.

In some embodiments, a "IL12 2pathway" signature comprises gene expression scores (e.g., GSEA scores) for the following genes: ATF2, B2M, CCL3, CCL4, CCR5, CD247, CD3D, CD3E, CD3G, CD4, CD8A, CD8B, EOMES, FASLG, FOS, GADD45B, GADD45G, GZMA, GZMB, HLA-A, HLA-DRA, HLX, IFNG, IL12A, IL12B, IL12RB1, IL12RB2, IL18, IL18R1, IL18RAP, IL1B, ILIR1, IL2, IL2RA, IL2RB, IL2RG, IL4, JAK2, LCK, MAP2K3, MAP2K6, MAPK14, MTOR, NFKB1, NFKB2, NOS2, PPP3CA, PPP3CB, PPP3R1, RAB7A, RELA, RELB, RIPK2, SOCS1, SPHK2, STAT1, STAT3, STAT4, STAT5A, STAT6, TBX21, and TYK2.

In some embodiments, a "Neutrophil degranulation" signature comprises gene expression scores (e.g., GSEA scores) for the following genes: A1BG, ABCA13, ACAA1, ACLY, ACP3, ACTR10, ACTR1B, ACTR2, ADA2, ADAM10, ADAM8, ADGRE3, ADGRE5, ADGRG3, AGA, AGL, AGPAT2, AHSG, ALAD, ALDH3B1, ALDOA, ALDOC, ALOX5, AMPD3, ANO6, ANPEP, ANXA2, AOC1, APIM1, AP2A2, APAF1, APEH, APRT, ARG1, ARHGAP45, ARHGAP9, ARL8A, ARMC8, ARPC5, ARSA, ARSB, ASAH1, ATAD3B, ATG7, ATP11A, ATP11B, ATP6AP2, ATP6VOA1, ATP6VOC, ATP6V1D, ATP8A1, ATP8B4, AZU1, B2M, B4GALT1, BIN2, BP1, BRI3, BST1, BST2, C1orf35, C3, C3AR1, C5AR1, C6orf120, CAB39, CALML5, CAMP, CAND1, CANT1, CAP1, CAPN1, CAT, CCT2, CCT8, CD14, CD177, CD300A, CD33, CD36, CD44, CD47, CD53, CD55, CD58, CD59, CD63, CD68, CD93, CDA, CDK13, CEACAM1, CEACAM3, CEACAM6, CEACAM8, CEP290, CFD, CFP, CHI3L1, CHIT1, CHRNB4, CKAP4, CLEC12A, CLEC4C, CLEC4D, CLEC5A, CMTM6, CNN2, COMMD3, COMMD9, COPB1, COTL1, CPNE1, CPNE3, CPPED1, CR1, CRACR2A, CREG1, CRISP3, CRISPLD2, CSNK2B, CST3, CSTB, CTSA, CTSB, CTSC, CTSD, CTSG, CTSH, CTSS, CTSZ, CXCL1, CXCR1, CXCR2, CYB5R3, CYBA, CYBB, CYFIP1, CYSTM1, DBNL, DDOST, DDX3X, DEFA1, DEFA1B, DEFA4, DEGS1, DERA, DGAT1, DIAPH1, DNAJC13, DNAJC3, DNAJC5, DNASEIL1, DOCK2, DOK3, DPP7, DSC1, DSG1, DSN1, DSP, DYN-CIH1, DYNCILI1, DYNLL1, DYNLT1, EEFIA1, EEF2, ELANE, ENPP4, EPX, ERP44, FABP5, FAF2, FCAR, FCER1G, FCGR2A, FCGR3B, FCN1, FGL2, FGR, FLG2, FOLR3, FPR1, FPR2, FRK, FRMPD3, FTH1, FTL, FUCA1, FUCA2, GAA, GALNS, GCA, GDI2, GGH, GHDC, GLA, GLB1, GLIPR1, GM2A, GMFG, GNS, GOLGA7, GP1, GPR84, GRN, GSDMD, GSN, GSTP1, GUSB, GYG1, HBB, HEBP2, HEXB, HGSNAT, HK3, HLA-B, HLA-C, HMGB1, HMOX2, HP, HPSE, HRNR, HSP90AA1, HSP90AB1, HSPA1A, HSPA1B, HSPA6, HSPA8, HUWE1, HVCN1, IDH1, IGF2R, ILF2, IMPDH1, IMPDH2, IQGAP1, IQGAP2, IRAG2, IST1, ITGAL, ITGAM, ITGAV, ITGAX, ITGB2, JUP, KCMF1, KCNAB2, KPNB1, KRT1, LAIR1, LAMP1, LAMP2, LAMTOR1, LAMTOR2, LAMTOR3, LCN2, LGALS3, LILRA3, LILRB2, LILRB3, LPCAT1, LRG1, LRRC7, LTA4H, LTF, LYZ, MAGT1, MAN2B1, MANBA, MAPK1, MAPK14, MCEMP1, METTL7A, MGAM, MGST1, MIF, MLEC, MME, MMP25, MMP8, MMP9, MNDA, MOSPD2, MPO, MS4A3, MVP, NAPRT, NBEAL2, NCKAP1L, NCSTN, NDUFC2, NEU1, NFAM1, NFASC, NFKB1, NHLRC3, NIT2, NME2, NPC2, NRAS, OLFM4, OLR1, ORM1, ORM2, ORMDL3, OSCAR, OSTF1, P2RX1, PA2G4, PADI2, PAFAHIB2, PDAP1, PDXK, PECAM1, PFKL, PGAM1, PGLYRP1, PGM1, PGM2, PGRMC1, PIGR, PKM, PKP1, PLAC8, PLAU, PLAUR, PLD1, PLEKHO2, PNP, PPBP, PP1A, PP1E, PRCP, PRDX4, PRDX6, PRG2, PRG3, PRKCD, PRSS2, PRSS3, PRTN3, PSAP, PSEN1, PSMA2, PSMA5, PSMB1, PSMB7, PSMC2, PSMC3, PSMD1, PSMD11, PSMD12, PSMD13, PSMD14, PSMD2, PSMD3, PSMD6, PSMD7, PTAFR, PTGES2, PTPN6, PTPRB, PTPRC, PTPRJ, PTPRN2, PTX3, PYCARD, PYGB, PYGL, QPCT, QSOX1, RAB10, RAB14, RAB18, RAB24, RAB27A, RAB31, RAB37, RAB3A, RAB3D, RAB44, RAB4B, RAB5B, RAB5C, RAB6A, RAB7A, RAB9B, RAC1, RAP1A, RAP1B, RAP2B, RAP2C, RETN, RHOA, RHOF, RHOG, RNASE2, RNASE3, RNASET2, ROCK1, S100A11, S100A12, S100A7, S100A8, S100A9, S100P, SCAMP1, SDCBP, SELL, SERPINA1, SERPINA3, SERPINB1, SERPINB10, SERPINB 12, SERPINB3, SER-PINB6, SIGLEC14, SIGLEC5, SIGLEC9, SIRPA, SIRPB1, SLC11A1, SLC15A4, SLC27A2, SLC2A3, SLC2A5, SLC44A2, SLCO4C1, SLP1, SNAP23, SNAP25, SNAP29, SPTAN1, SRP14, STBD1, STING1, STK10, STK111P, STOM, SURF4, SV1P, SYNGR1, TARM1, TBCID10C, TCIRG1, TCN1, TICAM2, TIMP2, TLR2, TMBIM1, TMC6, TMEM179B, TMEM30A, TMEM63A, TNFAIP6, TNFRSF1B, TOLL1P, TOM1, TRAPPC1, TRPM2, TSPAN14, TTR, TUBB, TUBB4B, TXNDC5, TYROBP, UBR4, UNC13D, VAMP8, VAPA, VAT1, VCL, VCP, VNN1, VPS35L, XRCC5, XRCC6, and YPEL5.

In some embodiments, a "Innate immune system" signature comprises gene expression scores (e.g., GSEA scores) for the following genes: A1BG, AAMP, ABCA13, ABI1, ABI2, ABL1, ACAA1, ACLY, ACP3, ACTB, ACTG1, ACTR10, ACTR1B, ACTR2, ACTR3, ADA2, ADAM10, ADAM8, ADGRE3, ADGRE5, ADGRG3, AGA, AGER, AGL, AGPAT2, AHCYL1, AHSG, AIM2, ALAD, ALDH3B1, ALDOA, ALDOC, ALOX5, ALPK1, AMPD3, ANO6, ANPEP, ANXA2, AOC1, APIM1, AP2A2, APAF1, APEH, APOB, APP, APRT, ARG1, ARHGAP45, ARHGAP9, ARL8A, ARMC8, ARPC1A, ARPC1B, ARPC2, ARPC3, ARPC4, ARPC5, ARSA, ARSB, ART1, ASAH1, ATAD3B, ATF1, ATF2, ATG12, ATG5, ATG7, ATOX1, ATPI1A, ATP11B, ATP6AP2, ATP6VOA1, ATP6VOA2, ATP6VOA4, ATP6VOB, ATP6VOC, ATP6VOD1, ATP6VOD2, ATP6VOE1, ATP6VOE2, ATP6V1A, ATP6VIB1, ATP6VIB2, ATP6VIC1, ATP6VIC2, ATP6V1D, ATP6VIE1, ATP6VIE2, ATP6VIF, ATP6VIG1, ATP6VIG2, ATP6VIG3, ATP6VIH, ATP7A, ATP8A1, ATP8B4, AZU1, B2M, B4GALT1, BAIAP2, BCL10, BCL2, BCL2L1, BIN2, BIRC2, BIRC3, BP1, BPIFA1, BPIFA2, BPIFB1, BPIFB2, BPIFB4, BPIFB6, BRI3, BRK1, BST1, BST2, BTK, BTRC, Clorf35, C1QA, C1QB, C1QC, C1R, C1S, C2, C3, C3AR1, C4A, C4B, C4B_2, C4BPA, C4BPB, C5, C5AR1, C5AR2, C6, C6orf120, C7, C8A, C8B, C8G, C9, CAB39, CALM1, CALML5, CAMP, CAND1, CANT1, CAP1, CAPN1, CAPZA1, CAPZA2, CARD11, CARD9, CASP1, CASP10, CASP2, CASP4, CASP8, CASP9, CAT, CCL17, CCL22, CCR2, CCR6, CCT2, CCT8, CD14, CD177, CD180, CD19, CD209, CD247, CD300A, CD300E, CD300LB, CD33, CD36, CD3G, CD4, CD44, CD46, CD47, CD53, CD55, CD58, CD59, CD63, CD68, CD81, CD93, CDA, CDC34, CDC42, CDK13, CEACAM1, CEACAM3, CEACAM6, CEACAM8, CEP290, CFB, CFD, CFH, CFHR1, CFHR2, CFHR3, CFHR4, CFHR5, CF1, CFL1, CFP, CGAS, CHGA, CHI3L1, CHIT1, CHRNB4, CHUK, CKAP4, CLEC1A, CLEC12A, CLEC4A, CLEC4C, CLEC4D, CLEC4E, CLEC5A, CLEC6A, CLEC7A, CLU, CMTM6, CNN2, CNPY3, COLEC10, COLEC11, COMMD3, COMMD9, COPB1, COTL1, CPB2, CPN1, CPN2, CPNE1, CPNE3, CPPED1, CR1, CR2, CRACR2A, CRCP, CREB1, CRE-BBP, CREG1, CRISP3, CRISPLD2, CRK, CRP, CSNK2B, CST3, CSTB, CTNNB1, CTSA, CTSB, CTSC, CTSD, CTSG, CTSH, CTSK, CTSL, CTSS, CTSV, CTSZ, CUL1, CXCL1, CXCR1, CXCR2, CYB5R3, CYBA, CYBB, CYFIP1, CYFIP2, CYLD, CYSTM1, DBNL, DCD, DDOST, DDX3X, DDX41, DEFA1, DEFA1B, DEFA3, DEFA4, DEFA5, DEFA6, DEFB1, DEFB103A, DEFB103B, DEFB104A, DEFB104B, DEFB105A, DEFB 105B, DEFB106A, DEFB106B, DEFB107A, DEFB107B, DEFB 108B, DEFB 109B, DEFB110, DEFB112, DEFB113, DEFB114, DEFB115, DEFB116, DEFB118, DEFB119, DEFB121, DEFB123, DEFB124, DEFB125, DEFB126, DEFB127, DEFB128, DEFB 129, DEFB130A, DEFB130B, DEFB131A, DEFB132, DEFB133, DEFB134, DEFB 135, DEFB 136, DEFB4A, DEFB4B, DEGS1, DERA, DGAT1, DHX36, DHX58, DHX9, DIAPH1, DNAJC13, DNAJC3, DNAJC5, DNASEIL1, DNM1, DNM2, DNM3, DOCK1, DOCK2, DOK3, DPP7, DSC1, DSG1, DSN1, DSP, DTX4, DUSP3, DUSP4, DUSP6, DUSP7, DYNCIH1, DYNCILI1, DYNLL1, DYNLT1, ECSIT, EEA1, EEFIA1, EEF2, ELANE, ELK1, ELMO1, ELMO2, ENPP4, ENSG00000284958, EP300, EPPIN, EPPIN-WFDC6, EPX, ERP44, F2, FABP5, FADD, FAF2, FBXW11, FCAR, FCER1A, FCER1G, FCGR1A, FCGR2A, FCGR3A, FCGR3B, FCN1, FCN2, FCN3, FGA, FGB, FGG, FGL2, FGR, FLG2, FOLR3, FOS, FPR1, FPR2, FRK, FRMPD3, FTH1, FTL, FUCA1, FUCA2, FYN, GAA, GAB2, GALNS, GCA, GDI2, GGH, GHDC, GLA, GLB1, GLIPR1, GM2A, GMFG, GNLY, GNS, GOLGA7, GP1, GPR84, GRAP2, GRB2, GRN, GSDMD, GSDME, GSN, GSTP1, GUSB, GYG1, GZMM, HBB, HCK, HEBP2, HERC5, HEXB, HGSNAT, HK3, HLA-B, HLA-C, HLA-E, HMGB1, HMOX1, HMOX2, HP, HPSE, HRAS, HRNR, HSP90AA1, HSP90AB1, HSP90B1, HSPA1A, HSPA1B, HSPA6, HSPA8, HTN1, HTN3, HUWE1, HVCN1, ICAM2, ICAM3, IDH1, IFI16, IFIH1, IFNA1, IFNA10, IFNA13, IFNA14, IFNA16, IFNA17, IFNA2, IFNA21, IFNA4, IFNA5, IFNA6, IFNA7, IFNA8, IFNB1, IGF2R, IGHE, IGHG1, IGHG2, IGHG4, IGHV1-2, IGHV1-46, IGHV1-69, IGHV2-5, IGHV2-70, IGHV3-11, IGHV3-13, IGHV3-23, IGHV3-30, IGHV3-33, IGHV3-48, IGHV3-53, IGHV3-7, IGHV4-34, IGHV4-39, IGHV4-59, IGKV1-12, IGKV1-16, IGKV1-17, IGKV1-33, IGKV1-39, IGKV1-5, IGKVID-12, IGKVID-16, IGKVID-33, IGKVID-39, IGKV2-28, IGKV2-30, IGKV2D-28, IGKV2D-30, IGKV2D-40, IGKV3-11, IGKV3-15, IGKV3-20, IGKV3D-20, IGKV4-1, IGKV5-2, IGLC2, IGLC3, IGLV1-40, IGLV1-44, IGLV1-47, IGLV1-51, IGLV2-11, IGLV2-14, IGLV2-23, IGLV2-8, IGLV3-1, IGLV3-19, IGLV3-21, IGLV3-25, IGLV3-27, IGLV6-57, IGLV7-43, IKB1P, IKBKB, IKBKE, IKBKG, IL1B, ILF2, IMPDH1, IMPDH2, IQGAP1, IQGAP2, IRAG2, IRAK1, IRAK2, IRAK3, IRAK4, IRF3, IRF7, ISG15, IST1, ITCH, ITGAL, ITGAM, ITGAV, ITGAX, ITGB2, ITK, ITLN1, ITPR1, ITPR2, ITPR3, JUN, JUP, KCMF1, KCNAB2, KIR2DL5A, KIR2DS1, KIR2DS2, KIR2DS4, KIR2DS5, KIR3DS1, KLRC2, KLRD1, KLRK1, KPNB1, KRAS, KRT1, LAIR1, LAMP1, LAMP2, LAMTOR1, LAMTOR2, LAMTOR3, LAT, LAT2, LBP, LCK, LCN2, LCP2, LEAP2, LGALS3, LGMN, LILRA3, LILRB2, LILRB3, LIMK1, LPCAT1, LPO, LRG1, LRRC14, LRRC7, LRRFIP1, LTA4H, LTF, LY86, LY96, LYN, LYZ, MAGT1, MALT1, MAN2B1, MANBA, MAP2K1, MAP2K3, MAP2K4, MAP2K6, MAP2K7, MAP3K1, MAP3K14, MAP3K7, MAP3K8, MAPK1, MAPK10, MAPK11, MAPK12, MAPK13, MAPK14, MAPK3, MAPK7, MAPK8, MAPK9, MAPKAPK2, MAPKAPK3, MASP1, MASP2, MAVS, MBL2, MCEMP1, MEF2A, MEF2C, MEFV, METTL7A, MGAM, MGST1, MIF, MLEC, MME, MMP25, MMP8, MMP9, MNDA, MOSPD2, MPO, MRE11, MS4A2, MS4A3, MUC1, MUC12, MUC13, MUC15, MUC16, MUC17, MUC20, MUC21, MUC3A, MUC4, MUC5AC, MUC5B, MUC6, MUC7, MUCL1, MVP, MYD88, MYH2, MYH9, MYO10, MYO1C, MYOSA, MYO9B, N4BP1, NAPRT, NBEAL2, NCF1, NCF2, NCF4, NCK1, NCKAP1, NCKAP1L, NCK-IPSD, NCR2, NCSTN, NDUFC2, NEU1, NF2, NFAM1, NFASC, NFATC1, NFATC2, NFATC3, NFKB1, NFKB2, NFKB1A, NFKB1B, NHLRC3, NIT2, NKIRAS1, NKI-RAS2, NLRC3, NLRC4, NLRC5, NLRP1, NLRP3, NLRP4, NLRX1, NME2, NOD1, NOD2, NOS1, NOS2, NOS3, NPC2, NRAS, OLFM4, OLR1, ORM1, ORM2, ORMDL3, OSCAR, OSTF1, OTUD5, P2RX1, P2RX7, PA2G4, PADI2, PAFAHIB2, PAK1, PAK2, PAK3, PANX1, PCBP2, PDAP1, PDPK1, PDXK, PDZD11, PECAM1, PELI1, PELI2, PELI3, PFKL, PGAM1, PGLYRP1, PGLYRP2, PGLYRP3, PGLYRP4, PGM1, PGM2, PGRMC1, PI3, PIGR, PIK3C3, PIK3CA, PIK3CB, PIK3R1, PIK3R2, PIK3R4, PIN1, PKM, PKP1, PLA2G2A, PLA2G6, PLAC8, PLAU, PLAUR, PLCG1, PLCG2, PLD1, PLD2, PLD3, PLD4, PLEKHO2, PLPP4, PLPP5, PNP, POLR1C, POLR1D, POLR2E, POLR2F, POLR2H, POLR2K, POLR2L, POLR3A, POLR3B, POLR3C, POLR3D, POLR3E, POLR3F, POLR3G, POLR3GL, POLR3H, POLR3K, PPBP, PP1A, PP1E, PPP2CA, PPP2CB, PPP2R1A, PPP2R1B, PPP2R5D, PPP3CA, PPP3CB, PPP3R1, PRCP, PRDX4, PRDX6, PRG2, PRG3, PRKACA, PRKACB, PRKACG, PRKCD, PRKCE, PRKCQ, PRKCSH, PRKDC, PROS1, PRSS2, PRSS3, PRTN3, PSAP, PSEN1, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PSTPIP1, PTAFR, PTGES2, PTK2, PTPN11, PTPN4, PTPN6, PTPRB, PTPRC, PTPRJ, PTPRN2, PTX3, PYCARD, PYGB, PYGL, QPCT, QSOX1, RAB10, RAB14, RAB18, RAB24, RAB27A, RAB31, RAB37, RAB3A, RAB3D, RAB44, RAB4B, RAB5B, RAB5C, RAB6A, RAB7A, RAB9B, RAC1, RAC2, RAF1, RAP1A, RAP1B, RAP2B, RAP2C, RASGRP1, RASGRP2, RASGRP4, RBSN, REG3A, REG3G, RELA, RELB, RETN, RHOA, RHOF, RHOG, RIG1, RIPK1, RIPK2, RIPK3, RNASE2, RNASE3, RNASE6, RNASE7, RNASE8, RNASET2, RNF125, RNF135, RNF216, ROCK1, RPS27A, RPS6KA1, RPS6KA2, RPS6KA3, RPS6KA5, S100A1, S100A11, S100A12, S100A7, S100A7A, S100A8, S100A9, S100B, S100P, SAA1, SARM1, SCAMP1, SDCBP, SELL, SEM1, SEMG1, SERPINA1, SERPINA3, SERPINB1, SER-PINB10, SERPINB 12, SERPINB3, SERPINB6, SERP-ING1, SFTPA1, SFTPA2, SFTPD, SHC1, SIGIRR, SIGLEC14, SIGLEC15, SIGLEC5, SIGLEC9, SIKE1, SIRPA, SIRPB1, SKP1, SLC11A1, SLC15A4, SLC27A2, SLC2A3, SLC2A5, SLC44A2, SLCO4C1, SLP1, SNAP23, SNAP25, SNAP29, SOCS1, SOS1, SPTAN1, SRC, SRP14, STAT6, STBD1, STING1, STK10, STK111P, STOM, SUGT1, SURF4, SV1P, SYK, SYNGR1, TAB1, TAB2, TAB3, TANK, TARM1, TAXIBP1, TBCIDIOC, TBK1, TCIRG1, TCN1, TEC, TICAM1, TICAM2, TIFA, TIMP2, TIRAP, TKFC, TLR1, TLR10, TLR2, TLR3, TLR4, TLR5, TLR6, TLR7, TLR8, TLR9, TMBIM1, TMC6, TMEM179B, TMEM30A, TMEM63A, TNFAIP3, TNFAIP6, TNFRSF1B, TNIP2, TOLL1P, TOM1, TOMM70, TP53, TRAF2, TRAF3, TRAF6, TRAPPC1, TREM1, TREM2, TREX1, TRIM21, TRIM25, TRIM32, TRIM4, TRIM56, TRPM2, TSPAN14, TTR, TUBB, TUBB4B, TXK, TXN, TXNDC5, TXN1P, TYROBP, UBA3, UBA52, UBA7, UBB, UBC, UBE2D1, UBE2D2, UBE2D3, UBE2K, UBE2L6, UBE2M, UBE2N, UBE2V1, UBR4, UNC13D, UNC93B1, USP14, USP18, VAMP8, VAPA, VAT1, VAV1, VAV2, VAV3, VCL, VCP, VNN1, VPS35L, VRK3, VTN, WAS, WASF1, WASF2, WASF3, WASL, WIPF1, WIPF2, WIPF3, XRCC5, XRCC6, YES1, YPEL5, and ZBP1.

In some embodiments, a "IL1 family signaling" signature comprises gene expression scores (e.g., GSEA scores) for the following genes: AGER, ALOX5, ALPK1, APP, BTRC, CASP1, CASP8, CHUK, CTSG, CUL1, FBXW11, GSDMD, HMGB1, IKB1P, IKBKB, IKBKG, IL13, IL18, IL18BP, IL 18R1, IL18RAP, IL1A, IL1B, ILIF10, ILIR1, ILIR2, ILIRAP, ILIRAPL1, ILIRL1, ILIRL2, ILIRN, IL33, IL36A, IL36B, IL36G, IL36RN, IL37, IL4, IRAK1, IRAK2, IRAK3, IRAK4, LRRC14, MAP2K1, MAP2K4, MAP2K6, MAP3K3, MAP3K7, MAP3K8, MAPK8, MYD88, N4BP1, NFKB1, NFKB2, NFKB1A, NFKB1B, NKIRAS1, NKI-RAS2, NLRC5, NLRX1, NOD1, NOD2, PELI1, *PELI2,* *PELI3*, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PTPN11, PTPN12, PTPN13, PTPN14, PTPN18, PTPN2, PTPN20, PTPN23, PTPN4, PTPN5, PTPN6, PTPN7, PTPN9, RBX1, RELA, RIPK2, RPS27A, S100A12, S100B, SAA1, SEM1, SIGIRR, SKP1, SMAD3, SQSTM1, STAT3, TAB1, TAB2, TAB3, TBK1, TIFA, TNIP2, TOLL1P, TP53, TRAF2, TRAF6, UBA52, UBB, UBC, UBE2N, UBE2V1, USP14, and USP18.

In some embodiments, a "Signaling by GPCR" signature comprises gene expression scores (e.g., GSEA scores) for the following genes: ABHD12, ABHD6, ABR, ACKR1, ACKR2, ACKR3, ACKR4, ADCY1, ADCY2, ADCY3, ADCY4, ADCY5, ADCY6, ADCY7, ADCY8, ADCY9, ADCYAP1, ADCYAPIR1, ADGRE1, ADGRE2, ADGRE3, ADGRE5, ADM, ADM2, ADORA1, ADORA2A, ADORA2B, ADORA3, ADRA1A, ADRA1B, ADRA1D, ADRA2A, ADRA2B, ADRA2C, ADRB1, ADRB2, ADRB3, AGT, AGTR1, AGTR2, AHCYL1, AKAP13, AKT1, AKT2, AKT3, ANXA1, APLN, APLNR, APP, ARHGEF1, ARHGEF10, ARHGEFIOL, ARHGEF11, ARHGEF12, ARHGEF15, ARHGEF16, ARHGEF17, ARHGEF18, ARHGEF19, ARHGEF2, ARHGEF25, ARHGEF26, ARHGEF3, ARHGEF33, ARHGEF35, ARHGEF37, ARHGEF38, ARHGEF39, ARHGEF4, ARHGEF40, ARHGEF5, ARHGEF6, ARHGEF7, ARHGEF9, ARRB1, ARRB2, AVP, AVPR1A, AVPR1B, AVPR2, BDKRB1, BDKRB2, BRS3, BTK, C3, C3AR1, C5, C5AR1, C5AR2, CALCA, CALCB, CALCR, CAL-CRL, CALM1, CAMK2A, CAMK2B, CAMK2D, CAMK2G, CAMK4, CAMKK1, CAMKK2, CASR, CCK, CCKAR, CCKBR, CCL1, CCL11, CCL13, CCL16, CCL17, CCL19, CCL2, CCL20, CCL21, CCL22, CCL23, CCL25, CCL27, CCL28, CCL3, CCL3L1, CCL3L3, CCL4, CCL4L2, CCL5, CCL7, CCR1, CCR10, CCR2, CCR3, CCR4, CCR5, CCR6, CCR7, CCR8, CCR9, CCRL2, CD55, CDC42, CDK5, CGA, CHRM1, CHRM2, CHRM3, CHRM4, CHRM5, CMKLR1, CNR1, CNR2, CORT, CREB1, CRH, CRHBP, CRHR1, CRHR2, CX3CL1, CX3CR1, CXCL1, CXCL10, CXCL11, CXCL12, CXCL13, CXCL16, CXCL2, CXCL3, CXCL5, CXCL6, CXCL8, CXCL9, CXCR1, CXCR2, CXCR3, CXCR4, CXCR5, CXCR6, CYSLTR1, CYSLTR2, DAGLA, DAGLB, DGKA, DGKB, DGKD, DGKE, DGKG, DGKH, DGK1, DGKK, DGKQ, DGKZ, DHH, DRD1, DRD2, DRD3, DRD4, DRD5, ECE1, ECE2, ECT2, EDN1, EDN2, EDN3, EDNRA, EDNRB, EGFR, F2, F2R, F2RL1, F2RL2, F2RL3, FFAR1, FFAR2, FFAR3, FFAR4, FGD1, FGD2, FGD3, FGD4, FN1, FPR1, FPR2, FPR3, FSHB, FSHR, FZD1, FZD10, FZD2, FZD3, FZD4, FZD5, FZD6, FZD7, FZD8, FZD9, GABBR1, GABBR2, GAL, GALR1, GALR2, GALR3, GAST, GCG, GCGR, GHRH, GHRHR, GHRL, GHSR, G1P, GIPR, GLP1R, GLP2R, GNA11, GNA12, GNA13, GNA14, GNA15, GNAI1, GNAI2, GNAI3, GNAL, GNAQ, GNAS, GNAT1, GNAT2, GNAT3, GNAZ, GNB1, GNB2, GNB3, GNB4, GNB5, GNG10, GNG11, GNG12, GNG13, GNG2, GNG3, GNG4, GNG5, GNG7, GNG8, GNGT1, GNGT2, GNRH1, GNRH2, GNRHR, GPBAR1, GPER1, GPHA2, GPHB5, GPR132, GPR143, GPR15, GPR150, GPR17, GPR176, GPR18, GPR183, GPR20, GPR25, GPR27, GPR31, GPR32, GPR35, GPR37, GPR37L1, GPR39, GPR4, GPR45, GPR55, GPR65, GPR68, GPR83, GPR84, GPRC6A, GPSM1, GPSM2, GPSM3, GRB2, GRK2, GRK3, GRK5, GRK6, GRM1, GRM2, GRM3, GRM4, GRM5, GRM6, GRM7, GRM8, GRP, GRPR, HBEGF, HCAR1, HCAR2, HCAR3, HCRT, HCRTR1, HCRTR2, HEBP1, HRAS, HRH1, HRH2, HRH3, HRH4, HTR1A, HTR1B, HTR1D, HTR1E, HTR1F, HTR2A, HTR2B, HTR2C, HTR4, HTR5A, HTR6, HTR7, IAPP, IHH, INSL3, INSL5, ITGA5, ITGB1, ITPR1, ITPR2, ITPR3, ITSN1, KALRN, KEL, KISS1, KISS1R, KNG1, KPNA2, KRAS, LHB, LHCGR, LPAR1, LPAR2, LPAR3, LPAR4, LPAR5, LPAR6, LTB4R, LTB4R2, MAPK1, MAPK3, MAPK7, MC1R, MC2R, MC3R, MC4R, MC5R, MCF2, MCF2L, MCHR1, MCHR2, MGLL, MLN, MLNR, MMP3, MTNR1A, MTNR1B, NBEA, NET1, NGEF, NLN, NMB, NMBR, NMS, NMU, NMUR1, NMUR2, NPB, NPBWR1, NPBWR2, NPFF, NPFFR1, NPFFR2, NPS, NPSR1, NPW, NPY, NPY1R, NPY2R, NPY4R, NPY5R, NRAS, NTS, NTSR1, NTSR2, OBSCN, OPN1LW, OPN1MW, OPN1SW, OPN3, OPN4, OPN5, OPRD1, OPRK1, OPRL1, OPRM1, OXER1, OXGR1, OXT, OXTR, P2RY1, P2RY10, P2RY11, P2RY12, P2RY13, P2RY14, P2RY2, P2RY4, P2RY6, PAK1, PCP2, PDE10A, PDE11A, PDE1A, PDE1B, PDE1C, PDE2A, PDE3A, PDE3B, PDE4A, PDE4B, PDE4C, PDE4D, PDE7A, PDE7B, PDE8A, PDE8B, PDPK1, PDYN, PENK, PF4, PIK3CA, PIK3CG, PIK3R1, PIK3R2, PIK3R3, PIK3R5, PIK3R6, PLA2G4A, PLCB1, PLCB2, PLCB3, PLCB4, PLEKHG2, PLEKHG5, PLPPR1, PLPPR2, PLPPR3, PLPPR4, PLPPR5, PLXNB1, PMCH, PNOC, POMC, PPBP, PPP1CA, PPP1R1B, PPP2CA, PPP2CB, PPP2R1A, PPP2R1B, PPP2R5D, PPP3CA, PPP3CB, PPP3CC, PPP3R1, PPY, PREX1, PRKACA, PRKACB, PRKACG, PRKAR1A, PRKAR1B, PRKAR2A, PRKAR2B, PRKCA, PRKCB, PRKCD, PRKCE, PRKCG, PRKCH, PRKCQ, PRKX, PRLH, PRLHR, PROK1, PROK2, PROKR1, PROKR2, PSAP, PTAFR, PTCH1, PTCH2, PTGDR, PTGDR2, PTGER1, PTGER2, PTGER3, PTGER4, PTGFR, PTG1R, PTH, PTH1R, PTH2, PTH2R, PTHLH, PYY, QRFP, QRFPR, RAMP1, RAMP2, RAMP3, RASGRF2, RASGRP1, RASGRP2, RGR, RGS1, RGS10, RGS11, RGS12, RGS13, RGS14, RGS16, RGS17, RGS18, RGS19, RGS2, RGS20, RGS21, RGS22, RGS3, RGS4, RGS5, RGS6, RGS7, RGS8, RGS9, RGSL1, RHO, RHOA, RHOB, RHOC, RLN2, RLN3, ROCK1, ROCK2, RPS6KA1, RPS6KA2, RPS6KA3, RRH, RXFP1, RXFP2, RXFP3, RXFP4, S1PR1, S1PR2, S1PR3, S1PR4, S1PR5, SAA1, SCT, SCTR, SHC1, SHH, SMO, SOS1, SOS2, SRC, SST, SSTR1, SSTR2, SSTR3, SSTR4, SSTR5, SUCNR1, TAAR1, TAAR2, TAAR5, TAAR6, TAAR8, TAAR9, TAC1, TAC3, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R46, TAS2R5, TAS2R50, TAS2R60, TAS2R7, TAS2R8, TAS2R9, TBXA2R, TIAM1, TIAM2, TRH, TRHR, TRIO, TRPC3, TRPC6, TRPC7, TSHB, TSHR, UCN, UCN2, UCN3, UTS2, UTS2B, UTS2R, VAV1, VAV2, VAV3, V1P, VIPR1, VIPR2, WNT1, WNT10A, WNT10B, WNT11, WNT16, WNT2, WNT2B, WNT3, WNT3A, WNT4, WNT5A, WNT6, WNT7A, WNT7B, WNT8A, WNT8B, WNT9A, WNT9B, XCL1, XCL2, XCR1, and XK.

In some embodiments, a "Signaling by receptor tyrosine kinases" signature comprises gene expression scores (e.g., GSEA scores) for the following genes: AAMP, ABI1, ABI2, ACTB, ACTG1, ADAM10, ADAM12, ADAM17, ADAP1, ADCYAP1, ADCYAP1R1, ADORA2A, AHCYL1, AKT1, AKT2, AKT3, ALK, ANOS1, AP2A1, AP2A2, AP2B1, AP2M1, AP2S1, APH1A, APH1B, APOE, ARC, AREG, ARF6, ARHGEF7, ASCL1, ATF1, ATF2, ATP6AP1, ATP6V0A1, ATP6V0A2, ATP6V0A4, ATP6V0B, ATP6V0C, ATP6V0D1, ATP6V0D2, ATP6V0E1, ATP6V0E2, ATP6V1A, ATP6V1B1, ATP6V1B2, ATP6V1C1, ATP6V1C2, ATP6V1D, ATP6V1E1, ATP6V1E2, ATP6V1F, ATP6V1G1, ATP6V1G2, ATP6V1G3, ATP6V1H, AXL, BAIAP2, BAX, BCAR1, BDNF, BRAF, BRK1, BTC, CALM1, CAV1, CBL, CD274, CDC37, CDC42, CDH5, CDK5, CDK5R1, CDK5R2, CHD4, CHEK1, CILP, CLTA, CLTC, CMA1, COL11A1, COL11A2, COL1A1, COL1A2, COL24A1, COL27A1, COL2A1, COL3A1, COL4A1, COL4A2, COL4A3, COL4A4, COL4A5, COL5A1, COL5A2, COL5A3, COL6A1, COL6A2, COL6A3, COL6A5, COL6A6, COL9A1, COL9A2, COL9A3, CREB1, CRK, CRKL, CSK, CSN2, CTNNA1, CTNNB1, CTNND1, CTSD, CUL5, CXCL12, CYBA, CYBB, CYFIP1, CYFIP2, DIAPH1, DLG4, DNAL4, DNM1, DNM2, DNM3, DOCK1, DOCK3, DOCK7, DUSP3, DUSP4, DUSP6, DUSP7, EGF, EGFR, EGR1, EGR2, EGR3, EGR4, ELK1, ELMO1, ELMO2, EP300, EPGN, EPN1, EPS15, EPS15L1, ERBB2, ERBB3, ERBB4, ERBIN, EREG, ESR1, ESRP1, ESRP2, F3, FER, FES, FGF1, FGF10, FGF16, FGF17, FGF18, FGF19, FGF2, FGF20, FGF22, FGF23, FGF3, FGF4, FGF5, FGF6, FGF7, FGF8, FGF9, FGFBP1, FGFBP2, FGFBP3, FGFR1, FGFR2, FGFR3, FGFR4, FGFRL1, FLRT1, FLRT2, FLRT3, FLT1, FLT3, FLT3LG, FLT4, FN1, FOS, FOSB, FOSL1, FRS2, FRS3, FURIN, FYN, GAB1, GAB2, GABRA1, GABRB1, GABRB2, GABRB3, GABRG2, GABRG3, GABRQ, GALNT3, GFAP, GGA3, GIPC1, GRAP, GRAP2, GRB 10, GRB2, GRB7, GRIN2B, GTF2F1, GTF2F2, HBEGF, HDAC1, HDAC2, HDAC3, HGF, HGFAC, HGS, HIF1A, HNRNPA1, HNRNPF, HNRNPH1, HNRNPM, HPN, HRAS, HSP90AA1, HSPB1, ID1, ID2, ID3, ID4, IDE, IGF1, IGF1R, IGF2, IL2RG, INS, INSR, IRS1, IRS2, IRS4, ITCH, ITGA2, ITGA3, ITGAV, ITGB1, ITGB3, ITPR1, ITPR2, ITPR3, JAK2, JAK3, JUNB, JUND, JUP, KDR, KIDINS220, KIT, KITLG, KL, KLB, KRAS, LAMA1, LAMA2, LAMA3, LAMA4, LAMA5, LAMB1, LAMB2, LAMB3, LAMC1, LAMC2, LAMC3, LCK, LRIG1, LYL1, LYN, MAP2K1, MAP2K2, MAP2K5, MAPK1, MAPK11, MAPK12, MAPK13, MAPK14, MAPK3, MAPK7, MAPKAP1, MAPKAPK2, MAPKAPK3, MATK, MDK, MEF2A, MEF2C, MEF2D, MEMO1, MET, MKNK1, MLST8, MMP9, MST1, MST1R, MTOR, MUC20, MXD4, MYC, MYCN, NAB1, NAB2, NCBP1, NCBP2, NCF1, NCF2, NCF4, NCK1, NCK2, NCKAP1, NCKAP1L, NCOR1, NCSTN, NEDD4, NELFB, NGF, NOS3, NRAS, NRG1, NRG2, NRG3, NRG4, NRP1, NRP2, NTF3, NTF4, NTRK1, NTRK2, NTRK3, PAG1, PAK1, PAK2, PAK3, PCSK5, PCSK6, PDE3B, PDGFA, PDGFB, PDGFC, PDGFD, PDGFRA, PDGFRB, PDPK1, PGF, PGR, PIK3C3, PIK3CA, PIK3CB, PIK3R1, PIK3R2, PIK3R3, PIK3R4, PLAT, PLCG1, PLG, POLR2A, POLR2B, POLR2C, POLR2D, POLR2E, POLR2F, POLR2G, POLR2H, POLR2I, POLR2J, POLR2K, POLR2L, PPP2CA, PPP2CB, PPP2R1A, PPP2R1B, PPP2R5D, PRDM1, PRKACA, PRKACB, PRKACG, PRKCA, PRKCB, PRKCD, PRKCE, PRKCZ, PRR5, PSEN1, PSEN2, PSENEN, PTBP1, PTK2, PTK2B, PTK6, PTN, PTPN1, PTPN11, PTPN12, PTPN18, PTPN2, PTPN3, PTPN6, PTPRF, PTPRJ, PTPRK, PTPRO, PTPRS, PTPRU, PTPRZ1, PXN, RAB4A, RAB4B, RAC1, RALA, RALB, RALGDS, RANBP10, RANBP9, RAP1A, RAP1B, RAPGEF1, RASA1, RBFOX2, REST, RHOA, RICTOR, RIT1, RIT2, RNF41, ROCK1, ROCK2, RPS27A, RPS6KA1, RPS6KA2, RPS6KA3, RPS6KA5, RRAD, S100B, SGK1, SH2B2, SH2B3, SH2D2A, SH3GL1, SH3GL2, SH3GL3, SH3KBP1, SHB, SHC1, SHC2, SHC3, SIN3A, SOCS1, SOCS6, SOS1, SPARC, SPHK1, SPINT1, SPINT2, SPP1, SPRED1, SPRED2, SPRY1, SPRY2, SRC, SRF, STAM, STAM2, STAT1, STAT3, STAT5A, STAT5B, STAT6, STMN1, STUB1, TAB2, TCF12, TCIRG1, TEC, TGFA, TGFBR3, THBS1, THBS2, THBS3, THBS4, THEM4, TIA1, TIAL1, TIAM1, TLR9, TNS3, TNS4, TPH1, TRIB1, TRIB3, UBA52, UBB, UBC, USP8, VAV1, VAV2, VAV3, VEGFA, VEGFB, VEGFC, VEGFD, VGF, VRK3, WASF1, WASF2, WASF3, WWOX, WWP1, YAP1, YES1, and YWHAB.

In some embodiments, a "KRAS signaling up" signature comprises gene expression scores (e.g., GSEA scores) for the following genes: ABCB1, ACE, ADAM17, ADAM8, ADAMDEC1, ADGRA2, ADGRL4, AKAP12, AKT2, ALDHIA2, ALDHIA3, AMMECR1, ANGPTL4, ANKH, ANOI, ANXA10, APOD, ARG1, ATG10, AVL9, BIRC3, BMP2, BPGM, BTBD3, BTC, C3AR1, CA2, CAB39L, CBL, CBR4, CBX8, CCL20, CCND2, CCSER2, CD37, CDADC1, CFB, CFH, CFHR2, CIDEA, CLEC4A, CMKLR1, CPE, CROT, CSF2, CSF2RA, CTSS, CXCL10, CXCR4, DCBLD2, DNMBP, DOCK2, DUSP6, EMP1, ENG, EPB41L3, EPHB2, EREG, ERO1A, ETS1, ETV1, ETV4, ETV5, EVI5, F13A1, F2RL1, FBXO4, FCER1G, FGF9, FLT4, FUCA1, GOS2, GABRA3, GADD45G, GALNT3, GFPT2, GLRX, GNG11, GPNMB, GPRC5B, GUCY1A1, GYPC, H2BC3, HBEGF, HDAC9, HKDC1, HOXD11, HSD11B1, ID2, IGF2, IGFBP3, IKZF1, ILIORA, IL1B, ILIRL2, IL2RG, IL33, IL7R, INHBA, IRF8, ITGA2, ITGB2, ITGBL1, JUP, KCNN4, KIF5C, KLF4, LAPTM5, LAT2, LCP1, LIF, LY96, MAFB, MALL, MAP3K1, MAP4K1, MAP7, MMD, MMP10, MMP11, MMP9, MPZL2, MTMR10, MYCN, NAPIL2, NGF, NIN, NROB2, NR1H4, NRP1, PCP4, PCSKIN, PDCD1LG2, PECAM1, PEG3, PIGR, PLAT, PLAU, PLAUR, PLEK2, PLVAP, PPBP, PPPIR15A, PRDM1, PRELID3B, PRKG2, PRRX1, PSMB8, PTBP2, PTCD2, PTGS2, PTPRR, RABGAP1L, RBM4, RBP4, RELN, RETN, RGS16, SATB1, SCG3, SCG5, SCN1B, SDCCAG8, SEMA3B, SERPINA3, SLP1, SNAP25, SNAP91, SOX9, SPARCL1, SPON1, SPP1, SPRY2, ST6GAL1, STRN, TFP1, TLR8, TMEM100, TMEM158, TMEM176A, TMEM176B, TNFAIP3, TNFRSF1B, TNNT2, TORIAIP2, TPH1, TRAF1, TRIB1, TRIB2, TSPAN1, TSPAN13, TSPAN7, USH1C, USP12, VWASA, WDR33, WNT7A, YRDC, ZNF277, and ZNF639.

In some embodiments, a "Negative regulation of the PI3K AKT network" signature comprises gene expression scores (e.g., GSEA scores) for the following genes: AKT1, AKT2, AKT3, AREG, BTC, CD19, CD28, CD80, CD86, EGF, EGFR, EPGN, ERBB2, ERBB3, ERBB4, EREG, ESR1, ESR2, FGF1, FGF10, FGF16, FGF17, FGF18, FGF19, FGF2, FGF20, FGF22, FGF23, FGF3, FGF4, FGF5, FGF6, FGF7, FGF8, FGF9, FGFR1, FGFR2, FGFR3, FGFR4, FLT3, FLT3LG, FRS2, FYN, GAB1, GAB2, GRB2, HBEGF, HGF, ICOS, IER3, ILIRAP, ILIRL1, IL33, INS, INSR, IRAK1, IRAK4, IRS1, IRS2, KIT, KITLG, KL, KLB, LCK, MAPK1, MAPK3, MET, MYD88, NRG1, NRG2, NRG3, NRG4, PDGFA, PDGFB, PDGFRA, PDG-FRB, PHLPP1, PHLPP2, PIK3AP1, PIK3CA, PIK3CB, PIK3CD, PIK3R1, PIK3R2, PIK3R3, PIP4K2A, PIP4K2B, PIP4K2C, PIP5K1A, PIP5K1B, PIP5K1C, PPP2CA, PPP2CB, PPP2R1A, PPP2R1B, PPP2R5A, PPP2R5B, PPP2R5C, PPP2R5D, PPP2R5E, PTEN, PTPN11, RAC1, RAC2, RHOG, SRC, STRN, TGFA, THEM4, TRAF6, TRAT1, TRIB3, and VAV1.

In some embodiments, a "VEGFR1 2 pathway" signature comprises gene expression scores (e.g., GSEA scores) for the following genes: AKAP1, AKT1, ARF1, BRAF, CAMKK2, CAV1, CBL, CDC42, CDH5, CTNNA1, CTNNB1, DNM2, FBXW11, FES, FLT1, FYN, GAB1, GRB10, GRB2, HGS, HSP90AA1, HSP90AB1, IQGAP1, ITGAV, ITGB3, KDR, MAP2K1, MAP2K2, MAP2K3, MAP2K6, MAPK1, MAPK11, MAPK14, MAPK3, MAPKAPK2, MYOF, NCK1, NCK2, NEDD4, NOS3, PAK2, PDPK1, PIK3CA, PIK3R1, PLCG1, PRKAA1, PRKAA2, PRKAB1, PRKACA, PRKAG1, PRKCA, PRKCB, PRKCD, PTK2, PTK2B, PTPN11, PTPN2, PTPN6, PTPRJ, PXN, RAF1, RHOA, ROCK1, SH2D2A, SHB, SRC, VCL, VEGFA, and VTN.

In some embodiments, a "Naive CD8 T cells versus PD-1 high CD8 T cells" signature comprises gene expression scores (e.g., GSEA scores) for the following genes: ACSS2, ACTN1, ADGRA3, ADPRM, AEBP1, AGBL2, AGMAT, AK5, AMIGO1, APBB1, ARHGEF4, ARMCX1, ATG9B, ATP6VOE2-AS1, AZIN2, BDH1, BEND5, BEX3, BPHL, C17orf67, C19orf18, C3orf18, CA6, CAPN5, CARS1, CAT-SPERE, CBR3, CCR7, CD248, CD55, CEP170, CEP41, CHCHD7, CHMP7, CLECI1A, CLN5, CLTRN, CNKSR1, CNKSR2, CT75, CYP2J2, DCHS1, DENNDSA, DSC1, ECRG4, EDAR, EFHC2, EFHD1, EFNA1, EIF2D, ENSG00000280119, EPB41L2, EPHA1, EPHA1-AS1, FAM117B, FAM184A, FAM216A, FBLN2, FBP1, FBXO15, FLNB, FOXO1, FOXP1, GAL3ST4, GIPC3, GNG7, GP5, GPRASP2, HAPLN3, HPCAL4, HSBPIL1, IGF1R, IL6R, IL6ST, IPCEF1, IRS1, ITGA6, KLF7, KLHL6, KRTCAP3, LDLRAP1, LEF1, LEF1-AS1, LINS1, LMF1, LRRN3, MAL, MAML2, MANIC1, MCF2L-AS1, MDS2, MEST, MICU3, MMEL1, MRRF, MYB, NAA16, NAT9, NDFIP1, NELL2, NEXMIF, NOG, NR3C2, NRCAM, NREP, NT5E, NUDT9P1, OBSCN, OVGP1, OXNAD1, PABPC3, PASK, PCSK5, PDCD4-AS1, PDE9A, PDK1, PIK3IP1, PK1A, PK1G, PLAG1, PLEKHG4, PLPP1, PRKCA, PRKCQ-AS1, PRRT1, PRXL2A, RAB43, RBM26-AS1, REG4, RETREG1, RFX2, RHPN2, RNF157, RNF175, ROBO3, SALL2, SARAF, SCML1, SCML2, SCOC-AS1, SELL, SERP1, SFXN4, SFXN5, SH3RF3, SH3YL1, SLC16A10, SLC22A17, SLC7A3, SNED1, SNHG32, SOX8, SPART, SPEG, SPEN-AS1, SPINK2, SPINT2, SREBF1, STRADB, STXBP1, SULTIB1, SUSD3, TAF4B, TBXA2R, TCEAL3, TCF3, TECPR1, THEM4, TKTL1, TMEM220, TMEM272, TNFRSF10D, TOPIMT, TP73-AS1, TPST1, TRABD2A, TSEN2, TXNRD3, UBE2E2, UBIAD1, UBQLN2, USP51, USP6NL, VIPR1, YPEL2, ZBTB10, ZBTB18, ZNF285, ZNF436-AS1, ZNF496, ZNF662, ZNF667-AS1, and ZNF93.

In some embodiments, a "Naive versus activated CD8 T cells" signature comprises gene expression scores (e.g., GSEA scores) for the following genes: ACADL, ACOT7, ACP1, ACTG1, AFG3L1P, AIF1, AKIP1, ALCAM, ALYREF, ANAPC15, ANXA1, ANXA4, APOBEC2, ASF1B, AURKA, BEX3, BSPRY, BUB3, C4orf3, CAB39L, CALM1, CALM3, CARHSP1, CCDC34, CD44, CD48, CD80, CDK2AP1, CDKN1A, CDKN2C, CENPP, CHST11, CISD1, CLIC1, COMMD3, COPS4, COPS5, CRELD2, CTLA4, CXCL10, CXCR3, DAPK2, DB1, DCK, DDOST, DDX39A, DEPDC1, DLAT, DPAGT1, DSCC1, DUSP5, E2F7, EME1, EMP1, EPAS1, ERG28, ERH, ETFB, FAM136A, FBX05, FCGRT, FIGNL1, FKBP2, FLNB, GABARAPL1, GCNT1, GEM, GGH, GLRX, GPR160, GRB7, GSAP, H1-1, H2BC4, H4C8, HIRIP3, HMGN2, HOPX, HPRT1, ID2, IDI1, IFITM1, IFNGR1, IL1B, ILIR2, INSL6, IRAK3, ITSN1, KIF22, KLF11, KLRC2, LAG3, LAIR1, LAMP2, LSM12, LSM2, LSM3, MDH2, MICOS10, MIS18BP1, MPHOSPH6, MRPL18, MRPL42, MXD3, MYADM, MYL4, NCALD, NDUFAF2, NDUFS6, NME1, NRP1, NUDT1, NUP37, NUP43, NUP54, ORC6, PANX1, PBK, PGAM1, PHF11, PLAC8, PMAIP1, PMM1, PNP, POLR3K, PPA1, PRELID1, PRF1, PRIM2, PSMA1, PSMA5, PSMB2, PSMC31P, PSMD8, PYCARD, RAD18, RAD51AP1, RAN, RANBP1, RBBP7, RBM47, RFC3, RGS1, RPA2, SAMSN1, SAR1B, SCRN3, SELENOS, SEPHS2, SERPINB9, SERPINE2, SF3B6, SIVA1, SMIM3, SNRPA1, SNX10, SPDL1, SURF4, SYCE2, SYPL1, SYTL3, TAF12, TBCB, TCEAL9, TEX15, TEX30, TFDP1, TIMM17A, TIMM23, TMBIM4, TMED10, TMEM163, TROAP, TTC39B, TTC9C, TUBB4B, TXNDC17, UBE2N, UBE2S, UCK2, UFC1, VDAC3, VIM, YBX3, and ZBTB32.

In some embodiments, a "PD-1 signaling" signature comprises gene expression scores (e.g., GSEA scores) for the following genes: CD247, CD274, CD3D, CD3E, CD3G, CD4, CSK, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, LCK, PDCD1, PDCD1LG2, PTPN11, PTPN6, TRAV19, TRAV29DV5, TRAV8-4, TRBV12-3, and TRBV7-9.

In some embodiments, a "Cancer immunotherapy by PD1 Blockade" signature comprises gene expression scores (e.g., GSEA scores) for the following genes: NFKB1, PTPN11, PDCD1, NFATC1, STAT3, NFATC2, HLA-DRB1, BATF, NFAT5, IFNG, HLA-A, CD274, PDCD1LG2, ZAP70, NFATC3, NFATC4, CD8A, CD3D, LCK, CD8B, CD3E, JUN, and CD3G.

In some embodiments, leukocyte immunoprofile types are characterized according to cytokine expression profiles. Table 12 of the Examples further describes additional features of leukocyte immunoprofile types, for example by Cell Type Enrichment, Functional Significance, and/or T cell receptor (TCR) repertoires.

In some embodiments, the present disclosure provides methods for identifying a subject having, suspected of having, or at risk of having cancer as having an as being likely to have a good prognosis (e.g., as measured by overall survival (OS) or progression-free survival (PFS). A good prognosis may refer to a subject with a first immunoprofile type having a decreased risk of cancer progressions, an increased chance of responding to therapeutic, and/or an increased lifespan prediction relative to a subject having a different leukocyte immunoprofile types. For example, in some embodiments, a subject having a Primed type HNSCC is expected to have a better response to immunotherapy (e.g., a PD1-inhibitor) than a subject having a different immunoprofile type of HNSCC.

In some embodiments, the method comprises determining a leukocyte immunoprofile type of the subject as described herein.

In some embodiments, the methods comprise identifying the subject as having a decreased risk of cancer progression relative to a subject having a different leukocyte immunoprofile types. In some embodiments, "decreased risk of cancer progression" may indicate better prognosis of cancer or decreased likelihood of having advanced disease in a subject. In some embodiments, "decreased risk of cancer progression" may indicate that the subject who has cancer is expected to be more responsive to certain treatments. For instance, "decreased risk of cancer progression" indicates that a subject is at least 10%, 20%, 30%, 40%, 50%, 60%, 70%, 80%, 90%, or 100% likely to experience a progression-free survival event (e.g., relapse, retreatment, or death) than another cancer patient or population of cancer patients (e.g., patients having cancer, but not the same cancer leukocyte immunoprofile type as the subject).

In some embodiments, the methods further comprise identifying the subject as having an increased risk of cancer progression relative to other leukocyte immunoprofile types. In some embodiments, "increased risk of cancer progression" may indicate less positive prognosis of cancer or increased likelihood of having advanced disease in a subject. In some embodiments, "increased risk of cancer progression" may indicate that the subject who has cancer is expected to be less responsive or unresponsive to certain treatments and show less or no improvements of disease symptoms. For instance, "increased risk of cancer progression" indicates that a subject is at least 10%, 20%, 30%, 40%, 50%, 60%, 70%, 80%, 90%, or 100% more likely to experience a progression-free survival event (e.g., relapse, retreatment, or death) than another cancer patient or population of cancer patients (e.g., patients having cancer, but not the same leukocyte immunoprofile type as the subject).

In some embodiments, the methods described herein comprise the use of at least one computer hardware processor to perform the determination.

In some embodiments, the present disclosure provides a method for providing a prognosis, predicting survival, or stratifying patient risk of a subject suspected of having, or at risk of having cancer. In some embodiments, the method comprises determining a leukocyte immunoprofile type of the subject as described herein.

Updating Leukocyte Immunoprofile Types Based on New Data

Techniques for generating leukocyte immunoprofile types are described herein. It should be appreciated that the clusters may be updated as additional signatures are computed for patients. In some embodiments, the leukocyte signature of the subject is one of a threshold number of leukocyte signatures for a threshold number of subjects. In some embodiments, when the threshold number of leukocyte signatures is generated the leukocyte immunoprofile types are updated. For example, once a threshold number of new leukocyte signatures are obtained (e.g., 1 new signature, 10 new signatures, 100 new signatures, 500 new signatures, any suitable threshold number of signatures in the range of 10-1,000 signatures), the new signatures may be combined with the leukocyte signatures previously used to generate the leukocyte immunoprofile types and the combined set of old and new leukocyte signatures may be clustered again (e.g., using any of the clustering algorithms described herein or any other suitable clustering algorithm) to obtain an updated set of leukocyte immunoprofile types.

In this way, data obtained from a future patient may be analyzed in a way that takes advantage of information learned from patients whose leukocyte signature was computed prior to that of the future patient. In this sense, the machine learning techniques described herein (e.g., the unsupervised clustering machine learning techniques) are adaptive and learn with the accumulation of new patient data. This facilitates improved characterization of the leukocyte immunoprofile type that future patients may have and may improve the selection of treatment for those patients.

Therapeutic Indications

Aspects of the disclosure relate to methods of identifying or selecting a therapeutic agent for a subject based upon determination of the subject's leukocyte immunoprofile type. The disclosure is based, in part, on the recognition that subjects having certain leukocyte immunoprofile types (e.g., Naïve immunoprofile type, Primed immunoprofile type) have an increased likelihood of responding to certain therapies (e.g., immunotherapeutic agents) relative to subjects having other leukocyte immunoprofile types (e.g., Suppressive). In some embodiments, a subject having Suppressive leukocyte immunoprofile type is not selected for immunotherapy. In some embodiments, a subject having Suppressive leukocyte immunoprofile type is administered a treatment that is not immunotherapy.

In some embodiments, a therapeutic agent is an immuno-oncology (IO) agent. An IO agent may be a small molecule, peptide, protein (e.g., antibody, such as monoclonal antibody), interfering nucleic acid, or a combination of any of the foregoing. In some embodiments, the IO agent comprises a PD1 inhibitor, PD-L1 inhibitor, or PD-L2 inhibitor. Examples of IO agents include but are not limited to cemiplimab, nivolumab, pembrolizumab, avelumab, durvalumab, atezolizumab, BMS1166, BMS202, etc. In some embodiments, the IO agent comprises a combination of atezolizumab and albumin-bound paclitaxel, pembrolizumab and albumin-bound paclitaxel, pembrolizumab and paclitaxel, or pembrolizumab and Gemcitabine and Carboplatin.

In some embodiments, methods described by the disclosure further comprise a step of administering one or more therapeutic agents to the subject based upon the determination of the subject's leukocyte immunoprofile type. In some embodiments, a subject is administered one or more (e.g., 1, 2, 3, 4, 5, or more) IO agents.

Aspects of the disclosure relate to methods of treating a subject having (or suspected or at risk of having) cancer based upon a determination of the leukocyte immunoprofile type of the subject. In some embodiments, the methods comprise administering one or more (e.g., 1, 2, 3, 4, 5, or more) therapeutic agents to the subject. In some embodiments, the therapeutic agent (or agents) administered to the subject are selected from small molecules, peptides, nucleic acids, radioisotopes, cells (e.g., CAR T-cells, etc.), and combinations thereof. Examples of therapeutic agents include chemotherapies (e.g., cytotoxic agents, etc.), immunotherapies (e.g., immune checkpoint inhibitors, such as PD-1 inhibitors, PD-L1 inhibitors, etc.), antibodies (e.g., anti-HER2 antibodies), cellular therapies (e.g., CAR T-cell therapies), gene silencing therapies (e.g., interfering RNAs, CRISPR, etc.), antibody-drug conjugates (ADCs), and combinations thereof.

In some embodiments, the disclosure relates to methods of treating a subject having (or suspected or at risk of having) head and neck squamous cell carcinoma (HNSCC) based upon a determination of the leukocyte immunoprofile type of the subject. For example, a subject having HNSCC and a Primed leukocyte immunoprofile type may have a higher response rate to immunotherapies (e.g., immune checkpoint inhibitors, for example PD-1 blocking antibodies such as nivolumab) than a subject having HNSCC and a different immunoprofile type (e.g., Naïve, Progressive, Chronic, or Suppressive). In some embodiments, a subject having HNSCC and a Chronic or Suppressive immunotype may have a lower response rate to an immunotherapy than a subject having HNSCC and a Primed immunotype.

In some embodiments, a subject is administered an effective amount of a therapeutic agent. "An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., leukocyte immunoprofile type, tumor microenvironment, tumor formation, tumor growth, etc.) may be analyzed.

Generally, for administration of any of the anti-cancer antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 ug/mg to about 2 mg/kg (such as about 3 ug/mg, about 10 ug/mg, about 30 ug/mg, about 100 ug/mg, about 300 ug/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays and/or by monitoring leukocyte immunoprofile type as described herein. The dosing regimen (including the therapeutic used) may vary over time.

Dosing of immuno-oncology agents is well-known, for example as described by Louedec et al. *Vaccines* (Basel). 2020 December; 8(4): 632. For example, dosages of pembrolizumab, for example, include administration of 200 mg every 3 weeks or 400 mg every 6 weeks, by infusion over 30 minutes.

When the anti-cancer therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically, the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward cancer.

Alleviating cancer includes delaying the development or progression of the disease, or reducing disease severity. Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively, or in addition to the clinical techniques known in the art, development of the disease may be detectable and assessed based on other criteria. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

Examples of an immunotherapy include, but are not limited to, a PD-1 inhibitor or a PD-L1 inhibitor, a CTLA-4 inhibitor, adoptive cell transfer, therapeutic cancer vaccines, oncolytic virus therapy, T-cell therapy, and immune checkpoint inhibitors.

In some aspects, the disclosure provides a method for treating cancer, the method comprising administering one or more therapeutic agents (e.g., one or more anti-cancer agents, such as one or more immunotherapeutic agents) to a subject identified as having a particular leukocyte immunoprofile type, wherein the leukocyte immunoprofile type of the subject has been identified by method as described by the disclosure.

EXAMPLES

Recent advances in immunotherapy demonstrate the need to further understand the characteristics of an individual cancer patient's immune system and how it influences responses to cancer treatment. These representative examples describe development of an immunoprofiling platform to evaluate the features in the blood of cancer patients to investigate use of peripheral immune cell heterogeneity to stratify patients into different categories or immunotypes to monitor disease progression and treatment response. To that end, a unique diagnostic immunoprofiling assay and analytical framework based on the analysis of leukocytes in the peripheral blood was established using multiparameter flow cytometry.

Supervised manual gating analysis of flow cytometry data from a cohort of 50 healthy donors identified 415 cell types and immune activation states that were used to train and later independently validate machine learning models to automatically identify immune cell subsets from raw cytometry data. A cohort of 650 patients was also analyzed by flow cytometry in the same manner. By applying this tool to peripheral blood (e.g., WBC) samples from a mixed cohort of 299 healthy donors and 323 cancer patients a machine learning classification model that can differentiate between these two groups with 91% accuracy (ROC-AUC) was developed. This model was further refined using spectral clustering with bootstrapping, revealing 5 clusters, or immunotypes, characterized by specific physiological immune profiles: (1) Naïve T and B lymphocytes, (2) Tregs and various CD4+ T helper cell subsets, (3) mature NK, CD8+ transitional memory and PD1+ TIGIT+ CD8+ T cells, (4) Terminally-differentiated Effector memory and TEMRA CD4 and CD8+ T cells, (5) Myeloid cells such as monocytes and neutrophils.

Very few healthy donors were assigned to clusters 4 and 5. Matched RNA-seq was used to further validate these profiles using the cellular deconvolution algorithm, Kassandra, and differential gene expression analysis revealed immunotype-specific signatures that are consistent with immune response potential. Patients in the terminally-differentiated CD8+ T cell cluster had a narrower range of HLA-types than the other clusters, and TCR repertoire analysis indicated significantly increased clonality and reduced clonotype diversity. Within this cluster there was a high degree of overlap between TCR sequences in the peripheral blood and the tumor, indicating a relationship between peripheral blood immunotype and tumor infiltration.

Example 1

The immune system plays an important role in protecting an organism from different diseases, including cancers. However, sometimes immunity fails to stop a tumor from developing. Moreover, immune cells can even support malignant growth being a part of a tumor microenvironment. Most of the immune cell populations are also present in the blood and can be analyzed after being collected as an easily accessible biopsy. Blood draws are almost non-invasive procedures that can give access to a person's immune cells. This representative example describes an overview of an analysis that was performed on blood samples collected from both cancer patients and healthy donors.

Figure 5A:
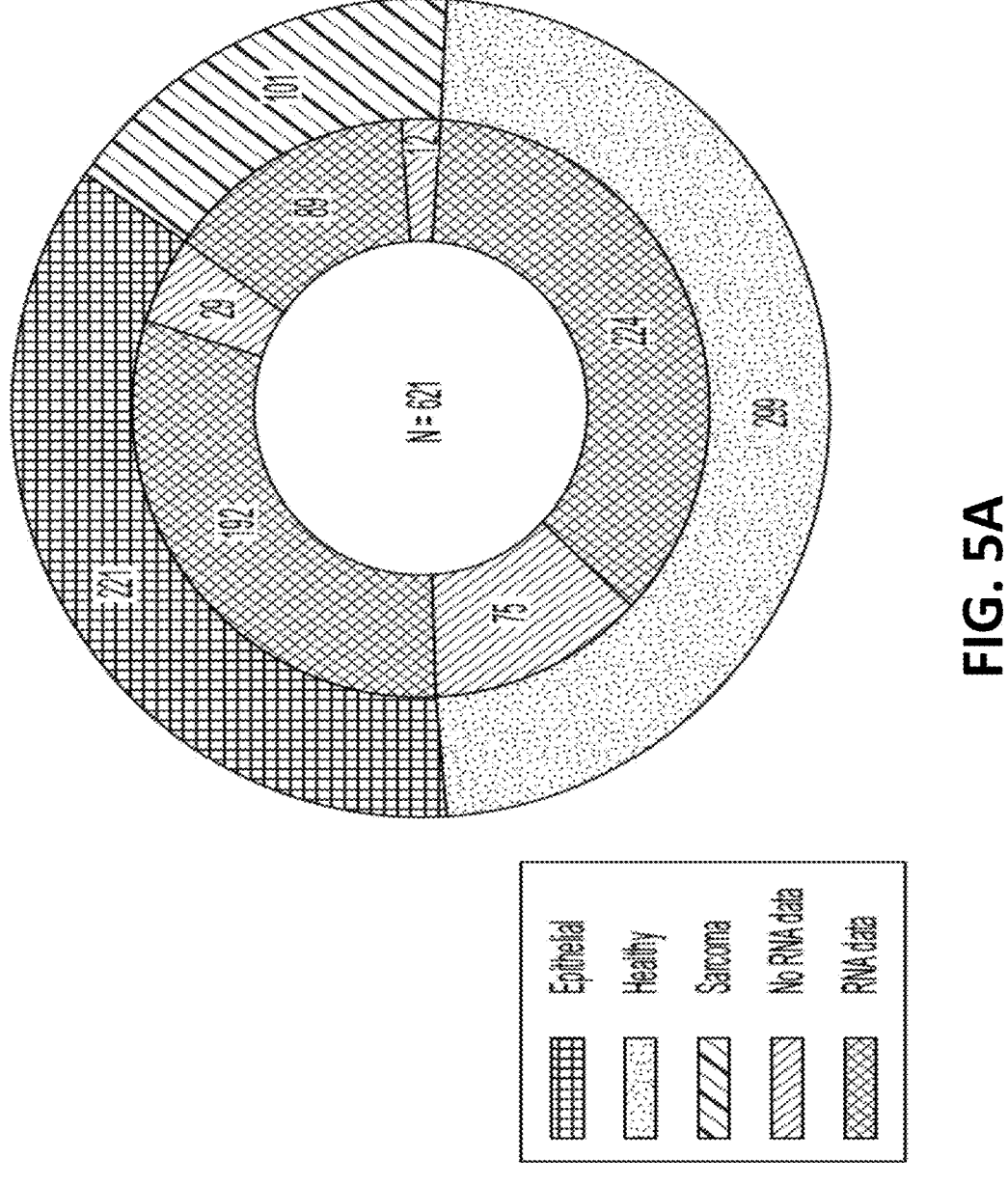

Samples from 621 blood draws in total were collected: 299 being from healthy donors, 221 from patients with epithelial cancers, and 101 from sarcoma patients. A second cohort was also analyzed-samples from 850 blood draws in total were collected: 408 being from healthy donors, 309 from patients with epithelial cancers, and 133 from sarcoma patients. Samples were subject to the crosslinking multi-panel flow cytometry (FC) analysis, as well as a hematology analyzer. For most of the samples, RNA sequencing was also performed (FIGS. 5A-5B). As a result, a cohort with multiple cell populations' percentages in blood (e.g., cell types set forth in Table 1) was generated. For most of the blood samples from cancer patients, corresponding RNA-seq of a tumor biopsy was available. For RNA-seq data, there were expression values calculated in TPM format for approximately 20,000 genes.

Figure 6A:
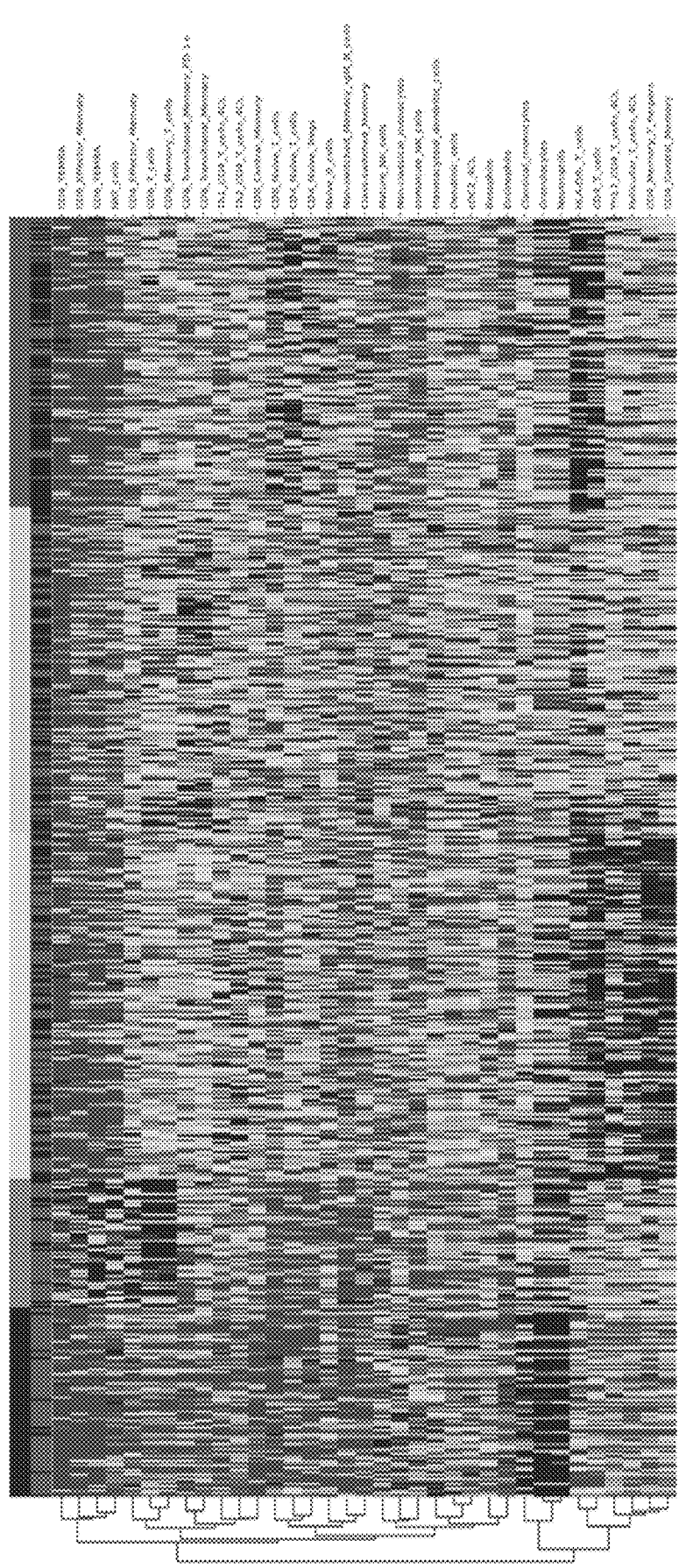
FIGS. 6A-6B are representative heatmaps of flow cytometry data obtained for the cohort described in FIGS. 5A-5B), according to some embodiments of the technology described herein.
Figure 6B:
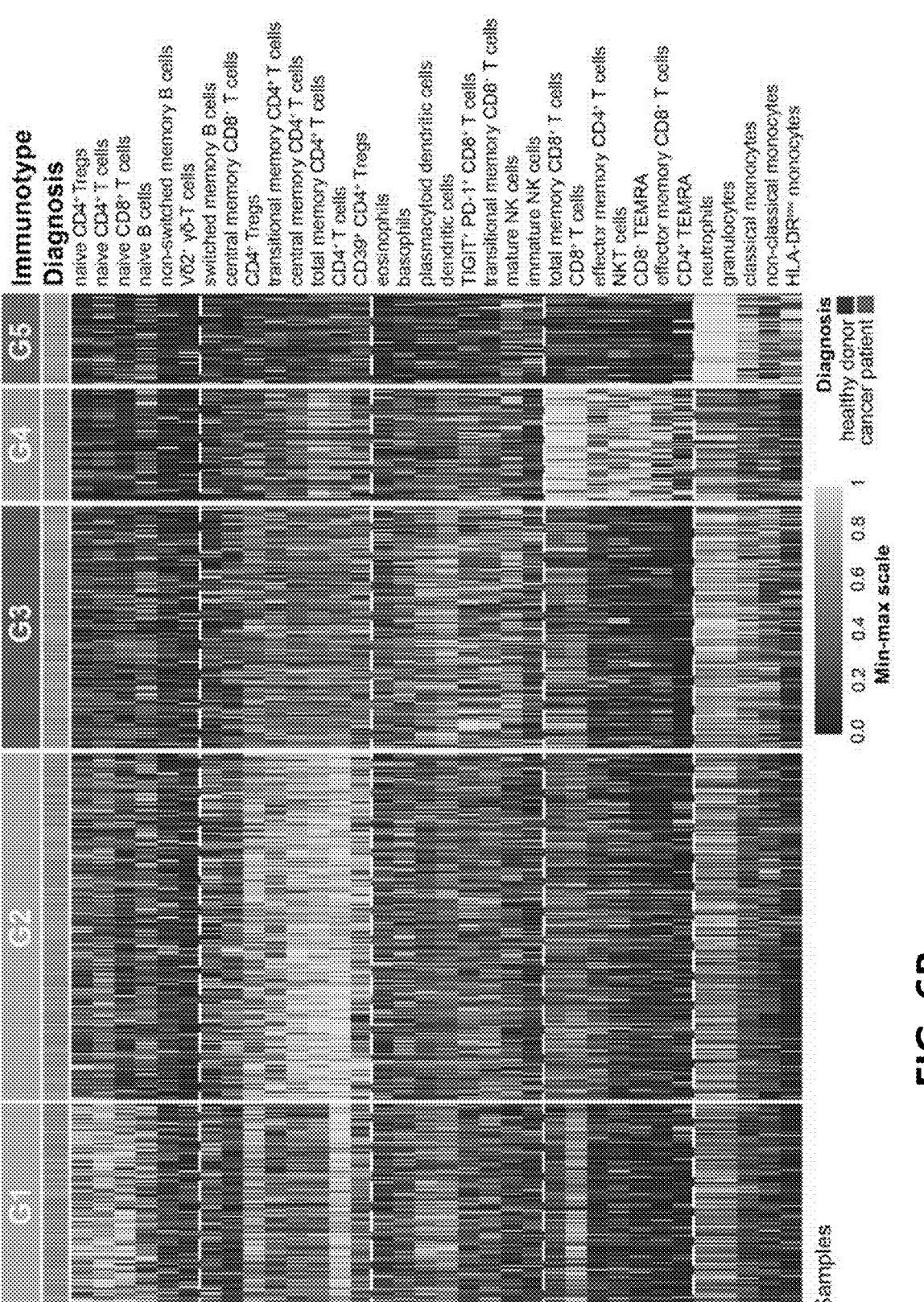

At first, flow cytometry data were analyzed using classical dimensional reduction methods, such as PCA, tSNE and uMAP. Spectral clustering analysis was performed on the data. The best stability of clusters was observed with the spectral clustering algorithm with the number of clusters being equal to 5. An uneven distribution was observed between the healthy donor and cancer patient samples between these clusters (see FIGS. 6A-6B). Some of the identified clusters consist of blood samples with different cell populations proportions, which are described below:

Cluster 1 (Myeloid derived suppressor/NK cell cluster; also referred to in this example as "Monocytes" or "G1" or "Suppressive"). This cluster is characterized by an increased number of myeloid cell populations, including classical monocytes and neutrophils, relative to the other clusters.

Cluster 2 (Terminally-differentiated CD8+ T cells cluster; also referred to in this example as "CD8 T cells" or "G2" or "Chronic"). This cluster is characterized by an increased number of CD8 memory and effector cells as well as the NKT cell population, relative to the other clusters.

Cluster 3 (Mixed CD4+ T helper cells cluster; also referred to in this example as "CD4 T cells" or "G3" or "Progressive"). This cluster is characterized by an increased number of T-helper memory cells, including CD4 central memory, relative to the other clusters.

Cluster 4 (CD4+ Th1 & CD8+ T cell memory cluster; also referred to in this example as "CD4/CD8 T cells" or "G4" or "Primed"). This cluster is characterized by an increased number of CD4 and CD8 memory cells, and high increase in CD8 transitional memory cells, relative to the other clusters.

Cluster 5 (Naïve T and B lymphocytes cluster; also referred to in this example as "G5" or "Naïve"). This cluster is characterized by an increased number of Naïve CD4, CD8 and B cells, relative to the other clusters.

The clusters may also be described statistically, as shown in Tables 5-7 below, which show, the 25%, 50% (median), and 75% quantiles for each of the five clusters for each of the cell types.

TABLE 5

| | G1 (Monocytes) 25% | G2 (CD8 T cells) 25% | G3 (CD4 T cells) 25% | G4 (CD4/CD8 T cells) 25% | G5 (Naïve T/B cells) 25% |
|---|---|---|---|---|---|
| HLA-DR-T cells | 0.106328 | 0.283683 | 0.5403 | 0.443324 | 0.596917 |
| CD4 T cells | 0.067698 | 0.267173 | 0.58441 | 0.374826 | 0.511845 |
| Th1 CD4 T cells | 0.036604 | 0.108995 | 0.26649 | 0.263428 | 0.152247 |
| Th2 CD4 T cells | 0.095003 | 0.142166 | 0.37654 | 0.185264 | 0.163 |
| Th17 CD4 T cells | 0.117065 | 0.153179 | 0.42137 | 0.230167 | 0.226913 |
| CD4 Naïve T cells | 0.034715 | 0.063445 | 0.23172 | 0.17332 | 0.439375 |
| CD4 Naïve Tregs | 0.032717 | 0.059123 | 0.19235 | 0.131932 | 0.289133 |
| CD4 Memory T helpers | 0.063865 | 0.375559 | 0.61633 | 0.382133 | 0.242293 |
| CD4 Effector Memory | 0.058556 | 0.456092 | 0.20736 | 0.229745 | 0.122493 |
| CD4 Central Memory | 0.123691 | 0.246346 | 0.60517 | 0.335551 | 0.291734 |
| CD4 TEMRA | 0.005659 | 0.11697 | 0.01225 | 0.013615 | 0.010809 |
| CD8 T cells | 0.039958 | 0.630845 | 0.19631 | 0.331358 | 0.295225 |
| CD8 Naïve T cells | 0.020406 | 0.046728 | 0.08689 | 0.108112 | 0.247128 |
| CD8 Memory T cells | 0.061191 | 0.659571 | 0.19163 | 0.284277 | 0.166347 |
| CD8 Transitional Memory PD-1+ | 0.036002 | 0.093951 | 0.20409 | 0.313713 | 0.174481 |
| CD8 Transitional Memory | 0.058921 | 0.231584 | 0.23021 | 0.340671 | 0.190939 |
| CD8 Central Memory | 0.036013 | 0.128753 | 0.20134 | 0.231671 | 0.160843 |
| CD8 Effector Memory | 0.010973 | 0.152987 | 0.05532 | 0.096939 | 0.041693 |
| Follicular T cells | 0.074380 | 0.192826 | 0.45744 | 0.326113 | 0.269109 |
| CD8 TEMRA | 0.009394 | 0.452182 | 0.02534 | 0.036895 | 0.02272 |
| CD8 TEMRA PD-1+ | 0.003883 | 0.069517 | 0.03595 | 0.052409 | 0.033727 |

TABLE 5-continued

| | G1 (Monocytes) 25% | G2 (CD8 T cells) 25% | G3 (CD4 T cells) 25% | G4 (CD4/CD8 T cells) 25% | G5 (Naïve T/B cells) 25% |
|---|---|---|---|---|---|
| Non-switched Memory IgM B cells | 0.035967 | 0.026193 | 0.07142 | 0.101036 | 0.145749 |
| Class-switched Memory | 0.042619 | 0.050361 | 0.10672 | 0.133283 | 0.13904 |
| Naïve B cells | 0.093303 | 0.062922 | 0.11898 | 0.14919 | 0.221864 |
| Classical Monocytes | 0.458568 | 0.244505 | 0.24327 | 0.248523 | 0.232693 |
| Non-classical Monocytes | 0.230355 | 0.156849 | 0.10795 | 0.143944 | 0.069608 |
| Mature NK cells | 0.200234 | 0.087801 | 0.18181 | 0.180878 | 0.103363 |
| Immature NK cells | 0.139125 | 0.058377 | 0.12202 | 0.116228 | 0.091874 |
| Dendritic cells | 0.106136 | 0.086082 | 0.15349 | 0.216583 | 0.160171 |
| Plasmacytoid Dendritic cells | 0.162407 | 0.128447 | 0.19228 | 0.236386 | 0.218051 |
| cDC2 | 0.090028 | 0.104803 | 0.1491 | 0.260122 | 0.169601 |
| NKT cells | 0.022841 | 0.359754 | 0.05384 | 0.090443 | 0.054794 |
| Basophils | 0.087037 | 0.133056 | 0.18685 | 0.203315 | 0.153611 |
| Eosinophils | 0.045604 | 0.036612 | 0.07923 | 0.108351 | 0.073041 |
| Neutrophils | 0.65833 | 0.368159 | 0.38571 | 0.26889 | 0.346164 |
| Granulocytes | 0.666864 | 0.353082 | 0.36287 | 0.239295 | 0.324922 |

TABLE 6

| | G1 (Monocytes) Median | G2 (CD8 T cells) Median | G3 (CD4 T cells) Median | G4 (CD4/CD8 T cells) Median | G5 (Naïve T/B cells) Median |
|---|---|---|---|---|---|
| HLA-DR-Tcells | 0.268192 | 0.500976 | 0.648245 | 0.591865 | 0.758814 |
| CD4 T cells | 0.209573 | 0.343746 | 0.68407 | 0.486548 | 0.651823 |
| Th1 CD4 T cells | 0.104613 | 0.204741 | 0.402059 | 0.396065 | 0.291833 |
| Th2 CD4 T cells | 0.147361 | 0.214283 | 0.479981 | 0.244601 | 0.25253 |
| Th17 CD4 T cells | 0.217881 | 0.272969 | 0.552144 | 0.332609 | 0.312792 |
| CD4 Naïve T cells | 0.113725 | 0.125276 | 0.351845 | 0.278363 | 0.600005 |
| CD4 Naïve Tregs | 0.099969 | 0.100974 | 0.293101 | 0.216797 | 0.426822 |
| CD4 Memory T helpers | 0.195943 | 0.466783 | 0.709288 | 0.486498 | 0.375563 |
| CD4 Effector Memory | 0.139278 | 0.61348 | 0.320537 | 0.310928 | 0.198333 |
| CD4 Central Memory | 0.206858 | 0.310895 | 0.688435 | 0.422796 | 0.396236 |
| CD4 TEMRA | 0.016302 | 0.246496 | 0.031503 | 0.035689 | 0.028403 |
| CD8 T cells | 0.158047 | 0.75256 | 0.312818 | 0.482671 | 0.408883 |
| CD8 Naïve T cells | 0.061372 | 0.098375 | 0.171853 | 0.266962 | 0.480484 |
| CD8 Memory T cells | 0.143213 | 0.795461 | 0.275231 | 0.390962 | 0.212354 |
| CD8 Transitional Memory PD-1+ | 0.108799 | 0.175897 | 0.302216 | 0.478071 | 0.277381 |
| CD8 Transitional Memory | 0.151472 | 0.385116 | 0.318796 | 0.534504 | 0.289327 |
| CD8 Central Memory | 0.082439 | 0.201114 | 0.31736 | 0.318617 | 0.248858 |
| CD8 Effector Memory | 0.049550 | 0.401219 | 0.095028 | 0.148906 | 0.073248 |
| Follicular T cells | 0.166301 | 0.283402 | 0.654542 | 0.418471 | 0.398618 |
| CD8 TEMRA | 0.043413 | 0.668858 | 0.069213 | 0.122074 | 0.056611 |
| CD8 TEMRA PD-1+ | 0.033842 | 0.221638 | 0.072429 | 0.112941 | 0.071543 |
| Non-switched Memory IgM B cells | 0.091232 | 0.071776 | 0.151122 | 0.199213 | 0.234955 |
| Class-switched Memory | 0.114907 | 0.128994 | 0.212951 | 0.237468 | 0.24639 |
| Naïve B cells | 0.213448 | 0.192368 | 0.262771 | 0.272111 | 0.388314 |
| Classical Monocytes | 0.655329 | 0.306156 | 0.342229 | 0.368947 | 0.294646 |
| Non-classical Monocytes | 0.389927 | 0.263495 | 0.202277 | 0.249826 | 0.128144 |
| Mature NK cells | 0.371677 | 0.235421 | 0.265459 | 0.317649 | 0.160494 |
| Immature NK cells | 0.240692 | 0.113474 | 0.218086 | 0.201711 | 0.135861 |
| Dendritic cells | 0.205308 | 0.185447 | 0.243487 | 0.326594 | 0.23602 |
| Plasmacytoid Dendritic cells | 0.321997 | 0.20106 | 0.275889 | 0.384948 | 0.296866 |
| cDC2 | 0.206457 | 0.187459 | 0.270574 | 0.383004 | 0.251595 |
| NKT cells | 0.119644 | 0.441513 | 0.115239 | 0.173497 | 0.103974 |
| Basophils | 0.186265 | 0.235332 | 0.26546 | 0.294347 | 0.249749 |
| Eosinophils | 0.108559 | 0.111721 | 0.163279 | 0.196355 | 0.161185 |
| Neutrophils | 0.764971 | 0.571629 | 0.517067 | 0.401948 | 0.456711 |
| Granulocytes | 0.792903 | 0.553052 | 0.521678 | 0.395461 | 0.438848 |

TABLE 7

| | G1 (Monocytes) 75% | G2 (CD8 T cells) 75% | G3 (CD4 T cells) 75% | G4 (CD4/CD8 T cells) 75% | G5 (Naïve T/B cells) 75% |
|---|---|---|---|---|---|
| HLA-DR-Tcells | 0.410735 | 0.690284 | 0.797729 | 0.716651 | 0.878565 |
| CD4 T cells | 0.312610 | 0.499894 | 0.769481 | 0.601961 | 0.780222 |
| Th1 CD4 T cells | 0.206641 | 0.288377 | 0.577651 | 0.556095 | 0.445013 |
| Th2 CD4 T cells | 0.231139 | 0.321658 | 0.659031 | 0.342858 | 0.348253 |
| Th17 CD4 T cells | 0.300610 | 0.394415 | 0.736429 | 0.467016 | 0.397839 |
| CD4 Naïve T cells | 0.287645 | 0.252189 | 0.457705 | 0.415348 | 0.748118 |
| CD4 Naïve Tregs | 0.194028 | 0.172061 | 0.434128 | 0.322284 | 0.672625 |
| CD4 Memory T helpers | 0.303711 | 0.658291 | 0.825779 | 0.616362 | 0.515244 |
| CD4 Effector Memory | 0.264000 | 0.767647 | 0.467317 | 0.476475 | 0.296753 |
| CD4 Central Memory | 0.304972 | 0.399709 | 0.837447 | 0.558918 | 0.509379 |
| CD4 TEMRA | 0.065253 | 0.755316 | 0.16683 | 0.113046 | 0.098802 |
| CD8 T cells | 0.249499 | 0.953605 | 0.412224 | 0.619756 | 0.551059 |
| CD8 Naïve T cells | 0.138573 | 0.166204 | 0.302362 | 0.420946 | 0.734749 |
| CD8 Memory T cells | 0.239187 | 0.952402 | 0.370278 | 0.566457 | 0.310643 |
| CD8 Transitional Memory PD-1+ | 0.291578 | 0.375086 | 0.426108 | 0.684213 | 0.401351 |
| CD8 Transitional Memory | 0.357580 | 0.538933 | 0.412406 | 0.731612 | 0.408541 |
| CD8 Central Memory | 0.166129 | 0.328062 | 0.459847 | 0.489201 | 0.344726 |
| CD8 Effector Memory | 0.106249 | 0.86332 | 0.168937 | 0.247834 | 0.125704 |
| Follicular T cells | 0.274724 | 0.379509 | 0.821956 | 0.593423 | 0.509134 |
| CD8 TEMRA | 0.135954 | 0.973296 | 0.171905 | 0.276018 | 0.126378 |
| CD8 TEMRA PD-1+ | 0.111959 | 0.384143 | 0.140749 | 0.249695 | 0.167744 |
| Non-switched Memory IgM B cells | 0.161719 | 0.135083 | 0.269189 | 0.323938 | 0.378774 |
| Class-switched Memory | 0.208408 | 0.189463 | 0.420818 | 0.453476 | 0.417536 |
| Naïve B cells | 0.315093 | 0.300502 | 0.386124 | 0.377916 | 0.565337 |
| Classical Monocytes | 0.829032 | 0.492836 | 0.463403 | 0.490062 | 0.379943 |
| Non-classical Monocytes | 0.636081 | 0.385348 | 0.318401 | 0.414433 | 0.224774 |
| Mature NK cells | 0.554361 | 0.479733 | 0.425762 | 0.529321 | 0.265483 |
| Immature NK cells | 0.385627 | 0.237602 | 0.355379 | 0.294723 | 0.228888 |
| Dendritic cells | 0.363509 | 0.258012 | 0.307069 | 0.466837 | 0.33715 |
| Plasmacytoid Dendritic cells | 0.524641 | 0.298336 | 0.408698 | 0.57627 | 0.471078 |
| cDC2 | 0.408302 | 0.287179 | 0.376809 | 0.540043 | 0.384745 |
| NKT cells | 0.218663 | 0.775325 | 0.255804 | 0.322626 | 0.189051 |
| Basophils | 0.298585 | 0.301003 | 0.391303 | 0.448906 | 0.330341 |
| Eosinophils | 0.214113 | 0.257368 | 0.272007 | 0.355815 | 0.267526 |
| Neutrophils | 0.865122 | 0.728919 | 0.654019 | 0.529779 | 0.616451 |
| Granulocytes | 0.911527 | 0.73119 | 0.653567 | 0.543972 | 0.612533 |

Figure 7A:
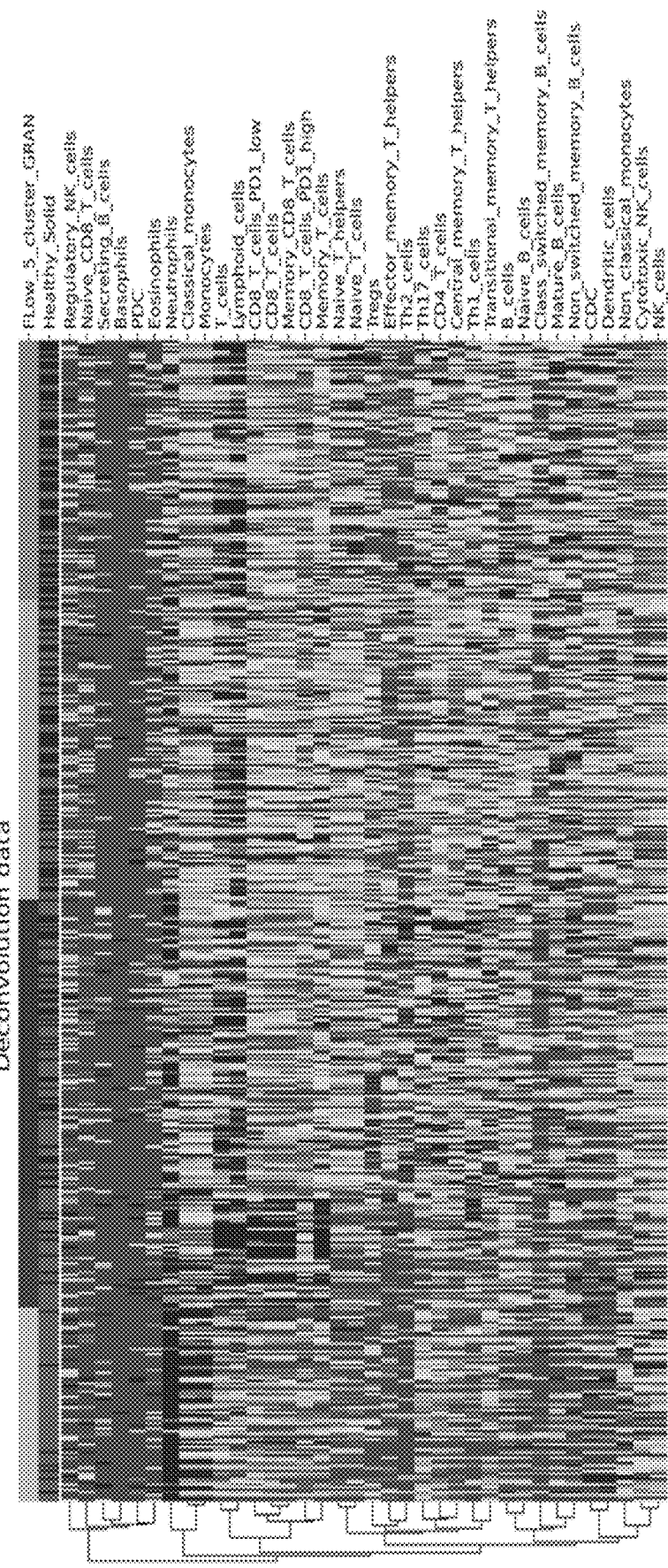
FIGS. 7A-7B are representative heatmaps of cell deconvolution analysis performed on RNA-seq data from samples belonging to different leukocyte immunoprofile types, according to some embodiments of the technology described herein.
Figure 7B:
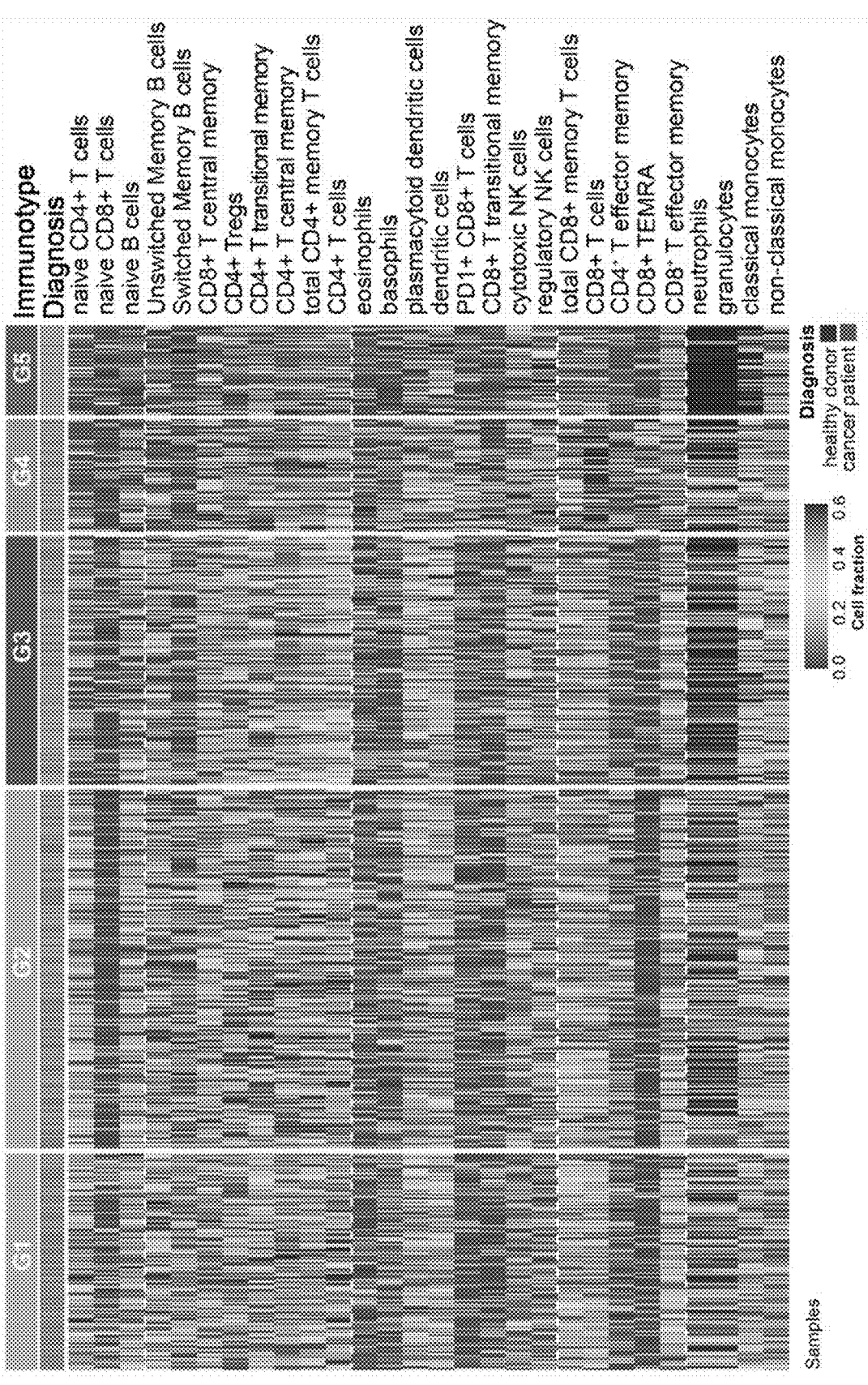
Figure 8:
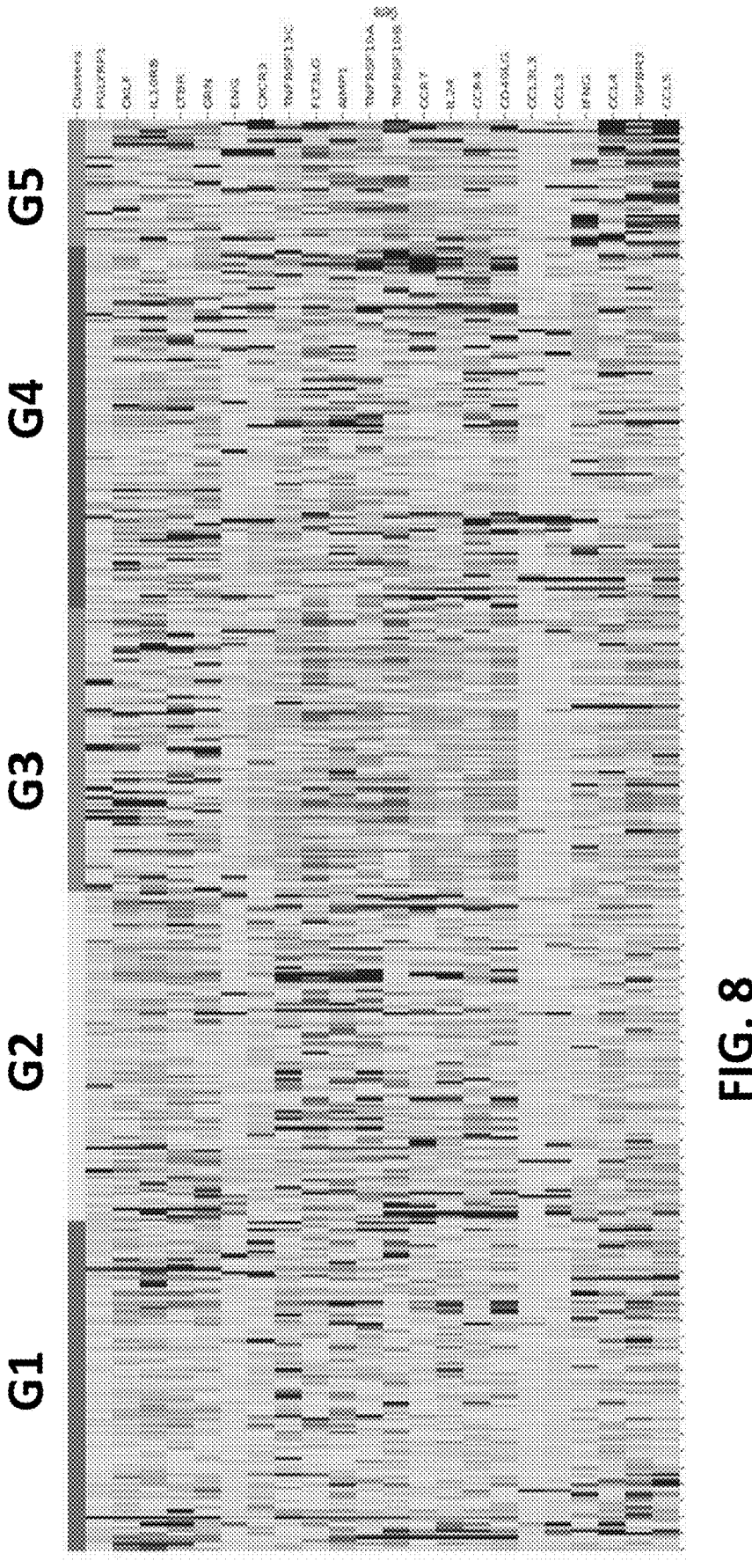
FIG. 8 is a representative heatmap showing differential gene expression analysis performed on RNA-seq data from samples belonging to leukocyte immunoprofile types, according to some embodiments of the technology described herein.

To validate these observations, an analysis of corresponding RNA-seq data of the blood samples belonging to different clusters (for those samples that had that RNA-seq data) was performed. RNA-seq data were processed with the BostonGene Kassandra cell deconvolution tool (e.g., as described in International Application No. PCT/US2021/022155, published as International Publication No. WO2021/183917 on Sep. 16, 2021; and International Application No. PCT/US2022/027088, published as International Publication No. WO2022/232615 on Nov. 3, 2022, the entire contents of each of which are incorporated by reference herein). Data indicate that flow cytometry analysis results were concordant with RNA-seq-based cell composition (FIGS. 7A-7B). Gene signature and cytokines differential expression analysis were also performed (FIG. 8).

Figure 9A:
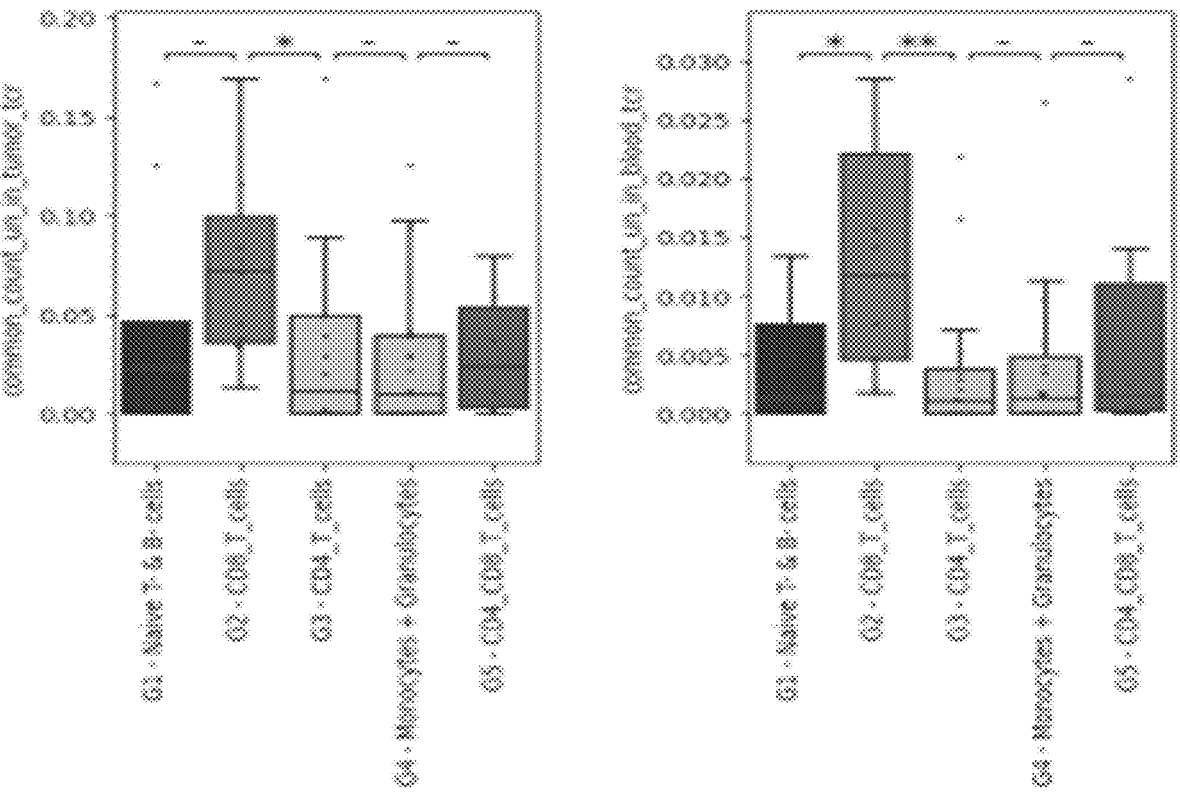
FIGS. 9A-9B show representative data for T cell receptor (TCR) and B cell receptor (BCR) analysis of leukocyte immunoprofile types, according to some embodiments of the technology described herein.
Figure 9B:
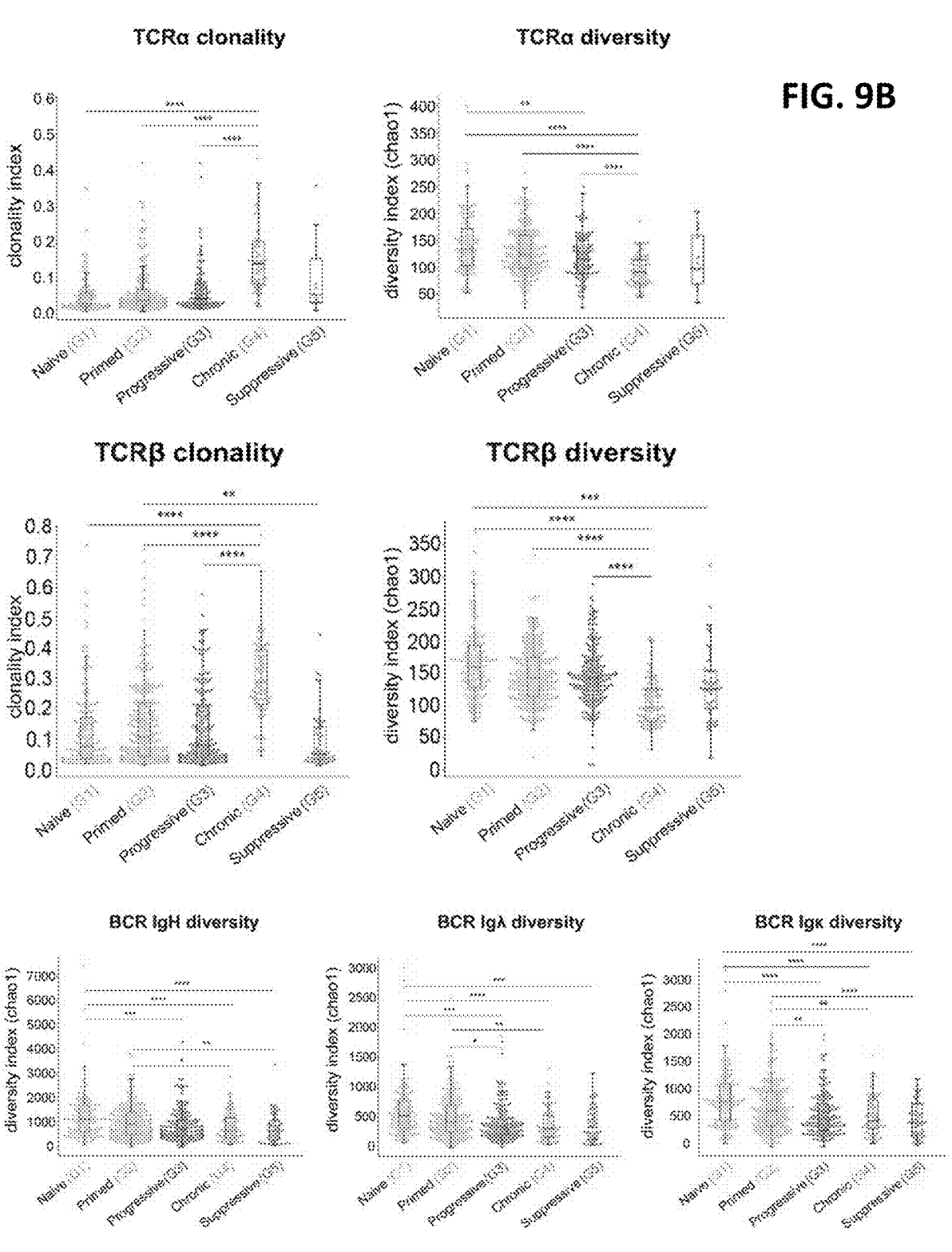

For blood RNA-seq sample data, T cell receptor and B cell receptor (TCR/BCR) analysis was also performed. In Cluster 2 described above, which is enriched for effector CD8 and CD4 cells, the variety of TCR was expectedly lower than in other clusters. Interestingly, the intersection between TCR clonotypes between tumor and blood samples was also higher in this cluster (FIGS. 9A-9B).

Example 2

Figure 10A:
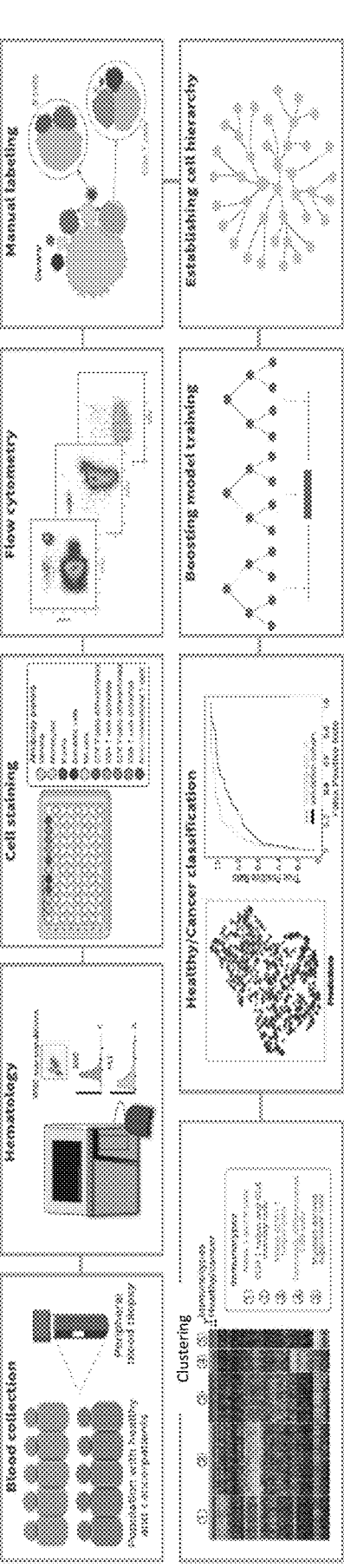
FIG. 10A shows a schematic depicting an example of an immunoprofiling pipeline, according to some embodiments of the technology as described herein.
Figure 10B:
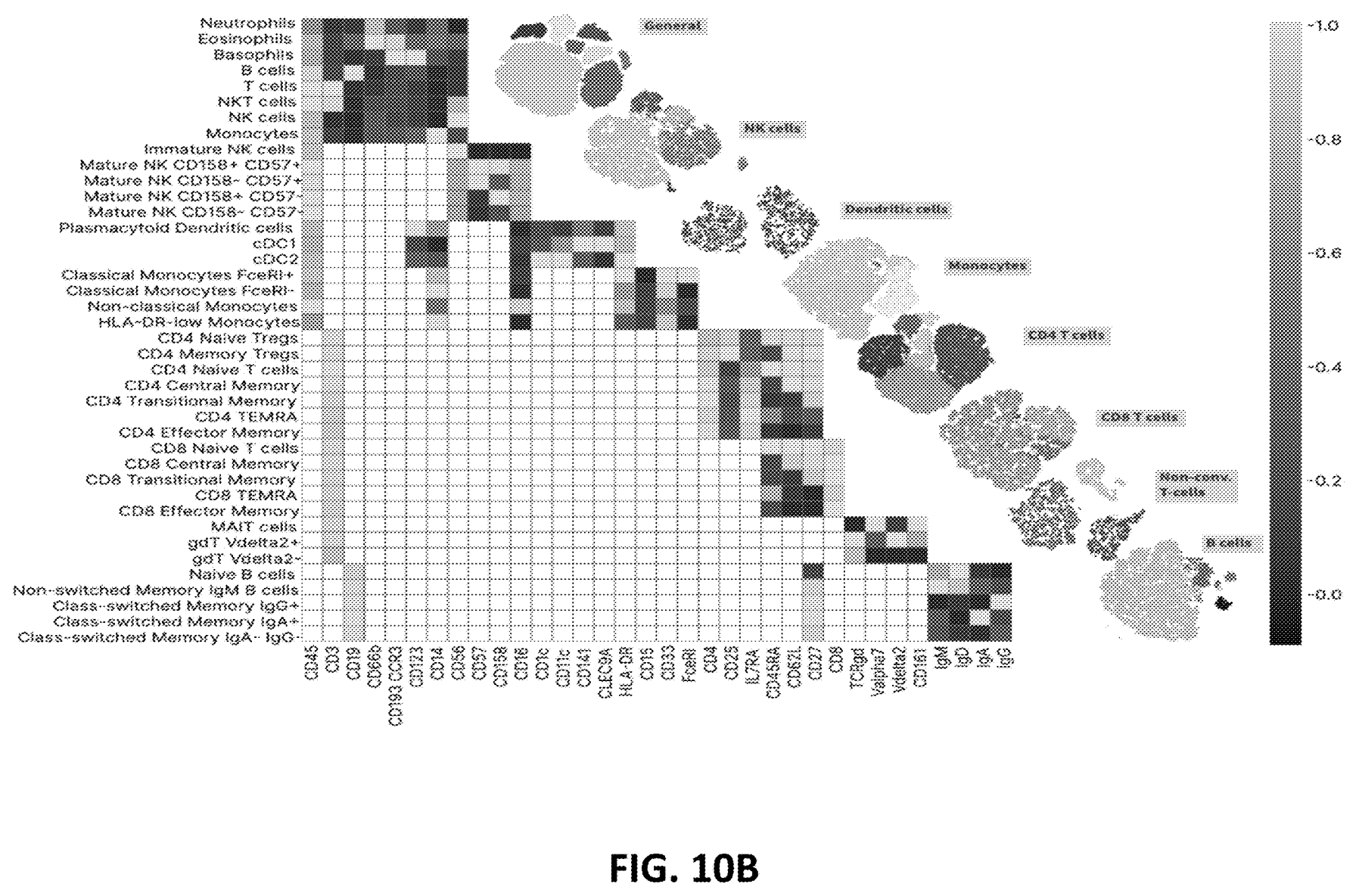
Figure 11A:
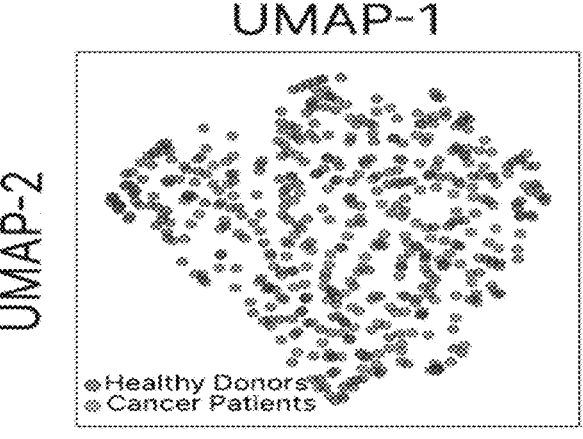
FIGS. 11A-11D show representative data relating to prediction of healthy and cancer samples using a machine learning (ML) classifier, according to some embodiments of the technology described herein.
Figure 11B:
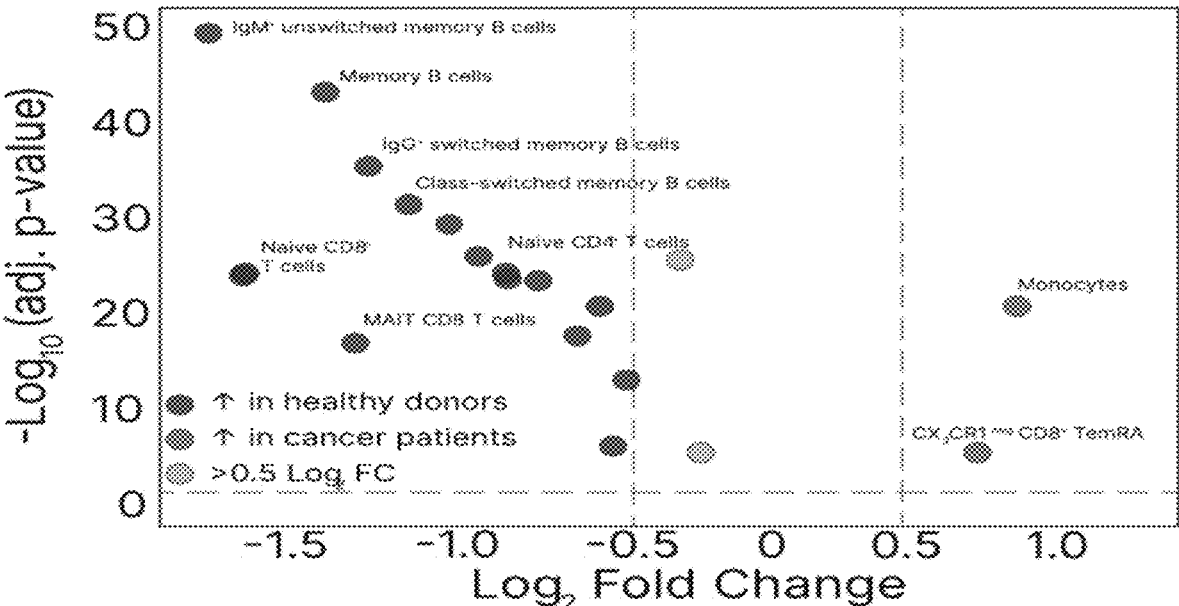
Figure 11C:
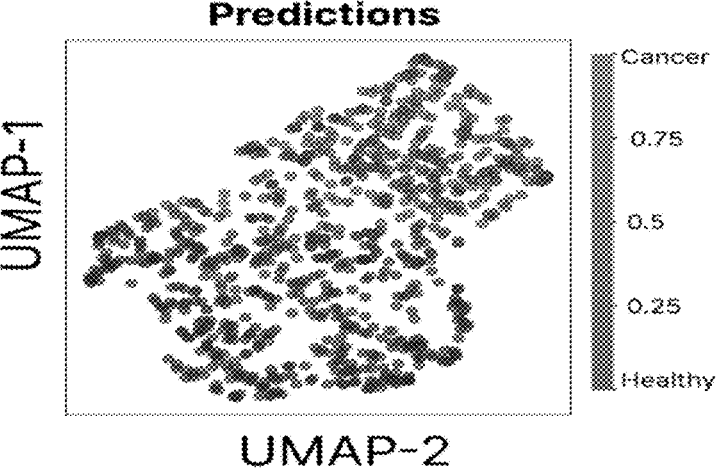
Figure 11D:
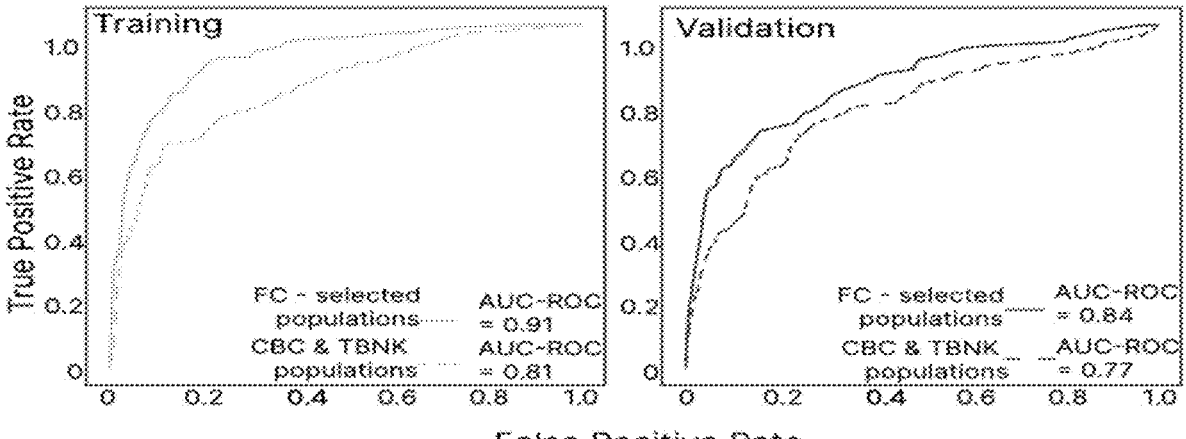
Figure 12A:
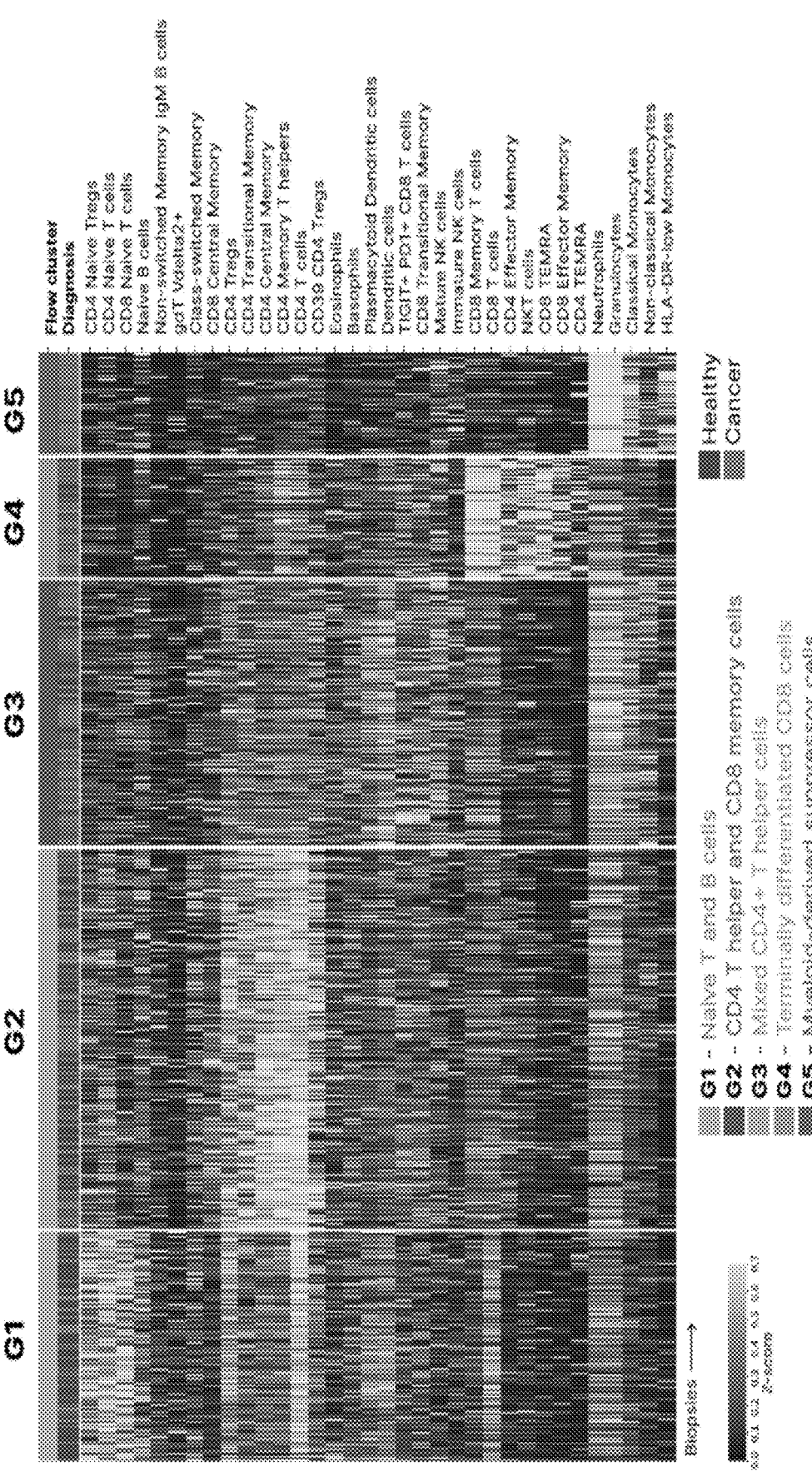
FIGS. 12A-12D show representative data for leukocyte signature clustering, according to some embodiments of the technology described herein.
Figure 12B:
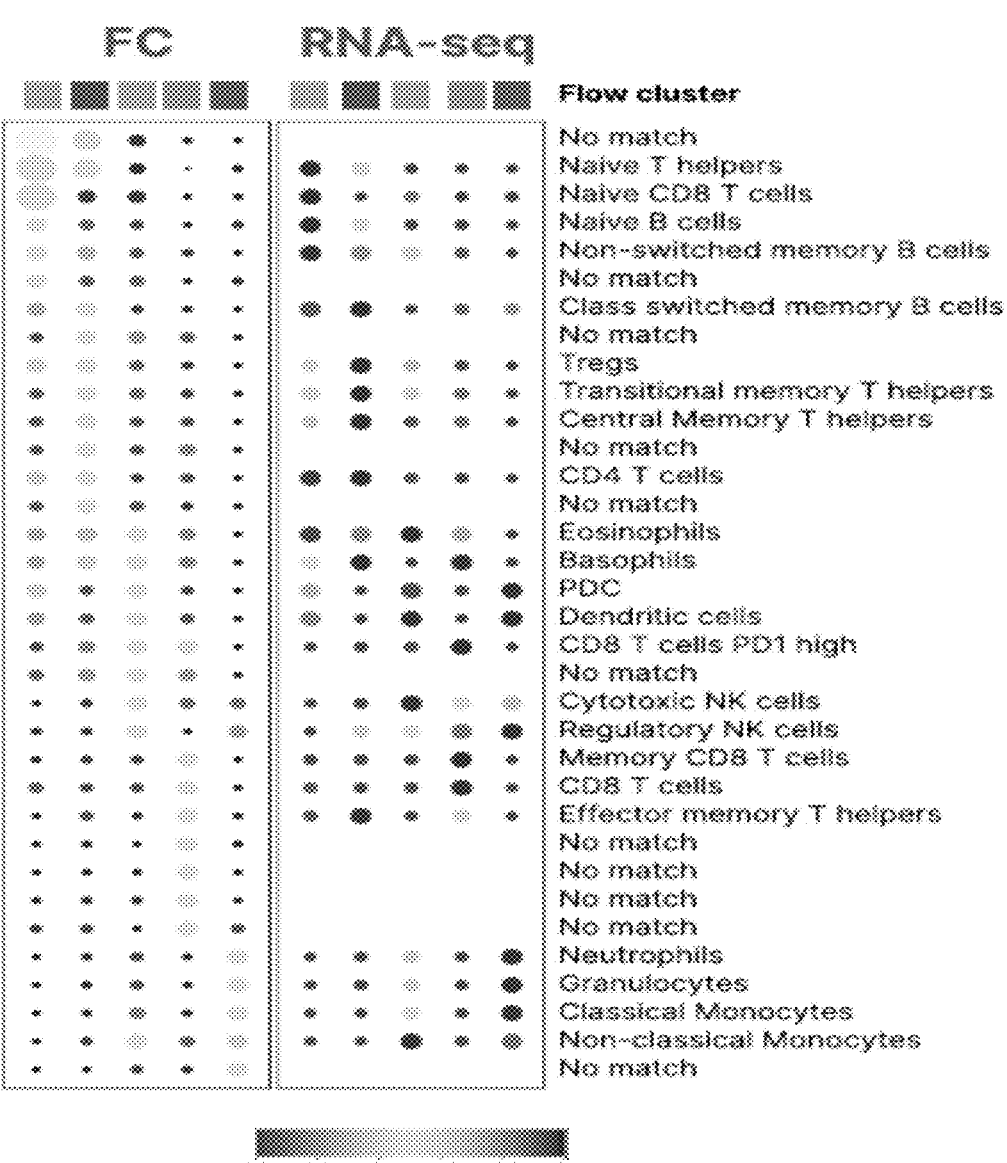
Figure 12C:
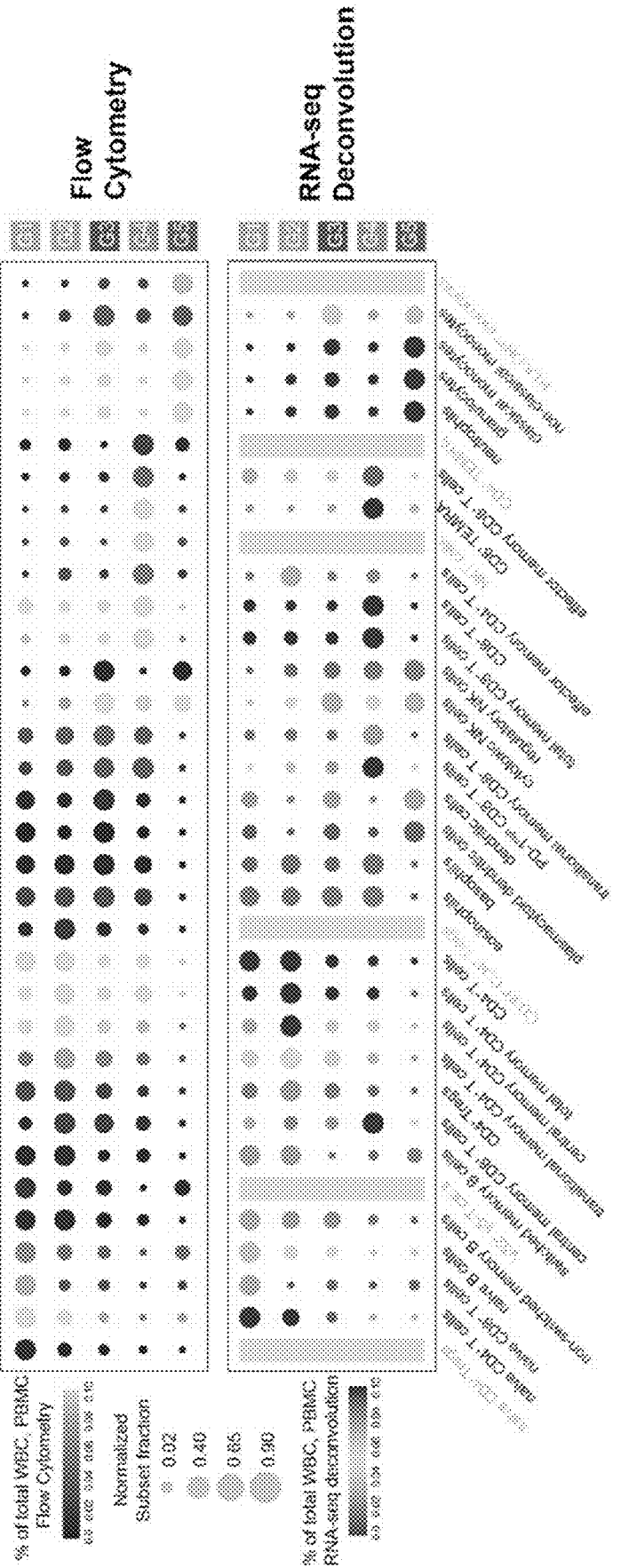
Figure 12D:
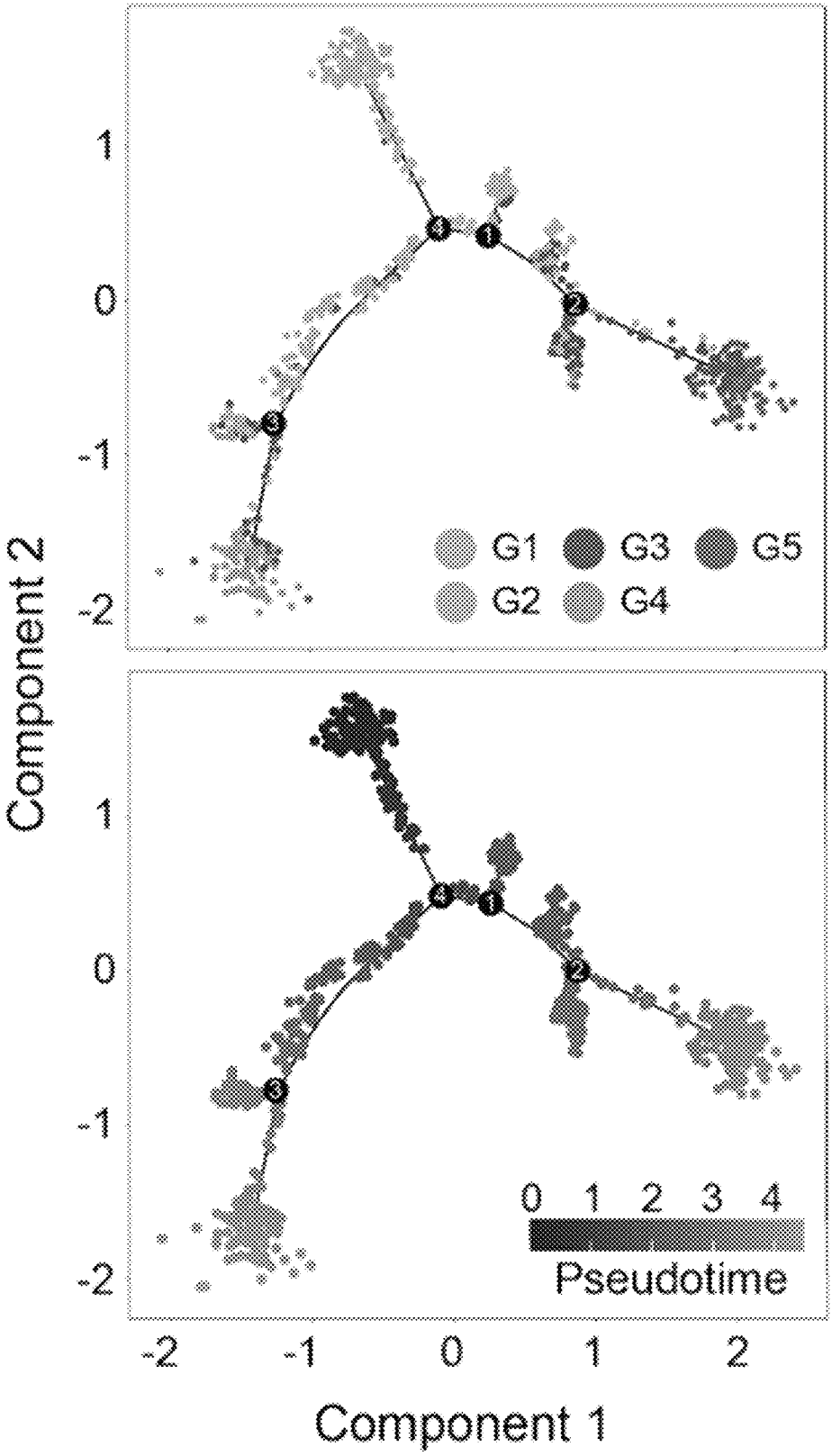

FIG. 10A shows a schematic depicting a representative example immunoprofiling pipeline. Peripheral blood samples of 442 cancer patients with differing diagnoses and of 408 healthy donors were collected from multiple centers. White blood cells (WBC) were isolated, stained with custom antibody panels in 96-well plates, and processed by multi-parameter flow cytometry (n=850). Each panel was labeled manually to then determine the percentages of cell populations (e.g., cell types set forth in Table 2). A machine-learning model was developed to classify healthy and cancer groups and refined to stratify immune profiles. FIG. 10B shows representative data for cytometry panels of cell populations shown as heatmaps of normalized signal intensities and tSNEs of immune cell populations.

Supervised manual gating analysis of flow cytometry data from a cohort of 50 healthy donors identified 415 cell types. Analysis of additional cancer samples led identified 650 cell types and immune activation states that were used to train and independently validate machine learning (ML) models to automatically identify immune cell subsets from raw cytometry data. Using the Max-Relevance and Min-Redundancy (MRMR) algorithm with stepwise leave-one-out cross-validation to identify cell populations that were the most significantly different between healthy donors and cancer patients, 20 significant features were selected from the flow cytometry data to distinguish between healthy donors and cancer patients. In another analysis, a Boruta feature selection algorithm (see e.g., M Kursa and W. Rudnicki, "Feature Selection with the Boruta Package", Journal of Statistical Software, vol. 36, issue 11, 2010) was used to select 78 significant features to distinguish between healthy donors and cancer patients, and a Random Forest model was further refined using spectral clustering with bootstrapping to identify immune profiles, and cluster stability was measured with Jaccard Index metrics.

The developed machine-learning classification models can differentiate between healthy individuals and cancer patients from flow cytometry analysis of peripheral blood samples (FIGS. 11A-11D).

The flow cytometry data was later analyzed with usage of spectral clustering and immune cell heterogeneity in the peripheral blood of individuals was grouped into five (5) leukocyte immunoprofile types, each characterized by specific physiological immune programs and supported by transcriptomic analysis. A brief description of the clusters is as follows:

Cluster 1 (Naïve T and B lymphocytes cluster or "Naïve" cluster; also referred to in this example as "G1"). This cluster is characterized by an increased number of Naïve CD4, CD8 and B cells, relative to the other clusters.

Cluster 2 (CD4+ T cells cluster or "Primed" cluster; also referred to in this example as "G2"). This cluster is characterized by an increased number of T-helper memory cells, including CD4 central memory, relative to the other clusters.

Cluster 3 (CD4+CD8+ T cell cluster or "Progressive" cluster; also referred to in this example as "G3"). This cluster is characterized by an increased number of CD4 and CD8 memory cells, increased dendritic cells, NK cells and high increase in CD8 transitional memory cells, relative to the other clusters.

Cluster 4 (CD8+ T cells cluster or "Chronic" cluster; also referred to in this example as "G4"). This cluster is characterized by an increased number of CD8 memory, increased number of effector memory cells re-expressing CD45RA (TEMRA), and effector cells as well as the NKT cell population, relative to the other clusters.

Cluster 5 (Myeloid derived suppressor/NK cell cluster or "Suppressive" cluster; also referred to in this example as "G5"). This cluster is characterized by an increased number of myeloid cell populations, including classical monocytes and neutrophils, relative to the other clusters.

The clusters may also be described statistically, as shown in Tables 8-10 below, which show, the 25%, 50% (median), and 75% quantiles for each of the five clusters for each of the cell types.

TABLE 8

| | G1 (Naïve) 25% | G2 (Primed) 25% | G3 (Progressive) 25% | G4 (Chronic) 25% | G5 (Suppressive) 25% |
|---|---|---|---|---|---|
| CD4 T cells | 0.516809 | 0.587592 | 0.27119 | 0.261428 | 0.077586 |
| CD4 Naïve T cells | 0.461229 | 0.225648 | 0.122336 | 0.055161 | 0.063215 |
| CD4 Naïve Tregs | 0.315621 | 0.167623 | 0.094701 | 0.052802 | 0.021256 |
| CD4 Memory T helpers | 0.240765 | 0.547057 | 0.262 | 0.330802 | 0.07266 |
| CD4 Effector Memory | 0.053214 | 0.131542 | 0.087894 | 0.287602 | 0.049874 |
| CD4 Central Memory | 0.246429 | 0.484443 | 0.221505 | 0.188642 | 0.064234 |
| CD4 TEMRA | 0.014031 | 0.021267 | 0.010106 | 0.078115 | 0.011735 |
| CD8 T cells | 0.328793 | 0.223175 | 0.182001 | 0.583353 | 0.062078 |
| CD8 Naïve T cells | 0.384364 | 0.086982 | 0.075898 | 0.042453 | 0.044037 |
| CD8 Memory T cells | 0.13253 | 0.19558 | 0.170497 | 0.630207 | 0.054764 |
| CD8 Transitional Memory | 0.138353 | 0.205539 | 0.214316 | 0.191516 | 0.051869 |
| CD8 Central Memory | 0.107956 | 0.175376 | 0.124022 | 0.122984 | 0.030678 |
| CD8 Effector Memory | 0.044591 | 0.064165 | 0.06174 | 0.205876 | 0.02561 |
| CD8 TEMRA | 0.030362 | 0.033965 | 0.032092 | 0.45737 | 0.019798 |
| Non-switched Memory IgM B cells | 0.124961 | 0.083798 | 0.040423 | 0.020677 | 0.021477 |
| Class-switched Memory | 0.145021 | 0.161367 | 0.071409 | 0.054709 | 0.065685 |
| Naïve B cells | 0.230684 | 0.187741 | 0.125653 | 0.072578 | 0.103146 |
| Classical Monocytes | 0.149244 | 0.1827 | 0.320377 | 0.154462 | 0.391395 |
| Non-classical Monocytes | 0.093421 | 0.125546 | 0.220434 | 0.132087 | 0.122624 |
| Mature NK cells | 0.099844 | 0.142419 | 0.222068 | 0.162549 | 0.144145 |
| Immature NK cells | 0.10621 | 0.09467 | 0.1418 | 0.072917 | 0.075758 |
| Dendritic cells | 0.320098 | 0.220471 | 0.32289 | 0.183333 | 0.039343 |
| Plasmacytoid Dendritic cells | 0.24047 | 0.157613 | 0.221469 | 0.126741 | 0.033319 |
| NKT cells | 0.083531 | 0.076961 | 0.073639 | 0.387684 | 0.04147 |
| Granulocytes | 0.247181 | 0.303666 | 0.429831 | 0.239702 | 0.789608 |
| Neutrophils | 0.240015 | 0.310561 | 0.398834 | 0.25917 | 0.771303 |
| Basophils | 0.177694 | 0.170987 | 0.214673 | 0.165205 | 0.044676 |
| Eosinophils | 0.106514 | 0.113121 | 0.139433 | 0.085996 | 0.005973 |
| CD4 Tregs | 0.367483 | 0.377588 | 0.244801 | 0.119928 | 0.053491 |
| CD4 Transitional Memory | 0.191683 | 0.352033 | 0.229838 | 0.160369 | 0.051402 |
| HLA DR low Monocytes | 0.02022 | 0.03144 | 0.049407 | 0.023268 | 0.23573 |
| TIGIT+ PD1+ CD8 T cells | 0.157494 | 0.207882 | 0.207871 | 0.186848 | 0.072178 |

TABLE 8-continued

|  | G1 (Naïve) 25% | G2 (Primed) 25% | G3 (Progressive) 25% | G4 (Chronic) 25% | G5 (Suppressive) 25% |
|---|---|---|---|---|---|
| CD39 CD4 Tregs | 0.220702 | 0.315876 | 0.194143 | 0.133377 | 0.124994 |
| gdT Vdelta2+ | 0.064997 | 0.034592 | 0.034595 | 0.022619 | 0.016564 |

TABLE 9

|  | G1 (Naïve) Median | G2 (Primed) Median | G3 (Progressive) Median | G4 (Chronic) Median | G5 (Suppressive) Median |
|---|---|---|---|---|---|
| CD4 T cells | 0.662711 | 0.685517 | 0.366451 | 0.413697 | 0.177509 |
| CD4 Naïve T cells | 0.556319 | 0.35091 | 0.224878 | 0.13328 | 0.130569 |
| CD4 Naïve Tregs | 0.501201 | 0.266506 | 0.190085 | 0.119554 | 0.075814 |
| CD4 Memory T helpers | 0.362402 | 0.648877 | 0.349596 | 0.488784 | 0.184368 |
| CD4 Effector Memory | 0.124962 | 0.243893 | 0.161168 | 0.460197 | 0.12102 |
| CD4 Central Memory | 0.335085 | 0.603169 | 0.323676 | 0.289721 | 0.147204 |
| CD4 TEMRA | 0.040028 | 0.048572 | 0.02456 | 0.208867 | 0.034468 |
| CD8 T cells | 0.467289 | 0.302725 | 0.332053 | 0.696135 | 0.136891 |
| CD8 Naïve T cells | 0.577479 | 0.184101 | 0.182589 | 0.092848 | 0.085994 |
| CD8 Memory T cells | 0.212876 | 0.288699 | 0.276308 | 0.753472 | 0.147294 |
| CD8 Transitional Memory | 0.256088 | 0.313295 | 0.340113 | 0.295304 | 0.135786 |
| CD8 Central Memory | 0.174808 | 0.296935 | 0.211254 | 0.204562 | 0.083402 |
| CD8 Effector Memory | 0.08312 | 0.108541 | 0.126585 | 0.463977 | 0.071121 |
| CD8 TEMRA | 0.075175 | 0.09858 | 0.073416 | 0.6324 | 0.079485 |
| Non-switched Memory IgM B cells | 0.195806 | 0.166557 | 0.125041 | 0.070817 | 0.056502 |
| Class-switched Memory | 0.256662 | 0.269578 | 0.173303 | 0.131577 | 0.135593 |
| Naïve B cells | 0.370449 | 0.298478 | 0.245035 | 0.213552 | 0.163953 |
| Classical Monocytes | 0.225279 | 0.252791 | 0.41498 | 0.269292 | 0.615564 |
| Non-classical Monocytes | 0.144156 | 0.204433 | 0.31591 | 0.238835 | 0.279489 |
| Mature NK cells | 0.176443 | 0.233585 | 0.401355 | 0.254386 | 0.301891 |
| Immature NK cells | 0.17347 | 0.167108 | 0.22399 | 0.157168 | 0.186185 |
| Dendritic cells | 0.437941 | 0.330493 | 0.480443 | 0.316261 | 0.157078 |
| Plasmacytoid Dendritic cells | 0.353953 | 0.254119 | 0.378514 | 0.234899 | 0.121252 |
| NKT cells | 0.171432 | 0.175771 | 0.129615 | 0.539552 | 0.129261 |
| Granulocytes | 0.382618 | 0.449489 | 0.561927 | 0.4229 | 0.850685 |
| Neutrophils | 0.387406 | 0.433641 | 0.529458 | 0.40581 | 0.830025 |
| Basophils | 0.262712 | 0.270411 | 0.301113 | 0.248018 | 0.112651 |
| Eosinophils | 0.20403 | 0.215491 | 0.242424 | 0.192835 | 0.066675 |
| CD4 Tregs | 0.492833 | 0.525276 | 0.366742 | 0.218896 | 0.163226 |
| CD4 Transitional Memory | 0.298263 | 0.497258 | 0.321826 | 0.255247 | 0.151531 |
| HLA DR low Monocytes | 0.065281 | 0.07846 | 0.125353 | 0.067239 | 0.477165 |
| TIGIT+ PD1+ CD8 T cells | 0.240903 | 0.306068 | 0.333351 | 0.342234 | 0.148581 |
| CD39 CD4 Tregs | 0.371016 | 0.520242 | 0.372921 | 0.296799 | 0.200762 |
| gdT Vdelta2+ | 0.140606 | 0.083826 | 0.088897 | 0.054894 | 0.050277 |

TABLE 10

|  | G1 (Naïve) 75% | G2 (Primed) 75% | G3 (Progressive) 75% | G4 (Chronic) 75% | G5 (Suppressive) 75% |
|---|---|---|---|---|---|
| CD4 T cells | 0.788032 | 0.786622 | 0.463021 | 0.564684 | 0.366608 |
| CD4 Naïve T cells | 0.741686 | 0.461062 | 0.327475 | 0.260051 | 0.375022 |
| CD4 Naïve Tregs | 0.764426 | 0.408182 | 0.288943 | 0.241674 | 0.185199 |

TABLE 10-continued

| | G1 (Naïve) 75% | G2 (Primed) 75% | G3 (Progressive) 75% | G4 (Chronic) 75% | G5 (Suppressive) 75% |
|---|---|---|---|---|---|
| CD4 Memory T helpers | 0.465098 | 0.761053 | 0.45632 | 0.655063 | 0.295012 |
| CD4 Effector Memory | 0.208899 | 0.378299 | 0.251368 | 0.772331 | 0.27798 |
| CD4 Central Memory | 0.466527 | 0.746517 | 0.437682 | 0.411724 | 0.223683 |
| CD4 TEMRA | 0.131756 | 0.220494 | 0.058863 | 0.639782 | 0.143112 |
| CD8 T cells | 0.589538 | 0.468197 | 0.48603 | 0.904461 | 0.352648 |
| CD8 Naïve T cells | 0.78544 | 0.323442 | 0.319262 | 0.170799 | 0.192921 |
| CD8 Memory T cells | 0.320078 | 0.409544 | 0.455537 | 0.915129 | 0.286708 |
| CD8 Transitional Memory | 0.415027 | 0.441222 | 0.5326 | 0.450074 | 0.244854 |
| CD8 Central Memory | 0.263697 | 0.444168 | 0.354911 | 0.280339 | 0.16354 |
| CD8 Effector Memory | 0.160068 | 0.198665 | 0.227355 | 0.809943 | 0.127967 |
| CD8 TEMRA | 0.176336 | 0.230469 | 0.21788 | 0.907577 | 0.221438 |
| Non-switched Memory IgM B cells | 0.307385 | 0.267483 | 0.227953 | 0.149117 | 0.14205 |
| Class-switched Memory | 0.42331 | 0.464562 | 0.289808 | 0.246844 | 0.248892 |
| Naïve B cells | 0.571189 | 0.43868 | 0.406178 | 0.360336 | 0.335013 |
| Classical Monocytes | 0.303541 | 0.362069 | 0.559735 | 0.365677 | 0.863046 |
| Non-classical Monocytes | 0.252922 | 0.299484 | 0.495174 | 0.390367 | 0.575074 |
| Mature NK cells | 0.326604 | 0.380774 | 0.617431 | 0.501855 | 0.440678 |
| Immature NK cells | 0.26615 | 0.274601 | 0.364978 | 0.262244 | 0.360084 |
| Dendritic cells | 0.551467 | 0.424051 | 0.646407 | 0.434698 | 0.306728 |
| Plasmacytoid Dendritic cells | 0.521473 | 0.349518 | 0.568588 | 0.380915 | 0.2793 |
| NKT cells | 0.264899 | 0.343661 | 0.256366 | 0.866944 | 0.344584 |
| Granulocytes | 0.517676 | 0.595496 | 0.685545 | 0.57367 | 0.991513 |
| Neutrophils | 0.52906 | 0.572942 | 0.656846 | 0.579071 | 0.988562 |
| Basophils | 0.396037 | 0.432851 | 0.431055 | 0.353198 | 0.207963 |
| Eosinophils | 0.333206 | 0.366476 | 0.423774 | 0.333555 | 0.155757 |
| CD4 Tregs | 0.663132 | 0.668141 | 0.478286 | 0.394052 | 0.306773 |
| CD4 Transitional Memory | 0.453336 | 0.648222 | 0.476315 | 0.372905 | 0.282151 |
| HLA DR low Monocytes | 0.140713 | 0.16051 | 0.304512 | 0.217529 | 0.882418 |
| TIGIT+ PD1+ CD8 T cells | 0.351118 | 0.425046 | 0.545905 | 0.51332 | 0.273978 |
| CD39 CD4 Tregs | 0.483579 | 0.682502 | 0.489588 | 0.389691 | 0.367768 |
| gdT Vdelta2+ | 0.28449 | 0.186779 | 0.200473 | 0.103883 | 0.126101 |

Figure 13A:
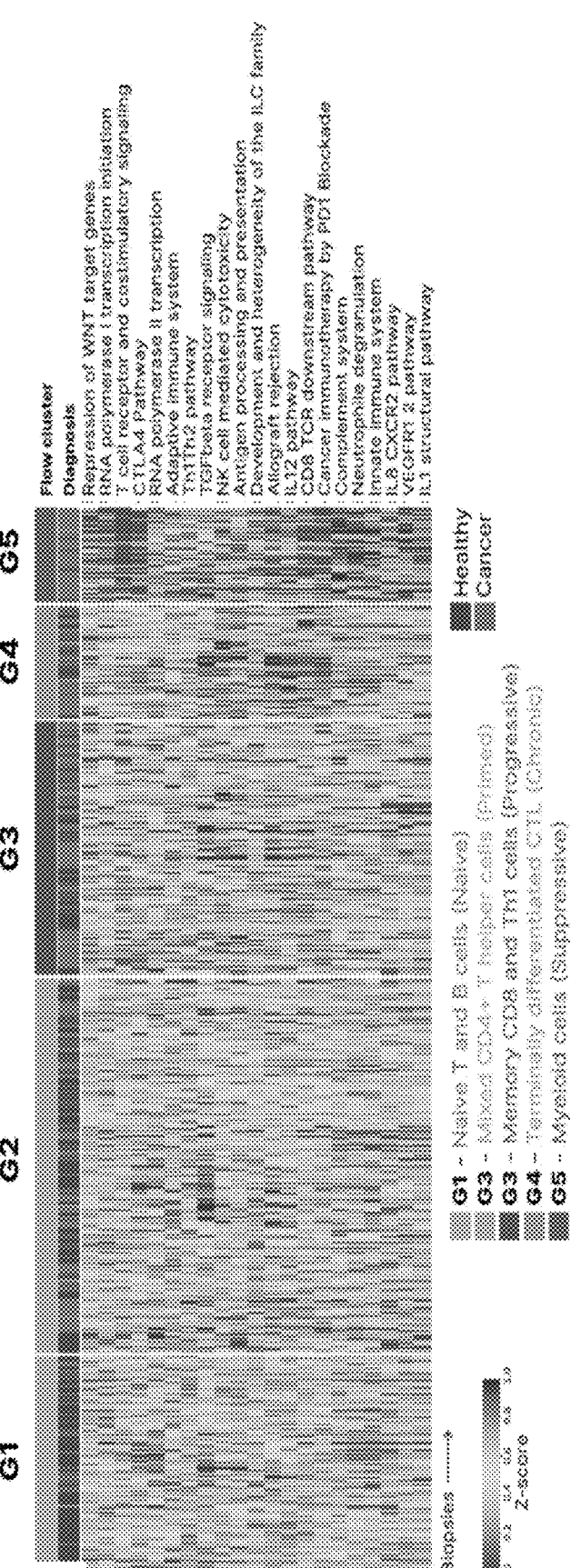
Figure 13B:
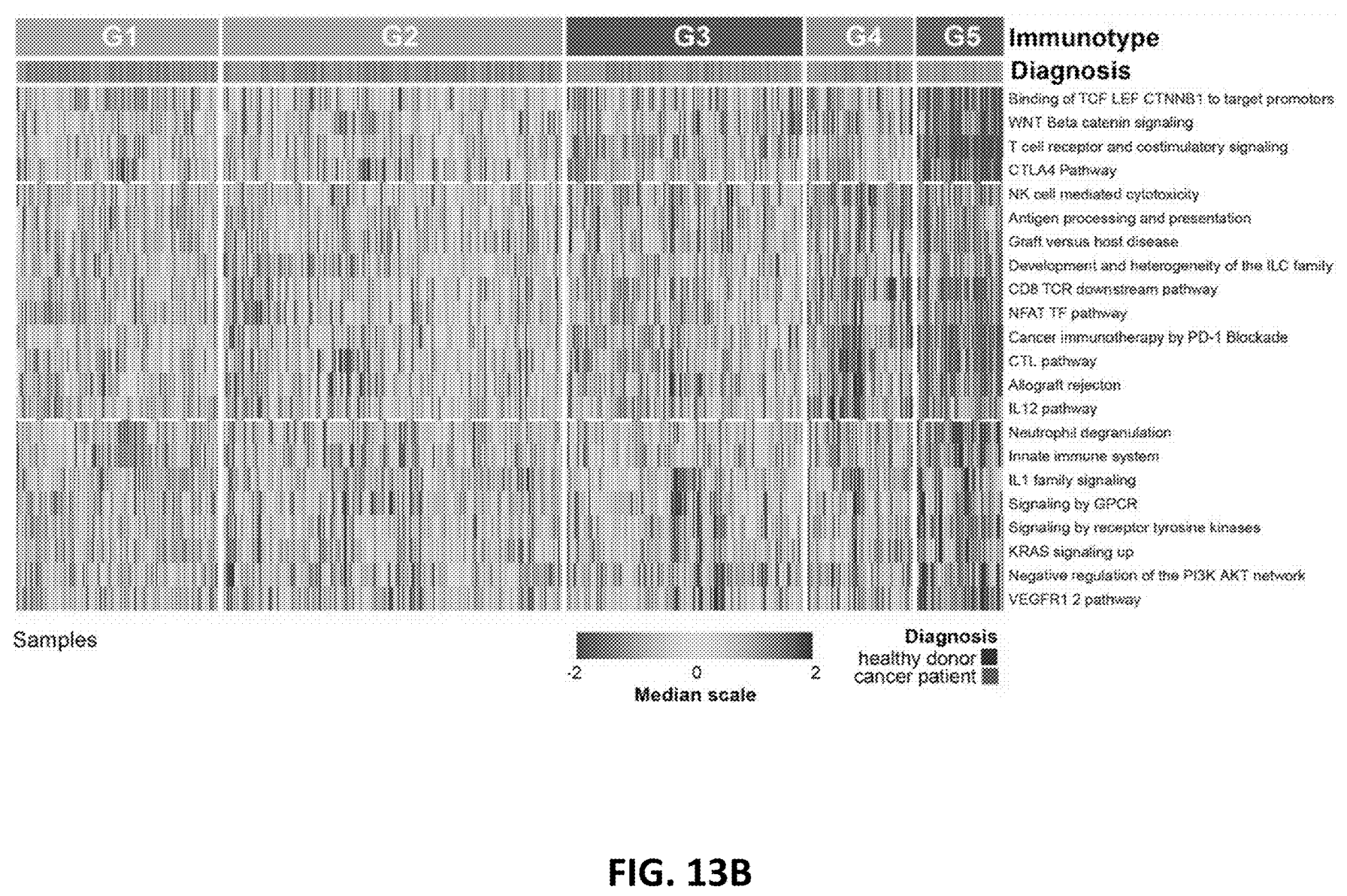
Figure 13C:
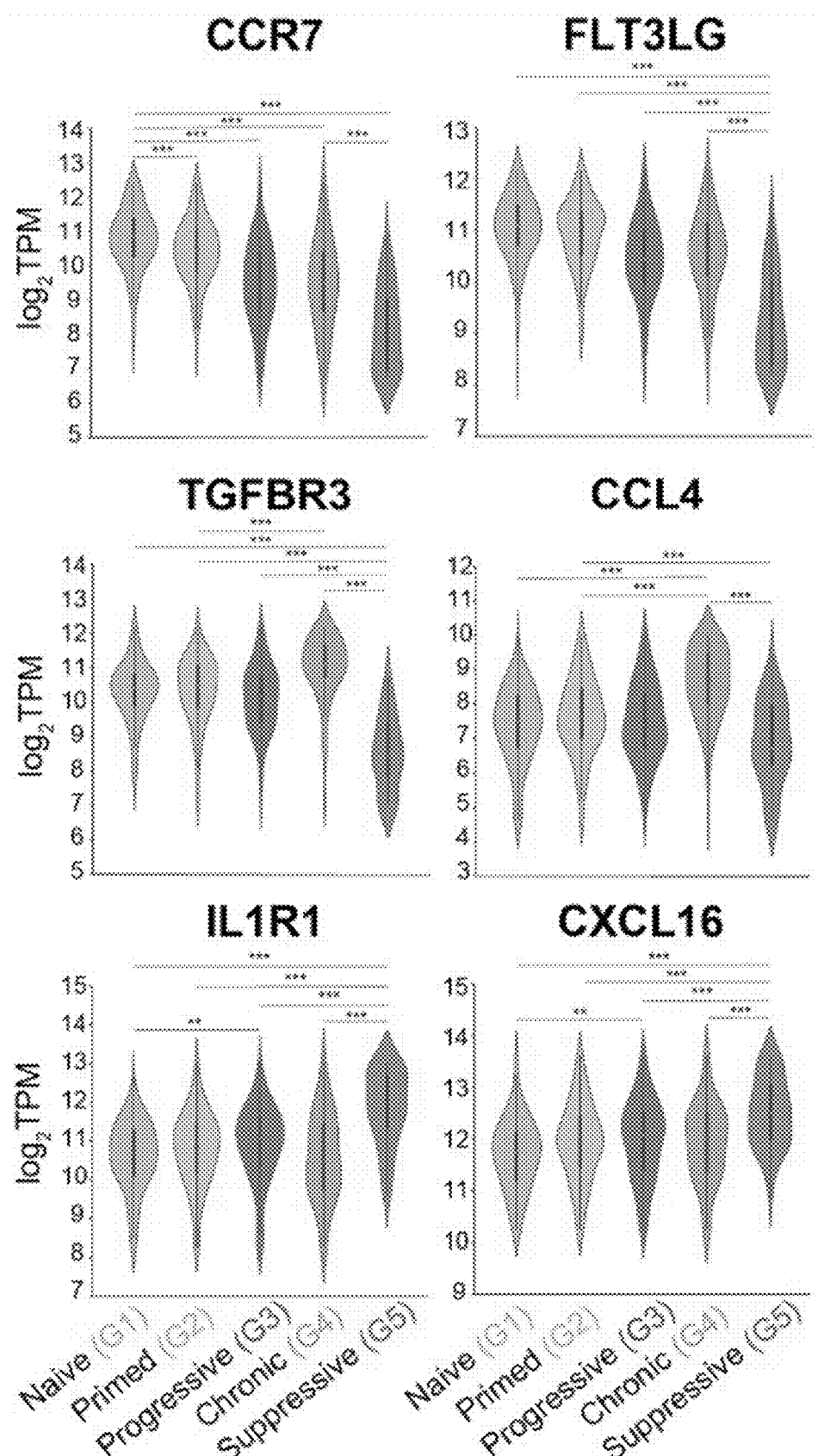

The first cluster, G1, was enriched by B and T Naïve cell populations; G2 with CD4 T helper memory subsets and CD4 Tregs; G3 with CD8 transitional memory T cells, dendritic cells, TIGIT and PD1-positive CD8 T cells; G4 with CD4/CD8 effector and TEMRA cells; and G5 was highly enriched in classical/non-classical monocytes, HLA-DR low monocytes, and neutrophils. The healthy-to-cancer ratio was the lowest in G1 cluster and is highest in G5, indicating its relevance as a characteristic of an individual's immune status (FIGS. 12A-12D). FIGS. 13A-13C show representative data indicating cytokine pathways are differentially expressed in leukocyte immunoprofile types. FIGS. 13A-13B show representative heatmaps indicating correlations between functional gene signatures from MSigDB database for cytokine-related pathways were found with leukocyte immunoprofile types G1-G5. The health status for each patient is also shown. FIG. 13C shows representative data indicating comparison of differential gene expression levels of cytokine and chemokine genes, FLT3LG, CCL4, CXCL16, CCR7, TGFBR3 and ILIR1, the 5 leukocyte immunoprofile types.

Figure 14:
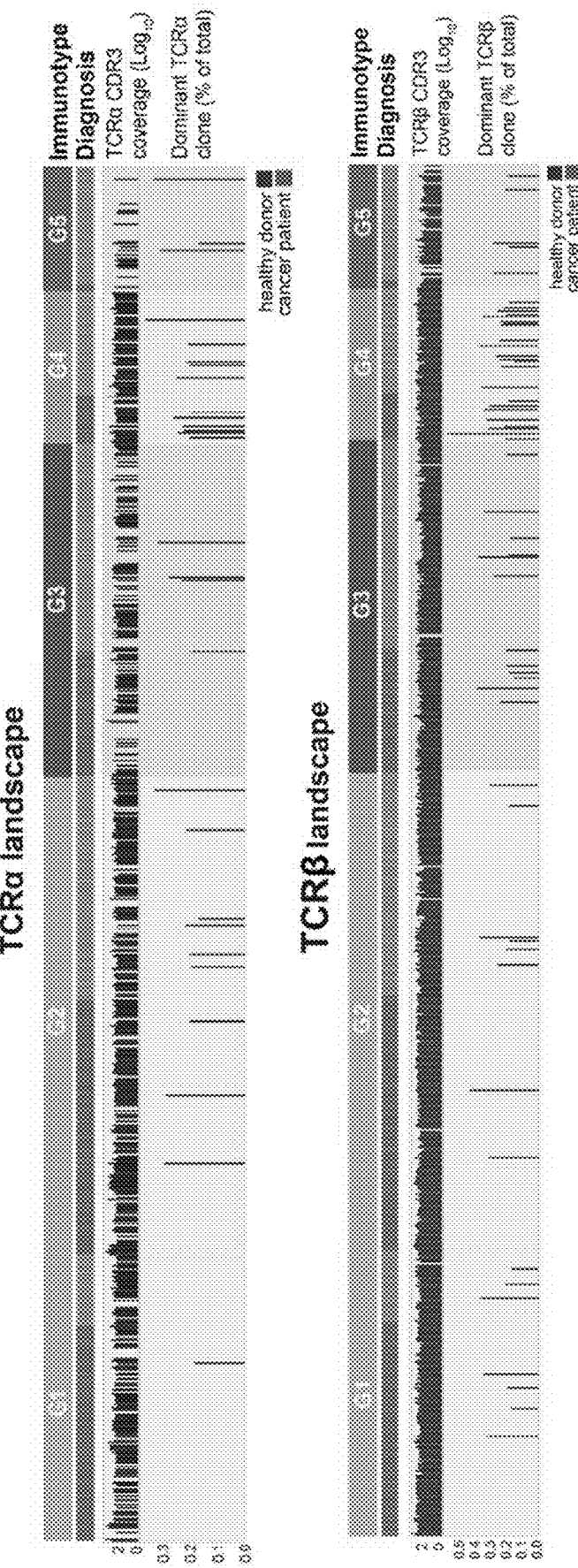
FIG. 14 shows representative data for TCR and BCR analysis of leukocyte immunoprofile types. Analysis of TCR (for both alpha and beta chains) landscape, stratified by leukocyte immunoprofile types (G1-G5) is shown, according to some embodiments of the technology described herein.

Evaluation of T cell receptor (TCR) and B cell receptor (BCR) content of leukocyte immunoprofile types was also performed. FIGS. 14A-14C show representative data for TCR and BCR analysis of PBC immunoprofile types. FIG. 14A shows a representative analysis of TCR (for both alpha and beta chains) landscape, stratified by PMBC immunoprofile types (G1-G5). FIG. 14B shows representative data for clonality and Chao1 indices for TCR beta chain. FIG. 14C shows a representative comparison of TCR analysis for blood and tumor RNA-seq data. The analysis of the distribution of HLA alleles of MHC I class indicated that the G2 (Primed) cluster was enriched with CD8+ T cells and showed a lower presence of HLA B in comparison with the other leukocyte immunoprofile types. Analysis of TCR landscape indicated that in the G2 (Primed) cluster, there were more samples with high fraction of the dominant clonotypes, for both chains a and B of TCR, relative to other leukocyte immunoprofile types.

Example 3

Recent advances in immune-based treatments for cancer demonstrate the need to further understand the molecular and cellular characteristics of an individual cancer patient's immune system. The lack of comprehensive diagnostics capable of describing the status of a patient's immune system is a major barrier in predicting and monitoring responses to immunotherapy. Here, a clinical immunoprofiling platform was developed to characterize the heterogencity of immune cells in the peripheral blood of healthy donors and patients with solid tumors. Robust cell populations that were differentially represented in these two groups were selected to train a machine learning (ML)-based classifier and identify groups or immunotypes with putative functional significance using unsupervised clustering. Five immunotypes were identified using flow cytometry that corresponded to immunological response states characterized by dominant cellular differentiation patterns. These observations were cross-validated using bulk RNAseq and T cell repertoire analysis to reveal conserved physiological states that can be easily interrogated from a single blood draw.

Human populations are genetically and developmentally diverse with immune systems that are shaped by a unique set of immunological challenges such as microbial exposure, metabolic changes, chronic diseases such as cancer, and aging. Regarding cancer, the immune system of each patient predisposes the patient's response to subsequent challenges and can critically inform how cancer patients will respond to various therapies, including immunotherapy. The success of immune checkpoint blockade (ICB) in cancer has been complicated by a lack of response in most patients. These treatments also produce immune-related adverse events (irAE) that often result in serious and life-long complications. Existing biomarkers such as PD-L1 expression by immunohistochemistry, microsatellite instability (MSI), DNA mismatch repair alterations (dMMR) and tumor mutational burden (TMB) obtained from the evaluation of tumor biopsies have only marginally improved response rates. Detailed investigation analysis of the tumor microenvironment (TME) that includes the analysis of tumor infiltrating T cells, inflammatory and immunosuppressive cell types, and different tissue microdomains have improved positive predictive value over these consensus biomarkers. However, beyond the TME, the contribution of the patient's immune system has not been factored into response prediction.

Surprisingly, there are no consensus methods for immune status evaluation. Many techniques that have been applied to this question favor reductionist approaches that considers individual cell populations one-at-a-time, but such methods often have confounding and biasing technical and natural variation. However, unbiased techniques, like single-cell RNAseq, are difficult to apply to large cohorts or individual patients in a clinical setting due to low throughput, high coefficients of variation, and considerable cost per sample.

This example describes a pan-cancer framework developed for patient stratification using an immunoprofiling assay based on flow cytometry using real-world samples from 408 healthy donors and 442 patients with solid tumors. Results show a comprehensive characterization of the immune system in the peripheral blood can be accomplished with flow cytometry. Using machine learning (ML) technology, a classification model capable of discriminating between healthy donors and solid cancer patients was developed with high accuracy. Five distinct immunotypes were identified using unsupervised clustering, each characterized by a different distribution of immune cell types and activation states, supported by paired bulk RNAseq analysis. Analysis of over 18,000 transcriptomes from PBMCs demonstrated that these clusters are highly conserved across different patient groups and diseases. These signatures were validated in a cohort of head and neck squamous cell carcinoma (HNSCC) treated with the PD-1 inhibitor nivolumab. In this cohort, objective responses were associated with an immunotype enriched in central and transitional memory CD4+ T cells, demonstrating the functional significance of this classification. Importantly, these characteristics represent functional meta-signatures that can be targeted for more effective immunotherapy selection. The identification of the tumor's immune profile or portrait, through an inexpensive blood test, is significantly associated with immunotherapy response and holds promise for effective patient stratification in clinical trials and treatment selection in a clinical setting.

Figure 16A:
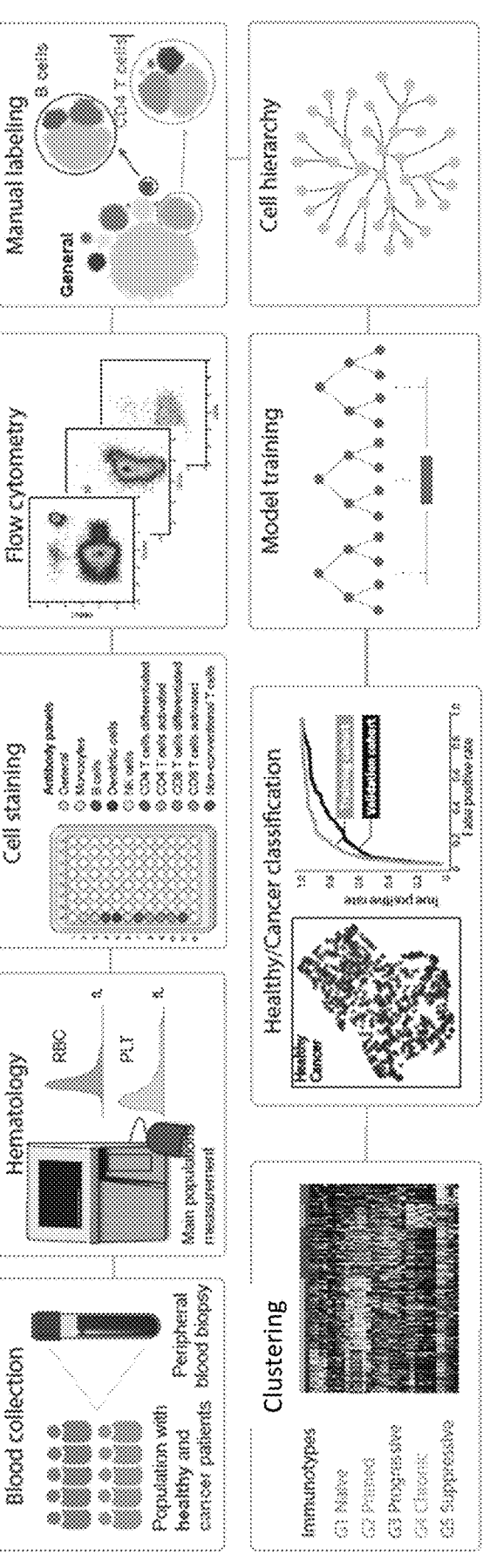
FIGS. 16A-16C show an overall description of one embodiment of a workflow cluster development, model training, cytometry data composition, and differences between healthy and cancer patients in the cytometry data, according to some embodiments of the technology described herein.
Figure 25:
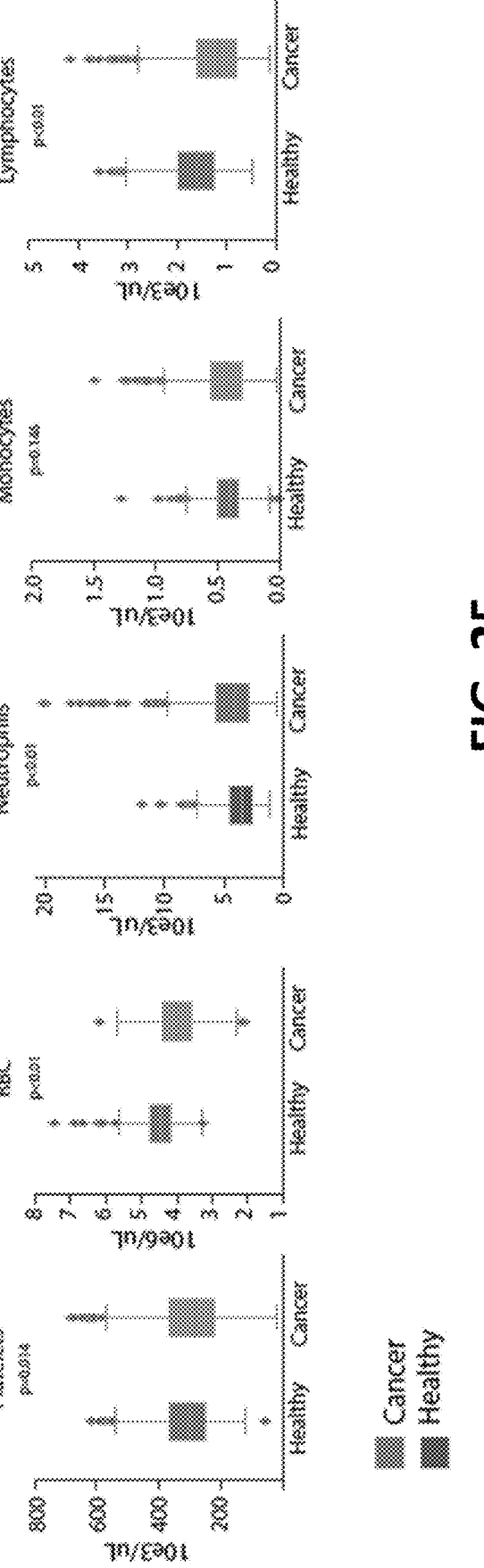
FIG. 25 shows absolute numbers of RBCs, platelets, neutrophils, and lymphocytes between healthy donors and cancer patients were significantly different, while the absolute number of monocytes were similar, according to some embodiments of the technology described herein.

Briefly, an immunoprofiling assay was developed using conventional flow cytometry on red blood cell (RBC)-depleted white blood cell (WBC) samples to evaluate the immune characteristics of cancer patients with a comprehensive pan-cancer analysis (FIG. 16A). This cohort represents a broad cross-section of patients with solid tumors and healthy donors (n=850). A clinical-grade end-to-end process was established, including steps for absolute quantification of blood cells using a standard hematology analyzer for complete blood count (CBC) analysis of whole blood (FIG. 16A). In agreement with published work, significant differences were observed with the absolute numbers of RBCs, platelets, neutrophils, and lymphocytes between healthy donors and cancer patients, while the absolute number of monocytes were similar (FIG. 25).

Figure 16B:
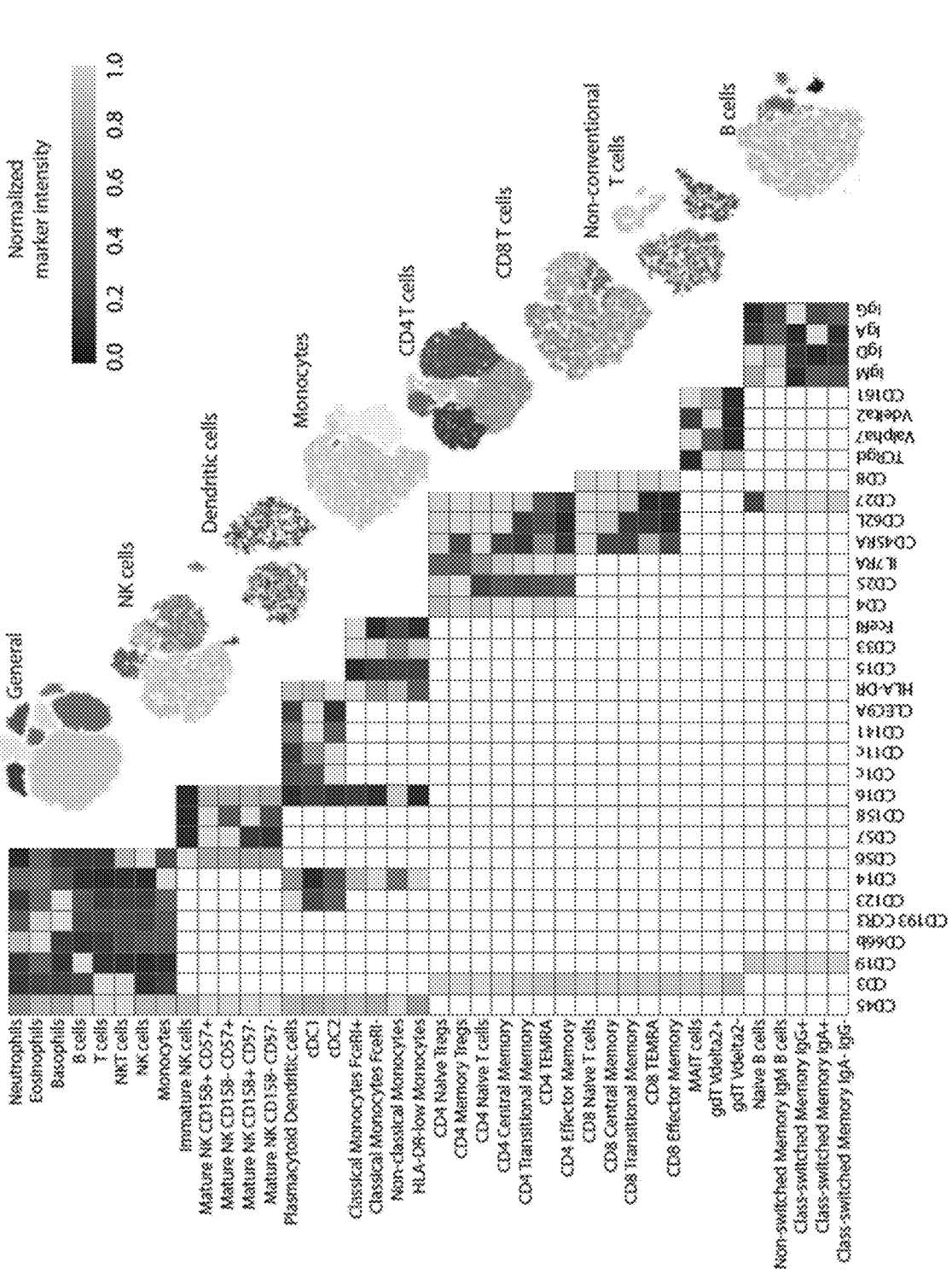

To ensure broad coverage of immune cell subpopulations across different immune cell lineages, a set of 10-overlapping antibody panels was developed, connected through a lineage backbone panel for quantitation of all CD45+ cells in the peripheral blood (Panel CP10—General, FIGS. 16A-16B). Multicolor flow cytometry was performed on the isolated WBCs stained with custom panels. Combination and alignment of those overlapping antibody panels allowed exhaustive cell typing, with cell-surface marker combinations assigned to each of different immune groups: NK cells, dendritic cells, monocytes, CD4 and CD8 T cells, nonconventional T cells and B-cells (FIG. 16B). Together, 650 cell types and immune activation states were differentiated based on surface markers combinations (FIG. 16B).

The manual analysis for cell typing defined an extensive hierarchy of cell types and subpopulations, which was then used to supervise the training of machine learning (ML) gradient boosting event type models to identify immune cell subsets reproducibly for each panel (FIG. 16A). The models for each panel accurately detected the various immune cell populations and activation states from peripheral blood by reproducing the manual supervised gating analysis in validation tests (F1-scores: 0.74-0.95, P4-metrics: 0.84-0.97, for the 10 panels).

Figure 16C:
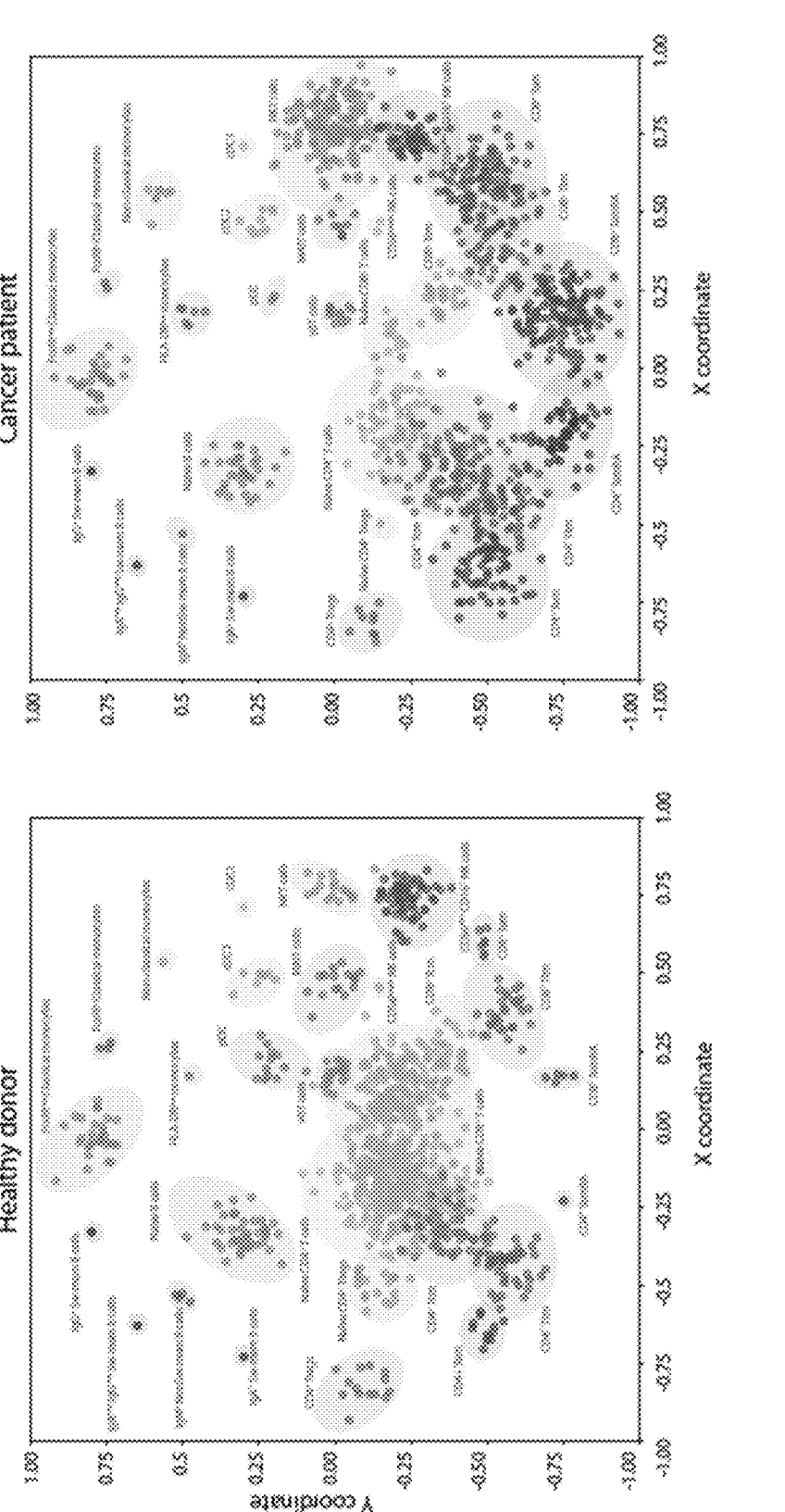

Preliminary comparisons between the peripheral blood of a healthy donor and a cancer patient showed several differences between the distribution of immune cell subsets, with striking differences in the frequencies of monocytes, Naïve, central memory and terminally-differentiated CD4+ and CD8+ T cells (FIG. 16C). This preliminary analysis, consistent with published reports, indicates that differences in overall immune cell composition between these two groups could be explored diagnostically in patients with solid tumors. Within this immunoprofiling flow cytometry-based platform, an ML-based classifier was developed to distinguish between healthy and cancer groups and refined the model to stratify immune profiles (FIG. 16A, FIG. 17, and FIG. 18).

To thoroughly analyze the immune status of cancer patients and distinguish features related specifically to tumorigenesis, independently of patient age, solid tumor type, and administered therapies, peripheral blood was collected from 408 healthy donors and 442 cancer patients aged 16 to 98 years old with 84 different solid tumor diagnoses within 7 major therapy groups (total n=850, FIGS. 17A and 17B, Supplementary cohort). Significant differences were previously shown between the peripheral blood samples of healthy donors and cancer patients, and between their immune cell composition analyzed with flow cytometry (FIG. 25, FIG. 16C). To accurately differentiate the content of immune cells in the peripheral blood of healthy donors from cancer patients, an ML-based classifier was developed.

The distribution of patients within the cohort was first evaluated relative to donor age, diagnosis, and therapy (FIG. 17C), using Uniform Manifold Approximation and Projections (UMAPs) to reduce the dimensionality of all 650 cytometry populations. The clusters defined by the absence or presence of cancer in patients, which also corresponded to age as healthy donors were generally younger than patients with solid tumors, revealed the greatest separation, whereas clusters based on diagnosis or treatment type were not distinguishable (FIG. 17C). Findings indicate that immune features differ between healthy donors and cancer patients, independently of specific cancer or treatment types.

Figure 17D:
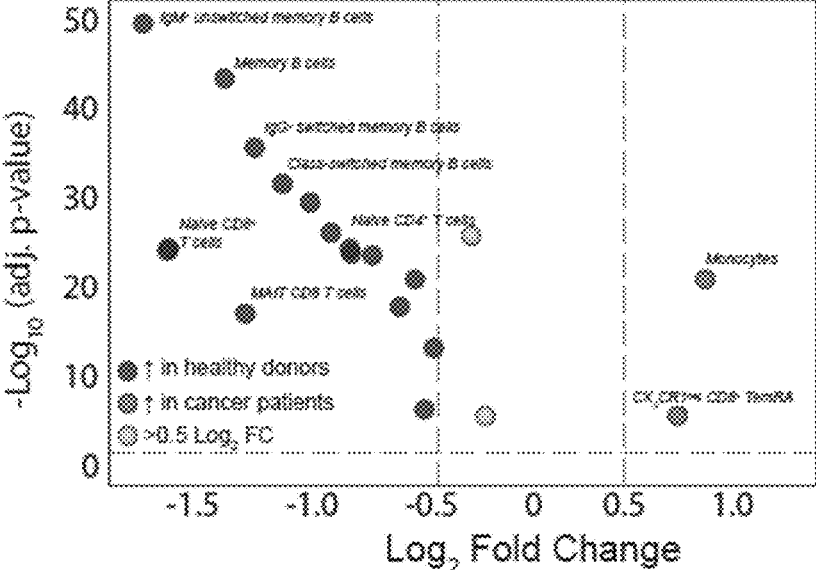
Figure 17E:
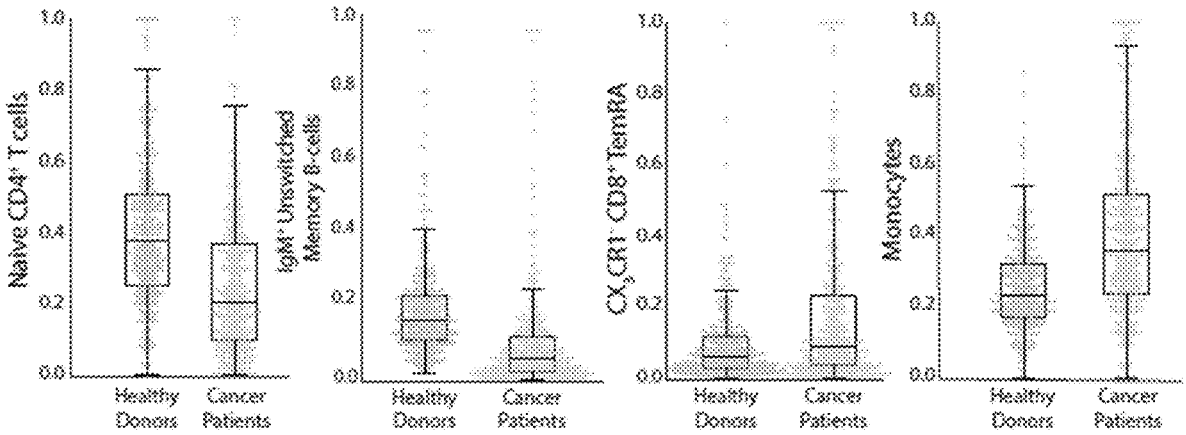
Figures 17F, 17G:
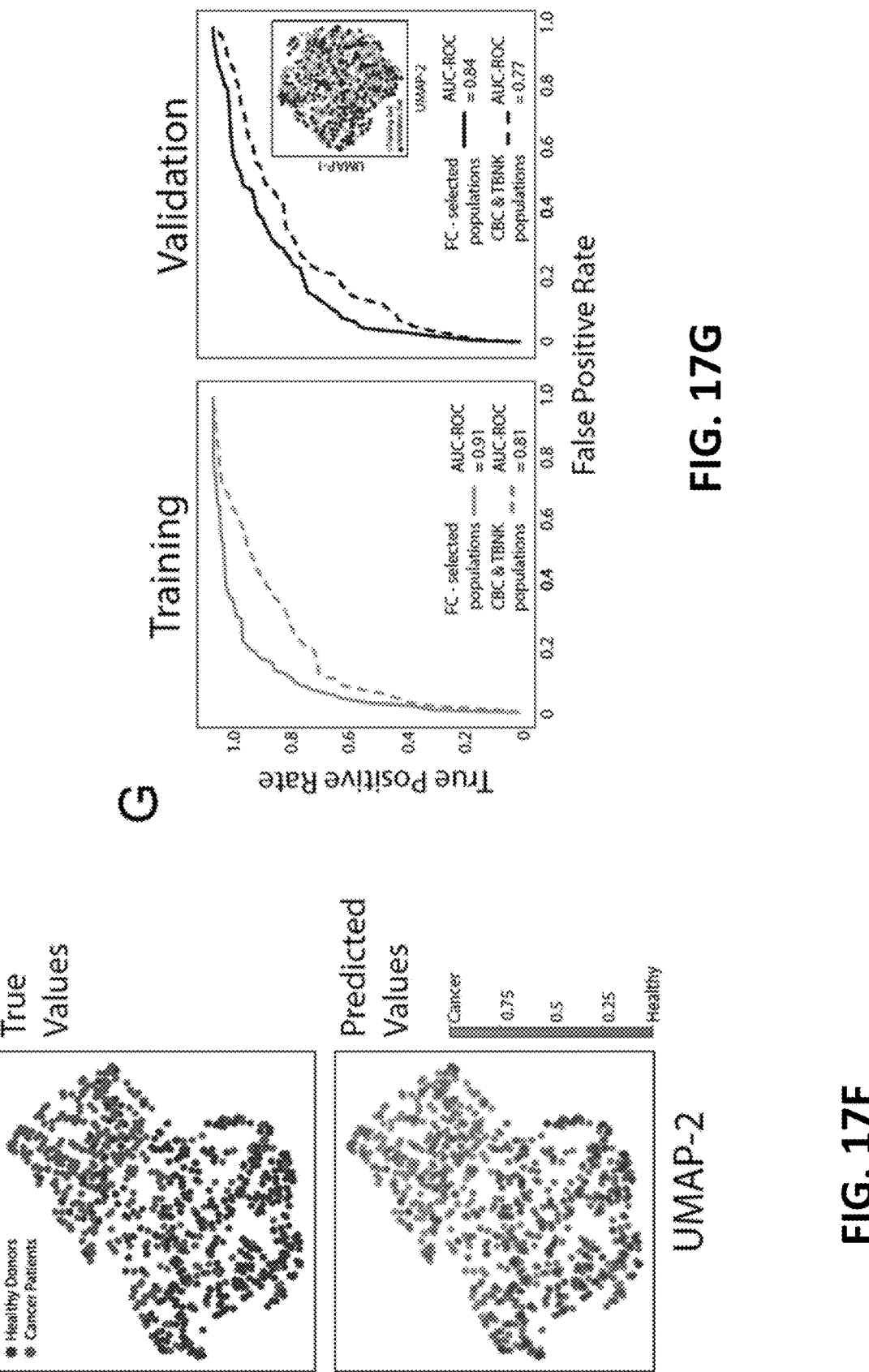

Twenty significantly different cell populations between the healthy donor and cancer patients were selected, using the Max-Relevance and Min-Redundancy (MRMR) algorithm with stepwise leave-one-out cross-validation (FIG. 17D, differentially distributed populations). Interestingly, these over- and under-represented cell populations contained Naïve CD4+ and CD8+ T cells, Naïve and memory B cells, and CD8+ TemRA and CD14+ classical monocytes respectively (FIG. 17E), which were highly significant between the two groups. The TabPFN-based (Hollman et al. 2022) classifier model was trained using the 20 selected populations as features on a set of 503 samples. The labels predicted by the classifier model (healthy or cancer) corresponded to the true labels, as observed in the gradient of healthy-cancer distribution of UMAPs on selected populations (FIG. 17F).

Figure 27A:
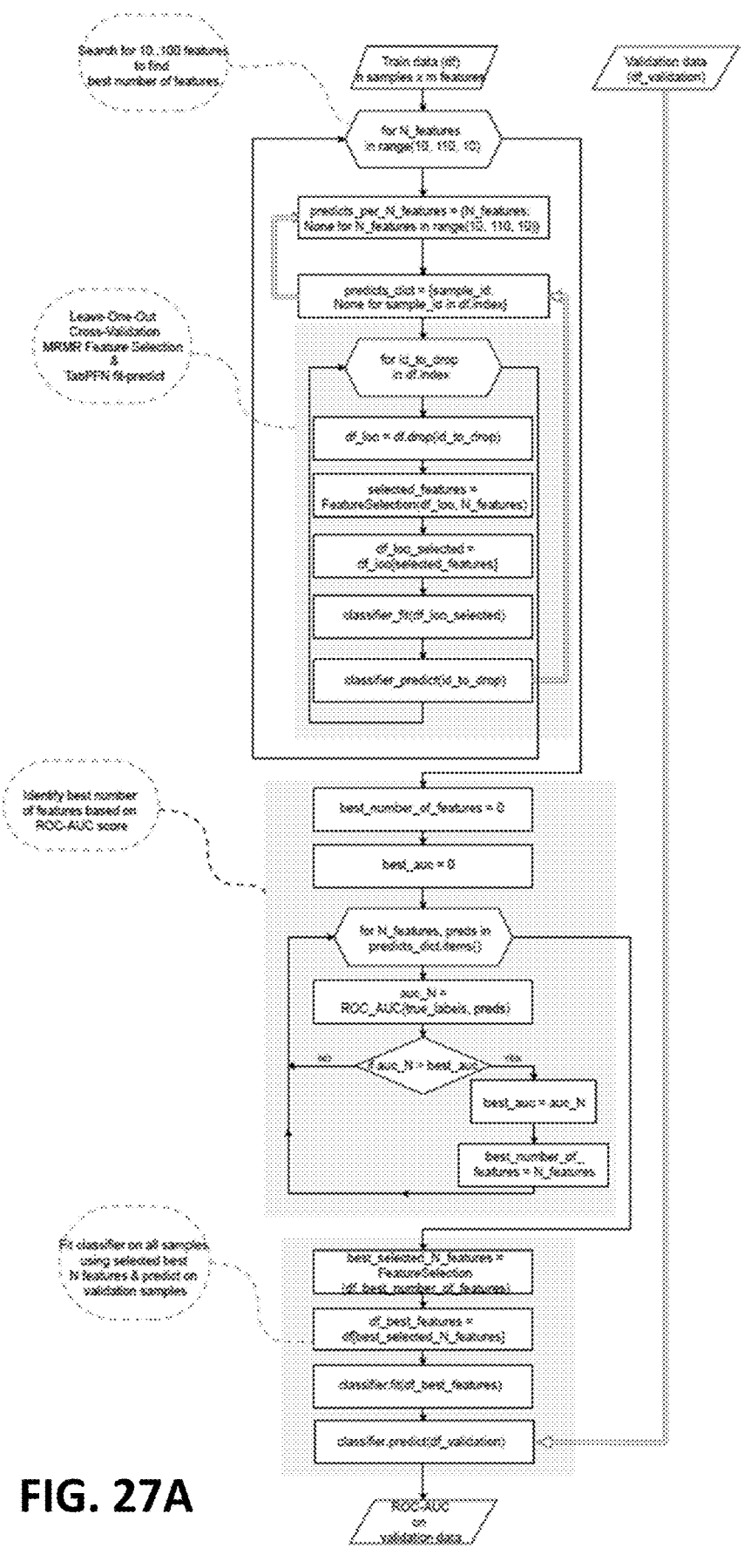
FIGS. 27A-27F show representative data for training and validation of a machine learning model for blood immunoprofile cluster identification, according to some embodiments of the technology described herein.
Figure 27B:
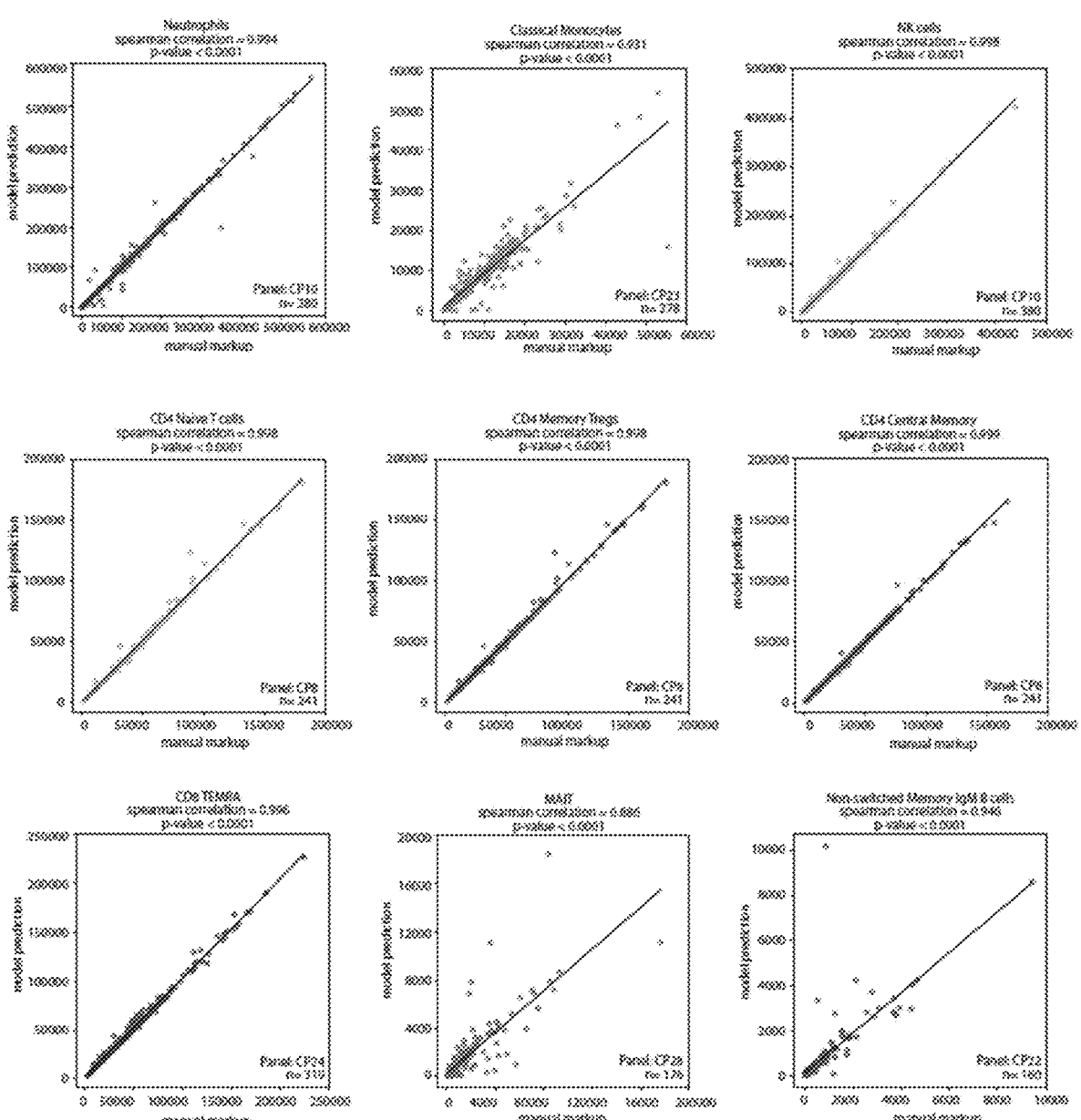

The classifier demonstrated a high performance in separating the healthy and cancer classes, assessed using leave-one-out cross validation on the training dataset (area under the curve for receiver operating characteristics (AUC-ROC) =0.91). The classifier model outperformed a simpler 'standard' model featuring general higher-level populations derived from a standard clinical cytometry panel (BD Multitest™ 6-color TBNK; e.g., as described by Omana-Zapata et al. *PLOS One* 2019 Jan. 28; 14 (1): e0211207) combined with major populations identified using CBC (basophils, cosinophils, neutrophils, monocytes, NK cells, NKT cells, B cells, CD4 T cells and CD8 T cells) (AUC-ROC=0.81, FIG. 17G left). Similarly, the healthy/cancer classifier model exhibited higher performance in classifying healthy donors and cancer patients on the validation subset of 347 patient samples, compared to the 'standard' panel (AUC=0.84 and 0.77, respectively, FIG. 17G right). Overall, cellular immunoprofiling can discriminate between healthy donors from patients with solid tumors based solely on the composition of white blood cell populations in the peripheral blood. FIG. 27A additionally shows an exemplary training workflow schema for the healthy/cancer classifier model. And FIG. 27B shows high correlations between model cell type predictions and the manual markups.

Figure 23A:
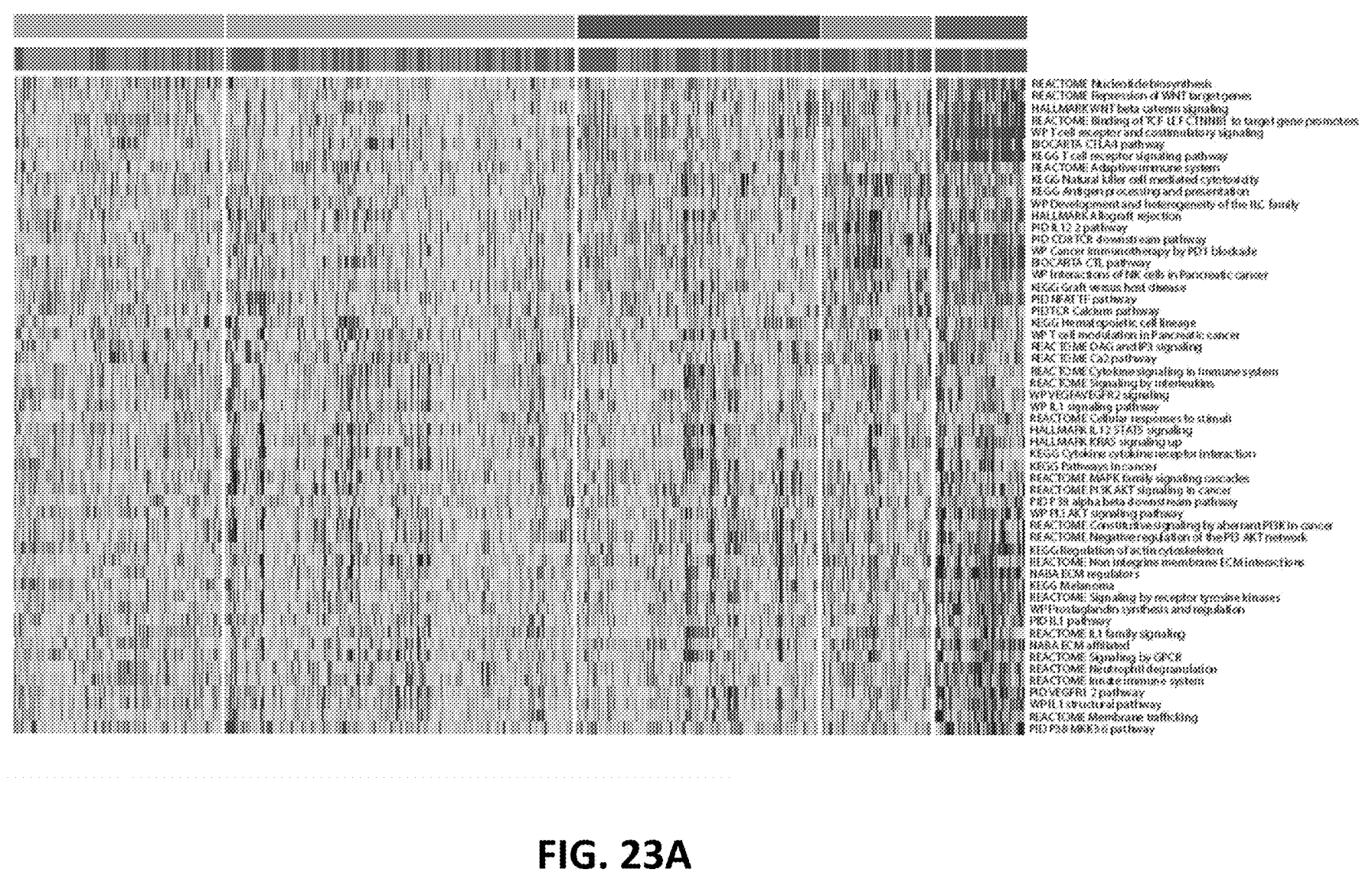

Next, the focus was on resolving the most robust immune features characterizing the heterogeneity of the cohort and consequently, to identify functional immune signatures that reflected physiological states associated with overall disease response rather than transient features corresponding to particular diagnoses or treatments. Unsupervised spectral clustering was applied to the normalized frequencies of 34 selected cell types obtained by flow cytometry to reveal immunologically distinct phenotypes. The immune cell types were selected from the hierarchy tree (FIG. 23B) that were congruent with the cell deconvolution of the Kassandra algorithm and cell populations previously identified as immunotherapy response biomarkers in studies across different cancer types: TIGIT+PD1+CD8 T cells, Vdelta2+ gamma-delta T cells, CD39+ Tregs, HLA-DR low monocytes.

Figure 18A:
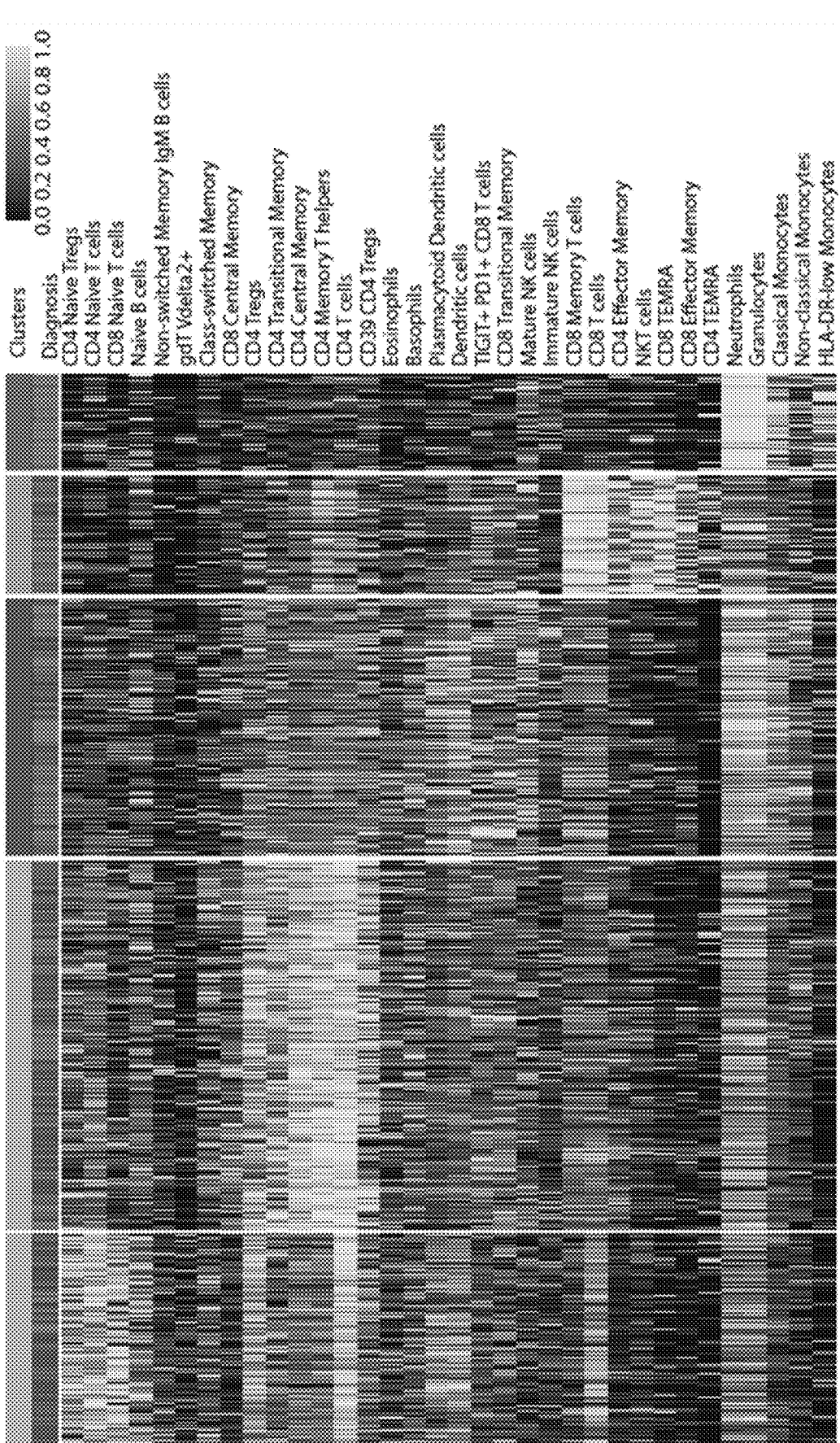
Figure 27C:
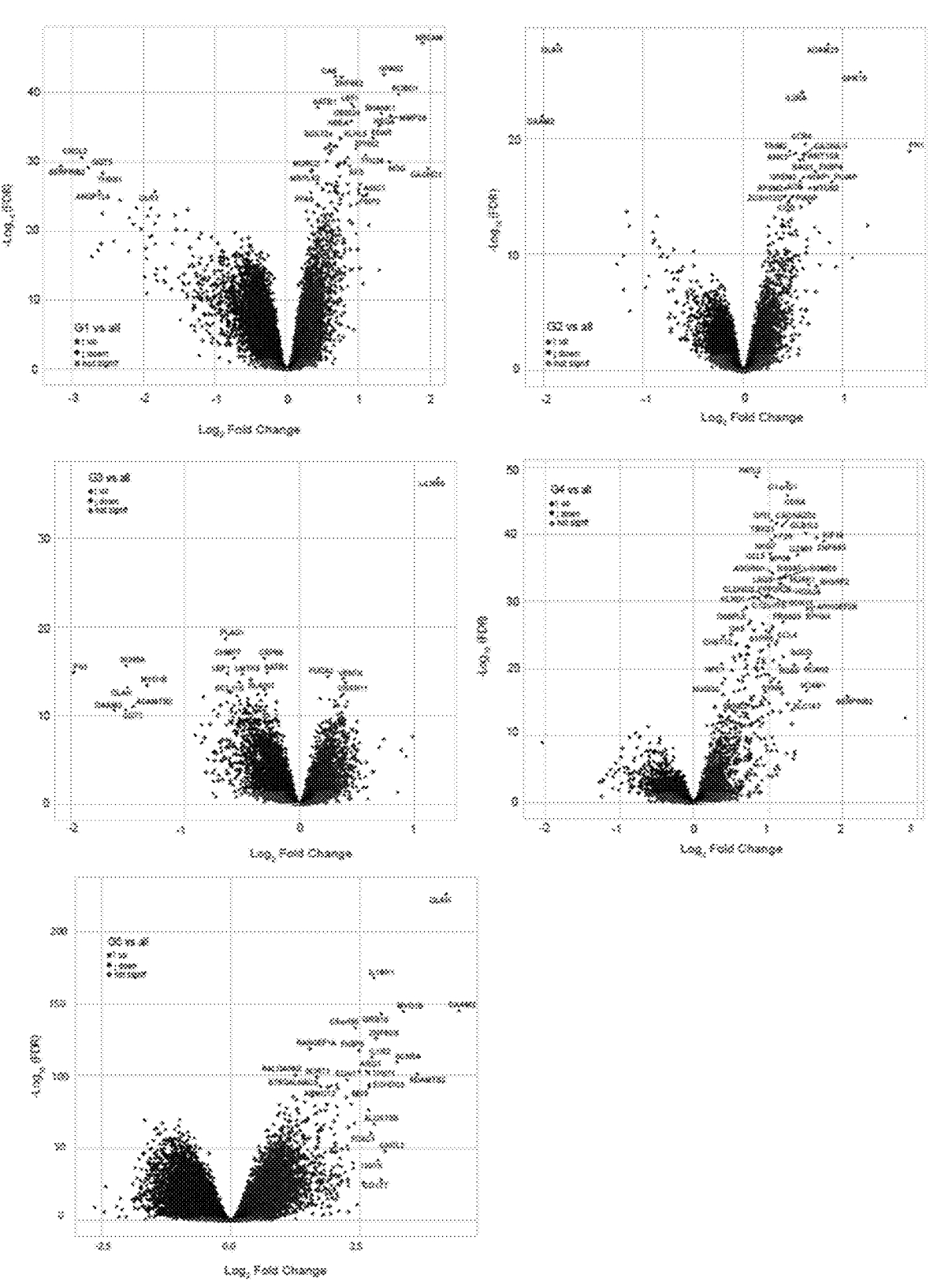

Five functional distinct immunotypes were identified, G1 to G5. G1-Naïve is characterized by a high frequency of Naïve CD4+, Naïve CD8+, and Naïve B cells. G2-Primed showed greater percentages of differentiated CD4+ central and transitional memory T cells, and CD39+ regulatory T cells (Tregs). G3-Progressive contained increased frequencies of mature NK cells, CD8 transitional memory and PD1+ TIGIT+CD8+ T cells. G4-Chronic was enriched with NKT and terminally-differentiated effector memory CD45RA+ (TemRA) and CD45RA-(Tem) of both CD4+ and CD8+ T cells. Finally, G5-Suppressive cluster was highly enriched in classical monocytes, HLA-DR low monocytes, and neutrophils and contained lower amounts of lymphocyte cell populations (FIG. 18A). Consistent with the UMAP analysis of the overall cohort (FIG. 17C), the presence or absence of a cancer diagnosis (healthy or cancer) and patient age were unevenly distributed within immunotype clusters (FIG. 18A). Importantly, clusters enriched with terminally differentiated CD8 T cells (G4) and classical monocytes (G5) contained very few healthy donors and a high proportion of cancer patients, while the G1 group with the highest percentage of Naïve T and B lymphocytes contained the largest proportion of healthy donors (FIG. 18A, top). Additionally, analysis was performed to determine the relationship between gene expression and TME group (FIG. 27C).

Figure 18B:
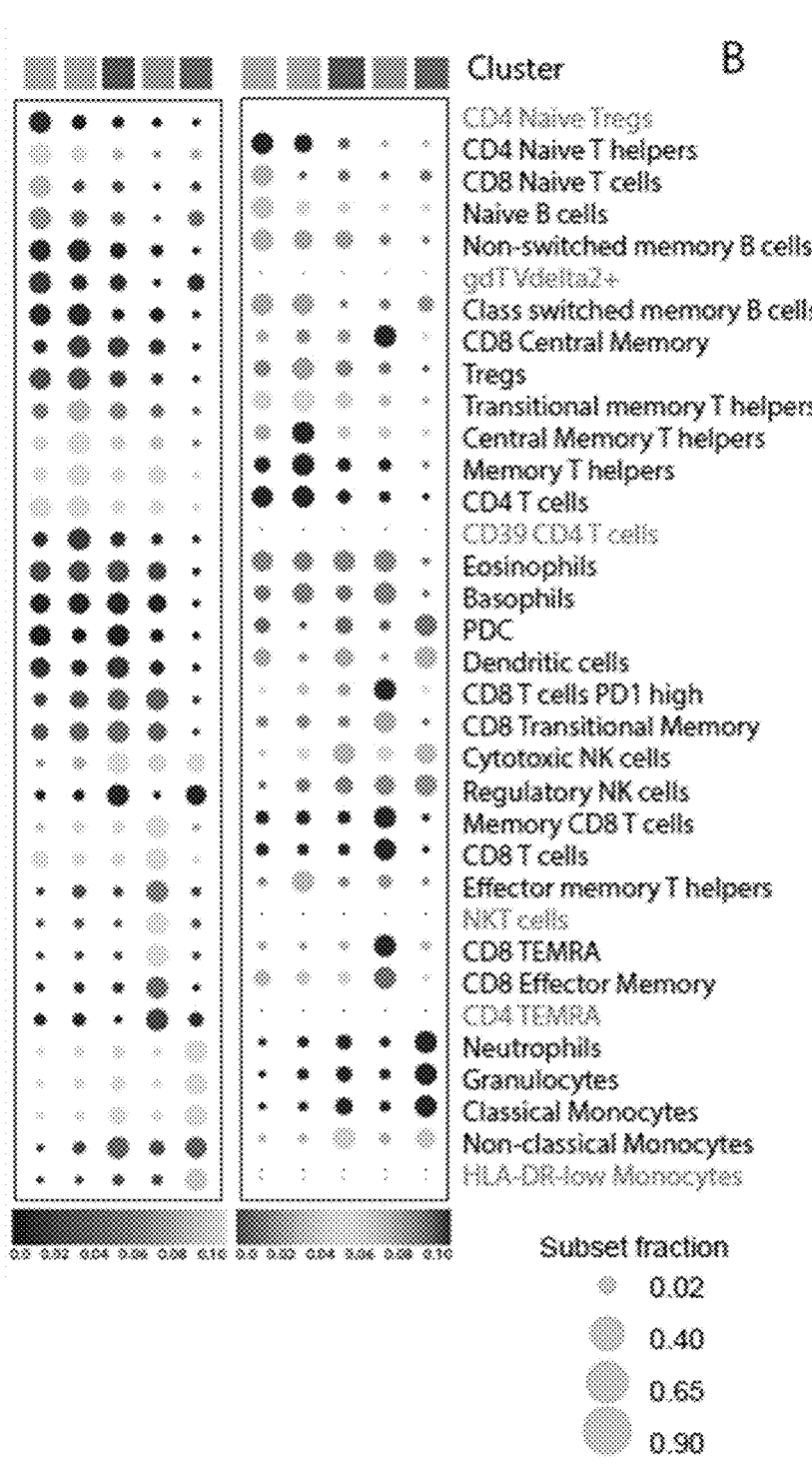
Figure 27D:
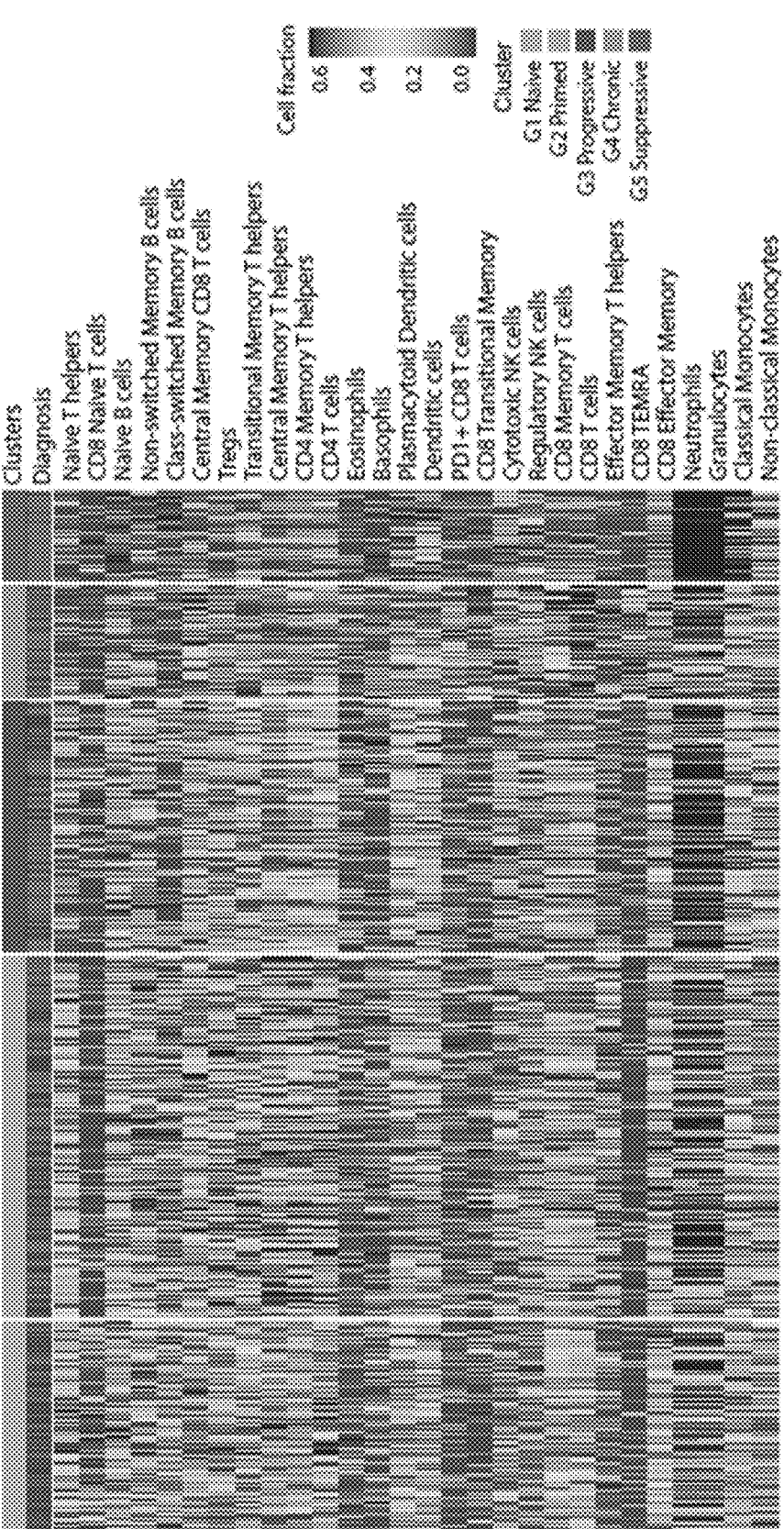
Figure 27E:
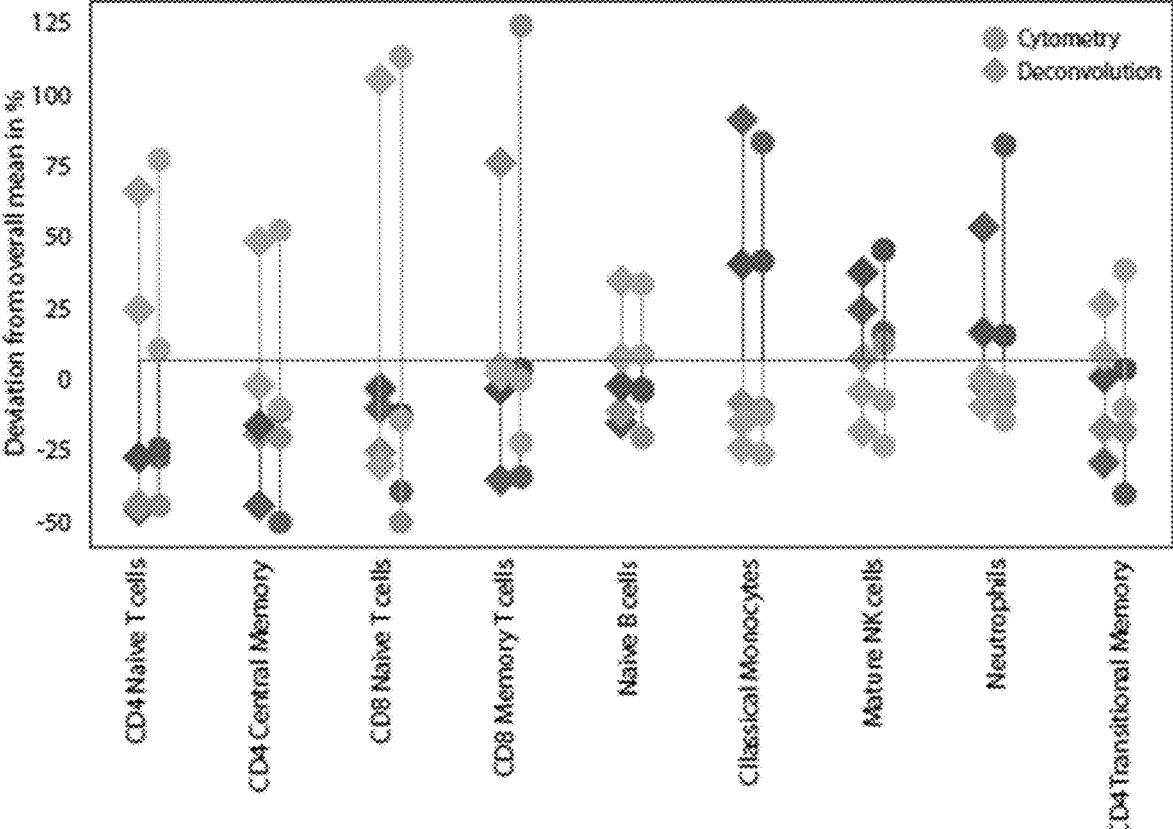
Figure 27F:
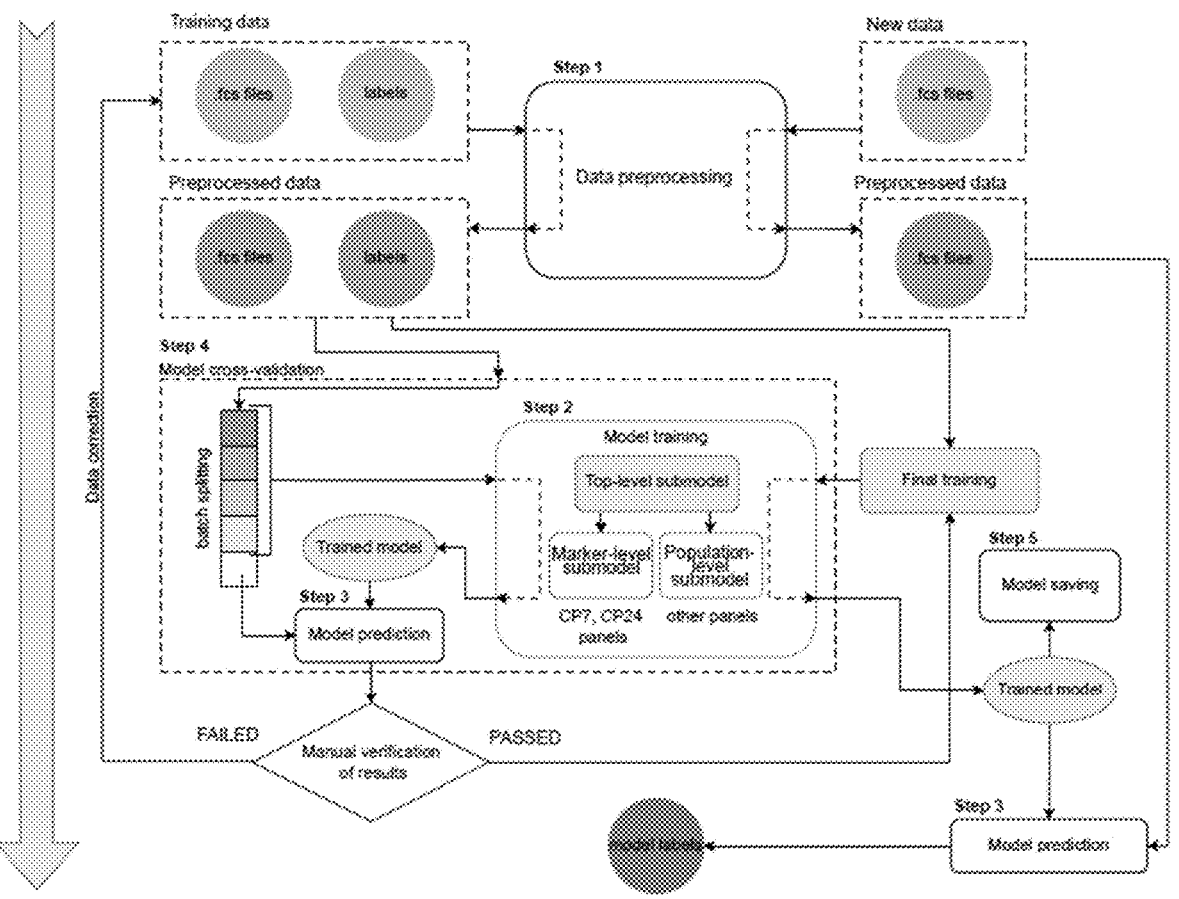

To analytically validate the immune groups, RNA-seq based cell deconvolution was compared to the G1-G5 immunotypes clustered from the flow cytometry data. Consistent with results published by Zaitsev et al (PMID: 35944503), the Kassandra algorithm's cellular deconvolution quantifying the cell population frequencies derived from bulk RNA-seq of paired samples (n=797, Supplementary cohort) were highly concordant with the frequencies obtained with flow cytometry (FIGS. 18A, 18B). FIG. 27D shows a representative Kassandra algorithm deconvolution heatmap with labels based on flow cytometry clustering. FIG. 27E further shows consistency between the cytometry-based quantification of cell population frequency distribution between the immunotypes and the corresponding predictions made by the deconvolution algorithm.

Figure 18D:
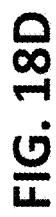

To demonstrate immunotype-associated gene expression profiles, the 200 most differentially expressed genes were selected from each cluster and performed gene-set enrichment analysis (GSEA) using curated functional gene signatures from MsigDB for immunologically relevant pathways. G1 and G2 were significantly enriched in signatures for TCF and LEF CTNNB 1 transcriptional regulation, TCR, and WNT/Beta catenin signaling. G4 was enriched in genes associated with cytotoxic effector T cell responses, and G5 contained multiple pathways associated with innate and myeloid cells (FIG. 18C). Immunotype comparison of individual gene expression levels of cytokine and chemokine signaling-related genes showed patterns of expression: FLT3LG and CCR7 expression was highest in G1-G4 relative to the low expression in G5; CCL4 and TGFBR3 expression was high in G4 and CXCL16 and ILIR1 in the G5 group (FIG. 18D).

Figure 18E:
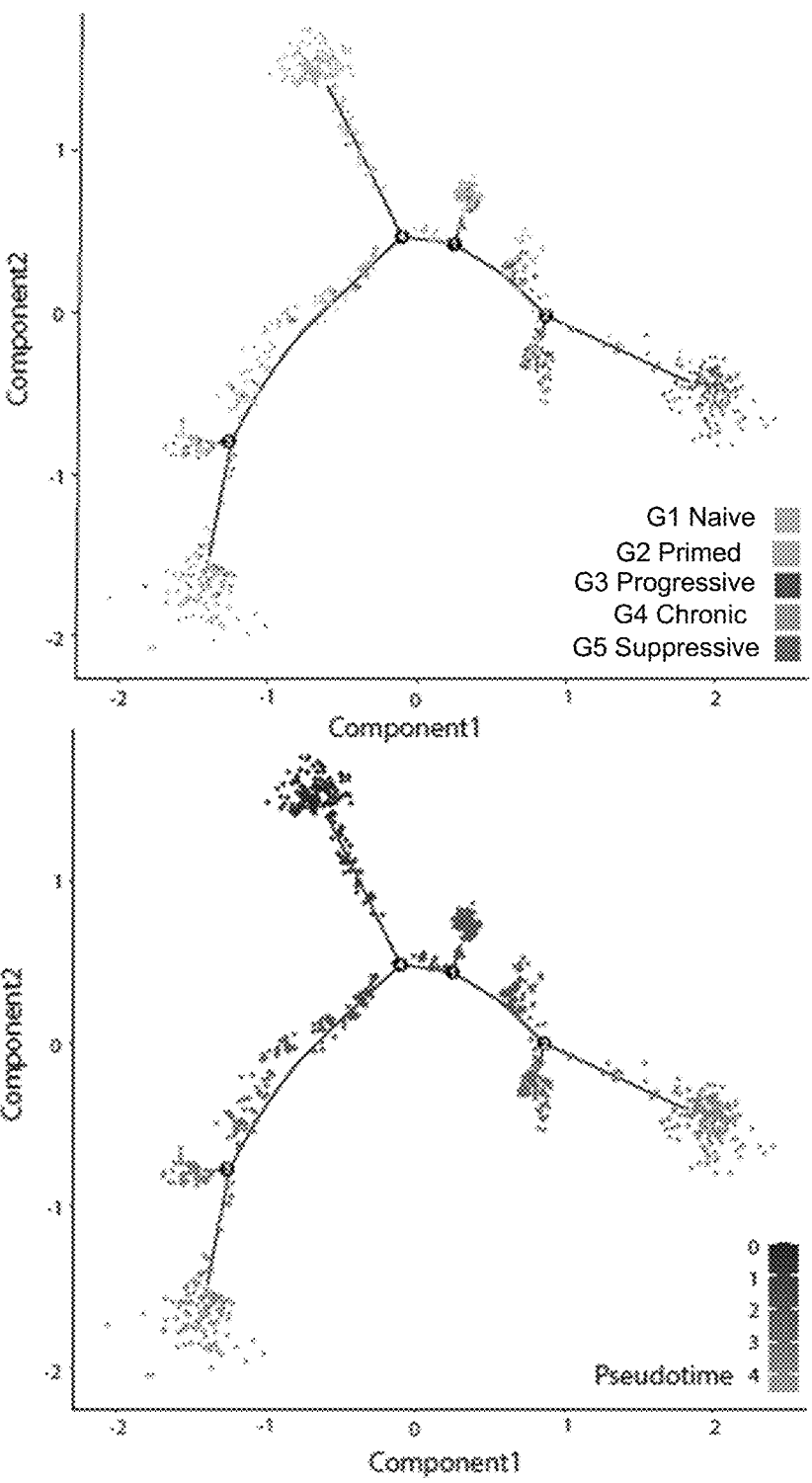

The developmental relationships between different T cell lineages have been characterized and could be used to infer the trajectory of immunotype evolution. Using peripheral immune cell composition data obtained from cytometry, a pseudotime analysis was performed to establish a developmental hierarchy of these response states (FIG. 18E). Patients in G1 and G2, containing the highest frequency of Naïve and central memory CD4+ T cells, clustered most frequently at the origin and bifurcated into two branches that terminated where groups G4 and G5 were most abundant. This analysis indicates that these immunotypes represent a continuum of functional response states and thereby potential to respond to subsequent immunological challenges.

Interestingly, patterns of gene signature overlap consistent with the immune cell population distribution by flow cytometry between the different clusters and in agreement with the pseudotime analysis was observed. For example, G3 appears to be a transitional state containing elements of both G4 and G5. These findings further indicate that these different immunotype groups are shaped by convergent responses to environmental and immunological stimuli. Therefore, each immunotype group was associated with a functional and developmental status: G1—Naïve, G2—primed, G3—progressive, G4—chronic, and G5—suppressive. These response characteristics, coupled with the fact that these clusters were present in both healthy donors and cancer patients, indicates that these immunotypes may be a conserved feature of immune physiology across different patient populations.

To further validate the immunotype classification, cell population percentages from Kassandra algorithm's cell deconvolution of bulk RNA-seq samples (n=18,712, Open-source datasets list) collected from the open-source GEO and ArrayExpress databases (Barrett et al., 2012) were stratified using a multiclass classifier trained on the cohort RNA-seq data. The open-source validation datasets consisted of whole blood samples from healthy donors and from patients with different diagnoses (>90 types), which were grouped based on their common features. Using the multiclass classifier, the samples were distinctly clustered into the 5 immune profiles G1-G5, as seen on the 3-dimensional PCA projection, indicating conservation of these immune categories across diverse diseases (FIG. 19A).

Figures 19A, 19B, 19C:
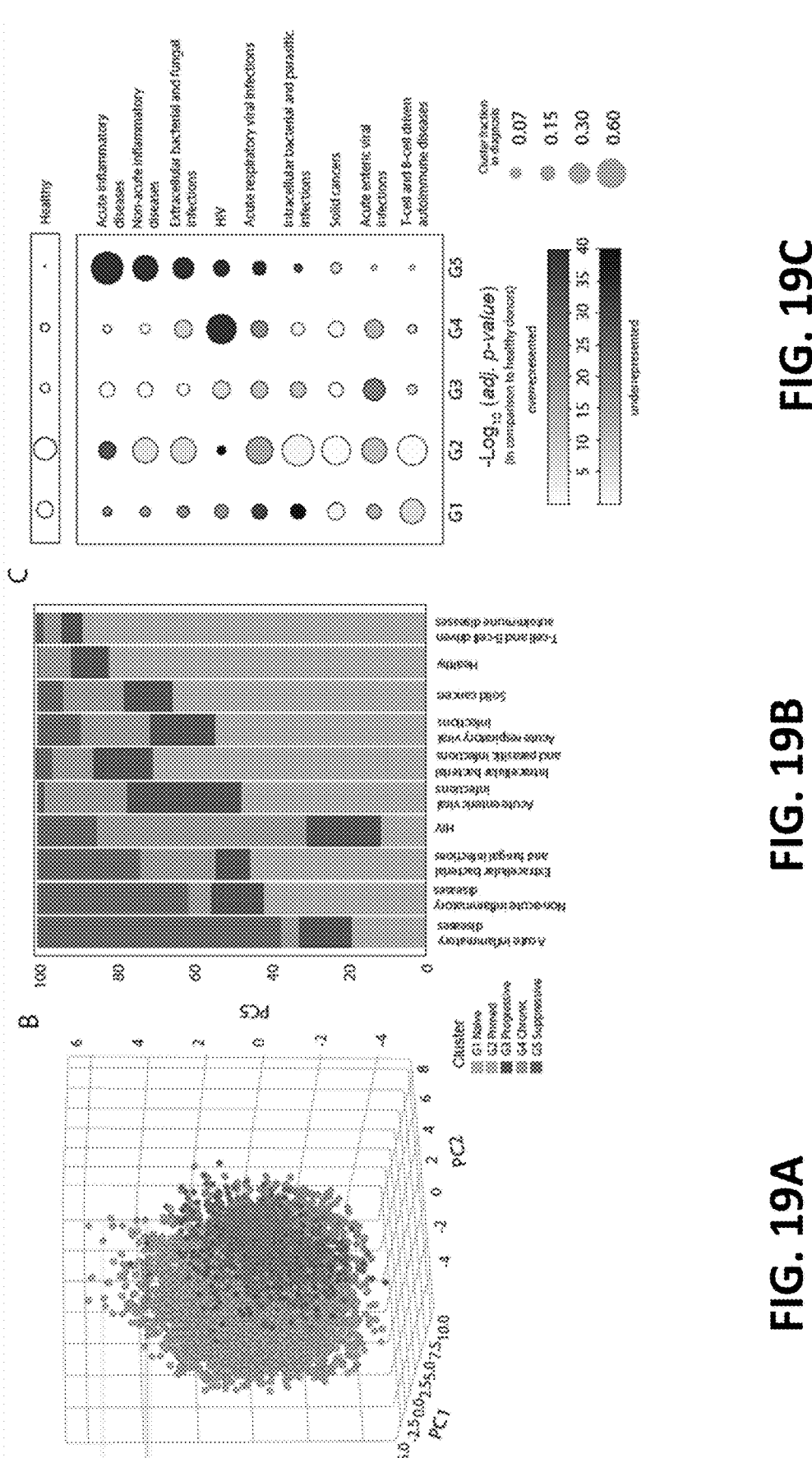
FIGS. 19A-19C show the representative data analysis of leukocyte immunoprofile clustering analysis, according to some embodiments of the technology described herein.

Each dataset was sub-grouped based largely on disease pathogenesis, such as assigning samples of patients with persistent *Mycobacterium tuberculosis* or *Leishmania* spp. infections in the 'intracellular bacterial and parasitic infections' group, and patients with influenza or coronavirus in the 'acute respiratory viral infections' group (FIG. 19B). In agreement with previous findings (FIG. 18A), the most frequent immunotypes for healthy donors were G1 and G2 (FIG. 19B). Patients with autoimmune diseases most commonly were classified to the Naïve (G1) immunotype. The primed immunotype (G2) containing abundant central and transitional memory CD4+ T cells was overall the most frequent immunotype across the cohort, and enriched particularly in patients with 'intracellular bacterial and parasitic infections', consistent with helper T cell responses being essential for phagosomal pathogen control. The progressive or transitional immunotype (G3) was enriched with samples of patients with viral infections, and most commonly linked to enteric tissues. Compared with healthy donors and patients with other viral infections, HIV patients were most frequently assigned to the chronic immunotype (G4). Interestingly, diseases known to be associated with high levels of systemic inflammation, such as bacterial sepsis, were most frequently classified into the suppressive (G5) subtype indicating inflammation-dependent mobilization of monocytes and neutrophils into the blood of these patients (FIG. 19B). Overall, a reciprocal relationship between patients assigned to the Naïve (G1) and suppressive (G5) immunotypes (FIG. 19C) was observed. The analysis of open-source data using deconvolution of bulk RNA-seq data demonstrated that the immunotypes were associated with conserved immunological response states that can be used to classify patient responses independently of specific diagnoses, based on immune cell heterogeneity in the peripheral blood.

Figure 20B:
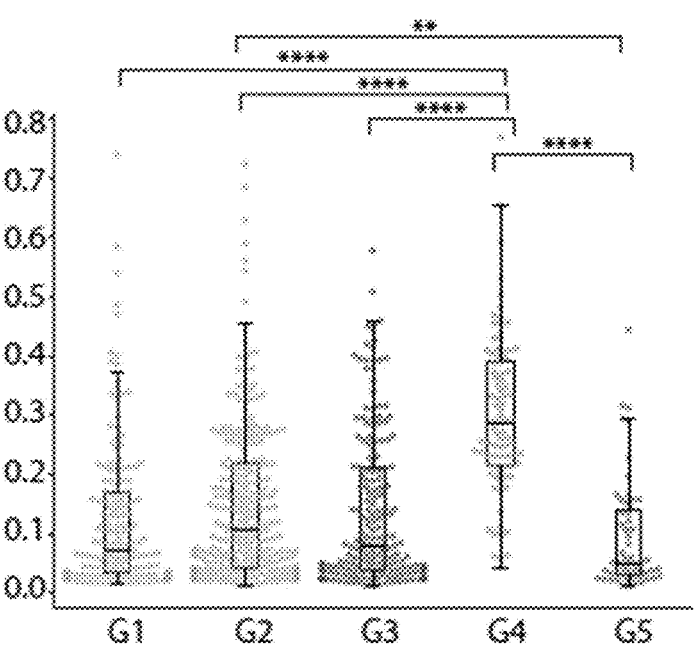
Figure 20C:
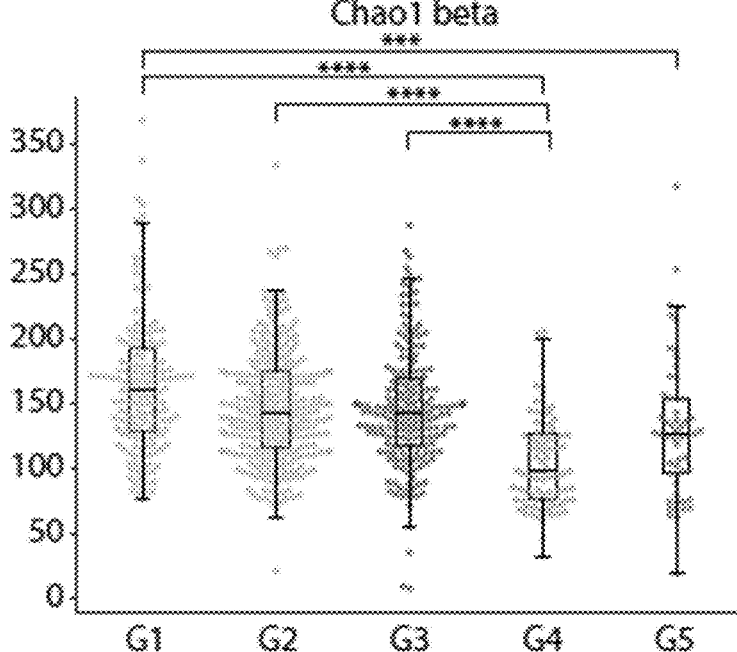

Clonal expansion of antigen-specific T cells is a fundamental characteristic of effective immune responses. This analysis of functional immunotype groups indicates an association between the dominant cellular phenotypes in each cluster and T-cell receptor (TCR) repertoire composition; and, therefore T-cell repertoires were evaluated using bulk RNA-seq data generated for most patients. Coverage of CDR3 sequences from TCRβ-chains were consistent across the cohort and reflected the overall frequency of T cells in each sample (FIG. 20A, top). Dominant clones that occupied more than 10% of total CDR3 in each patient (FIG. 20A, bottom), while infrequent in the cohort, were enriched in the chronic (G4) subtype. TCRβ repertoire clonality of individuals in G4 was 3-fold greater than all other immunotype groups (FIG. 20B), in agreement with the abundance of terminally-differentiated T cells in this group (FIG. 20B). Conversely, the Naïve, primed, and progressive immunotypes (G1-G3) had significantly higher TCRβ diversity than immunotypes G4 and G5, with decreasing Chao1 richness index from G1 to G3 (FIG. 20C), consistent with the frequency of Naïve, central, and transitional memory T cells in each group. These differences in TCRβ-chain clonality and diversity were also similar for TCRα CDR3 sequences (FIGS. 24A-24H, and 24M).

Figure 20D:
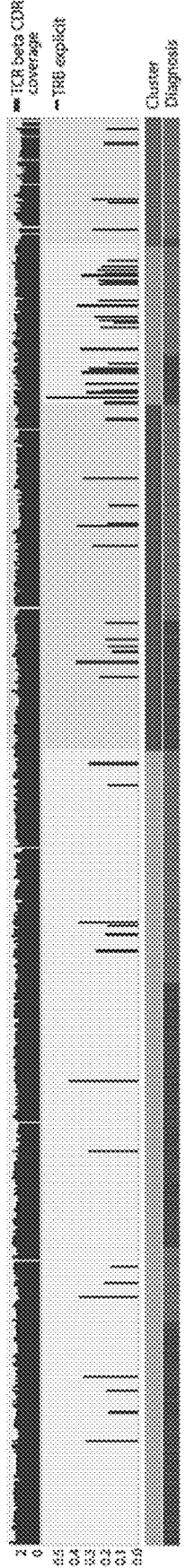

The distribution of MHC Class I HLA-alleles A, B, and C within the different functional immunotype groups (FIG. 20D, HLA-B) was then analyzed, as HLA-type skewing within different immunotype groups could lead to the changes seen in repertoire diversity. The distribution of HLA-alleles from this cohort were heterogeneous (FIG. 20D). Fewer patients with the HLA-B 07:02 allele were found in comparison to all other groups FIG. 20D, right), while other HLA alleles were not significantly different. This analysis provides further evidence that functional immunotype categories are shaped by convergent responses to immunological stimuli. Overall, this indicates that these categories might be relevant when evaluating responses to immune checkpoint blockade (ICB).

Figure 20E:
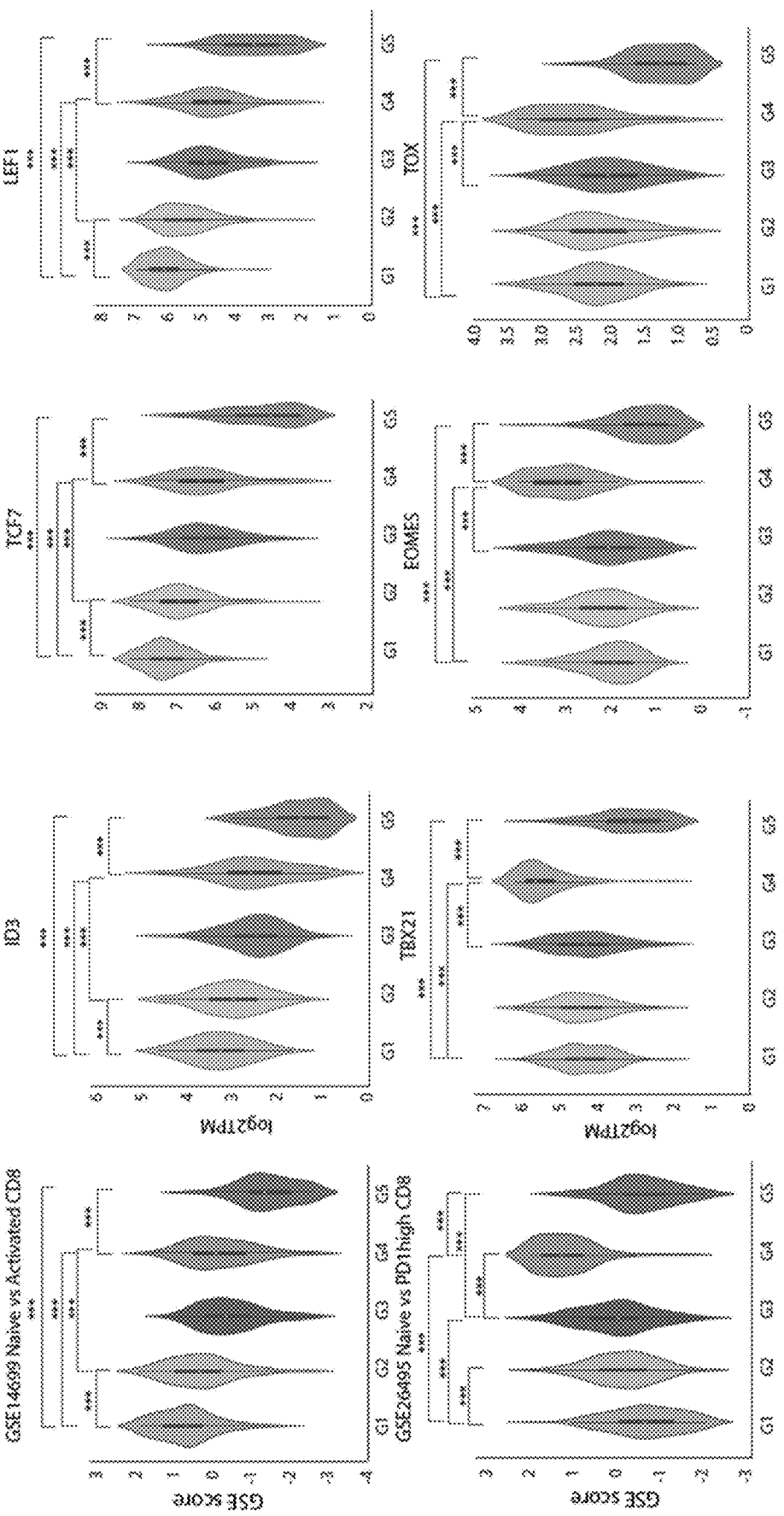

To further test this, the GSEA analysis was expanded to evaluate the functional immunotype groups using annotated gene signatures that correspond to gene expression patterns that are consistent with T-cell differentiation state, repertoire diversity, and immune checkpoint blockade (ICB) targeted PD-1-expressing T cells. First, an enrichment pattern of the general T-cell differentiation signature was observed, which comprises genes differentially expressed between Naïve and activated CD8+ T cells, that was similar to TCRβ repertoire diversity (FIG. 20D). In addition, individual gene expression levels of prominent transcription factors, TCF-7, LEF1, and ID3, associated with Naïve and self-renewing memory T cells, were the highest in G1-Naïve and G2-primed groups, reflecting the T-cell differentiation signature scores (FIG. 20E) (PMIDs: 21383243, 19204323). In agreement with TCRβ clonality and the frequency of terminally-differentiated T cells in the cluster, the chronic (G4) group had the highest enrichment score for the PD-1 high CD8+ T cell signature FIG. 20F). Transcription factors TBX21, EOMES, and TOX, that are critical regulators of effector T cell differentiation and exhaustion, had the highest expression in the G4 group as well (FIG. 20E). Collectively, this analysis suggests that patients in the chronic (G4) immunotype have characteristics of prolonged antigen exposure consistent with the evolution of an anti-tumor response and have been associated with ICB response in the peripheral blood and the TME.

BCR repertoire diversity analysis showed similar trends to the TCR repertoire (FIG. 24A-24M). The G1-Naïve cluster had the highest chao1 diversity score for BCR heavy chain and both of lambda and kappa light chains compared to other clusters, with significant differences from G3, G4 and G5 clusters. BCR clonality did not show significant differences between clusters them did not reach significance levels (FIG. 24I-24L).

Figure 20F:
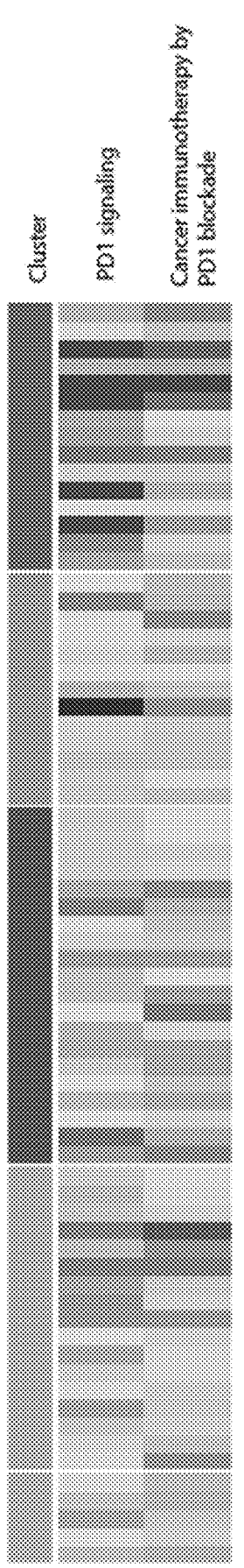
Figure 20G:
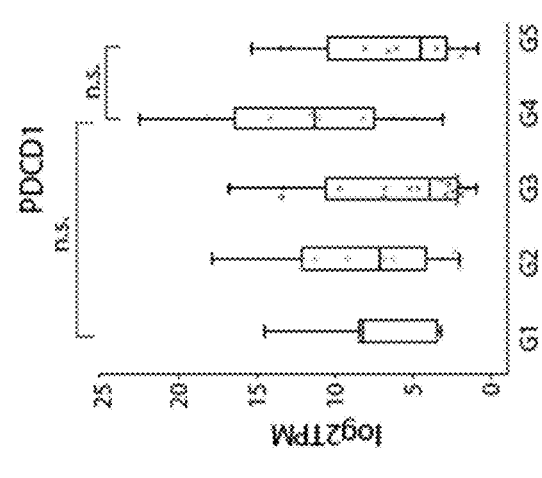
FIG. 20G shows representative data for $log_2TPM$ of PDCD1 gene group across the five clusters.

It was hypothesized that patients in this cohort with different cancer diagnoses that were on-treatment with ICB alone or in combination (n=72) would be assigned most frequently to the chronic (G4) immunotype. While there was an increased frequency of patients in clusters G3 and G4, this distribution was not significantly different from the patients with a cancer diagnosis on the whole, and there were no PDCD1 expression levels by RNA-seq were not significantly different between immune groups (FIG. 20G), patients in G1, G2, and G4 groups had the highest expression of annotated genes associated with PD1 signaling and cancer immunotherapy by PD1 blockade (FIG. 20F).

Figure 21A:
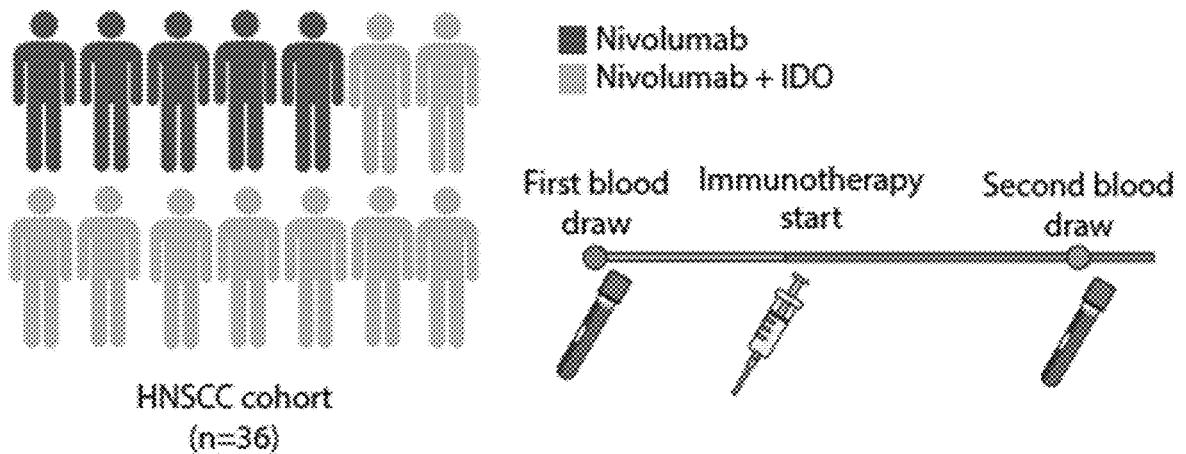
FIGS. 21A-21F shows representative data for PBMC immunoprofile typing of Head and neck squamous cell carcinoma (HNSCC) subjects, according to some embodiments of the technology described herein.
Figure 21B:
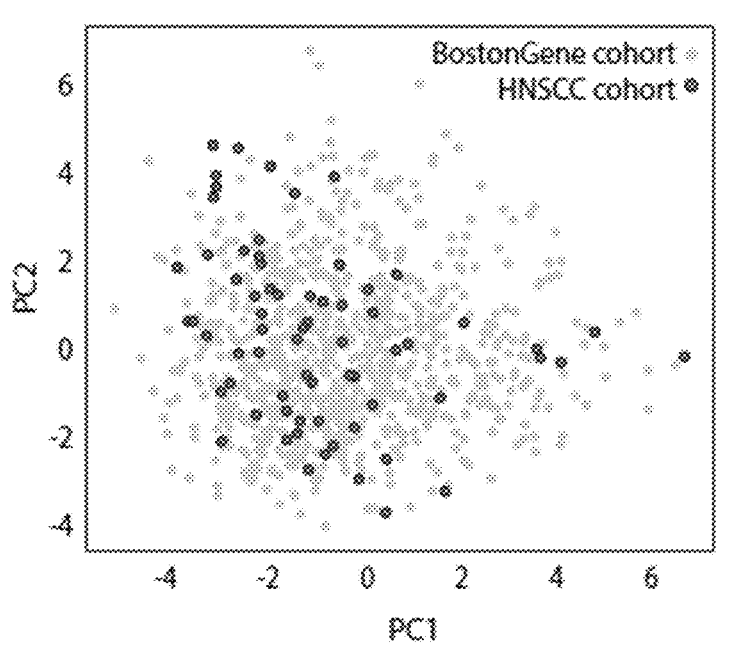

Importantly, this immunoprofiling platform was tested with a clinical cohort of 36 patients with advanced head and neck squamous cell carcinoma (HNSCC), treated with the PD-1 blocking antibody nivolumab. Cryopreserved peripheral blood samples were obtained prior to nivolumab infusion (baseline or pre-treatment) and post-treatment for the retrospective analysis for each patient. (FIG. 21A). 22/36 patients (64%) had responded to therapy (responders), according to an objective radiological and pathological assessment. The HNSCC clinical cohort showed a similar distribution on the UMAP to the internal cohort (FIG. 21B).

Figure 21C:
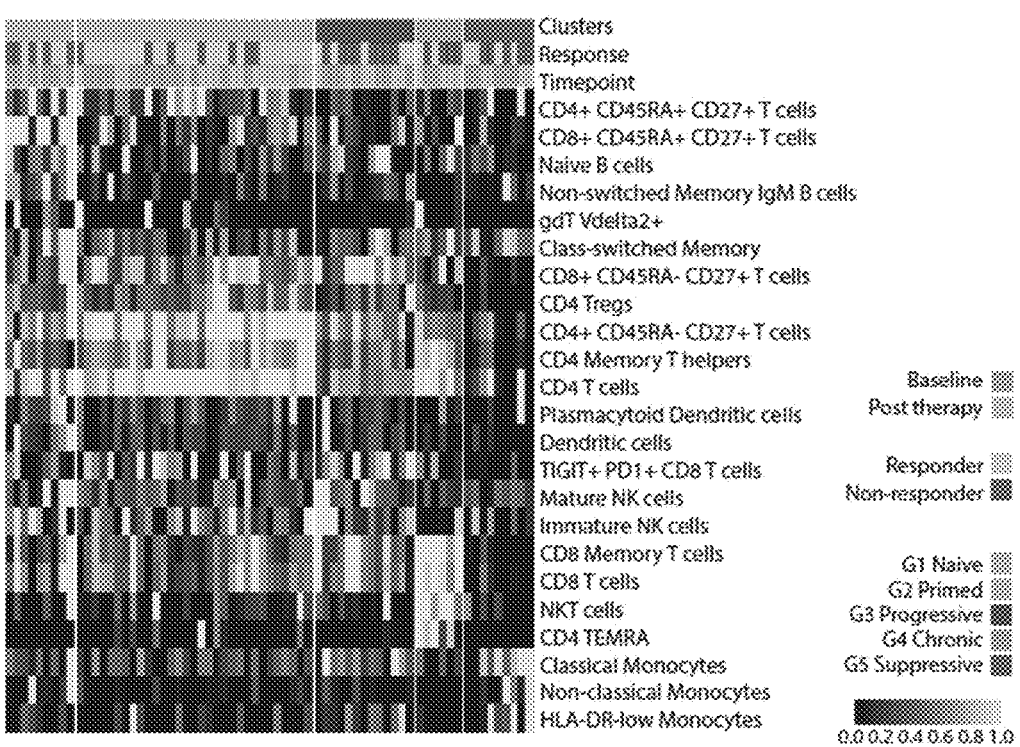
Figure 21D:
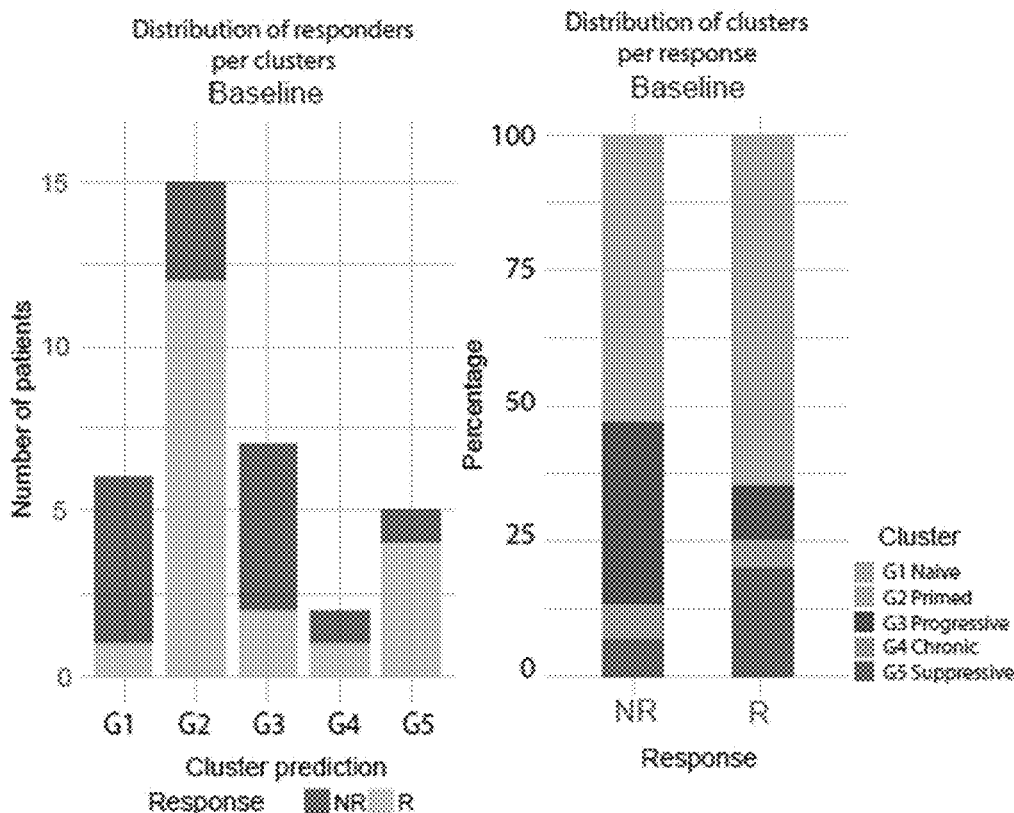
Figure 21E:
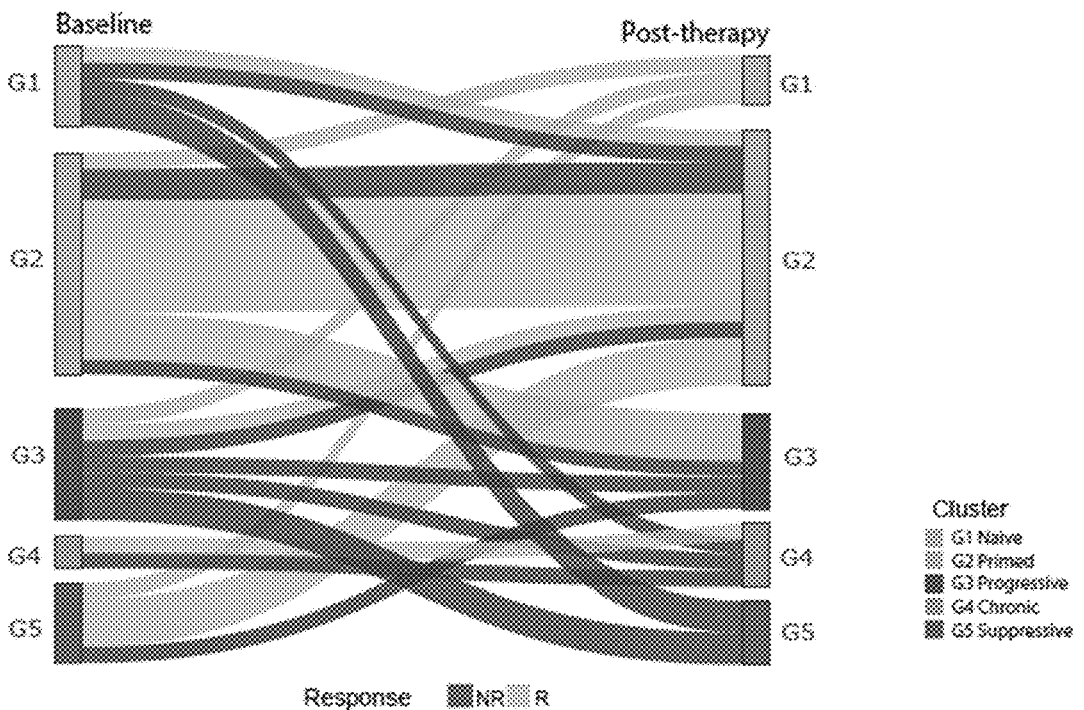
Figure 21F:
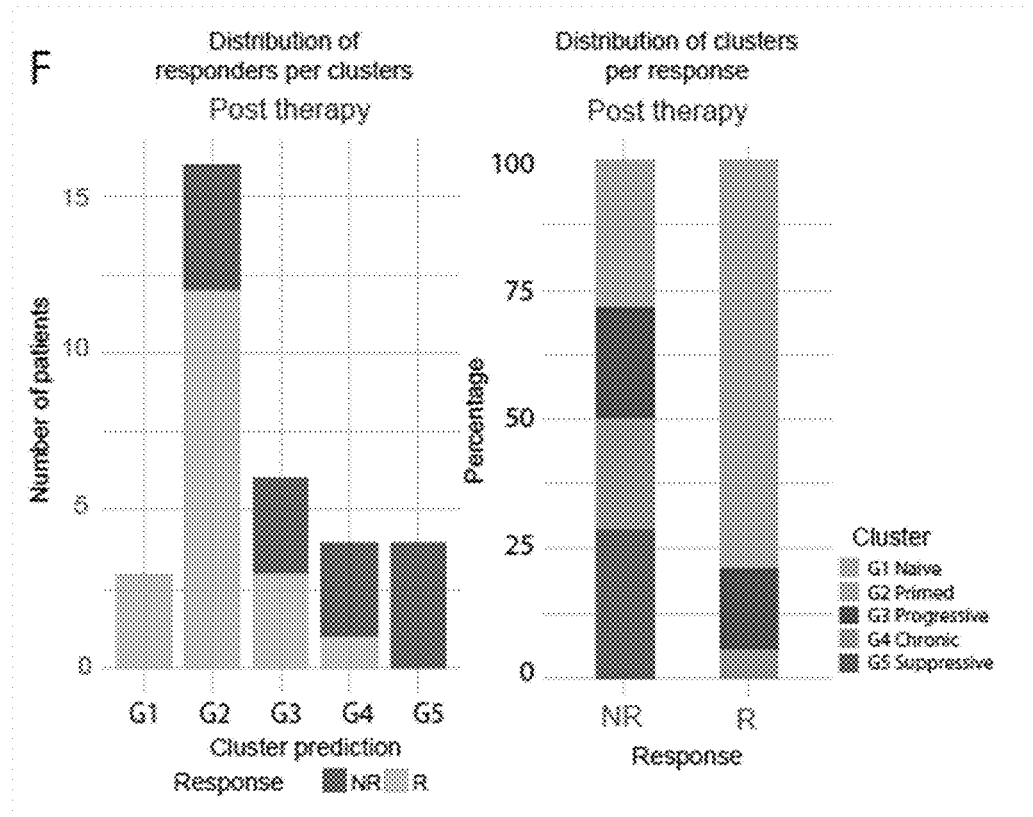

The multi-class immunotype classification model was applied to clinical cohort samples to assign patients to immunotype groups (FIG. 21C). The largest proportion of patient samples were classified into the G2-primed immunotype (FIG. 22C), consistent with previous analyses (FIGS. 17-18). Response to anti-PD-1 therapy was significantly associated with the G2 immunotype at baseline (prior to treatment). While non-responders were found within each group, the Naïve immunotype group (G1) contained predominantly non-responders at baseline (FIG. 21D). Dynamic analysis with post-treatment samples showed that 39% (14/36) of patients remained within the same functional immunotype group. Patients in the G2-primed immunotype at baseline that remained in this group post-treatment administration had a high response rate to therapy (FIG. 21E). Patients in the G2-primed immunotype in the on-treatment timepoint had a significant proportion of responders compared with the cohort overall, while non-responders dominated chronic (G4) and suppressive (G5) immunotypes (FIG. 21F). Collectively, this analysis demonstrates that functional immunotype assignment can effectively stratify patients that will respond to ICB based on the composition of immune cell types in the peripheral blood.

Figure 22A:
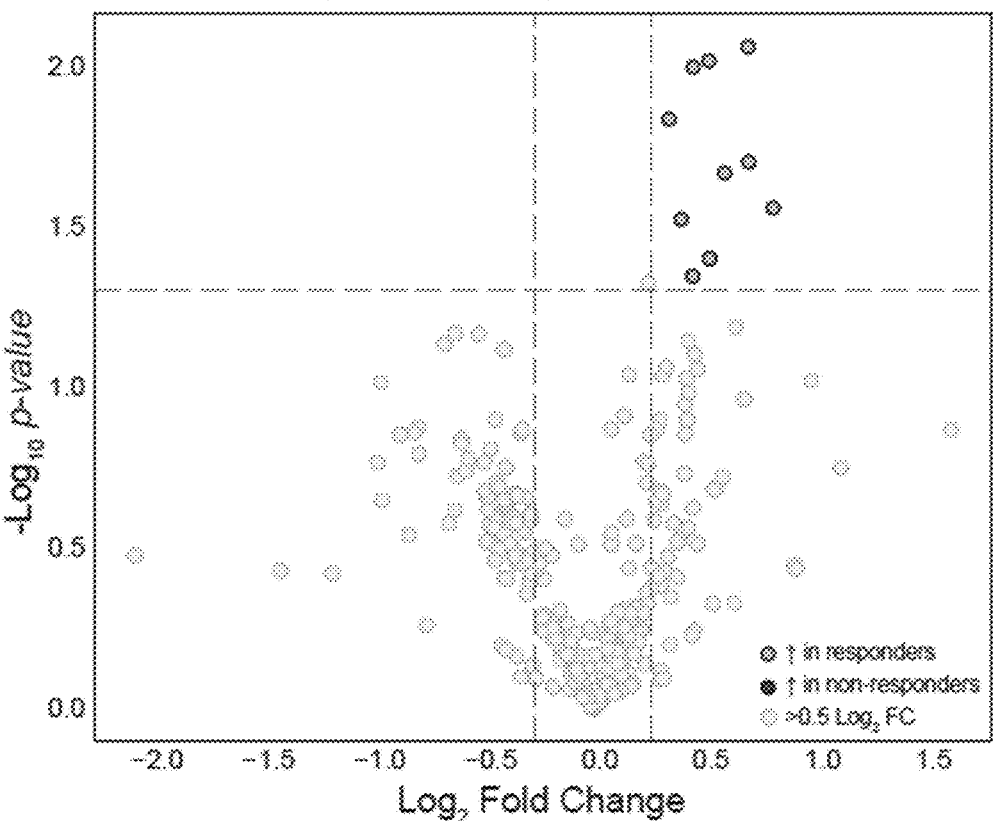
Figure 22B:
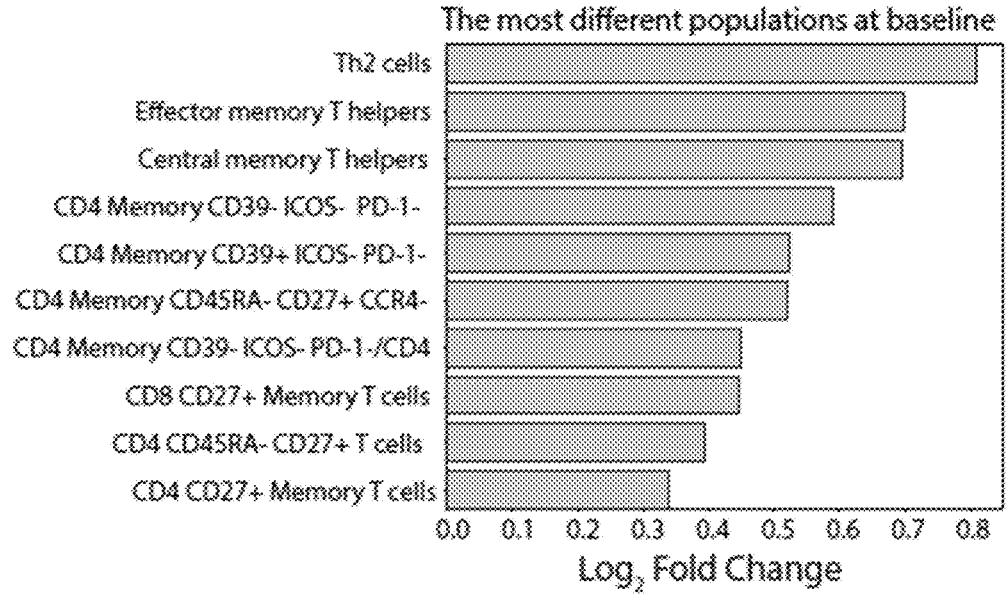
Figure 22C:
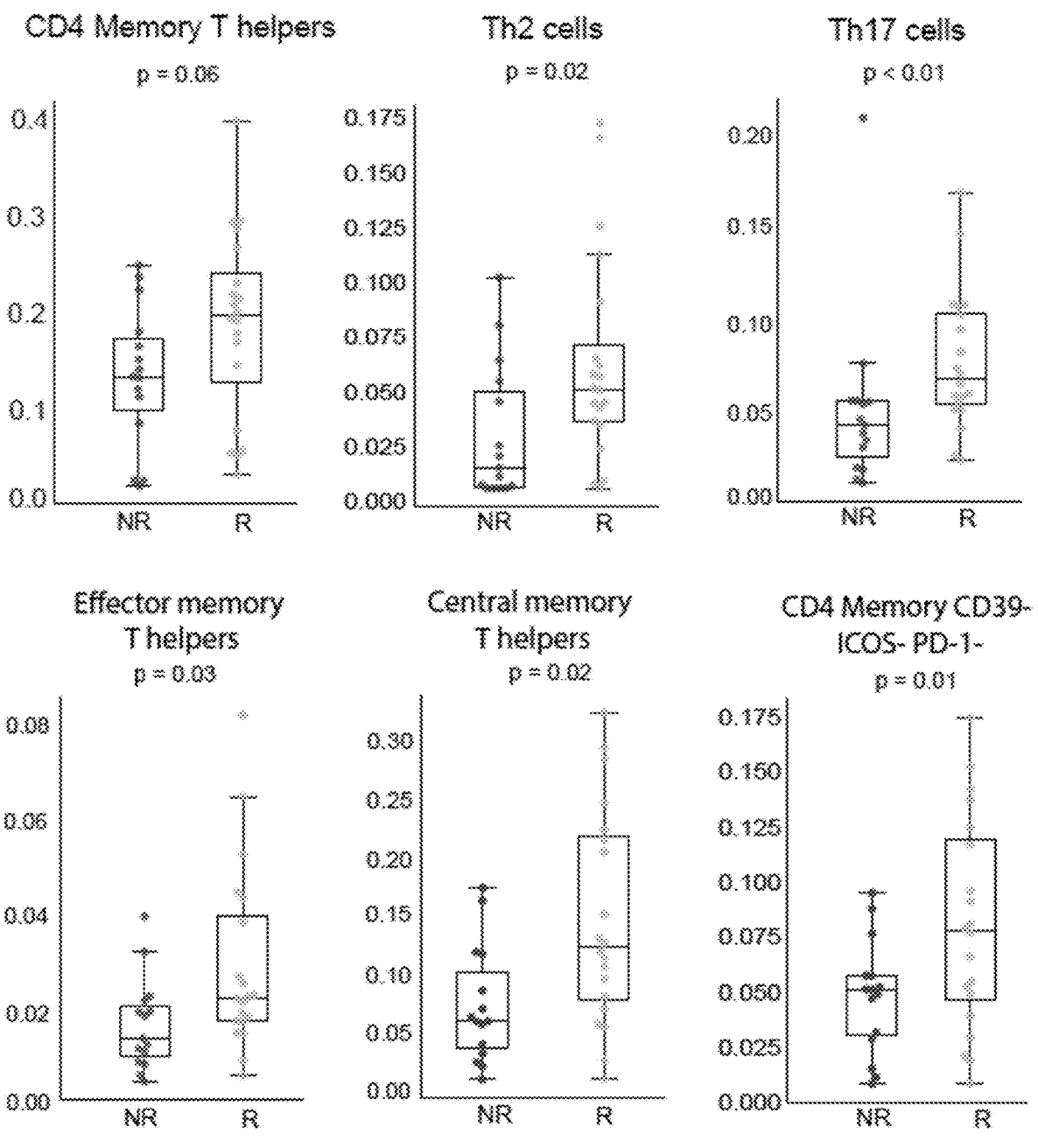

The responsive G2-Primed immunotype was enriched in central and transitional memory CD4+ T cells in the peripheral blood of the HNSCC cohort, which led us to further evaluate all immune cell populations between responders and non-responders to validate the findings. Upon differential population analysis of baseline samples between responders and non-responders, 10 cell populations were significantly increased in the peripheral blood of responders, of which 9 belong to the CD4+ T cell lineage (FIG. 22A, 22B). Th2, Th17, central memory T helper, and effector CD4+ T helper cell populations were significantly enriched in the blood of responders compared to non-responders (FIG. 22C), in contrast to the overall proportions of Naïve and total CD4+ T cells. Overall, these results further support the relationship between the enrichment of memory CD4+ T cells in the peripheral blood and response to ICB in HNSCC.

Figure 22F:
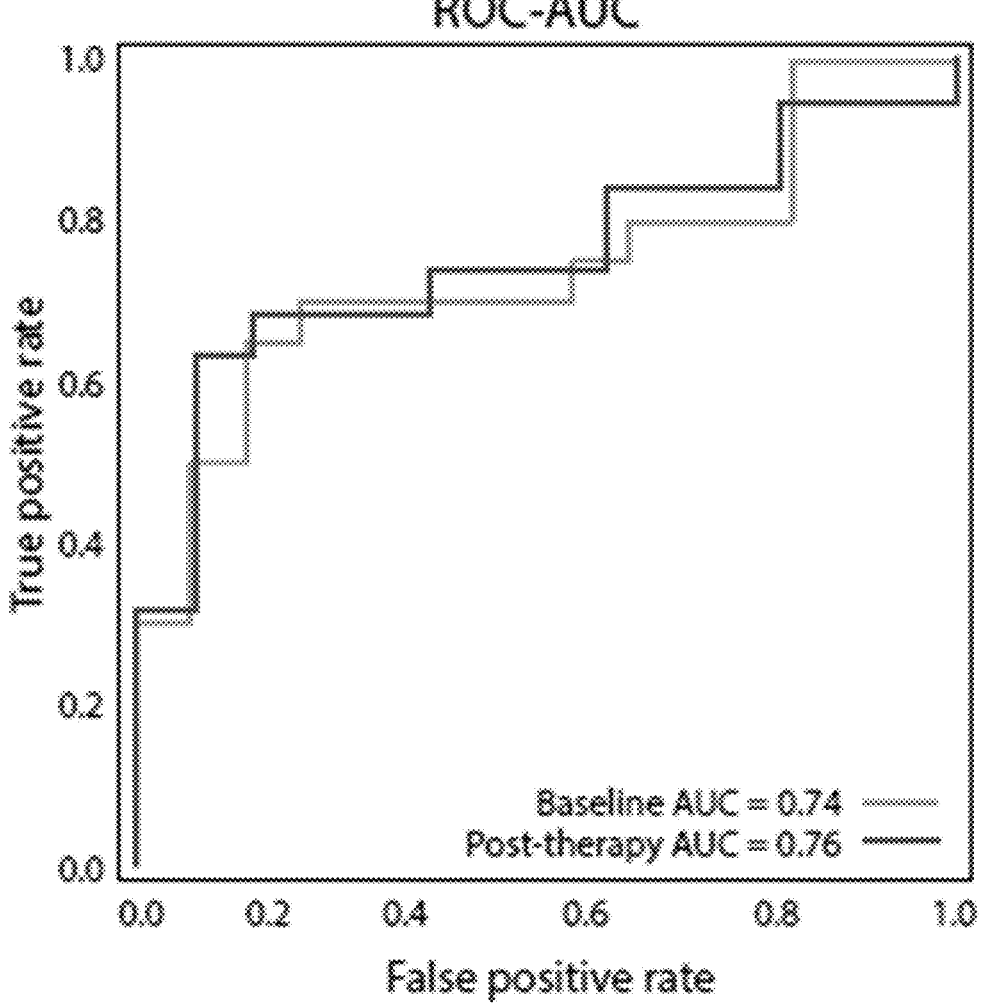
Figure 24A:
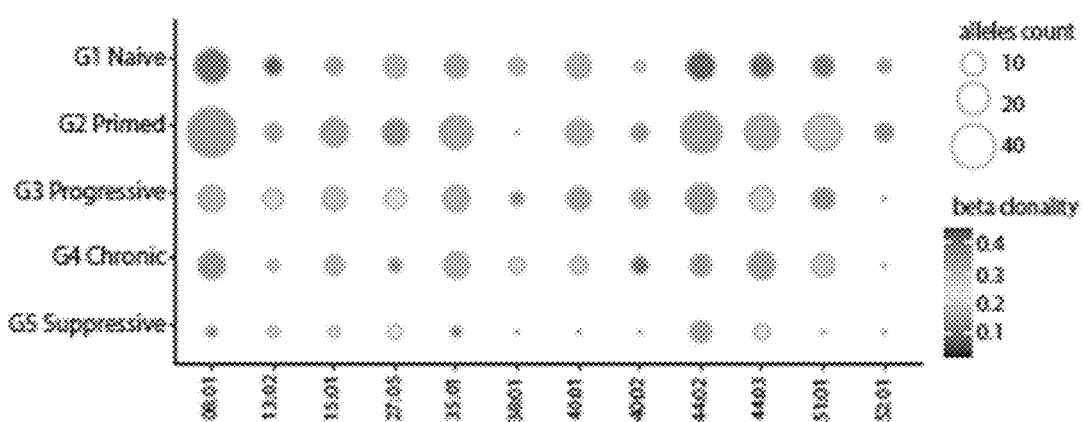
FIGS. 24A-24M show representative data comparing the five clusters (G1-G5) to TCR/BCR compositions, according to some embodiments of the technology described herein.
Figure 24B:
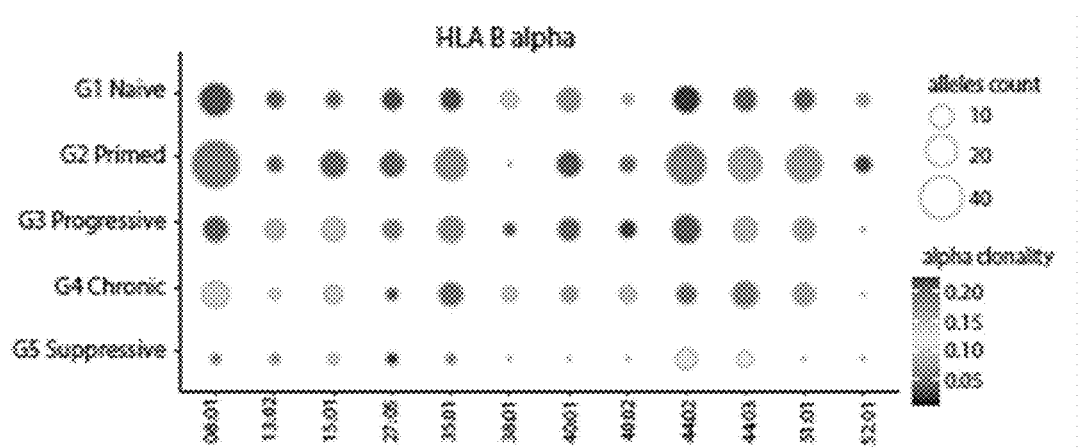
Figure 24C:
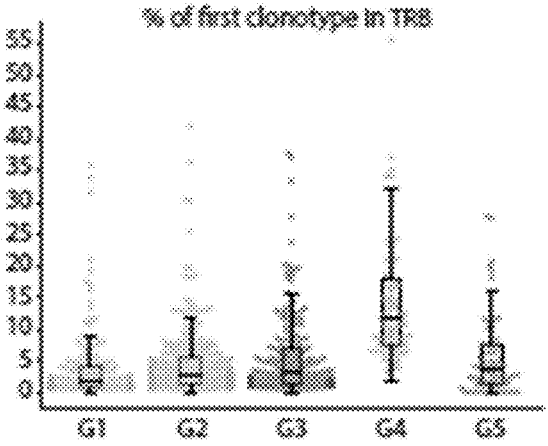
Figure 24D:
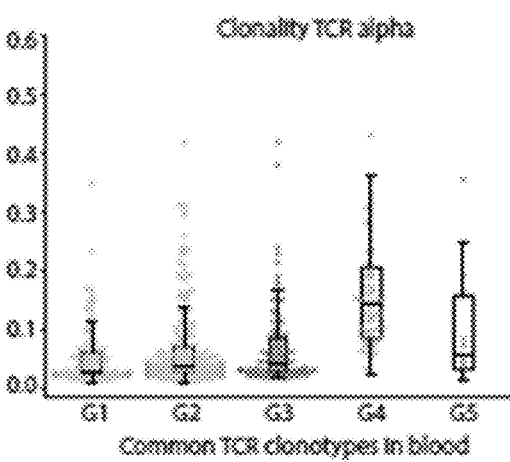
Figure 24E:
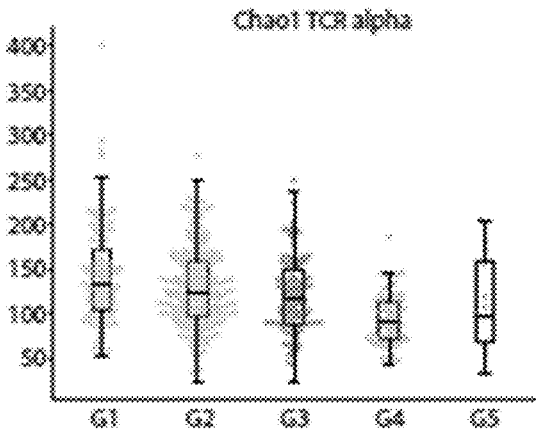
Figure 24F:
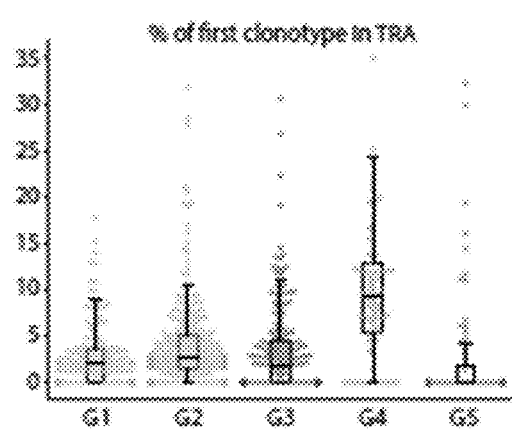
Figure 24G:
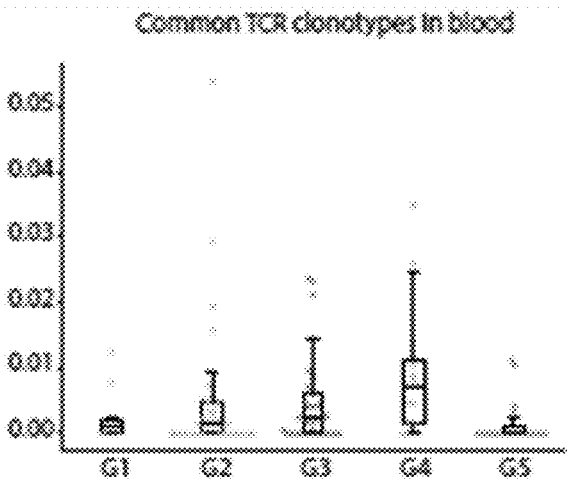
Figure 24H:
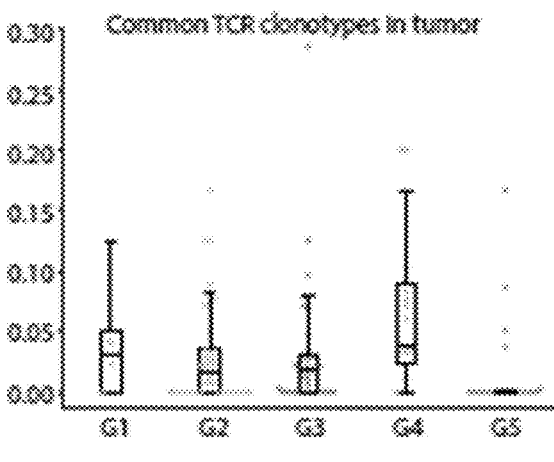
Figure 24I:
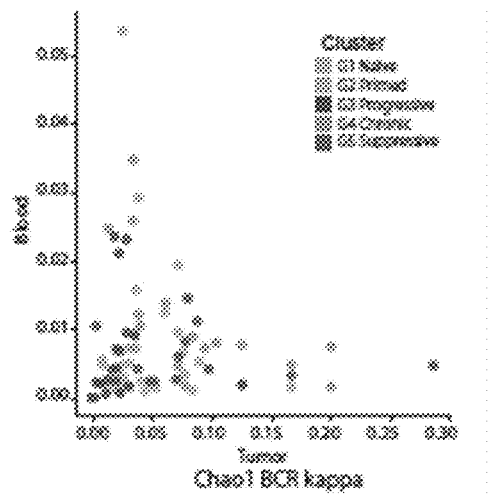
Figure 24J:
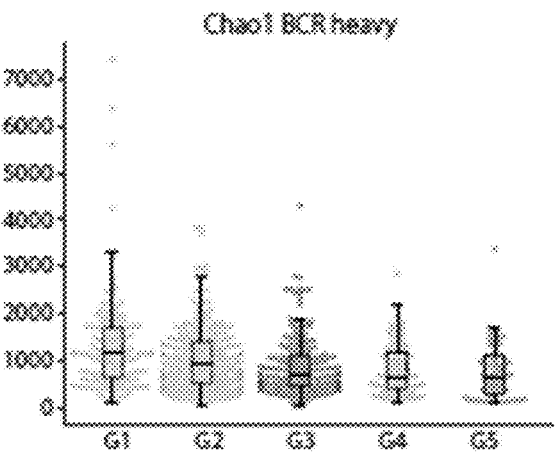
Figure 24K:
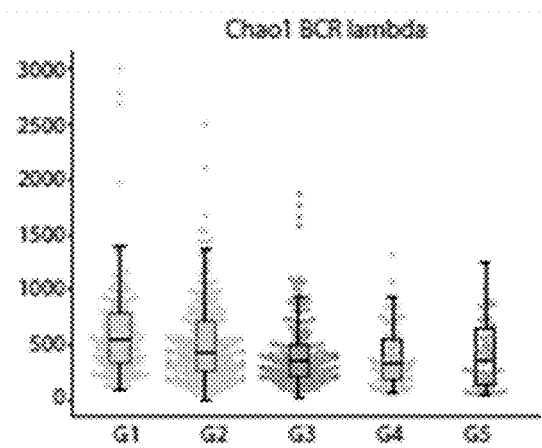
Figure 24L:
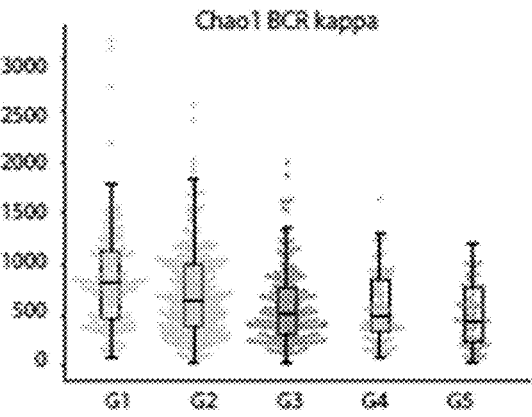
Figure 24M:
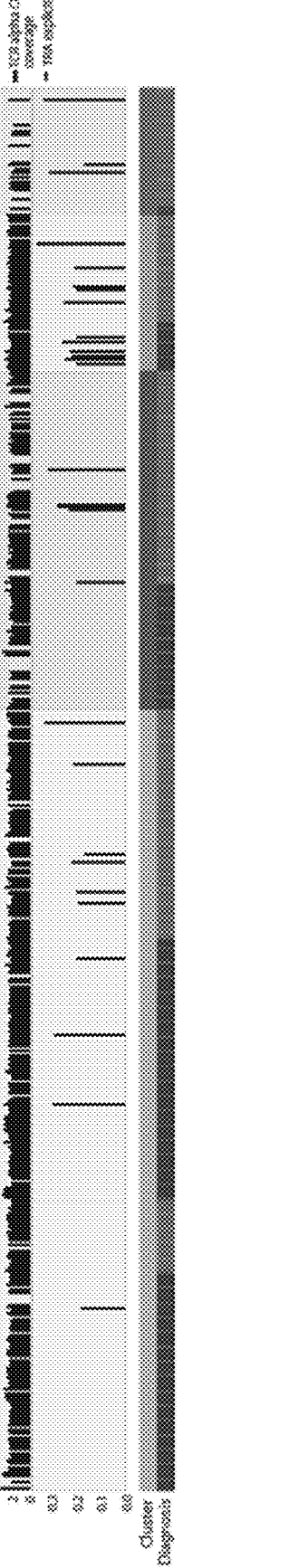

The distribution of the internal cohort based on the frequencies of different immune cell subpopulations demonstrated a continuous gradient of the distinct immunotype clusters on the UMAP. However, the assignment of patients to a discrete cluster is limited in capturing the dynamic transition of immune responses across immunotype clusters. (FIG. 22D, left). It was reasoned that the creation of a linear continuous score reflecting the similarity of samples within and across that individual immunotype clusters would increase the utility of this framework as a predictive biomarker. Using machine learning to identify the most differentially enriched populations in each cluster (Table 9), population frequency-based coefficients were generated for each subpopulation and used them to calculate a functional immunotype signature score from 0 to 10, based on the degree of similarity to the specific cluster phenotyped with the internal cohort (FIG. 22D, right). The G2-primed signature score was significantly higher in ICB responders in the HNSCC cohort at both baseline and post-treatment administration, compared to non-responders (p-values=0.017 and 0.014, respectively, Mann-Whitney U-Test) (FIG. 22E). The G2-primed signature scores were then used to train a binary classifier to predict ICB response of HNSCC patients and revealed a positive predictive value of 74% for pre-treatment and 76% for on-treatment samples FIG. 22F). As such, the newly developed G2-primed signature holds promising clinical utility.

TABLE 11

| | | Immune Score Coefficients | | | |
|---|---|---|---|---|---|
| Population | G1 Naïve coefficient | G2 Primed coefficient | G3 Progressive coefficient | G4 Chronic coefficent | G5 Suppressive coefficient |
| CD8 Naïve T cells | 0.33742649 | −0.156647155 | −0.076862524 | −0.05236322 | −0.029326534 |
| CD4 Naïve T cells | 0.232403532 | 0 | −0.132617553 | −0.04571792 | −0.027904185 |
| CD4 Naïve Tregs | 0.228427432 | −0.086948227 | −0.108340891 | −0.022989995 | −0.025704646 |
| CD8 T cells | 0.108241988 | −0.174387014 | −0.042607284 | 0.109818523 | −0.054050754 |
| CD4 T cells | 0.095259697 | 0.215526942 | −0.193752596 | −0.028538679 | −0.070096498 |

TABLE 11-continued

Immune Score Coefficients

| Population | G1 Naïve coefficient | G2 Primed coefficient | G3 Progressive coefficient | G4 Chronic coefficent | G5 Suppressive coefficient |
|---|---|---|---|---|---|
| Non-switched Memory IgM B cells | 0.066993785 | 0.045948912 | −0.015544489 | −0.027638555 | −0.046632291 |
| gdT Vdelta2+ | 0.06273697 | 0.009429867 | −0.014079771 | −0.036565974 | −0.011357972 |
| Plasmacytoid Dendritic cells | 0.056279012 | −0.121178908 | 0.153549497 | −0.01722038 | −0.056114463 |
| Naïve B cells | 0.053441882 | 0 | 0.003825776 | −0.016744509 | −0.016298942 |
| Dendritic cells | 0.053222172 | −0.157621855 | 0.255819387 | −0.015951048 | −0.096821076 |
| CD4 Tregs | 0.036759171 | 0.102593375 | −0.025694246 | −0.047559658 | −0.058998861 |
| Class-switched Memory | 0.01220796 | 0.117373102 | −0.092700616 | −0.026291331 | −0.007362301 |
| CD8 Effector Memory | −0.003321572 | 0 | −0.096379379 | 0.115194425 | −0.037154436 |
| CD4 TEMRA | −0.005601548 | 0 | −0.10036199 | 0.072835181 | 0.024215902 |
| Eosinophils | −0.017917277 | 0.015342879 | 0.068151539 | −0.00644313 | −0.051737814 |
| NKT cells | −0.023825925 | 0 | −0.084034898 | 0.108773222 | −0.008193872 |
| Basophils | −0.02965354 | 0.001928193 | 0.06220684 | −0.015438069 | −0.032767623 |
| CD8 Transitional Memory | −0.035025536 | 0 | 0.147885833 | −0.031874899 | −0.036938607 |
| CD8 TEMRA | −0.035107476 | −0.029169686 | −0.10118076 | 0.162266995 | −0.02080568 |
| Immature NK cells | −0.041617555 | −0.009830579 | 0.073373127 | −0.001551498 | −0.003313088 |
| CD4 Effector Memory | −0.049761049 | 0.016088349 | −0.093577096 | 0.090148464 | −0.019019483 |
| CD39 CD4 Tregs | −0.056591099 | 0.191174965 | −0.048748769 | −0.031846182 | −0.032916215 |
| Neutrophils | −0.059768388 | 0 | 0.000240949 | −0.025728408 | 0.093765225 |
| TIGIT+ PD1+ CD8 T cells | −0.064566669 | −0.05271506 | 0.189112025 | 0.001499926 | −0.037551525 |
| HLA-DR-low Monocytes | −0.066556219 | −0.018491814 | −0.073489973 | 0.000498086 | 0.136060987 |
| CD8 Memory T cells | −0.070528112 | −0.019370727 | 0.016686055 | 0.131824351 | −0.045640349 |
| Non-classical Monocytes | −0.072251524 | −0.025348313 | 0.122793758 | −0.001533621 | 0.009235295 |
| CD4 Transitional Memory | −0.073212119 | 0.186126199 | 0.034732583 | −0.045688383 | −0.054536799 |
| Granulocytes | −0.073359547 | 0 | 0.017347461 | −0.028183278 | 0.091932557 |
| Classical Monocytes | −0.075091382 | −0.012600798 | 0.120883564 | −0.033912086 | 0.062730277 |
| Mature NK cells | −0.083726253 | −0.013746556 | 0.198974754 | −0.00437679 | −0.022748525 |
| CD8 Central Memory | −0.093233991 | 0.094361388 | 0.093569764 | −0.035597838 | −0.031454879 |
| CD4 Memory T helpers | −0.147896635 | 0.33934971 | −0.107936973 | 0.012827493 | −0.059224879 |
| CD4 Central Memory | −0.153621053 | 0.436650167 | −0.093698578 | −0.03479063 | −0.061408384 |

TABLE 12

Immune profiles identified by cytometry-based immunoprofiling pipeline

| Number | Immunotype | Cell Type Enrichment | Functional Significance | TCR repertoires |
|---|---|---|---|---|
| G1 | Naïve | Naïve CD4+ CD8+ T cells, Naïve Tregs, and Naïve B cells | Undifferentiated, high response potential | Diverse +++ |
| G2 | Primed | Central and Transitional memory CD8+ T cells, and NK cells | Early clonal expansion, acute antigen exposure | Diverse ++ |
| G3 | Progressive | Dendritic Cells, Transitional memory CD8+ | Prolonged antigen exposure, | Diverse + |

TABLE 12-continued

Immune profiles identified by cytometry-based immunoprofiling pipeline

| Number | Immunotype | Cell Type Enrichment | Functional Significance | TCR repertoires |
|---|---|---|---|---|
| G4 | Chronic | T cells, and NK cells. Effector memory CD8+ T cells, NKT cells, and TEMRA | persistent viral infection Chronic antigen exposure, persistent viral infection | Clonal |
| G5 | Suppressive | Monocytes, MDSC, and Granulocytes | Immunosuppressive cell types and gene signatures | Mixed |

Methods

Internal Cohort Description

Peripheral blood samples of cancer patients were collected in multiple medical centers across the United States and delivered to BostonGene Laboratory. Blood of healthy donors were purchased from multiple collection centers around the Research Blood Components (Watertown, MA), STEMCELL Technologies (Vancouver, BC, Canada), and Discovery Life Sciences (Huntsville, AL). All patients provided written consent under IRB-approved protocols. Initially, 960 blood samples were collected for flow cytometry analysis, among them 470 patients with different cancer types (145 with sarcoma cancer subtypes and 325 with cancers of epithelial origin) and 449 healthy donor samples. 145 patients had sarcoma cancer subtype, 325 cancer of epithelial origin. After exclusion of samples based on insufficient quality, a total of 850 flow cytometry samples were analyzed in this study. For all patients, white blood cell analysis was performed using a unique flow cytometry approach (FIG. 16A).

The median age in the cohort was 47 years for healthy donors and 61.5 for cancer patients. Only patients with sarcomas and carcinomas were included, with the most frequent epithelial origin diagnoses: Pancreatic cancer (n=37), Breast neoplasm (n=65), Non-small cell lung carcinoma (n=32), Colorectal neoplasm (n=41), Melanoma (n=19) and Prostate (n=18). Therapeutic information was available for 417 (417/442, 94.3%) patients. Previous treatments were administered within a year of blood draw to 211 (211/417, 50.6%) patients including chemotherapy, radiotherapy, ICI or systemic therapy classified otherwise. 234 (234/417, 56.1%) patients were on ongoing therapy during material collection. Based on provided data, 44 (44/417, 10.55%) patients had no evidence of therapy administration after cancer diagnosis. Additionally, 797 RNA samples were analyzed from both healthy and cancer blood donors. This diverse cohort was used for multi-scale analysis of the relationship between cancer and peripheral blood immunity.

Head and Neck Squamous Cell Carcinoma Cohort

To further investigate the implications of newly discovered immune clusters to cancer immunotherapy, this flow cytometry analytical framework was applied to a cohort of 36 Head and Neck Squamous Cell Carcinoma (HNSCC) patients. The HNSCC cohort was part of a prospective phase II trial conducted in Thomas Jefferson University Hospital. During this trial, patients received anti-PD1 monoclonal antibody treatment (nivolumab) or nivolumab in combination with a specific IDO inhibitor (BMS986205). Pre- and post-treatment cryopreserved PBMCs were thawed and subjected to a multicolor flow cytometry staining. In total, 70 samples were analyzed with two of the patients having only pre-therapy samples due to poor quality of post-treatment PBMCs.

Blood Samples Processing and White Blood Cell (WBC) Isolation

Upon receipt, all fresh peripheral blood samples underwent a complete blood count using the DxH 500 Hematology Analyzer (Beckman Coulter, Brea, CA). Samples received within 24 hours of collection underwent red blood cell (RBC) lysis of 3 ml whole blood to isolate white blood cells (WBCs) using 42 ml nuclease-free HyPure water mixed with 5 ml 10× RBC lysis buffer (eBioscience). Samples were lysed at RT for 10 minutes, continuously mixing on a tube rotator. Cells were then centrifuged at 300×g for 5 minutes and washed with Sorter Buffer (2% NBCS in PBS+1 mM EDTA).

Cryopreserved PBMC Thawing

Cryopreserved peripheral blood mononuclear cell (PBMC) samples were stored in a vapor phase liquid nitrogen tank and thawed at 37° C. with premade thawing media (20% NBCS in 500 mL RPMI 1640 media+10 mL HEPES+10 mL PENSTREP+10 mL MEMNEAA+10 mL NAHEP+5 mL GlutaMAX). Prior to thawing, a 15 mL aliquot of thawing media was pre-warmed to 37° C. in a water bath and supplemented with 75 uL DNAse (20 mg/mL) and 75 uL Glutathione (200 mM). Samples were removed from the liquid nitrogen tank and immediately dipped into a 37C water bath, without submerging the cap in the water. Thawing was visually monitored, samples were swirled in the water bath for ~1 min until only a small ice crystal remained. Using a wide bore 1 ml pipette, each sample was transferred to an empty 15 mL tube. Pre-warmed, supplemented thawing media was slowly pipette into the tube, gently layering the media over the sample. After 3-4 mLs of layering, warmed media was slowly pipetted directly into the sample and simultaneously swirled until the sample was homogenous. Once homogenous, the sample was topped off with warm, supplemented thawing media until a final volume of 15 mL. PBMC samples were then centrifuged at 300×g for 8 minutes and washed with thawing media at 300×g for 8 minutes before staining.

Cell Staining and Flow Cytometry

Isolated WBCs or PBMCs were centrifuged at 300×g for 5 minutes, resuspended and blocked with Blocking Buffer (IMDM+10% NBCS+DNAse I (1:200)+Human TrueStain FcX (1:50)+Monocyte Blocker (1:50)+Unlabeled Normal Mouse IgG (1:200)) for 10 minutes at RT. After blocking, each sample was aliquoted into 10 unique wells in 96-well plate, centrifuged at 300×g for 3 minutes to remove supernatant. Each well was stained with Ghost Dye Violet 510 Viability Dye in PBS (1:400, Tonbo) at RT for 10 minutes. After staining with viability dye, 200 μL of Sorter Buffer was added to each well, centrifuged at 300×g for 3 minutes with the supernatant removed subsequently. Samples were stained with 10 custom flow cytometry panels (Table 13) for 20 minutes at RT. Once stained, 200 μL of Sorter Buffer was added to each well, centrifuged at 300×g for 3 minutes followed by supernatant removal. Cells were then fixed in a 1% paraformaldehyde solution (Cytofix/Cytoperm, BD Biosciences) overnight at 4° C. The fixation solution was then washed with Sorter Buffer and resuspended in Acquisition Buffer (PBS+0.5% (w/v) BSA+0.75% (w/v) Glycine+5 mM EDTA+ Tween-20 (1:2000)+Sodium Azide (1:100)).

Stained and fixed cells were acquired on the BD FACSCelesta Flow Cytometer. Prior to each acquisition, performance of BD FACSCelesta was checked using CS&T Research Beads (BD Biosciences). Compensation matrix was generated through the FACSDiva software by calculating spectral overlap from single stained controls. Single stained controls were prepared in-house by staining a set of 13 samples of Ultracomp eBeads Compensation Beads (Thermofisher) with unique antibodies in each channel.

TABLE 13

Flow Cytometry Panel Antibodies

| Reagent | Antibody Conjugate | Antibody Clone | Catalog # |
|---|---|---|---|
| CP10-Lineage | | | |
| Mouse Anti-Human CD14 | AF488 | M5E2 | 301811 |
| Mouse Anti-Human CD13 | BB700 | L138 | 746057 |
| Mouse Anti-Human CCR3 | BV421 | 5E8 | 310714 |
| Mouse Anti-Human CD123 | BV605 | 6H6 | 306026 |
| Mouse Anti-Human HLA-DR | BV650 | L243 | 307650 |
| Mouse Anti-Human CD3 | BV711 | OKT3 | 317328 |
| Mouse Anti-Human CD45 | BV786 | HI30 | 304048 |
| Mouse Anti-Human CD66b | PE | 6/40c | 392904 |
| Mouse Anti-Human CD56 | PE-CF594/ PEDazzle | 5.1H11 | 362544 |
| Mouse Anti-Human CD11c | PE-Cy7 | 3.9 | 301608 |
| Mouse Anti-Human CD19 | PE-Cy5 | HIB19 | 302210 |
| CP16 - Dendritic Cells | | | |
| Mouse Anti-Human FceR1 | AF488 | AER-37 (CRA-1) | 334640 |
| Mouse Anti-Human CD13 | BB700 | L138 | 746057 |
| Mouse Anti-Human CD1c | BV421 | L161 | 331526 |
| Mouse Anti-Human CD15 | BV510 | W6D3 | 563141 |
| Mouse Anti-Human CD3 | BV510 | OKT3 | 317332 |
| Mouse Anti-Human CD19 | BV510 | HIB19 | 302242 |
| Mouse Anti-Human CCR3 | BV510 | 5E8 | 310721 |
| Mouse Anti-Human CD7 | BV510 | M-T701 | 563650 |
| Mouse Anti-Human CD123 | BV605 | 6H6 | 306026 |
| Mouse Anti-Human HLA-DR | BV650 | L243 | 307650 |
| Mouse Anti-Human CD16 | BV711 | 3G8 | 302044 |
| Mouse Anti-Human CD45 | BV786 | HI30 | 304048 |
| Mouse Anti-Human CLEC9A | PE | 8F9 | 353804 |
| Mouse Anti-Human CD141 | PE-Daz | M80 | 344120 |
| Mouse Anti-Human CD11c | PE-Cy7 | 3.9 | 301608 |
| Mouse Anti-Human CD14 | PE-Cy5 | M5E2 | 301864 |
| CP22 - B Cells | | | |
| Mouse Anti-Human CD19 | BB515 | HIB19 | 564456 |
| Mouse Anti-Human IgD | BB700 | IA6-2 | 566538 |
| Mouse Anti-Human CD138 | BV421 | MI15 | 356516 |
| Mouse Anti-Human CD3 | BV510 | OKT3 | 317332 |
| Mouse Anti-Human CD7 | BV510 | M-T701 | 563650 |
| Mouse Anti-Human CD13 | BV510 | WM15 | 740162 |
| Mouse Anti-Human IgG | BV605 | G18-145 | 563246 |

TABLE 13-continued

Flow Cytometry Panel Antibodies

| Reagent | Antibody Conjugate | Antibody Clone | Catalog # |
|---|---|---|---|
| Mouse Anti-Human CD39 | BV650 | TU66 | 563681 |
| Mouse Anti-Human CD24 | BV711 | ML5 | 311136 |
| Mouse Anti-Human CD10 | BV786 | HI10a | 564960 |
| Goat Anti-Human IgA | PE | N/A (goat) | 2050-09 |
| Mouse Anti-Human IgM | PE-Daz | MHM-88 | 314529 |
| Mouse Anti-Human CD27 | PE-Cy7 | M-T271 | 356412 |
| Mouse Anti-Human CD38 | PE-Cy5 | HIT2 | 303508 |
| CP23 - Monocytes | | | |
| Mouse Anti-Human CD14 | AF488 | M5E2 | 301811 |
| Mouse Anti-Human CD9 | BB700 | M-L13 | 745827 |
| Mouse Anti-Human CD16 | BV421 | 3G8 | 562874 |
| Mouse Anti-Human CD3 | BV510 | OKT3 | 317332 |
| Mouse Anti-Human CCR3 | BV510 | 5E8 | 310722 |
| Mouse Anti-Human CD19 | BV510 | HIB19 | 302242 |
| Mouse Anti-Human CD7 | BV510 | M-T701 | 563650 |
| Mouse Anti-Human FceR1 | BV605 | AER-37 (CRA-1) | 334628 |
| Mouse Anti-Human HLA-DR | BV650 | L243 | 307650 |
| Mouse Anti-Human CD33 | BV711 | WM53 | 303424 |
| Mouse Anti-Human CD45 | BV786 | HI30 | 304048 |
| Mouse Anti-Human CD84 | PE | CD84.1.21 | 326008 |
| Mouse Anti-Human CD15 | PE-Daz | W6D3 | 323038 |
| Mouse Anti-Human CD169 | PE-Cy7 | 7-239 | 346014 |
| Mouse Anti-Human CD206 | PE-Cy5 | 15-2 | 321108 |
| CP26 - Natural Killer Cells (NK Cells) | | | |
| Mouse Anti-Human CD45 | AF488 | HI30 | 564585 |
| Mouse Anti-Human NKp44 | BB700 | p44-8 | 624381 |
| Mouse Anti-Human CD16 | BV421 | 3G8 | 562874 |
| Mouse Anti-Human CD19 | BV510 | HIB19 | 302242 |
| Mouse Anti-Human CD123 | BV510 | 6H6 | 306022 |
| Mouse Anti-Human CD13 | BV510 | WM15 | 740162 |
| Mouse Anti-Human CD3 | BV510 | OKT3 | 317332 |
| Mouse Anti-Human NKG2A | BV605 | 131411 | 747921 |
| Mouse Anti-Human CD158 | BV650 | HP-MA4 | 752506 |
| Mouse Anti-Human NKG2C | BV711 | 134591 | 748164 |
| Mouse Anti-Human CD57 | BV786 | QA17A04 | 393329 |
| Mouse Anti-Human CD161 | PE | HP-3G10 | 339904 |
| Mouse Anti-Human CD56 | PE-Dazzle594 | 5.1H11 | 362544 |

TABLE 13-continued

Flow Cytometry Panel Antibodies

| Reagent | Antibody Conjugate | Antibody Clone | Catalog # |
|---|---|---|---|
| Mouse Anti-Human NKG2D | PE-Cy7 | 1D11 | 320812 |
| Mouse Anti-Human CD107a | PE-Cy5 | eBioH4A3 | 15-1079-42 |
| CP24 - CD8 T Cell Differentiation | | | |
| Mouse Anti-Human CD27 | BB515 | M-T271 | 564642 |
| Mouse Anti-Human CD8 | BB700 | RPA-T8 | 566452 |
| Mouse Anti-Human CXCR3 | BV421 | G025H7 | 353716 |
| Mouse Anti-Human gdTCR | BV510 | B1 | 331220 |
| Mouse Anti-Human CD4 | BV510 | L200 | 563094 |
| Mouse Anti-Human CD19 | BV510 | HIB19 | 302242 |
| Mouse Anti-Human CD13 | BV510 | WM15 | 740162 |
| Mouse Anti-Human CD3 | BV605 | OKT3 | 317322 |
| Mouse Anti-Human CD62L | BV650 | DREG-56 | 304832 |
| Mouse Anti-Human CD95 | BV711 | DX2 | 305644 |
| Mouse Anti-Human CD57 | BV786 | QA17A04 | 393329 |
| Mouse Anti-Human CX3CR1 | PE | 2A9-1 | 341604 |
| Mouse Anti-Human PD-1 | PE-Daz | EH12.2H7 | 329940 |
| Mouse Anti-Human CXCR5 | PE-Cy7 | J252D4 | 356924 |
| Mouse Anti-Human CD45RA | PE-Cy5 | HI100 | 304110 |
| CP7 - CD8 T Cell Cancer Biomarker | | | |
| Mouse Anti-Human ICOS | BB515 | DX29 | 564549 |
| Mouse Anti-Human CD8 | BB700 | RPA-T8 | 566452 |
| Mouse Anti-Human Tim-3 | BV421 | F38-2E2 | 345008 |
| Mouse Anti-Human gdTCR | BV510 | 11F2 | 745026 |
| Mouse Anti-Human CD4 | BV510 | L200 | 563094 |
| Mouse Anti-Human CD19 | BV510 | HIB19 | 302242 |
| Mouse Anti-Human CD13 | BV510 | WM15 | 740162 |
| Mouse Anti-Human CD3 | BV605 | OKT3 | 317322 |
| Mouse Anti-Human CD62L | BV650 | DREG-56 | 304832 |
| Mouse Anti-Human CD27 | BV711 | M-T271 | 356430 |
| Mouse Anti-Human Lag-3 | BV786 | 11C3C65 | 369322 |
| Mouse Anti-Human TIGIT | PE | A15153G | 372704 |
| Mouse Anti-Human PD-1 | PE-Daz | EH12.2H7 | 329940 |
| Mouse Anti-Human CD39 | PE-Cy7 | A1 | 328212 |
| Mouse Anti-Human CD45RA | PE-Cy5 | HI100 | 304110 |
| CP25 - CD4 Treg Biomarker | | | |
| Mouse Anti-Human CTLA-4 | BB515 | BNI3 | 566918 |
| Mouse Anti-Human CD4 | BB700 | L200 | 566479 |

TABLE 13-continued

Flow Cytometry Panel Antibodies

| Reagent | Antibody Conjugate | Antibody Clone | Catalog # |
|---|---|---|---|
| Mouse Anti-Human CD25 | BV421 | BC96 | 302630 |
| Mouse Anti-Human gdTCR | BV510 | 11F2 | 745026 |
| Mouse Anti-Human CD8 | BV510 | RPA-T8 | 563256 |
| Mouse Anti-Human CD19 | BV510 | HIB19 | 302242 |
| Mouse Anti-Human CD13 | BV510 | WM15 | 740162 |
| Mouse Anti-Human CD3 | BV605 | OKT3 | 317322 |
| Armenian Hamster Anti-Human ICOS | BV650 | C398.4A | 313550 |
| Mouse Anti-Human CD27 | BV711 | M-T271 | 356430 |
| Mouse Anti-Human Lag3 | BV786 | 11C3C65 | 369322 |
| Mouse Anti-Human IL-7RA | PE | A019D5 | 351340 |
| Mouse Anti-Human PD-1 | PE-Daz | EH12.2H7 | 329940 |
| Mouse Anti-Human CD39 | PE-Cy7 | A1 | 328212 |
| Mouse Anti-Human CD45RA | PE-Cy5 | HI100 | 304110 |
| CP8 - CD4 T Cell Differentiation | | | |
| Mouse Anti-Human CD4 | BB515 | RPA-T4 | 564419 |
| Mouse Anti-Human CCR6 | BB700 | 11A9 | 746139 |
| Mouse Anti-Human CXCR3 | BV421 | G025H7 | 353716 |
| Mouse Anti-Human gdTCR | BV510 | 11F2 | 745026 |
| Mouse Anti-Human CD8 | BV510 | RPA-T8 | 563256 |
| Mouse Anti-Human CD19 | BV510 | HIB19 | 302242 |
| Mouse Anti-Human CD13 | BV510 | WM15 | 740162 |
| Mouse Anti-Human CD3 | BV605 | OKT3 | 317322 |
| Mouse Anti-Human CD62L | BV650 | DREG-56 | 304832 |
| Mouse Anti-Human CD27 | BV711 | M-T271 | 356430 |
| Mouse Anti-Human CD45RA | BV786 | HI100 | 304140 |
| Mouse Anti-Human IL-7RA | PE | A019D5 | 351340 |
| Mouse Anti-Human CCR4 | PE-Daz | L291H4 | 359420 |
| Mouse Anti-Human CXCR5 | PE-Cy7 | J252D4 | 356924 |
| Mouse Anti-Human CD25 | PE-Cy5 | BC96 | 302608 |
| CP28 - Nonconventional T Cells | | | |
| Mouse Anti-Human CD27 | BB515 | M-T271 | 564643 |
| Mouse Anti-Human CD8 | BB700 | RPA-T8 | 566452 |
| Mouse Anti-Human gdTCR | BV421 | 11F2 | 744870 |
| Mouse Anti-Human CD19 | BV510 | HIB19 | 302242 |
| Mouse Anti-Human CD13 | BV510 | WM15 | 740162 |
| Mouse Anti-Human CD3 | BV605 | OKT3 | 317322 |
| Mouse Anti-Human iNKT | BV650 | 6B11 | 744000 |

TABLE 13-continued

Flow Cytometry Panel Antibodies

| Reagent | Antibody Conjugate | Antibody Clone | Catalog # |
|---|---|---|---|
| Mouse Anti-Human TCR Vd2 | BV711 | B6 | 331412 |
| Mouse Anti-Human CD57 | BV786 | QA17A04 | 393329 |
| Mouse Anti-Human CD161 | PE | HP-3G10 | 339904 |
| Mouse Anti-Human CD56 | PE-Dazzle594 | 5.1H11 | 362544 |
| Mouse Anti-Human TCR Va7.2 | PE-Cy7 | 3C10 | 351712 |
| Mouse Anti-Human CD45RA | PE-Cy5 | HI100 | 304110 |
| Single Stain Controls | | | |
| ICOS (BB515, BD) | BB515 | DX29 | 337387 |
| CD13 | BB700 | L138 | 1169613 |
| CCR3 | BV421 | 5E8 | B281316 |
| CD19 | BV510 | SJ25C1 | B331406 |
| CD123 | BV605 | 6H6 | B322655 |
| HLA-DR | BV650 | L243 | 307650 |
| CD3 (OKT-3, Biolegend) | BV711 | OKT3 | B317956 |
| CD25 | BV786 | BC96 | B322204 |
| CD66b (Biolegend) | PE | 6/40c | B284868 |
| CD56 | PE-CF594 (Dazzle-594) | 5.1H11 | B325724 |
| CD11c | PE-Cy7 | 3.9 | B308581 |
| CD19 | PE-Cy5 | HIB19 | B311874 |

RNA Isolation

Isolated WBC for RNA sequencing were centrifuged at 300×g for 5 minutes with a maximum of 1e6 cells per vial. The supernatant was removed, and the cells were resuspended in cold Homogenization Buffer (2% 1-Thioglycerol, Promega). Samples were then frozen at −80° C. until extraction. RNA extraction was performed from frozen samples according to Maxwell RSC simplyRNA Cells Kit (Promega) using the benchtop automated Maxwell RSC Instrument (Promega).

Library Preparation and Sequencing of Samples

Libraries were prepared with Illumina TruSeq® Stranded mRNA Library Prep (Poly-A mRNA; stranded). Libraries were sequenced on NovaSeq 6000 as Paired-End Reads (2×150) with targeted coverage of 50 mln reads.

Flow Cytometry Data Processing

Flow cytometry data went through several quality control steps to ensure the consistency and overall high quality of the input in the analysis. All the selected patient samples contained no less than 10k cells in one panel. Files with poor compensation or occasional PMT failure were excluded. Flow cytometry data was exported in fcs 3.0 file format and analyzed as Pandas DataFrames (v 1.1.4) with compensation matrices applied using FlowKit (v. 0.5.0, github.com/mal-commac/FlowKit/releases) software for data processing and analysis. The values of all fluorochrome-marker channels were divided by a coefficient of 190 with the following inverse hyperbolic sine: $\text{arcsinh } x = \ln(x + \sqrt{(x^2 + 1)})$ transformation. Forward scatter and side scatter values (FCS-A/H/W and SSC-A/H/W) were divided by 105 to meet the order of data transformed with arcsinh.

Manual Data Analysis

A framework was developed for a precise manual analysis of cell populations combining classical gating within 2D scatter plots and clustering steps. Each panel was analyzed separately in accordance with its own specific strategy. Every strategy consists of several consecutive steps performed of the following cell selection/labeling methods:

Clustering approach. Events were clustered using Flow-SOM (v0.1.1, pypi.org/project/FlowSom/). Data was visualized with tSNE algorithm (openTSNE, v 0.6.2, pypi.org/project/openTSNE/) and coloured both by clustering result and by all markers intensity enabling to see the combination of markers intensities on specific clusters. Each cluster was matched with cell population manually based on a combination of markers intensities on this cluster.

Prior to clustering, processing the cytometry data may include a noise transformation. Noise transformation adjusts the intensity of the markers to reduce the influence of noise on the clustering results and includes reducing the intensity of the marker lower than a certain threshold. Threshold of noise for the marker is defined manually based on a 2-dimensional plot of the intensity of the marker versus intensity of another marker in the panel. The boundary between the noise and positive signal of the marker is chosen at the point of visually observed local minimum of the distribution by markers. Equations below describe the intensity of a marker after the noise transformation:

$$I_{after\ transform} = I_{initial}, \text{ if } I_{initial} \geq \text{border}$$

$$I_{after\ transform} = \frac{I_{initial}}{k}$$

where I_initial is the initial intensity of the marker from the cytometry data file, border is the threshold of noise for the intensity of the marker, and k is the coefficient of noise reduction. The coefficient of reduction is not a constant, it linearly increases from 1 at the selected threshold of noise to its maximum value (defined as 20) at the minimum intensity of the marker.

Population selection by two-dimensional plot shows pairwise projections of data distribution histograms and colored by distribution density of events (the same as done with classical gating process). The boundary between the positive and negative population is manually chosen at the point visually observed local minimum of the distribution by markers. In order to simplify the visual observation of local minimum of the distribution, kernel density estimate plots are used, above density plot.

The final results of manual data labeling were cell population labels for every event in the fcs file.

Model Training for Flow Cytometry Data Analysis

Manually labeled data was used to train LightGBM decision tree boosting machine learning models (with default parameters lightgbm.readthedocs.io/en/latest/Parameters.html). These models were trained to predict labels for each cytometry event. Approximately 200-300 labeled FCS samples were utilized for models for each cytometry panel. Forward scatter, side scatter and compensated fluorescence channel signal values were used as input along with ones being normalized on max and selected quantiles different for each panel (Table 14). A voting model was trained for each panel. The base model for voting was composed from two types of submodels each represented by LightGBM decision tree boosting classifier (LightGBM, v 3.3.2, pypi.org/project/lightgbm/3.3.2/). The first type predicted "top-level" populations such as Leukocytes in the general panel and CD8 T cells in the CD8 T cells panel. The second type classified the target population into subtypes. Overall model training process is shown in the Supplementary models figure.

Models performance was checked on validation sets of samples (~30 samples for each panel) not used in model training. For each of the validation samples predictions were generated. These predictions were then compared to the manual labels of these samples based on f1-score and p4-score metrics (see: Cytometry_supplement.xlsx, list "models_quality", average f1-scores and p4-scores are shown for each panel among all populations used in the article).

in the same way using ratio to number of WBC of three reference populations with hematology analyzer (Monocytes, Lymphocytes and Granulocytes).

TABLE 15

Reference populations used for combining results from different panels

| Panel | Reference population in CP10 | Reference population in corresponding panel |
|---|---|---|
| CP7 | CD3+_T_cells | CD3+_T_cells |
| CP8 | CD3+_T_cells | CD3+_T_cells |
| CP16 | PBMC_cells | PBMC_cells |
| CP22 | CD19+_B_cells | CD19+_B_cells |
| CP23 | Monocytes | Monocytes |
| CP24 | CD3+_T_cells | CD3+_T_cells |
| CP25 | CD3+_T_cells | CD3+_T_cells |

TABLE 14

Cytometry model parameters

| | CP7 | CP8 | CP10 | CP16 | CP22 | CP23 | CP24 | CP25 | CP26 | CP28 |
|---|---|---|---|---|---|---|---|---|---|---|
| quantile | 0.76027 | 0.5217 | 0.4927 | 0.4423 | 0.8192 | 0.72115 | 0.88009 | 0.67494 | 0.72468 | 0.78215 |
| Num leaves | 632 | 357 | 251 | 31 | 442 | 1000 | 215 | 367 | 190 | 836 |
| Max depth | 16 | 26 | 30 | 58 | 50 | 58 | 35 | 17 | 24 | 27 |
| Learning rate | 0.11942 | 0.0416 | 0.1 | 0.3176 | 0.0292 | 0.12183 | 0.05704 | 0.03002 | 0.22566 | 0.05934 |
| N estimators | 306 | 363 | 100 | 220 | 368 | 400 | 357 | 202 | 355 | 187 |
| Min child weight | 0.00396 | 2E−05 | 0.001 | 32.478 | 0.077 | 0.00033 | 0.00006 | 0.00291 | 0.60356 | 0.0006 |
| Min child samples | 131 | 283 | 121 | 20 | 289 | 99 | 67 | 108 | 58 | 122 |
| subsample | 0.38049 | 0.1994 | 0.1999 | 1 | 0.1731 | 0.46803 | 0.26537 | 0.60335 | 0.14877 | 0.46523 |
| Colsample bytree | 0.18997 | 0.2058 | 0.6839 | 1 | 0.2135 | 0.46819 | 0.6954 | 0.49554 | 0.95497 | 0.69627 |
| Reg alpha | 0.00125 | 2.0192 | 0.8841 | 0 | 0.2233 | 0.01003 | 0.11387 | 0.08093 | 0.04779 | 0.02603 |

Quality Control of Predicted Labels

All predicted labels, generated by models, underwent the procedure of manual quality control. Quality of predicted labels was assessed using a panel-specific set of 2-dimensional plots with the intensity of one marker against the intensity of another marker. Key populations for the panel were plotted in distinct colors on these plots to check the accuracy of selection of the populations and the accuracy of separation of the populations from one another. In case of any errors in the predicted label of the file, the gating of this population was corrected manually.

Determination of Cell Percentages

To calculate the final population percentages from labeled data, the results from different cytometry panels were combined together via the general panel (CP10). The cell count values in corresponding populations from other panels were multiplied by normalization coefficients to match results from the linear panel. The normalization coefficient was obtained by dividing the number of cells in the reference population in the linear panel by the number of cells in the reference population in the other panels ((Monocytes for monocytes panel, T cells for CD4 T cells panel, etc.). Table 15 contains the full list of reference populations used to combine results from different panels in order to calculate cell percentages for subpopulations. After this procedure, the percentage of Leukocytes for each cell population was calculated. The final percentages were obtained after multiplying percentages by normalization coefficient calculated

TABLE 15-continued

Reference populations used for combining results from different panels

| Panel | Reference population in CP10 | Reference population in corresponding panel |
|---|---|---|
| CP26 | NK_cells | NK_cells |
| CP28 | CD3+_T_cells | CD3+_T_cells |

RNA-Seq Quality Metrics

Raw FASTQ files quality was analyzed using FastQC (version 0.11.9), FastQ Screen (0.11.1) and MultiQC (version 1.14) software tools. The reference genomes utilized for the creation of BWA aligner indices (for FastQ Screen) included *Homo sapiens* (GRCh38), *Mus musculus, Danio rerio, Drosophila melanogaster, Caenorhabditis elegans, Saccharomyces cerevisiae, Arabidopsis thaliana, Mycoplasma arginini, Escherichia* virus phiX174, microbiome (downloaded from NIH Human Microbiome Project website), adapters (provided with FastQC v0.11.9), and UniVec (NCBI). All open source blood RNA-seq type datasets went through the same quality metric procedure as well.

RNA-Seq Processing

Bulk RNA-seq fastq files were processed by Kallisto, version (PMID: 27043002). The Kallisto index file was downloaded from the Xena project (PMID: 28398314), this index file was built based on GENCODE transcriptome annotation version 23 and the human reference genome GRCh38 with genes from the PAR locus removed (chrY: 10,000-2,781,479 and chrY: 56,887,902-57,217,415) (Vivian et al., 2017). In contrast to paired-end fastq files, single-end fastq files were processed by Kallisto with additional options -1 200 -s 15 in line with Xena. Calculated expression results were presented in the TPM format. All open source blood RNA-seq type datasets obtained from GEO or ArrayExpress were processed the same way as internal RNA-seq data. For further details of RNA-seq processing see deconvolution publication (PMID: 35944503).

Cell Deconvolution with Kassandra Algorithm

Kassandra is a cell deconvolution algorithm used for the digital reconstruction of the cellular composition of samples from gene expression data (PMID: 35944503). That is a decision tree machine learning technique trained on artificial mixes made from a broad collection of 9,414 tissue and blood sorted cell RNA seq samples. From profiles of sorted cells 150 000 of artificial transcriptomes were generated to train each cell type model. In each artificial mix, the fractions of all cell types were selected from a Dirichlet distribution with concentration parameters inversely proportional to the number of types. Each model was trained to predict the percent RNA fraction of each cell type represented in the mix using LightGBM version 2.3.1. The proportions predicted by the regressors were rescaled to sum up to 1. RNA seq proportions were recalculated into cell proportions using rna-per-cell coefficients derived from literature data.

TCR/BCR Analysis

The extraction of TCR or BCR clonotypes data from raw FASTQ files was executed with MiXCR software (version 3.0.12) (www.nature.com/articles/nmeth.3364) with default parameters for bulk RNA-seq extraction. For each clonotype, subsequent fractions were recalculated by chain summarized numbers. Additionally, clonotype groups, which correspond to similar (differ by 1 amino acid) CDR3 sequence in clonotypes, were identified for BCR. The diversity of TCR and BCR was estimated by calculation of Shannon index (www.ncbi.nlm.nih.gov/pmc/articles/PMC7331625/), Chao1 index and Clonality index (www.ncbi.nlm.nih.gov/pmc/articles/PMC93182/). The estimation was performed using downsampled to 100 clonotypes repertoire in order to exclude coverage bias in 10 replicates, for final analysis an average value was taken.

CDR3 specificity of TCR was analyzed using a comprehensive internal database which consists of data from VDJdb, McPAS, TBAdb and data for identified CDR3 sequences in different experiments from manually annotated articles.

HLA alleles of MHC I class were extracted by OptiType (v 1.0) (pubmed.ncbi.nlm.nih.gov/25143287/). This data was used for the analysis of allele distributions.

Tumor/Healthy Classifier

Transformer-based TabPFN model (paper: arxiv.org/abs/2207.01848, python package: github.com/automl/TabPFN, version 0.1.8) was used for cancer/healthy classification of the data samples. To determine the optimal number of features, a stepwise leave-one-out cross-validation approach was employed, utilizing the minimal-optimal feature selection algorithm MRMR (minimum-redundancy-maximum-relevance) (original paper: Ding, Chris, and Hanchuan Peng. Journal of bioinformatics and computational biology 3.02 (2005): 185-205, recent Uber paper: arxiv.org/pdf/1908.05376.pdf, python package: github.com/smazzanti/mrmr, version 0.2.5 was used in this research). Different variants of feature numbers ranging from 10 to 100 in increments of 10 were tested, aiming to find the subset of features that yielded the best model performance (FIG. 25).

Using the MRMR algorithm, the most significant number of features (cell populations) in discriminating between healthy donors and cancer patients were identified in a leave-one-out cross validation for values from 10 to 100 in increments of 10. It was determined that 20 features provided the optimal selection between these two groups (FIG. 17D, Differentially distributed populations).

To ensure data similarity between the training and validation datasets, the UMAP (Uniform Manifold Approximation and Projection) technique (paper: arxiv.org/abs/1802.03426, python package: github.com/lmcinnes/umap, version 0.5.3 was used in this research) was applied. This technique was employed on a substantial corpus of data points-specifically, 503 samples in the training dataset and 347 in the validation dataset. This process allowed us to visualize both datasets and compare them for any discrepancies. By verifying data similarity, quality of the trained model accurately was assessed using the features sampled from the training dataset for the validation dataset.

Clustering Algorithm

Flow cytometry data were represented as cell percentages (from total number of WBC for granulocyte populations and from total number of PBMC percentages for all other populations) see Table 16. Major cell populations (also represented in Kassandra deconvolution method) were selected for the cluster analysis with addition of manually selected ICI-relevant cell populations based on extensive publication analysis: TIGIT+PD1+CD8 T cells (PMID: 33188038), Vdelta2+gamma-delta T cells (PMID: 27400322), CD39+ Tregs (PMID: 32117275), HLA-DRlow monocytes (PMID: 26787752, 33842304, 32939320, 26873574, 31592989, 24844912, 24357148).

TABLE 16

Cluster populations and normalization

| Cluster_populations | Normalization |
|---|---|
| CD4_Naïve_Tregs | PBMC |
| CD4_Naïve_T_cells | PBMC |
| CD8_Naïve_T_cells | PBMC |
| Naïve_B_cells | PBMC |
| Non-switched_Memory_IgM_B_cells | PBMC |
| gdT_Vdelta2+ | PBMC |
| Class-switched_Memory | PBMC |
| CD8_Central_Memory | PBMC |
| CD4_Tregs | PBMC |
| CD4_Transitional_Memory | PBMC |
| CD4_Central_Memory | PBMC |
| CD4_Memory_T_helpers | PBMC |
| CD4_T_cells | PBMC |
| CD39_CD4_Tregs | PBMC |
| Eosinophils | WBC |
| Basophils | WBC |
| Plasmacytoid_Dendritic_cells | PBMC |
| Dendritic_cells | PBMC |
| TIGIT+_PD1+_CD8_T_cells | PBMC |
| CD8_Transitional_Memory | PBMC |
| Mature_NK_cells | PBMC |
| Immature_NK_cells | PBMC |
| CD8_Memory_T_cells | PBMC |
| CD8_T_cells | PBMC |
| CD4_Effector_Memory | PBMC |
| NKT_cells | PBMC |
| CD8_TEMRA | PBMC |
| CD8_Effector_Memory | PBMC |
| CD4_TEMRA | PBMC |

TABLE 16-continued

| Cluster populations and normalization | |
| --- | --- |
| Cluster_populations | Normalization |
| Neutrophils | WBC |
| Granulocytes | WBC |
| Classical_Monocytes | PBMC |
| Non-classical_Monocytes | PBMC |
| HLA-DR-low_Monocytes | PBMC |

Prior to clustering the data was rescaled just as for min-max normalization but with 2nd and 98th percentiles instead of 0 and 1 respectively. All values outside 0-1 range were clipped to the closest value.

Formula for Normalization $$\text{scaled value } Vx = \frac{Px - Pq02}{Pq98 - Pq02}$$

Spectral clustering approach (scikit-learn version 1.1.2) was selected for clustering technique as a better performing method. Spectral clustering is more robust and can be more suitable clustering algorithm for the data where expected clusters form irregular shape [pubmed.ncbi.nlm.nih.gov/35652725/] (probably a link should be provided, something like ieeexplore.ieee.org/document/6019693).

Evaluation of Cluster Number

To find the optimal number of clusters it decided to test which decomposition produces the most distinct immunotypes. For this clustering technique with the various number of clusters starting with 2 up to 14 was tested. For each decomposition all possible pairs of subtypes were compared between each other with the Further Mann Whitney U test being applied for each pair of clusters for each feature (34 populations) to check if these clusters statistically differ from each other by this population. Then for p-values from all comparisons (number of features×number of permutations without repetitions) Bonferroni correction has been applied. Finally for each pair of clusters the number of p-values lower than the selected threshold (0.05) was calculated and the median number of those significant p-values in every clustering iteration was found. In Table 17 median number of features which significantly distinguish each pair of clusters for the decompositions with number of clusters from 2 to 14 is presented. It can be noticed that for the decompositions with number of clusters 4 and 5 this median number of features is the same and the highest across all options. Decomposition with 5 clusters was chosen as the highest number of clusters which covers all diversity of data and still produces significantly different groups.

TABLE 17

| median number of features per cluster | |
| --- | --- |
| Number of clusters | Number of features |
| 2 | 27 |
| 3 | 27 |
| 4 | 28 |
| 5 | 28 |
| 6 | 22 |
| 7 | 24 |
| 8 | 25 |
| 9 | 25 |
| 10 | 23 |
| 11 | 25 |

TABLE 17-continued

| median number of features per cluster | |
| --- | --- |
| Number of clusters | Number of features |
| 12 | 22 |
| 13 | 23 |
| 14 | 22 |

Optimal cluster number was evaluated for the cohort and found out that clustering with 4 and 5 clusters gives a maximum score of distinct features between each pair of clusters and that score drops with 6 clusters, Therefore, spectral clustering was performed with 5 clusters, as 5 clusters was the highest number of clusters which covers maximal observable diversity of the cohort data.

This immunophenotyping assay was evaluated for sensitivity, reproducibility, and repeatability on fresh whole blood. Populations detected in frequencies greater than 0.01% displayed coefficients of variation that were on average less than 10%.

Differential Expression Analysis

Differential expression (DE) analysis was conducted using the edgeR tool (bioconductor.org/packages/release/bioc/html/edgeR.html). Heat shock genes and sex genes were excluded from the analysis.

Gene Set Enrichment Analysis (GSEA) of Differentially Expressed Genes

GSEA analysis was performed on an unfiltered list of 200 genes, ranked in descending order of differential expression test statistics. The Compute Overlaps tool (www.gsea-msigdb.org/gsea/msigdb/help_annotations.jsp #overlap) was used to compare the gene sets with the H gene set (hallmark gene sets) and the CP gene set (canonical pathways) from the MSigDB collection. For each cluster genset, 22 gene sets were chosen in the collections that best overlap with the gene set (see FIG. 18C). These results and chose N signatures were chosen that are most interesting from the point of view of cluster characterization.

Signature values were calculated using ssGSEA, normalized and shown as a heatmap. The ssGSEA score of PD1 related signatures was also calculated for patients on PD1 therapy. (FIG. 20)

Pseudotime Analysis

Pseudotime analysis was performed with the usage of Monocle software [PMID: 24658644]. Monocle is an unsupervised algorithm initially developed to perform on a single-cell RNA-seq data to analyze the cell fate decisions based on gene expression data. Since the analysis aimed to analyze the connection not between different cells, but between different blood samples, it was run again on cell percentages obtained from flow cytometry data analysis.

Cluster-Aligning Multiclass Classifier

The TabPFN multiclass classification model with default parameters was employed to analyze the comprehensive cohort data. The model was trained on the complete dataset, which was labeled with corresponding clusters using a selected list of features. To enhance the model's performance, the Leave-One-Out cross-validation method for model evaluation was utilized.

Classifier for HNSCC Data

In case of missing some surface cell markers presence in thawed samples, some of cell populations were replaced to those populations that were corresponding parents on the hierarchy tree. After proving that the internal and HNSCC cohorts data have similar distribution using a Kernel Maximum Mean Discrepancy (MMD), a multiclass classification TabPFN model was trained on the initial cohort with the same cross-validation approach. The model achieved a macro average F1-score of 0.84 and a weighted average F1-score of 0.82.

As the TabPFN model turned out to be suitable for the cohort, it was applied to the HNSCC dataset to align each sample to the corresponding cluster.

RNA-seq deconvolution-based classifier: A multiclass classifier was also trained based on deconvolution analysis of RNA-seq data (FIGS. 26A-26C). Predicted cell percentages were renormalized to PBMC fraction, and then the data was rescaled for min-max normalization and clipped in the same way as for the clustering method (see Clustering method). The LightGBM classifier was trained on (lightgbm.readthedocs.io/en/v3.3.2/#) populations intersecting between cluster cytometry and deconvolution (35 populations, see FIG. 18B legend). To validate this model, a leave-one-out cross-validation (academic.oup.com/bioinformatics/article/21/15/3301/195433?login=false) was used.

More than 20,000 bulk whole blood RNA-seq samples across several diagnoses from the GEO and ArrayExpress databases (Barrett et al., 2012) (Open-source datasets list) were gathered. The raw RNA-seq datasets were combined, homogeneously annotated, and bioinformatically recalculated for comparable measurements of transcript expression within each cell type to reduce batch effects. After quality control in total (n=18,712) purified RNA-seq of blood samples were analyzed including healthy donors and patients with more than 90 different diagnoses grouped based on diagnosis common features. After extensive QC, cell population percentages were extracted from each data set using Kassandra, those cell percentages were processed by the trained multiclass classifier, splitting the data into 5 clusters.

Cluster-Based Signatures Score

Cluster signature score is a linear metric that separates all samples belonging to the given cluster from all other samples in the multidimensional space of percentages of cells. For each of the clusters there was a separate signature-related model.

Prior to implementing this technique, the cytometry data was rescaled for min-max normalization and clipped the same way as it was done for the clustering method (see Clustering method). Then Elastic Net regression was used to identify coefficients that linearly transform percentages of cell populations to a number from 0 to 1 (separating samples from the chosen cluster and other clusters). Features were normalized percentages of cell populations. 1 was assigned to samples from the chosen cluster and 0 to samples from other clusters. Model parameters alpha and 11_ratio were selected by grid search. The score for grid search was cross-validated AUC. Cross-validation was made with StratifiedShuffleSplit (n_splits=5, test_size=0.3). After the model was trained, predictions for all cohort samples were obtained and calculated 0.01 and 0.99 quantiles of cohort predictions for normalization (q01 and q99, respectively) were determined. The final score was counted as a=9.9* (prediction−q01)/(q99−q01)+0.1, with all predictions being clipped at those quantile values. Therefore the presented signature score always lies between 0.1 and 10. These signature scores were counted for the whole internal cohort as well for the HNSCC cohort.

Training Cohort (Current Set)→[Validation Cohort, Next 347 Patients and Healthy Donors]

Clusters were established and then showed that these patients cluster with the same distribution and then follow up with these patients (potentially) and obtain clinical outcome dataEach cluster defines different immune response states, do these states reflect a condition that is stable or are these clusters in flux.

Processing of HNSCC Cohort Flow Cytometry Data

As mentioned previously, out of 72 cytometry samples (pre- and post-treatment combined), 2 samples were excluded from the further analysis due to low sample quality. Cytometry data for all panels of this HNSCC cohort was analyzed using both predicted by model labels and manually acquired labels.

All markers for all panels underwent thorough analysis of their performance after cryopreservation. A list of markers with significantly decreased intensity (decrease in median of 95-percentile of intensity more than 1.5 times with p-value less than 0.05) in comparison with internal fresh PBMC and WBC cohorts were detected. The list of such markers include CD62L, CXCR3, CXCR5, CCR6 and CD161. Populations defined by those markers were excluded from further analysis.

Remaining populations were finally sorted by median count of cells, detected in each population. Populations with median count less than 50, were removed from the analysis, as their counts are less than the limit of detection.

Figure 28:
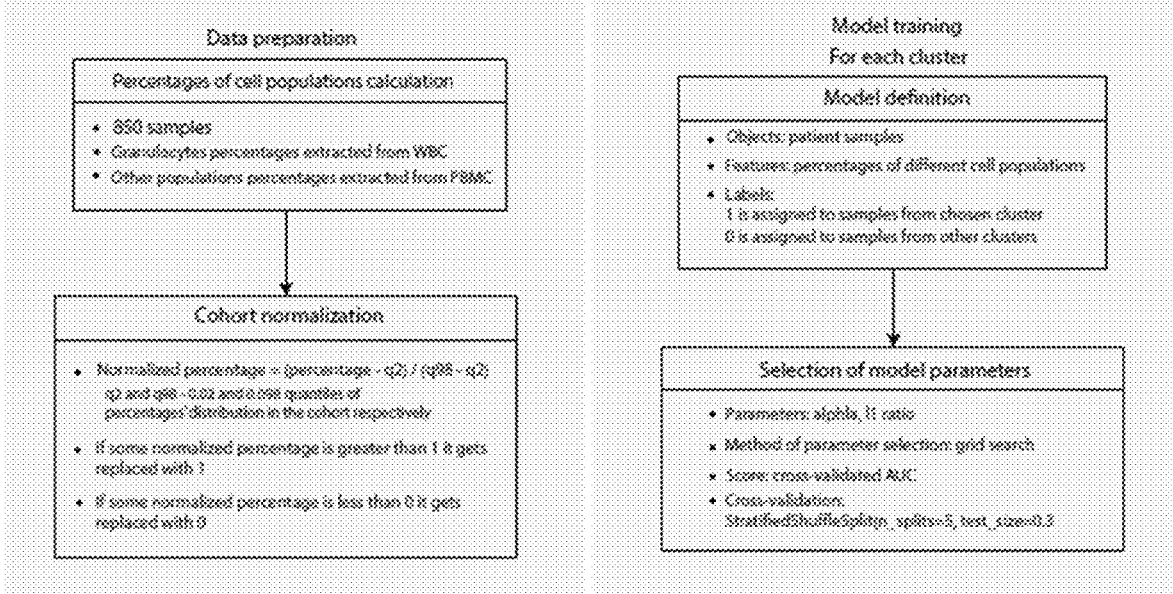
FIG. 28 shows a flow chart describing data preparation, model training, and signature calculation for a new blood sample, in accordance with some embodiments of the technology described herein.

FIG. 28 shows a flow chart describing data preparation, model training, and signature calculation for a new blood sample, in accordance with some embodiments of the technology described herein.

Computer Implementation

Figure 15:
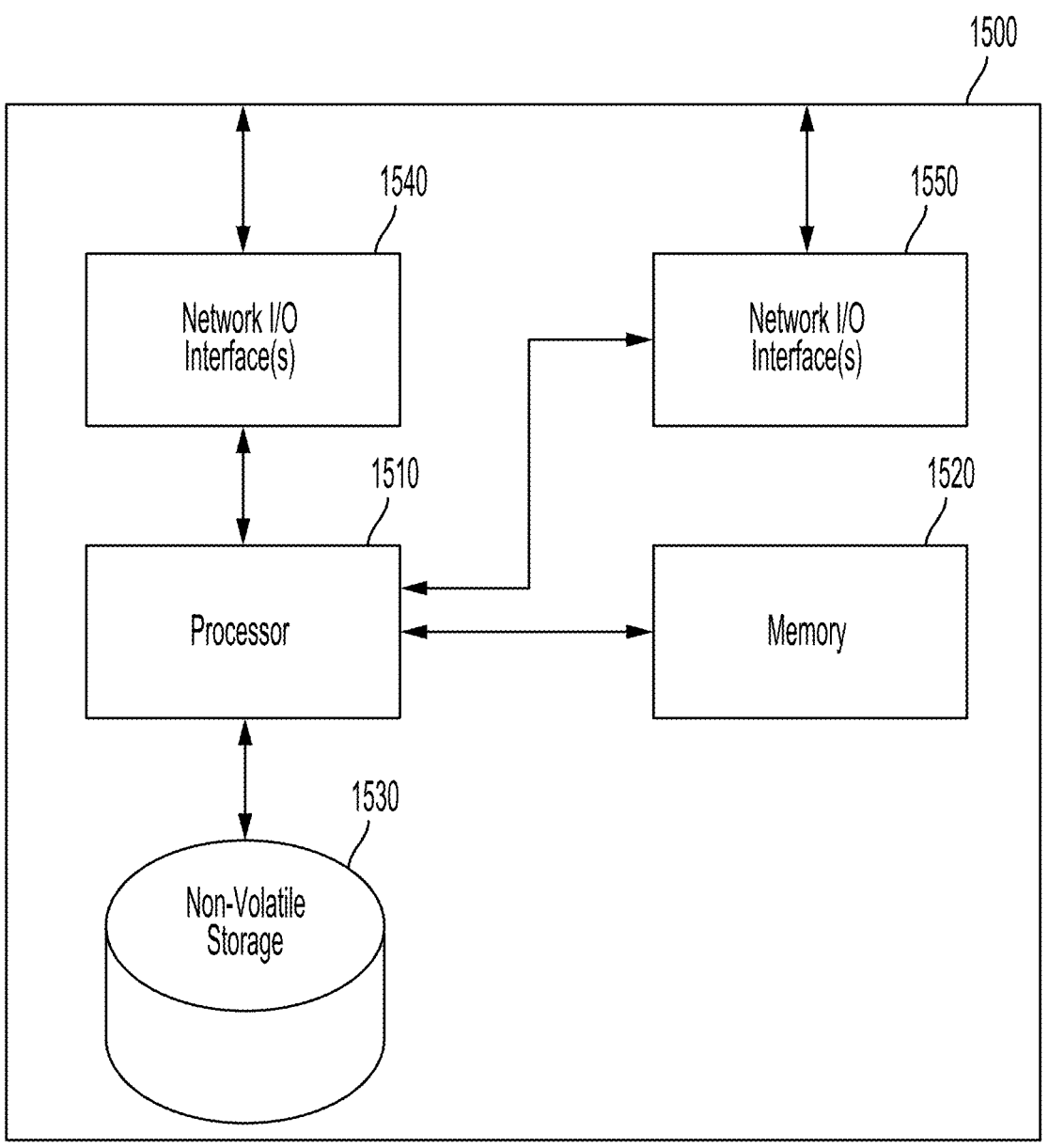
FIG. 15 depicts an illustrative implementation of a computer system that may be used in connection with some embodiments of the technology described herein.

An illustrative implementation of a computer system 1500 that may be used in connection with any of the embodiments of the technology described herein (e.g., such as the method of FIG. 1, FIG. 2, FIG. 3, FIG. 4, etc.) is shown in FIG. 15. The computer system 1500 includes one or more processors 1510 and one or more articles of manufacture that comprise non-transitory computer-readable storage media (e.g., memory 1520 and one or more non-volatile storage media 1530). The processor 1510 may control writing data to and reading data from the memory 1520 and the non-volatile storage device 1530 in any suitable manner, as the aspects of the technology described herein are not limited to any particular techniques for writing or reading data. To perform any of the functionality described herein, the processor 1510 may execute one or more processor-executable instructions stored in one or more non-transitory computer-readable storage media (e.g., the memory 1520), which may serve as non-transitory computer-readable storage media storing processor-executable instructions for execution by the processor 1510.

Computing device 1500 may also include a network input/output (I/O) interface 1540 via which the computing device may communicate with other computing devices (e.g., over a network), and may also include one or more user I/O interfaces 1550, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software, or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

The foregoing description of implementations provides illustration and description but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel.

It will be apparent that example aspects, as described above, may be implemented in many different forms of software, firmware, and hardware in the implementations illustrated in the figures. Further, certain portions of the implementations may be implemented as a "module" that performs one or more functions. This module may include hardware, such as a processor, an application-specific integrated circuit (ASIC), or a field-programmable gate array (FPGA), or a combination of hardware and software.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone, a tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

TABLE 18

Example genes that are specific or semi-specific to cell types.

| Cell Type | Genes |
|---|---|
| Basophils | ACTR8, ADCY7, AKAP12, ALDH16A1, ALOX5, ALS2, ANAPC4, APOBEC3A, ARHGEF6, ASL, ATF7, ATP10D, ATP2C1, BRE, C11orf21, C1orf186, CASP3, CCNA1, CHPT1, CLEC2D, CPA3, CPEB3, CPNE3, CSF2RB, CTAGE9, CTNNBL1, CYP11A1, DHX15, DPP9, E2F2, ECSIT, EFHC2, ENPP3, FAM110A, FCER1A, GAB1, GAB2, GAB3, GATA2, GCSAML, GLG1, GPATCH2L, HDC, HIPK2, HLX, HPGDS, HRH4, IDH3G, IFFO1, IGF1R, IKBKAP, IL3RA, IL4, INPP5D, ITGA2B, ITSN1, JAK2, KANSL3, KIAA1147, LIN7A, MAPK14, MILR1, MLX, MS4A2, MS4A3, NAALADL1, NDST1, NLK, NLRC3, NTRK1, OR6K3, OSBPL1A, PDLIM7, PHC1, PLA2G6, PLAGL1, PPP1R26, PRKCD, PTGER3, PTGS1, REPS2, RIPK3, RYR3, S1PR1, SBF2, SCCPDH, SCUBE1, SEMA3C, SLC2A10, SLC35A2, SLC45A3, SPECC1, ST3GAL4, ST6GAL1, STAM, SUMO3, SUPT20H, SV2C, TAL1, TCN1, TCP11L2, TEC, TEX101, TNFSF11, TPCN1, TPGS2, TRIM51, TRIM62, TRIM64B, TTN, UBXN4, VPS13A, WBP2, ZNF521 |
| CD4+ T cells | ADGRE1, AGMAT, ANKRD55, BCL11B, BCL2L14, BCL2L2, C11orf95, CCR4, CCR7, CD2, CD248, CD28, CD3D, CD3E, CD4, CD40LG, CD5, CD6, CD8A, CD8B, CISH, CRTAM, CTBP2, CTLA4, EEF1B2, FAM184A, FAM19A1, FBLN7, FCER1G, FEZ1, FHIT, FOXP3, GJB6, GNG8, GPR171, GTDC1, GYPC, GZMK, HAPLN3, HIP1, HLADQB1, HMSD, HOXC4, ICOS, IL2RA, IL32, KLRC4, KLRK1, LAT, LDHB, LRRN3, MAL, MAN1C1, PIGT, PRPF19, PTGIR, RCAN3, RGS10, RHOBTB2, RHOC, RNF144A, RPL10, RPL32, RPL36, RPL39, RPL7, RPS12, RPS29, SERPINB9, SLC25A53, SLC4A10, SMAD5, SSTR3, ST6GALNAC1, SUSD3, TESPA1, TIAM1, TNFAIP8L2, TNFRSF4, TRABD2A, TRAC, TRAT1, TRBC2, TRBV251, TSHZ2, UBASH3A, USP11, XCL1, XCL2, ZNF101 |
| CD8+ T cells | ADGRE1, AGMAT, ANKRD55, BCL11B, BCL2L14, BCL2L2, C11orf95, CCR4, CCR7, CD2, CD248, CD28, CD3D, CD3E, CD4, CD40LG, CD5, CD6, CD8A, CD8B, CISH, CRTAM, CTBP2, CTLA4, EEF1B2, FAM184A, FAM19A1, FBLN7, FCER1G, FEZ1, FHIT, FOXP3, GJB6, GNG8, GPR171, GTDC1, GYPC, GZMK, HAPLN3, HIP1, HLADQB1, HMSD, HOXC4, ICOS, IL2RA, IL32, KLRC4, KLRK1, LAT, LDHB, LRRN3, MAL, MAN1C1, PIGT, PRPF19, PTGIR, RCAN3, RGS10, RHOBTB2, RHOC, RNF144A, RPL10, RPL32, RPL36, RPL39, RPL7, RPS12, RPS29, SERPINB9, SLC25A53, SLC4A10, SMAD5, SSTR3, ST6GALNAC1, SUSD3, TESPA1, TIAM1, TNFAIP8L2, TNFRSF4, TRABD2A, TRAC, TRAT1, TRBC2, TRBV251, TSHZ2, UBASH3A, USP11, XCL1, XCL2, ZNF101 |
| PD1high CD8+ T cells | CBLB, CD2, CD226, CD244, CD27, CD38, CD8A, CD8B, CRTAM, CTLA4, ENTPD1, FASLG, HAVCR2, ICOS, IL2RA, IL2RB, IRF4, ITGAE, KLRC1, KLRK1, LAG3, LTA, PDCD1, PRDM1, PRKCQ, PVRIG, SH2D1A, SIRPG, TIGIT, TMIGD2, TNFRSF9 |
| Central memory CD8+ T cells | ABCB1, ADAM23, ADGRG4, ADTRP, AGAP1, ALOX5AP, ARG1, ARHGAP25, BATF, BCL2, BEX2, C10orf128, C2orf40, C4orf50, CACNA1I, CCL17, CCL5, CCR2, CCR5, CCR7, CD2, CD28, CD4, CD40LG, CD83, CD8A, CDH9, CEP295, CHN2, CLDND1, CLECL1, CLIC3, COTL1, CPA5, CREBL2, CST7, CTLA4, CYP1A2, DHRS3, DSC1, DSEL, EOMES, EVL, FBXL16, FCRL6, FGFBP2, FGFR1, FHIT, FHL3, FLJ20019, FRMD4B, GALM, GALT, GLB1L3, GRAP2, GRM2, GZMA, GZMH, GZMK, GZMM, HLADOA, HLF, HTR4, HYPK, ICOS, ID2, IGHG3, IL2RA, IL3RA, IL4I1, IL5RA, IL7R, IMPDH2, ITGA1, JAKMIP1, KCNJ10, KIR2DL2, KIR2DL3, KIR3DL2, KLRB1, KLRC2, KLRD1, KLRG1, KLRK1, KRT1, KRTAP212, LAG3, LDLRAP1, LEF1, LEPROTL1, LIMS2, LPAR6, LRRC75A, LRRN3, MALT1, METTL4, MICAL2, MLC1, MPPED2, MYO7A, MZB1, NCALD, NCR3, NDUFC2KCTD14, NEFL, NFATC2, NGDN, NMUR1, NT5E, NUAK1, OR2H2, PDCD1, PDE3B, PDE4DIP, PDZD4, PIK3R1, PIM1, PRDM1, PRF1, PRSS35, PRSS50, PRY2, PTF1A, PTPRM, PURG, RBM3, RBM39, RCAN2, RGPD5, RPH3A, RPL10A, RPL3, S1PR5, SAMD3, SEC31B, SELL, SIRPB1, SNTG2, SORBS1, SPN, SPON2, SRY, STYK1, SV2A, TBC1D2B, TCAF2, TESPA1, TIAM1, TMC6, TMPRSS3, TOE1, TPRG1, TRA2B, TRAC, TRGC1, TTC23L, TXNIP, WNT7A, ZNF33A, ZNF365, ZNF496, ZNF683, ZNF709, ZNF90 |
| Central memory CD4+ T cells | ACAP3, ACSS2, ADAM19, ADAM23, ADGRE1, ADPRM, ADTRP, AHNAK, AIFM3, AKR1E2, AMN, ANKRD55, AP3M2, APH1A, AQP3, ARHGAP31, ATP10A, B3GAT1, B4GALT5, BACH2, BCL2L14, BEST4, BLK, C10orf128, C2orf40, C8orf44, C9orf89, CA6, CACNA1I, CAMK4, CAPN12, CARD17, CCL5, CCR2, CCR3, CCR4, CCR5, CCR7, CCR9, CD19, CD2, CD247, CD27, CD28, CD3D, CD3G, CD4, CD40LG, CD5, CD58, CD6, CD69, CD7, CD70, CD79A, CD82, CER1, CHDH, CIAPIN1, CLDND1, CLECL1, CPA5, CR2, CRHR1, CSF2, CSGALNACT1, CTLA4, CTSW, CXCR5, CYLD, CYP1A2, CYSLTR1, DACT1, DDB2, DERL2, DNAH6, DSC1, EDAR, EPHA1, FAM134B, FAM153A, FAM19A1, FAM98B, FAS, FBLN7, FCRL1, FCRL3, FGFBP2, FLT3LG, FMN1, FOXP3, FXYD5, GAL3ST4, GALM, GALT, GATA3, GKN1, GLB1L3, GNAO1, GNG8, GP5, GPA33, GPD1, GRAP2, GRM2, GSTK1, GZMH, GZMK, HDC, HLF, HPCAL4, HPGDS, ICOS, IGHG1, IGHG3, IGKC, IKZF2, IL17A, IL2RA, IL32, IL5RA, IL7R, INPP4B, IRF4, ITGAE, ITGB1, ITK, JAKMIP1, JPH4, KBTBD3, KCNA6, KCNQ3, KIT, KLF8, KLRB1, KLRG1, KRT1, KRT10, KRT73, LCK, LEF1, LILRA4, LIMS2, LRRN3, LTA, MAN1C1, MAP2K5, MCOLN3, MDFIC, MDS2, MGST1, MS4A1, MT1X, MTRF1, MYB, MYO7A, NEFL, NFATC2, NFKBIZ, NIPAL2, NOSIP, NPM2, OR1L4, OR2T3, OR4D9, OR56A5, OR5H15, PAGE2, PASK, PBX4, PDCD1, PDE4DIP, PDZD4, PFDN5, PGA4, PIK3R1, PKIA, PLA2G4F, PLCG1, POU2AF1, POU3F1, PPIAL4F, PRDM1, PRF1, PROM1, PRSS35, PRY2, PTGDR, PTGER2, PTP4A3, RCAN3, RGPD5, RIC3, RORA, RPL14, RPL39L, RPL4, RPS13, RPS25, RPS26, RPS6, |

TABLE 18-continued

Example genes that are specific or semi-specific to cell types.

| Cell Type | Genes |
|---|---|
| | RPS6KA5, RSBN1, SAMD3, SELL, SIRPG, SIT1, SLC18A2, SLC35E3, SLC5A11, SLC7A3, SLX1B, SOAT2, SOX5, SOX8, SRY, SSTR3, STAC3, STAP1, TBC1D2B, TBC1D3C, TBC1D4, TCEA3, TCF7, TESPA1, THBS4, TIAM1, TLCD2, TMEM155, TMEM169, TMEM205, TMEM45B, TMIGD2, TMPRSS11E, TNFRSF25, TNFRSF4, TOX2, TP53, TPRG1, TRAC, TRAT1, TRBV251, TSHZ2, TULP2, UAP1L1, UBASH3A, USHBP1, VIPR1, VSIG8, WDR53, WNT7A, WNT9A, ZBED2, ZBTB2, ZNF365, ZNF490, ZNF683, ZNF709, ZXDB |
| Class-switched memory B cells | AADACL3, AANAT, ACAN, ACP5, ADCY4, ADCY5, ADORA2A, AIM2, ARHGEF3, ARNT, BAIAP3, BANK1, BCAS4, BCL7A, BEND4, BLK, BTNL9, C10orf128, C12orf74, C16orf86, C17orf107, C6orf47, CACNA1E, CCDC106, CCNG2, CCR6, CD1C, CD27, CD37, CD72, CD79B, CDHR3, CHD3, CLEC2B, CLVS2, CNR1, COCH, COL21A1, COL4A3, CRHBP, CXCR5, DCT, DEFA3, DGKD, DLGAP2, DLK1, DNAH8, DNAJC1, DNAJC5B, DTX1, DUSP15, DUSP8, DUX4, ERN1, ESR2, FAM231D, FBXW8, FCER2, FCMR, FCRL5, FMO2, FOLR2, GAGE12F, GAGE13, GDF7, GHRH, GIPR, GPM6A, GPR25, GRIK3, GYLTL1B, HBE1, HBG1, HBG2, HBZ, HCRT, HDAC10, HDC, HLADQA2, HLAG, HMCES, HOMER3, HRASLS2, HTR3A, IFNLR1, IGHD, IGHM, IL21R, IL4R, IL5RA, INSL4, KCNH8, KCNN4, KIAA0319, KIR2DS5, KIR3DX1, KLF13, KLHL40, KNOP1, KRT1, KRT6A, KRT6B, LONRF1, LRMP, LTB, LY86, MAGEA10, MAP3K7CL, MARCKS, METTL7A, MIIP, MYBPC2, MYO15A, N4BP3, NAPSA, NEB, NRK, OR1N1, OSTN, OXCT2, P2RY14, PCDH9, PCSK5, PDHB, PGPEP1, PIP5K1B, PKIG, PLA2G2D, PLEKHG7, PPAPDC1B, PRKD2, PRM2, PVRIG, PXDC1, RAB30, RAD51D, RASSF6, RHAG, RPL36A, RPL37A, RPS25, S100Z, SCN4A, SDR16C5, SGCA, SH3BP2, SLAMF1, SLC17A3, SLCO4C1, SOWAHD, SOX10, SPEM1, SPINK3, SRPR, ST6GAL1, T, TAS1R3, TBC1D26, TBC1D28, TBC1D3, TBC1D3K, TCF7, TCL1A, TCTE1, TFAP2E, TFEB, TMEM163, TMPRSS11D, TNFRSF13B, TNFRSF1B, TNNT3, TOX2, TRAK1, TYW5, UBALD2, USP17L11, VANGL2 |
| Classical monocytes | ACP5, ADAMTS5, AOC1, AP1S2, ARF6, ASB2, ASGR1, ASGR2, ATXN7L1, BATF2, C12orf57, C1QC, C9orf89, CASQ1, CCDC149, CCL3, CCR2, CD14, CD163, CD1D, CD22, CD300E, CD36, CD5, CD68, CDKN1A, CEACAM3, CEBPD, CHST13, CHST2, CLEC11A, CLEC17A, CLEC4F, CLEC5A, CMKLR1, COL9A2, COX6C, CPAMD8, CPVL, CRTAP, CXCL9, CYBB, DHRS4, DOC2B, DUSP5, DYSF, EGR1, EIF2B1, ENHO, FAM198B, FBN2, FCER1A, FCER2, FCGR1A, FCGR1B, FCN1, FOLR2, FPR3, FXYD6, GABBR1, GFI1B, GLT1D1, GPR34, GPR35, GSTM1, HIC1, HIVEP2, HLADQA2, HNMT, IFI30, IFITM3, IL15, IL1RN, IL21R, IL4I1, JPH4, KCNH3, KLF10, KLF11, KLHL22, L1TD1, LGALS2, LGALS3, LGALS9B, LILRB4, LPPR4, LRRC37A2, LTA4H, LYZ, MAFB, MEFV, MGAT1, MN1, MS4A6A, MSR1, NCF1, OLFM4, OSCAR, PID1, PIK3AP1, PLA2G7, PLD4, POFUT1, PRR5L, PSMD6, PTGIR, PTPRN2, RBBP6, REEP4, RGL4, RNASE2, RNASEL, RXFP2, S100A12, S1PR3, SARS2, SERPINB6, SEZ6L, SH3BP5, SIGLEC1, SIGLEC14, SIGLEC5, SIGLEC6, SIK1, SIK3, SLC28A3, SLX1ASULT1A3, SNAI1, SNX4, SPNS3, STAB1, SULT1A3, TBATA, TBC1D3, TLR7, TMEM176B, TMEM255B, TNFSF12, TNFSF13, TNNT3, TSHZ1, TYMP, TYW5, UAP1L1, ULK4, UMODL1, UPK3A, VSIG4, WDR49, XPC, ZDHHC7, ZNF469, ZNF706 |
| Cytotoxic NK cells | ACSL6, ADGRG3, AGK, AGPAT4, ARVCF, B3GNT7, B3GNT8, BAALC, CCL4, CCR1, CCR5, CD160, CD247, CD27, CD84, CD8B, CEP78, CHST2, CLIC3, COLQ, CPXM1, CRTAM, CXCR6, CYP4F22, DTHD1, FCGR3A, FCRL6, FEZ1, FGFBP2, GAS7, GIMAP1, GIMAP6, GNG2, GRIK4, GZMK, HAVCR2, HERPUD2, HSH2D, IL18RAP, IL1RL1, IL23R, IL2RB, KIR2DL1, KIR3DL3, KIR3DX1, KIT, KLRB1, KLRC3, KLRC4KLRK1, KLRF1, LAG3, LDB2, LGALS9B, LIM2, LITAF, LPAR6, MAPRE2, MGAM, MIB2, MLC1, NHSL2, NKG7, NMUR1, PAK6, PDGFRB, PIK3R6, PITPNM2, PODN, PROK2, PYHIN1, RCBTB2, RNF165, S1PR5, SH2D1B, SH2D2A, SLC4A10, SPON2, STOM, TCF7, TFDP2, TIGIT, TKTL1, TOX2, TRGC2, TTC38, TXK, UBASH3A, ZNF683 |
| Dendritic cells | AANAT, ACVRL1, ADAM28, ADAM33, AIFM3, APOBR, ARHGAP24, ARRDC3, ASGR1, ASGR2, ATP1A4, C1orf54, C9orf91, CALCRL, CASQ1, CCDC88A, CD68, CD74, CES1, CHST15, CIITA, CLEC10A, CLEC9A, CLIC2, CLNK, COL9A2, CST3, CTSO, CYBB, CYP2S1, EFCAB2, EMB, ENHO, F13A1, FCER1A, FLT3, FMO5, FRMD3, GPRIN3, H2AFY, HIGD2A, HLADOA, HLADPA1, HLADPB1, HLADQA1, HLADRA, HLADRB1, HOMER2, HTR7, HVCN1, ICOSLG, ID2, IFNLR1, IL15, ITIH4, KCNH8, KMO, L3MBTL3, LAIR1, LGALS2, LILRB1, LMNA, LY86, MAFB, MAP4K1, MBD2, MRC1, MS4A7, MTSS1, NDRG2, NEURL1, OLIG1, P2RX7, P2RY6, PARVG, PNOC, PRCP, PRKAR2B, PTPRO, RASA4, RASA4B, RASGEF1B, RASL11A, RHBDF2, RHOB, RPL14, RPL15, RPL18A, RPS11, RPS24, S100A10, SCNM1, SEMA4A, SERINC1, SEZ6L, SIGLEC1, SIK1, SLC12A7, SLC37A2, SLC46A2, SNAI1, SNED1, SPNS3, ST18, STARD8, TCTA, TIFAB, TLR7, TMSB10, TOP1MT, TTC7A, TYK2, UBE2J1, UBQLN2, UPK3A, VAMP8, VASH1, YIF1B, ZNF366, ZNF385A, ZNF469 |
| Effector memory CD8+ T cells | ABHD17A, ADAM19, ADAM23, ADGRG4, ADPRM, ADTRP, AGAP1, AGAP6, AHNAK, AIF1, ALOX5AP, ANXA1, AQP3, ARHGAP25, ATP10A, B3GAT1, BATF, BEND4, BLK, C10orf53, C1QC, CA6, CACNA1I, CAMK4, CARNS1, CASP3, CCL17, CCL23, CCL5, CCR2, CCR3, CCR4, CCR9, CD160, CD27, CD28, CD4, CD48, CD7, CD72, CD80, CD8A, CD8B, CD99, CDH9, CEACAM8, CENPC, CER1, CHDH, CHST2, CLDND2, CLEC2B, CLECL1, CPXM1, CR2, CRACR2A, CRBN, CRHR1, CSGALNACT1, CST7, CTLA4, CTSW, CX3CR1, CYLD, DERL2, DHRS3, DHX8, DPPA4, DSC1, DUSP4, EDAR, EOMES, EPHA1, EPX, EVL, FAM212A, FAM45A, FAM90A1, FAS, FBLN7, FBXO39, FCRL3, FGFBP2, FGFR1, FHL3, FLT3LG, FNDC5, FRMD4B, GALNT11, GALT, GATA1, GATA3, GNLY, GNRH2, GP5, GPLD1, GRM2, GZMA, GZMH, GZMK, GZMM, HDC, HLADRB1, HPGDS, HSH2D, HTR4, HUS1B, HYPK, ICOS, ID2, IFNG, IFNK, IFNLR1, IGHG1, IGLL5, IKZF2, IL2RA, IL2RB, IL5, IL5RA, IQCA1, IRF4, ITGAE, ITGB1, ITM2C, JAKMIP1, JPH4, KCNJ10, KCNJ5, KIF1A, KIF5A, KIR2DL3, KIR3DL1, KLF8, KLLN, KLRB1, KLRC3, KLRK1, KRTAP212, LAG3, LAIR1, LAIR2, LDLRAP1, LECT1, LIM2, LIMS2, LMO4, LYG1, MDFIC, MDS2, METTL4, MGAT4A, MICAL2, MMP25, MPPED2, MXI1, MYCBPAP, MYF6, MYO16, MYO7A, MYSM1, MZB1, NCALD, NCR1, NCR3, NFATC2, NFKBIZ, NKX63, NOSIP, NPRL2, NRBP2, NRDE2, NT5E, OR11H4, OR2H2, P2RY14, PDCD1, PDE3B, PDLIM2, PDZD4, PIK3R1, PIM1, PINLYP, PRDM1, PRG3, PRSS35, PRSS50, PRY2, PTF1A, PTGDR, PTGER2, PTPRM, PURG, PYHIN1, RBM3, RBM39, RCAN3, RGL4, RHOC, RHOT2, RIC3, ROBO2, RORA, RPH3A, RPL10A, RPL18, RPL21, RPL37, RPS13, RPS14, RPS26, RPS27A, RPS28, RPS5, RSBN1, S100A4, S100B, S1PR5, SAMD3, SARAF, SEC11C, SEC31B, SELL, SERTAD3, SH2D1B, SIGLEC6, SIGLEC7, SIRPB1, SIRPG, SLC17A9, SLC2A7, SLC34A2, SLC7A3, SLPI, SLX1B, SMG1, SMIM24, SMPD3, SMURF2, SNTG2, SOAT2, SOX8, SPDYE5, SPEF2, SPN, SPON2, SV2A, TBC1D2B, TBC1D3C, TBPL2, TCAF2, TCERG1L, TESPA1, TIAM1, TMC6, TMEM11, TMEM151B, TMEM155, TMEM182, TMEM39B, TMPRSS3, TNF, TPRG1, TPT1, TRA2B, TRAC, TRAT1, TRGC1, TRPM2, TRPS1, TSHZ2, TULP2, UBASH3A, USHBP1, VIPR1, VWA5B2, ZCCHC14, ZNF345, ZNF35, ZNF365, ZNF414, ZNF496, ZNF548, ZNF709, ZNF853, ZNF880, ZNF90 |

TABLE 18-continued

Example genes that are specific or semi-specific to cell types.

| Cell Type | Genes |
|---|---|
| Effector memory CD4+ T cells | ABCB1, ABHD17A, ADAM19, ADAM23, AHNAK, ALOX5AP, AMY2A, AMZ1, ANKRD20A1, ANKRD55, AP3M2, AQP3, B2M, B3GAT1, BACH2, BATF, C10orf128, C1QC, C1orf100, C1orf54, C4orf50, CA6, CACNA1I, CACNA2D2, CAPN12, CARD17, CCL19, CCL4, CCL5, CCR1, CCR2, CCR3, CCR4, CCR5, CCR7, CCR9, CD163, CD1C, CD1E, CD2, CD207, CD244, CD27, CD28, CD3E, CD3G, CD4, CD40LG, CD5, CD52, CD6, CD69, CD7, CD80, CD8A, CD8B, CD99, CER1, CHDH, CLDND2, CLEC10A, CLEC2B, CLEC4F, CLEC9A, CPA5, CPNE5, CRBN, CRHR1, CRTAM, CSF3R, CSGALNACT1, CST7, CTLA4, CTSW, CX3CR1, CXCR1, CXCR2, CXCR5, CYLD, DNAH6, EDAR, F13A1, FAM153A, FAM19A1, FAM45A, FAS, FBLN7, FBXL16, FBXO39, FCER1A, FCGR3B, FCRL3, FCRL6, FGFBP2, FOSB, FOXP3, GALM, GALNT8, GALT, GATA3, GBP1, GKN1, GNAO1, GNLY, GPA33, GPBAR1, GPR132, GPR34, GPR87, GRAP2, GSE1, GSTK1, GZMA, GZMH, GZMK, GZMM, HLADOA, HLADOB, HLADRB1, HLF, HPCAL4, HPGDS, HRH2, HSD11B1, HTR4, ICOS, IDO1, IFNG, IKZF2, IL2RA, IL32, IL4I1, IL5RA, IL7R, IRF5, ITGA1, ITGAE, ITGAM, ITGB1, ITK, JAKMIP1, KCNA6, KIAA0825, KIT, KLF8, KLRB1, KLRD1, KLRF1, KLRG1, KLRK1, KRT1, KRT17, KRT73, LAG3, LAIR2, LBHD1, LGALS8, LILRA4, LMO4, LPAR6, LRRN3, MAGEB3, MGAT4A, MNDA, MS4A1, MS4A6A, MYO16, MYO7A, MYSM1, MZB1, NCAM1, NCR3, NEFL, NFKBIZ, NGDN, NKG7, NMUR1, OGN, OR10G2, P2RY14, PADI2, PDCD1, PDE3B, PDE4DIP, PDZD4, PGA4, PHOSPHO1, PKIA, PLCG1, PLVAP, PRDM1, PRF1, PRSS35, PRY2, PSAP, PTGDR, PTGER2, PYHIN1, RASA4B, RCAN2, RCBTB2, RORA, RPL14, RPL4, RPLP1, RPS19, RSBN1, S1PR1, S1PR5, SAMD3, SELL, SERPINB9, SIRPG, SIT1, SLAMF7, SLC18A2, SLC35F3, SMPD3, SNTG2, SPEF2, SPN, SPON2, SRY, SV2A, TBC1D3C, TBC1D4, TCF7, TESPA1, TLCD2, TMEM155, TMPRSS3, TNF, TNFRSF10C, TNFRSF25, TNFRSF4, TNFSF13B, TPRG1, TRAC, TRAT1, TRBC2, TRBV251, TRGC1, TRPM2, TSHZ2, TTC39B, TULP2, UBASH3A, WNT7A, WNT9A, ZEB2, ZNF250, ZNF365, ZNF683, ZNF90 |
| Eosinophils | ABCB10, ABTB2, ADAMTS7, ADGRE1, AJAP1, AKNA, AKT1, ANKRD13A, APOBEC3A, ARHGAP10, ATP2A3, AXIN1, BCL2A1, C1D, CASP10, CCDC112, CD300LB, CD300LF, CEBPE, CEP85, CLCF1, CNKSR2, COTL1, CYSLTR2, DAPK2, DBP, DEFA1B, DEFA3, DUSP6, DYNLT1, EHD1, FBN1, FFAR2, FHL3, FRRS1, GAB3, GATA1, GFI1B, GPR160, GRHL1, GSTM2, GSTM4, H1FX, HDAC1, HIC1, HLAA, INPP1, IQSEC2, ITGA4, ITGB2, KCNH2, KIAA0040, LAIR1, LAT2, LGALS12, MAP4K4, MCPH1, MPZL3, MSRA, MTFR1L, MTMR1, MYCT1, NAPA, NTAN1, ORMDL3, OSBPL11, OSTF1, P2RY2, PDK4, PIK3IP1, PMM2, PRSS33, PTGER4, RGS1, RIPK3, RNF122, RPS6KA2, SELPLG, SEPT5, SIGLEC10, SIGLEC8, SLC29A1, SMPD3, SNX27, SOAT1, SORD, SPG21, SULF2, SYNE1, TCEB2, THBS4, TKTL1, TMEM140, TMEM50B, TRIB1, TTC7B, TXLNB, UBASH3B, UGT2A3, USP3, VPS45, WDR91, XKR8, ZNF397, ZSCAN29 |
| Granulocytes | A2M, ABCB10, ABHD12, ABTB2, ACP2, ACSL1, ADAMTS7, ADAP2, ADM, ADORA3, AJAP1, AK5, AKNA, AKT1, ALDH16A1, ALOX5, ALOX5AP, ALPL, ALS2, ANAPC4, APOC1, ARAP2, ARHGAP18, ARSB, ATP10D, ATP6V0D1, AXIN1, BCL2L11, BCL7A, C10orf128, C11orf21, C15orf39, C19orf38, C1D, C1QC, C1orf186, C1orf54, C2, C6orf48, CAMP, CCDC109B, CCDC112, CCDC71L, CCL2, CCL23, CCL5, CCNA1, CCR3, CD101, CD14, CD274, CD300LF, CD36, CD3D, CD52, CD68, CD83, CD86, CEACAM3, CEACAM4, CEP63, CEP85, CEP85L, CFD, CHPT1, CIR1, CLEC2D, CLEC4E, CNKSR2, COMT, COTL1, CPA3, CPAMD8, CPM, CPNE3, CSF1, CSF2RB, CSTA, CTNNBL1, CTSO, CUL1, CXCL2, CXCR2, CYBA, CYP11A1, DBP, DDX54, DEFA1B, DEFA3, DHRS9, DHX15, DPEP2, DPP9, DUSP6, ECSIT, EEF1B2, EEF1G, EEPD1, EFHC2, ENHO, ENOPH1, ENPP3, EPB41L3, ERCC1, EVI2B, EXOSC5, FABP5, FAM110A, FAM198B, FAM35A, FARS2, FCER1A, FCN1, FGFBP2, FGFR1OP, FHL3, FKBP9, FPR1, FPR2, FXYD6, GAB3, GCSAML, GHRL, GNG2, GNL2, GPATCH2L, GPNMB, GPR160, GPR183, GPR84, GPX1, GRHL1, GSN, H3F3A, H3F3B, HDAC1, HIC1, HLAC, HLAE, HNMT, HNRNPA1, HRH4, IDH3G, IFI30, IFITM2, IFNGR2, IGF1R, IGHD, IKBKAP, IL13RA1, IL1R2, IL3RA, INPP1, INPP5A, IQSEC2, IRF2, ITGA4, ITGB2, ITSN1, JAK2, JUN, KANSL3, KATNBL1, KCNH2, KCNK13, KCTD12, KIAA0319, KLF11, LAIR1, LAT2, LCP2, LILRB3, LIN7A, LITAF, LRG1, LST1, LTF, LY96, LYN, LYZ, MAFB, MAP4K4, March1, MBOAT7, MCPH1, METTL7A, MMP9, MNDA, MRC1, MS4A2, MS4A3, MS4A7, MTA2, MTFR1L, NAAA, NDST1, NFAM1, NINJ2, NKG7, NLK, NLRP6, NPC2, NPL, NTRK1, NUP214, OAZ2, OLR1, OR6K3, ORM1, ORMDL3, OSBPL1A, OSTF1, OXER1, PADI4, PANX2, PECAM1, PFDN1, PFDN5, PGLYRP1, PIK3IP1, PLA2G7, PLAC8, PLAGL1, PLBD2, PMM2, PON2, PRKCD, PRR13, PSAP, PSMB8, PTGER4, PTMA, R3HDM4, RASA4, RASGRP3, RASGRP4, RBP7, REPS1, REPS2, RGL4, RNF122, RNF19B, RNPS1, ROPN1L, RPL19, RPL23, RPL5, RPS5, RPS6KA1, RPS6KA2, RYR3, S100A13, S1PR3, SAT1, SBF2, SCRN1, SEC11A, SELPLG, SEPP1, SEPT2, SEPT5, SETD7, SHC1, SLC11A1, SLC15A3, SLC1A3, SLC25A37, SLC29A1, SLC2A10, SLC37A2, SLC43A2, SLC45A3, SLC46A2, SLC4A3, SMCO4, SMPD3, SMPDL3A, SNAI3, SNX18, SNX27, SOD2, SPECC1, SPI1, SRGN, ST6GAL1, STX3, SULF2, SUPT20H, SUSD1, SV2C, SYNE1, TBC1D9B, TCEB2, TCIRG1, TCN1, TCN2, TEC, TFEC, TKTL1, TMEM140, TMEM176A, TMEM50B, TMEM51, TMEM8B, TMTC2, TNFRSF10C, TNFSF11, TPGS2, TREM1, TRGC2, TRIB1, TRIM51, TRIM62, TTC7B, TTN, TYROBP, UBASH3B, UBE2E2, UBXN4, UGT2A3, UNC119, UQCRFS1, USP3, VPS45, WAS, WBP2, WDR49, WDR5, WDR91, XKR8, YIF1B, ZNF397, ZNF469, ZNF521, ZSCAN29 |
| Memory CD8+ T cells | ABHD17A, ADAM19, ADTRP, AGAP1, AHNAK, ALOX5AP, ANKRD55, AOAH, AP3M2, AQP3, ARG1, ARHGAP25, ATP6V1C2, B3GAT1, BACH2, BATF |
| Naive B cells | AIM2, ALPL, ARHGAP31, BANK1, BCL11A, BCL7A, BLOC1S2, BTG1, C10orf128, C12orf74, C16orf74, CACNA1E, CASP10, CBFA2T3, CD1A, CD27, CD69, CD80, CD83, CDIP1, CDK5R1, CLCN4, COL4A3, CR1, CS, CSF2RB, CXCR4, CXCR5, DAAM1, DNAH7, EHD3, ELOF1, ERAP1, ERCC5, EVI2B, FAM126A, FAM53B, FFAR1, FOLR2, FXYD1, GDF7, GOLGA8B, GPR132, GPR18, GRAPL, GSX2, HDAC9, HLA-DQA2, HLA-DQB1, HSH2D, IGHD, IGHM, IL18BP, IL21R, IL2RA, IL4R, ITGAM, KCNG1, KDM5D, LAPTM5, LARGE, LSP1, MACROD2, MMP17, MYZAP, NAPSA, NCK2, NEK6, NOL4L, NUAK2, P2RY10, PCBP3, PIP4K2A, PLCG2, PLEK, PLEKHG7, PNPLA7, POTEG, REL, RFTN1, RHOH, RPL18A, SCN3A, SH3BP1, SIK1, SLITRK2, TAGAP, TAPBP, TAPT1, TBC1D28, TBC1D3F, TBC1D9, TCF4, TCL1A, TCL1B, TEX9, TNFRSF13B, TSPAN33, TXLNB, UGT2B17, UTS2B, UTY, WSCD2, ZNF154 |
| Naive CD8+ T cells | ADAM23, ADPRM, AIF1, ANKRD55, AP3M2, BACH2, BCL2, C2orf40, C4orf50, CA6, CACNA1I, CAMK4, CAPN12, CARD17, CARNS1, CCL5, CCR4, CCR5, CCR7, CD2, CD27, CD28, CD3D, CD3E, CD3G, CD40LG, CD48, CD5, CD7, CD79A, CD8A, CD8B, CD99, CDH9, CDKN2AIP, CENPC, CLDND1, CLEC11A, CPA5, CR2, CSGALNACT1, CTLA4, CYLD, CYP1A2, DACT1, DBH, DSC1, DSEL, EDAR, EEF1A1, EOMES, EPHA1, EXOC8, FAM129C, FAM134B, FAM153A, FBLN7, FCRL3, FHIT, FLT3LG, FOXP3, GAL3ST4, GALT, GLB1L3, GP5, GPA33, GSTK1, GZMA, GZMH, GZMK, HPCAL4, HTR4, HYPK, ICOS, IL7R, IMPDH2, IRF4, ITGA1, ITK, JAKMIP1, KCNJ10, KCNJ5, KLRB1, KLRC2, KLRC3, KLRG1, KLRK1, KRT1, KRT17, LAG3, LAIR2, LDLRAP1, LEF1, LEPROTL1, LPAR6, LRRN3, MALT1, MAN1C1, MDS2, MXI1, MYB, MYF6, NOSIP, NT5E, OR10G2, PCMTD2, PDCD1, PDE3B, PDZD4, PIK3R1, PIM1, PRDM1, PRDM2, PYHIN1, RCAN3, RNASEH2B, RORA, |

TABLE 18-continued

Example genes that are specific or semi-specific to cell types.

| Cell Type | Genes |
|---|---|
| | RPL10A, RPL14, RPL18, RPL19, RPL21, RPL3, RPS12, RPS13, RPS14, RPS27A, RPS28, RPS3A, RPS5, RPS6, RPS8, RSBN1, S100B, SCTR, SFRP5, SIRPG, SIT1, SLC7A3, SMG1, SMIM24, SORBS1, SPDYE5, SSTR3, SV2A, TBC1D2B, TCF7, TESPA1, TGFBR2, TIAM1, TMEM155, TMIGD2, TNFRSF13C, TRAC, TRAT1, TSHZ2, UBASH3A, VIPR1, ZNF33A, ZNF496, ZNF683, ZNF853 |
| Naive CD4+ T cells | ABCA2, ABCC10, ACE, ACVR1C, ADAM19, ADAMTS10, ADAMTSL2, AHNAK, AK5, AKAP11, AKR1C4, ALS2CL, ANKRD55, C15orf53, C9orf153, CA6, CACNA1I, CARD17, CBLL1, CCDC154, CCNI2, CCR10, CCR4, CCR8, CD7, CD84, CHD3, CLIC5, COL18A1, COL6A3, CORO7PAM16, CPA5, DACT1, DCHS1, DPYSL4, DSC1, DTX1, EDAR, EPHA4, FAM153A, FAM153B, FBLN2, FUT7, FXYD7, GDPD5, GKN1, GPR155, GPR55, GPRASP1, GRAP2, HBG1, IKZF2, IL10RA, KCNA2, KDM5D, KIAA2022, KLF8, KRT72, KRT73, LDOC1L, LIPF, LMTK3, LTBP3, MACF1, MAGEB3, MAN1C1, MAPK10, MCF2L2, MDN1, MMP28, MTUS2, NBPF15, NPIPA1, NUPR1L, OBSCN, OGDH, OTOF, PDCD1, PI16, PIWIL1, PLAG1, PSMB11, RASGRF2, RGPD1, RPL11, RPS15A, RPS25, RPS27, RPS4Y1, S100B, SAMD3, SAP25, SCML1, SFRP5, SLC25A53, SNED1, SNPH, SOCS3, SORCS3, SSTR3, ST8SIA1, STX1B, SV2C, TBC1D4, TCEA3, THEM5, TMIGD2, TRABD2A, TRERF1, TRIM35, TSHZ2, UPK3BL, USP46, VSNL1, WDR86, WSCD2, ZNF80 |
| Neutrophils | ADGRE3, ADGRG3, C5AR1, CCR3, CEACAM8, CLEC7A, CSF3R, CXCR1, CXCR2, EVI2B, IFITM2, FCGR2A, FCGR3B, FFAR2, FPR1, FPR2, KCNJ15, MEFV, MMP25, MNDA, PADI2, PADI4, PGLYRP1, RASGRP4, SIGLEC5, TNFRSF10C, VNN2, VNN3, WAS, GLT1D1, P2RY13, PHOSPHO1, LILRB3 |
| Non-classical monocytes | ABI3, ACP5, ADA, ADD2, ADGRE1, ASB2, C1QA, CABP4, CD14, CD300LB, CD37, CD79B, CD99, CDKN1C, CEACAM3, CHST2, CLEC4F, CRTC3, CSF1R, CSTB, CTSL, CX3CR1, DRAP1, ERICH1, FAM118A, FCGR3A, FCN1, GSAP, GUCY1B3, HK1, HMOX1, ICAM4, IFITM3, IL21R, IL27, IL27RA, KDM5D, KNDC1, L1TD1, LILRA1, LILRB1, LST1, LYNX1, LYPD2, MBD2, MMP17, MOB1A, MRAS, MS4A14, MS4A7, MTPN, MTSS1, NAP1L1, NAPSA, NEURL1, NLRX1, NPIPB9, OAS1, OPRL1, ORAI2, OSBPL7, OSCAR, P2RX7, PHF19, PIK3AP1, PPM1N, PPP1R17, PRR5, PTMA, PTP4A3, PXN, RHOC, RNF122, SERPINB1, SERPINB9, SFTPD, SH2D1B, SIGLEC10, SIGLEC7, SIRPB1, SLC46A2, SOD1, SPN, SYT17, TADA3, TBC1D3, TBC1D3E, TBC1D3L, TCF7L2, TESC, TNFRSF8, TSKS, UTY, VMO1, ZBTB4 |
| Non-switched Memory IgM B cells | ACAN, ACKR1, ACYP2, ADCY4, ALOX5, ALPL, ANGPTL1, ARHGAP17, ARHGAP24, ARHGAP5, BMF, BMP3, BTNL2, C16orf74, CACFD1, CCDC17, CCR6, CCR7, CD1C, CD1E, CD70, CD79B, CD86, CEND1, CHAD, CHMP7, CLEC17A, COCH, COL4A3, CORO2B, CRB2, CRHBP, CTSH, CYB5R2, DEFA3, DLGAP1, DNAH7, DPF3, DSCAML1, EEF1B2, ERICH3, ESPNL, ESR2, ETV7, FFAR1, FOXO1, FRZB, FXYD1, GCSAM, GEN1, GNG7, GPM6A, GPR25, GRIK3, GTSF1L, HDC, HRK, HTR3A, IGHD, IGHM, IGLL1, IL21R, IL2RA, IL4R, IL6, IRGM, JAM3, KCNG1, KCNH8, KIAA0226L, KLRK1, LCE1A, MACROD2, MAP3K7CL, MARC2, MARCKS, MAST4, MMP17, NCR3, NLGN4Y, NR3C2, NUDT3, OSBPL10, OXCT2, PARM1, PARP15, PCBP3, PITPNM2, PLA2G2D, PLEKHF2, POTED, PPAPDC1B, PTPRJ, RASGRF1, RASSF6, RBMY1A1, RBMY1B, RBMY1D, RFTN1, RIMBP2, RNF103CHMP3, RNGTT, RPL17, RPL23A, RPS27A, RPS8, S1PR4, SCIMP, SCN3A, SCPEP1, SEMA3D, SH2B2, SH3BP2, SLC12A9, SLC23A2, SLC25A42, SLC2A5, SLC7A3, SNX22, SOX7, SSBP3, SSPN, SYNGR3, TAF4B, TAS1R3, TBC1D3E, TBC1D9, TCEB3, TCL1A, TEX9, TNFRSF13B, TNFSF9, TNS3, TOP1MT, TOX, TOX2, TP53INP1, TRAF5, TRAK2, TSPAN7, TTN, TXLNB, UGT2B17, UTS2B, VSIG1, WNT16, WSCD2, ZFPM1, ZNF318, ZNF804A |
| Plasmacytoid dendritic cells | ABHD15, ACP2, ADAM28, AJAP1, ALOX5AP, ARMC5, ASL, ATG101, BCL11A, C12orf45, C12orf75, CADM4, CCDC50, CCND3, CD164, CD4, CD68, CIB2, CLEC4C, CLIC3, CNPY3, COMMD5, CSF2RA, CUX2, CYP46A1, CYYR1, DCANP1, DERL3, DNASE1L3, DRD4, DUS2, DUSP5, DYNLT1, EIF4EBP3, EPHB1, ERCC1, ERP29, FAM213A, FAM96A, FANCE, FCER1A, FCER1G, FERMT3, GAS6, GLT1D1, GRN, GUCY2D, GZMB, IGFLR1, IKBKE, IL3RA, IRF7, IRF8, ITM2C, JCHAIN, KCNA5, KCNK10, KCNK17, KCTD5, KPTN, KRT5, LAMP5, LGMN, LILRA4, LIME1, LRFN4, MAPK13, MAPKAPK2, MBD6, MS4A6A, NALP7, NAPSA, NEK8, NOTCH4, NR5A1, NREP, P2RY14, PACSIN1, PALD1, PDXP, PECR, PHEX, PLAC8, PLD4, PLP2, PLVAP, PMM1, PPIB, PPM1J, PPP1R14B, PROC, PSEN2, PTCRA, PTGDS, RNF11, RPS6KA4, RPS8, SCAMP5, SCT, SEC61B, SELL, SERPINB6, SERPINF1, SHD, SIDT1, SLA2, SLC12A3, SLC32A1, SMIM5, SMIM6, SMPD3, SPCS1, SPNS3, ST14, ST3GAL2, ST3GAL4, STX18, SULF2, TAGLN2, TIFAB, TLR7, TLR9, TMEM106B, TMEM109, TMEM206, TMEM8B, TMIGD2, TRAF4, TSPAN13, TTC39A, UGCG, VIMP, VPS37B, WDFY1, WNT10A, ZC2HC1A, ZDHHC17, ZFAT |
| Regulatory NK cells | ACTL9, ADGRG3, C3AR1, CCL25, CCL4, CCL4L2, CCL5, CD244, CD3G, CD8B, CD96, CDCA7, CLDND1, CNN2, CNR2, CPXM1, CXCR1, CXCR4, DFNB31, DLL1, DTHD1, EFHC2, EIF3G, ESR2, F12, FCGR3A, FGFBP2, GPR171, GREM2, GZMB, GZMK, HAVCR2, HSPA6, IGHG1, IGHG3, IL12RB2, IL18R1, IL18RAP, IL1RL1, IL23R, IL2RB, IL32, KIR2DL4, KIT, KLRB1, KLRC1, KLRC3, KLRC4, KLRC4KLRK1, KLRF1, KRT3, LDB2, LGALS9B, LGALS9C, LGR6, LPAR5, MAF, MAP3K8, MATK, MGAM, MGAM2, MMRN1, MTSS1, NCR1, NTNG2, PDGFRB, PFN1, PLEKHF1, PODN, PRDM1, ROBO3, SAMD3, SCML1, SH2D1A, SLC4A10, SLC4A4, SPON2, STYK1, TBC1D3E, TC2N, TCF7, TENM1, TIE1, TIGIT, TNFRSF11A, TNFSF11, TOX2, TRBV251, TRDC, UBXN10, XCL1, XCL2, ZBTB16, ZFYVE28, ZMAT4 |
| CD8+ TEMRA | ABCB1, ABHD17A, ADGRG4, AGAP1, ALOX5AP, AOAH, B3GAT1, BHLHE40, BLK, C10orf128, C10orf53, C1orf100, C4orf50, CA6, CACNA1I, CACNA2D2, CAMK4, CARNS1, CASP3, CCL3, CCL3L3, CCL4, CCL5, CCR4, CCR5, CD160, CD247, CD27, CD28, CD3D, CD3E, CD3G, CD40LG, CD5, CD6, CD7, CD70, CD72, CD80, CD8A, CD8B, CDH9, CEP290, CER1, CHST2, CLDND1, CLDND2, CLEC10A, CLECL1, CLIC3, CPA5, CRACR2A, CRTAM, CSF3R, CST7, CTLA4, CTSW, DBH, DERL2, EOMES, EPX, ERP29, EVL, FBXL16, FCRL3, FCRL6, FGFBP2, FGFR1, FHL3, FOSB, FRMD4B, GALM, GALT, GATA1, GATA3, GNAO1, GNLY, GP5, GRAP2, GRIN2C, GZMA, GZMH, GZMK, GZMM, HSH2D, IFNG, IFNK, IKZF2, IL2RB, IL32, IL4I1, IL5RA, IL7R, ITGA1, ITGAE, ITGAM, ITK, JAKMIP1, JPH4, KIR2DL1, KIR2DL2, KIR2DL3, KIR2DS2, KIR3DL1, KIR3DL2, KIT, KLRB1, KLRC2, KLRC3, KLRD1, KLRF1, KLRG1, KLRK1, KRT1, KRT73, LAG3, LAIR2, LDLRAP1, LEF1, LEPROTL1, LIM2, LPAR5, LRRN3, MAMDC4, MATK, MGAT4A, MLC1, MPPED2, NCALD, NCAM1, NCR1, NCR3, NFATC2, NKG7, NKX63, NMUR1, NRBP2, NUAK1, OLIG3, OR10G2, OR2H2, OR6C70, OSBPL7, PDCD1, PDE3B, PDZD4, PLAC8, PPIAL4F, PRDM1, PRF1, PRG3, PRSS33, PRSS35, PRY2, PTGDR, PTGER2, PTPRM, PYHIN1, RASA4, RORA, RPS26, RPS6KA4, RSPH10B2, RXFP2, S100B, S1PR5, SAMD3, SARAF, SARDH, SEC31B, SELL, SERTAD3, SH2D1B, SIGLEC7, SIRPG, SLC7A3, SLX1B, SNTG2, SOAT2, SPOCK2, SPON2, SRY, TCERG1L, TEKT1, TESPA1, THBS4, TLE1, TMC6, TMEM151B, TMEM155, TMIGD2, TMPRSS3, TNF, TNFRSF9, TRA2B, TRAC, TRAT1, TRBC2, TRBV251, TRGC1, TRPM2, TULP2, XCL2, ZEB2, ZMAT1, ZMAT4, ZNF337, ZNF365, ZNF414, ZNF683, ZNF709, ZNF814, ZNF90 |

TABLE 18-continued

Example genes that are specific or semi-specific to cell types.

| Cell Type | Genes |
| --- | --- |
| Transitional memory CD8+ T cells | ABCB1, ADAM19, ADGRG4, ALOX5AP, ANKRD20A1, AOAH, AP3M2, ARMC4, B3GAT1, BCL2, BEND4, BHLHE40, BLK, C10orf128, C2orf40, C4orf50, CA6, CACNA1I, CACNA2D2, CALN1, CAMK4, CARD17, CCL3, CCL3L3, CCL4, CCL5, CCL8, CCR1, CCR2, CCR4, CCR5, CCR7, CCR9, CD160, CD2, CD27, CD28, CD3D, CD3E, CD3G, CD40LG, CD52, CD6, CD69, CD7, CD70, CD83, CD8A, CD8B, CD99, CHN2, CHRNB3, CLDND1, CLEC2B, CLECL1, CPA5, CPXM1, CR2, CRACR2A, CRBN, CRTAM, CSGALNACT1, CST7, CTLA4, CTSW, CYLD, DBH, DNTTIP2, DSC1, EOMES, FAM153A, FAM19A1, FBXO39, FCRL3, FCRL6, FGFBP2, FHL3, FOSB, FOXP3, FRMD4B, GALNT11, GALT, GATA3, GCK, GLB1L3, GNLY, GP5, GPA33, GPLD1, GRM2, GSTK1, GZMA, GZMH, GZMK, GZMM, HLADOB, HLAE, HLF, HPCAL4, HTR4, HUNK, ICOS, IKZF2, IL2RA, IL2RB, IL32, IL4I1, IL5, IL5RA, IL7R, ITGA1, ITGAE, ITGAM, ITGB1, ITK, JAKMIP1, KCNK10, KCNQ3, KIF1A, KIF5A, KIR2DL1, KIR2DL2, KIR2DL3, KIR2DL4, KIR2DS2, KIR3DL1, KIR3DL2, KIT, KLRB1, KLRC2, KLRC3, KLRD1, KLRF1, KLRG1, KLRK1, KRT1, KRT73, KRTAP1010, LAG3, LAIR2, LEF1, LEPROTL1, LIM2, LPAR6, LRRC75A, LRRN3, LTA, MALT1, MATK, MDS2, MGAT4A, MLC1, MPPED2, MREG, MYCBPAP, MYO7A, MYSM1, MZB1, NCALD, NCAM1, NCR1, NCR3, NDUFC2KCTD14, NGDN, NKG7, NMUR1, NOSIP, NRBP2, NRDE2, NT5E, OLIG3, OR10G2, OR11H4, OSBPL7, P2RY14, PCDHGA8, PDCD1, PDE3B, PDLIM2, PDZD4, PIK3R1, PKIA, PLCG1, PPIAL4F, PRDM1, PRF1, PRG3, PRSS35, PTGDR, PTGER2, PTPRM, RCAN2, RCAN3, RGPD5, RHOT2, RNF130, RORA, RPS26, RPS6KA3, S1PR1, S1PR5, SAMD3, SEC31B, SELL, SH3BGRL2, SIRPB1, SIRPG, SIT1, SLC17A9, SLX1B, SNTG2, SOAT2, SPOCK2, SPON2, SRY, SSTR3, SV2A, TBC1D4, TBPL2, TCF7, TEKT1, TESPA1, TIAM1, TMC6, TMEM155, TMIGD2, TMPRSS11E, TMPRSS3, TNFRSF13C, TNFRSF4, TNFRSF9, TOE1, TPRG1, TRA2B, TRAC, TRAT1, TRBC2, TRBV251, TRGC1, TRPM2, TRPS1, TTC23L, TUBB4A, TULP2, UBASH3A, USP20, VWA5B2, XCL2, ZBED2, ZCCHC14, ZMAT1, ZNF35, ZNF365, ZNF414, ZNF683, ZNF853, ZNF90 |
| Transitional memory CD4+ T cells | ABCB1, ACSS2, ADAM19, ADAM23, ADRB3, AGMAT, AHNAK, ALOX5AP, AMICA1, ANKRD39, ANKRD55, AP3M2, AQP3, ARL4A, B2M, B3GAT1, BACH2, BEST4, BHLHE22, BLK, C10orf128, C4orf50, C9orf89, CA6, CACNA1I, CACNA2D2, CAMK4, CAPN12, CARD17, CARNS1, CCL5, CCR2, CCR4, CCR5, CCR7, CCR9, CD2, CD207, CD247, CD27, CD28, CD3D, CD3E, CD3G, CD4, CD40LG, CD5, CD6, CD69, CD7, CD70, CD8A, CD8B, CEACAM8, CER1, CHDH, CHRNB3, CLEC4F, CMTM6, COCH, COL4A3, CPA3, CPA5, CRHR1, CRTAM, CSGALNACT1, CST7, CTLA4, CX3CR1, CXCR2, CXCR5, CYLD, DACT1, DBH, DERL2, DLG4, DNAH6, DPPA4, DSC1, DSCR8, EDAR, EOMES, EPHA1, ERICH3, FAM153A, FAM19A1, FAM65A, FAS, FBLN7, FBXL16, FCER1A, FCRL3, FCRL6, FGFBP2, FHIT, FLT3LG, FMN1, FOSB, FOXP3, FRMD4B, GADD45G, GAL3ST4, GALT, GATA3, GBP4, GJC3, GKN1, GLB1L3, GLDC, GNAO1, GNLY, GP5, GPA33, GPM6B, GRAP2, GZMA, GZMH, GZMK, GZMM, HDC, HDDC3, HLADOA, HLF, HPCAL4, ICOS, IDO1, IFNG, IFNK, IGHG1, IKZF2, IL17A, IL2RA, IL2RB, IL3, IL32, IL4I1, IL5RA, IL7R, ILDR2, INPP4B, IRF4, ITGAE, ITGB1, ITK, JAKMIP1, JPH4, KBTBD3, KCNQ3, KIT, KLF8, KLRB1, KLRF1, KLRG1, KRT1, KRT73, KRTAP212, LAG3, LCK, LECT1, LEF1, LEPROTL1, LPAR6, LRRN3, LTA, MALT1, MAN1C1, MCOLN3, MDFIC, MDS2, MITD1, MS4A1, MTRF1, MYBPC2, MYO16, MZB1, NEFL, NKG7, NKX63, NOSIP, NPM2, OR1L4, OR4D9, OR56A5, PAGE2, PDCD1, PDE3B, PDZD4, PGA4, PIFO, PIK3R1, PKIA, PLK3, POLR3G, POU2AF1, PPIAL4F, PRDM1, PRF1, PRG3, PRSS35, PRY2, PTGDR, PTGER2, PTP4A3, PTPRM, PYHIN1, RCAN2, RCAN3, RGPD5, RIC3, RNASEH2B, RORA, RPL14, RPL21, RPL4, RPS26, RPS27, RPS7, S1PR1, S1PR5, SAMD3, SEC31B, SELL, SIRPG, SIT1, SLAIN1, SLC2A7, SLC5A11, SNTG2, SOAT2, SOX5, SOX8, SPDYE2B, SPG20, SPN, SPOCK2, SPRR3, SSTR3, STAC3, TBC1D3C, TBC1D4, TCEA3, TCEB3CL2, TCF7, TESPA1, THBS4, TIAM1, TMEM155, TMEM182, TMEM218, TMEM45B, TMIGD2, TMPRSS3, TNF, TNFAIP8L2, TNFRSF13C, TNFRSF25, TNFRSF4, TNFSF13B, TPRG1, TRAC, TRAT1, TRBC2, TRBV251, TRGC1, TSHZ2, UBASH3A, USHBP1, VIPR1, WNK4, WNT7A, ZCCHC14, ZFP82, ZMAT1, ZNF365, ZNF524, ZNF683, ZNF775, ZNF853 |
| CD4+ Tregs | A2M, ACAP1, ADAM29, ANKRD55, AP3M2, APOL3, AQP3, ATHL1, AXIN2, B2M, B3GALT2, BCL11B, BFSP2, BHLHE40, C1QTNF7, C2CD4A, CASP10, CCDC23, CCND2, CCR10, CCR3, CCR4, CCR5, CCR6, CD247, CD27, CD40LG, CD52, CD69, CD96, CEACAM4, CEP85L, CHD2, CHD7, CISH, CTLA4, DDX3Y, DGKA, DLEC1, DNAH8, DUSP16, EIF3CL, EPSTI1, ETS1, F5, FANK1, FCMR, FCRL3, FOXP3, GCNT4, GIMAP4, GPA33, GPRIN3, HMCN1, ICOS, IKZF1, IKZF2, IL24, IL2RA, IL4R, IL7R, ITGA4, KCNA3, KLHL34, KRT28, LAIR2, LBH, LRRC32, LTA, LZTS1, MAL, MEOX1, NLRP6, NOG, OSM, PIM1, PKIA, PLAG1, PLCL1, PLXDC1, POU2F2, PRAMEF5, PRR5L, RBMS1, RGPD1, RGS10, RORC, RPL17C18orf32, RPL32, RPS26, RTKN2, RUFY3, SCML4, SELL, SELP, SEMA3G, SIRPG, SLC22A12, SOCS1, SORBS3, SOS1, STAT4, TBC1D3K, TESPA1, TFAP2B, THEMIS, TIGIT, TMEM169, TMSB4X, TNFRSF25, TNFRSF4, TNFSF14, TRAC, TRADD, TSHR, WNT1, ZFP36L2 |

EQUIVALENTS

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation many equivalents to the specific embodiments described herein. It is, therefore, to be understood that the foregoing embodi- ments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately," "substantially," and "about" may be used to mean within +20% of a target value in some embodiments, within +10% of a target value in some embodiments, within +5% of a target value in some embodiments, within +2% of a target value in some embodiments. The terms "approximately," "substantially," and "about" may include the target value.

What is claimed is:

1. A method for determining a leukocyte immunoprofile type of a subject having, suspected of having, or at risk of having cancer, the method comprising:
   using at least one computer hardware processor to perform:
   obtaining flow cytometry data for white blood cells (WBC) isolated from a biological sample obtained from the subject;
   processing the flow cytometry data to determine cell composition percentages for at least 20 of the following cell types:
   Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, memory CD4+ T cells, CD4+ T cells, CD39+ CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, and HLA-DRlow monocytes;
   generating a leukocyte signature for the subject using the determined cell composition percentages for the at least 20 cell types, the leukocyte signature comprising the cell composition percentages for the at least 20 cell types;
   identifying, using the leukocyte signature and from among a plurality of leukocyte immunoprofile types, a Primed leukocyte immunoprofile type for the subject; and
   administering an immune checkpoint inhibitor (ICI) to the subject when the subject is identified as having the Primed leukocyte immunoprofile type.

2. The method of claim 1, wherein the WBC consist of granulocyte white blood cells and agranulocyte white blood cells.

3. The method of claim 1, wherein processing the flow cytometry data comprises applying one or more machine learning models to the flow cytometry data to obtain the cell composition percentages for the at least 20 cell types.

4. The method of claim 1, wherein processing the flow cytometry data comprises determining cell composition percentages for: Naive CD4+ Tregs, Naive CD4+ T cells, Naive CD8+ T cells, Naive B cells, Effector memory CD4+ T cells, Effector memory CD8+ T cells, Classical monocytes, and Non-classical monocytes.

5. The method of claim 1, wherein processing the flow cytometry data comprises determining the cell composition percentages for: Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, memory CD4+ T cells, CD4+ T cells, CD39+CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, and HLA-DRlow monocytes.

6. The method of claim 1, wherein the leukocyte signature comprises the cell composition percentages for: Naive CD4+ Tregs, Naive CD4+ T cells, Naive CD8+ T cells, Naive B cells, Effector memory CD4+ T cells, Effector memory CD8+ T cells, Classical monocytes, and Non-classical monocytes.

7. The method of claim 1, wherein the leukocyte signature comprises the cell composition percentages for: Naive CD4+ Tregs, Naive CD4+ T cells, Naive CD8+ T cells, Naive B cells, Non-switched memory IgM B cells, Vδ2+ γδ T cells, Class-switched memory B cells, Central memory CD8+ T cells, CD4+ Tregs, Transitional memory CD4+ T cells, Central memory CD4+ T cells, memory CD4+ T cells, CD4+ T cells, CD39+ CD4+ Tregs, Eosinophils, Basophils, Plasmacytoid dendritic cells, Dendritic cells, PD1high CD8+ T cells, Transitional memory CD8+ T cells, Cytotoxic NK cells, Regulatory NK cells, memory CD8+ T cells, CD8+ T cells, Effector memory CD4+ T cells, NKT cells, CD8+ TEMRA, Effector memory CD8+ T cells, CD4+ TEMRA, Neutrophils, Granulocytes, Classical monocytes, Non-classical monocytes, and HLA-DRlow monocytes.

8. The method of claim 1, wherein identifying, using the leukocyte signature and from among a plurality of leukocyte immunoprofile types, the Primed leukocyte immunoprofile type for the subject comprises:

associating the leukocyte signature of the subject with a particular one of the plurality of leukocyte immunoprofile types, and identifying the Primed leukocyte immunoprofile type for the subject as the leukocyte immunoprofile type corresponding to the particular one of the plurality of leukocyte immunoprofile types to which the leukocyte signature of the subject is associated.

9. The method of claim 8, wherein associating the leukocyte signature of the subject with a particular one of the plurality of leukocyte immunoprofile types comprises:

processing the leukocyte signature with a trained classifier to obtain an output indicative of the particular one of the plurality of leukocyte immunoprofile types.

10. The method of claim 9, wherein the trained classifier comprises a trained neural network classifier, optionally, a tabular prior-data fitted network transformer (TabPFN) classifier.

11. The method of claim 8, wherein the associating the leukocyte signature of the subject with a particular one of the plurality of leukocyte immunoprofile types comprises:

determining, for each particular one of the plurality of leukocyte immunoprofile types, a score indicating whether the leukocyte signature of the subject is associated with that particular leukocyte immunoprofile type, wherein determining the score for a particular leukocyte immunoprofile type comprises applying a linear regression model associated with the particular leukocyte immunoprofile type, to the cell composition percentages in the leukocyte signature.

12. The method of claim 1, further comprising generating the plurality of leukocyte immunoprofile types, the generating comprising:

obtaining multiple sets of flow cytometry data from white blood cells (WBC) isolated from biological samples obtained from multiple respective subjects, each of the multiple sets of flow cytometry data indicating cell composition percentages for the at least 20 cell types;

generating multiple leukocyte signatures from the multiple sets of flow cytometry data, each of the multiple leukocyte signatures comprising cell composition percentages for the at least 20 cell types, the generating comprising, for each particular one of the multiple leukocyte signatures:

determining the leukocyte signature by determining the cell composition percentages using the flow cytometry data in the particular set of flow cytometry data for which the particular one leukocyte signature is being generated; and clustering the multiple leukocyte signatures to obtain the plurality of leukocyte immunoprofile types.

13. The method of claim 1, wherein the plurality of leukocyte immunoprofile types comprises: a Naïve leukocyte immunoprofile type, the Primed leukocyte immunoprofile type, a Progressive leukocyte immunoprofile type, a Chronic leukocyte immunoprofile type, and a Suppressive leukocyte immunoprofile type.

14. The method of claim 1, wherein the subject has head and neck squamous cell carcinoma (HNSCC).

* * * * *